(12) United States Patent
Biswas et al.

(10) Patent No.: US 8,952,009 B2
(45) Date of Patent: Feb. 10, 2015

(54) CHROMAN DERIVATIVES AS TRPM8 INHIBITORS

(71) Applicant: Amgen Inc., Thousand Oaks, CA (US)

(72) Inventors: Kaustav Biswas, Agoura Hills, CA (US); Jian J. Chen, Camarillo, CA (US); Vijay Keshav Gore, Aliso Viejo, CA (US); Scott Harried, Pittsburgh, PA (US); Daniel B. Horne, Simi Valley, CA (US); Matthew R. Kaller, Ventura, CA (US); Vu Van Ma, Oak Park, CA (US); Kelvin Sham, Thousand Oaks, CA (US); Wenge Zhong, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/958,478

(22) Filed: Aug. 2, 2013

(65) Prior Publication Data
US 2014/0045855 A1  Feb. 13, 2014

Related U.S. Application Data

(60) Provisional application No. 61/680,199, filed on Aug. 6, 2012.

(51) Int. Cl.
| | | |
|---|---|---|
| C07D 491/052 | (2006.01) | |
| C07D 401/12 | (2006.01) | |
| C07D 311/68 | (2006.01) | |
| C07D 215/40 | (2006.01) | |
| C07D 471/04 | (2006.01) | |
| C07D 491/04 | (2006.01) | |

(52) U.S. Cl.
CPC .......... *C07D 491/052* (2013.01); *C07D 401/12* (2013.01); *C07D 311/68* (2013.01); *C07D 215/40* (2013.01); *C07D 471/04* (2013.01); *C07D 491/04* (2013.01)
USPC ........................................................ 514/249

(58) Field of Classification Search
None
See application file for complete search history.

(56) References Cited

U.S. PATENT DOCUMENTS

| | | | |
|---|---|---|---|
| 2,483,250 A | 9/1949 | Suter | |
| 3,995,044 A | 11/1976 | Kabbe et al. | |
| 4,006,239 A | 2/1977 | Mayer et al. | |
| 5,081,131 A | 1/1992 | Tomcufcik et al. | |
| 5,223,499 A | 6/1993 | Greenlee et al. | |
| 5,296,495 A | 3/1994 | Matsuo et al. | |
| 5,344,813 A | 9/1994 | Theobald et al. | |
| 5,380,721 A | 1/1995 | Johnson et al. | |
| 5,395,840 A | 3/1995 | Miiller et al. | |
| 5,468,882 A | 11/1995 | Schohe-Loop et al. | |
| 5,698,554 A | 12/1997 | Ishida et al. | |
| 5,728,699 A | 3/1998 | Toriyabe et al. | |
| 5,817,677 A | 10/1998 | Linz et al. | |
| 5,891,872 A | 4/1999 | Doll et al. | |
| 5,892,030 A | 4/1999 | Alig | |
| 5,910,595 A | 6/1999 | Durrwachter | |
| 5,916,906 A | 6/1999 | Shaskan | |
| 5,977,090 A | 11/1999 | Slusher et al. | |
| 6,075,029 A | 6/2000 | Klein et al. | |
| 6,200,993 B1 | 3/2001 | Cote et al. | |
| 6,268,384 B1 | 7/2001 | Novak et al. | |
| 6,302,921 B1 | 10/2001 | Delroisse et al. | |
| 6,329,405 B1 | 12/2001 | Kurata et al. | |
| 6,369,227 B1 | 4/2002 | Lam et al. | |
| 6,413,979 B1 | 7/2002 | Hayama et al. | |
| 6,448,281 B1 | 9/2002 | Beaulieu et al. | |
| 6,451,752 B1 | 9/2002 | Delroisse et al. | |
| 6,555,561 B2 | 4/2003 | Bloom et al. | |

(Continued)

FOREIGN PATENT DOCUMENTS

| | | |
|---|---|---|
| CA | 2135536 A1 | 5/1995 |
| CA | 2761639 A1 | 12/2010 |
| CN | 1733708 | 2/2006 |
| CN | 101343313 | 6/2009 |
| EP | 0459730 A2 | 12/1991 |

(Continued)

OTHER PUBLICATIONS

International Search Report and Written Opinion for PCT Application No. PCT/US2013/053514, mailed on Sep. 18, 2013.

(Continued)

*Primary Examiner* — Soren Harward
*Assistant Examiner* — Jeanmaire Calvillo
(74) *Attorney, Agent, or Firm* — Bernard P. Friedrichsen

(57) ABSTRACT

Chroman compounds and derivatives of Formula I are useful inhibitors of TRPM8. Such compounds are useful in treating a number of TRPM8 mediated disorders and conditions and may be used to prepare medicaments and pharmaceutical compositions useful for treating such disorders and conditions. Examples of such disorders include, but are not limited to, migraines and neuropathic pain. Compounds of Formula I have the following structure:

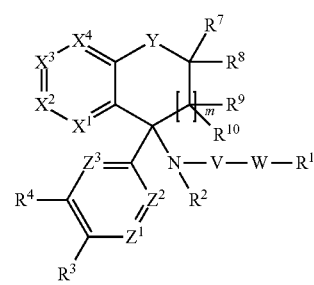

where the definitions of the variables are provided herein.

57 Claims, No Drawings

(56) References Cited

U.S. PATENT DOCUMENTS

| | | |
|---|---|---|
| 6,617,351 B1 | 9/2003 | Arnold et al. |
| 6,630,495 B1 | 10/2003 | Cooke et al. |
| 6,630,509 B2 | 10/2003 | Fagerhag et al. |
| 6,696,467 B2 | 2/2004 | Mattei et al. |
| 6,903,128 B2 | 6/2005 | Duplantier et al. |
| 7,087,617 B2 | 8/2006 | Corbett et al. |
| 7,091,371 B2 | 8/2006 | Ducray et al. |
| 7,179,823 B1 | 2/2007 | Momose et al. |
| 7,273,856 B2 | 9/2007 | Sisto et al. |
| 7,291,641 B2 | 11/2007 | Chabrier De Lassauniere et al. |
| 7,351,713 B2 | 4/2008 | Chan Chun Kong et al. |
| 7,375,093 B2 | 5/2008 | Tice et al. |
| 7,405,221 B2 | 7/2008 | Kopka et al. |
| 7,550,499 B2 | 6/2009 | Tuerdi et al. |
| 7,601,868 B2 | 10/2009 | Ishihara et al. |
| 7,618,959 B2 | 11/2009 | Axten et al. |
| 7,625,937 B2 | 12/2009 | Ali et al. |
| 7,834,023 B2 | 11/2010 | Scarborough et al. |
| 7,888,376 B2 | 2/2011 | Salvati et al. |
| 7,947,718 B2 | 5/2011 | Carruthers et al. |
| 7,964,204 B2 | 6/2011 | Lahm et al. |
| 7,968,542 B2 | 6/2011 | Miyaji et al. |
| 8,017,635 B2 | 9/2011 | Lyga et al. |
| 8,268,754 B2 | 9/2012 | Mita et al. |
| 2002/0019527 A1 | 2/2002 | Wang et al. |
| 2002/0042516 A1 | 4/2002 | Tom et al. |
| 2003/0050211 A1 | 3/2003 | Hage et al. |
| 2003/0195212 A1 | 10/2003 | Lundstedt et al. |
| 2005/0026991 A1 | 2/2005 | Cholody et al. |
| 2005/0038035 A1 | 2/2005 | Takasugi et al. |
| 2005/0159450 A1 | 7/2005 | Dargazanli et al. |
| 2006/0063775 A1 | 3/2006 | Pajouhesh et al. |
| 2006/0117994 A1 | 6/2006 | Ryu et al. |
| 2006/0173183 A1 | 8/2006 | Powes et al. |
| 2007/0066604 A1 | 3/2007 | Herold et al. |
| 2007/0155738 A1 | 7/2007 | Steeneck et al. |
| 2007/0185152 A1 | 8/2007 | Yamashita et al. |
| 2008/0045589 A1 | 2/2008 | Kelley |
| 2008/0051418 A1 | 2/2008 | Maekawa et al. |
| 2008/0146612 A1 | 6/2008 | Thompson et al. |
| 2008/0214552 A1 | 9/2008 | Fischer et al. |
| 2008/0293674 A1 | 11/2008 | Schwarz et al. |
| 2008/0293687 A1 | 11/2008 | Gibson et al. |
| 2008/0312278 A1 | 12/2008 | Schadt et al. |
| 2009/0069320 A1 | 3/2009 | Reich et al. |
| 2009/0082358 A1 | 3/2009 | Nishimura et al. |
| 2009/0239876 A1 | 9/2009 | Clements et al. |
| 2009/0286765 A1 | 11/2009 | Blackaby et al. |
| 2010/0063100 A1 | 3/2010 | Chen et al. |
| 2010/0125062 A1 | 5/2010 | Allen et al. |
| 2010/0179166 A1 | 7/2010 | Bell et al. |
| 2010/0261723 A1 | 10/2010 | Finlay |
| 2010/0261728 A1 | 10/2010 | Norman et al. |
| 2010/0292263 A1 | 11/2010 | Wood |
| 2011/0028507 A1 | 2/2011 | Kim et al. |
| 2011/0028509 A1 | 2/2011 | Crosignani et al. |
| 2011/0105532 A1 | 5/2011 | Heil et al. |
| 2011/0105549 A1 | 5/2011 | Wood et al. |
| 2011/0212969 A1 | 9/2011 | Blackburn et al. |
| 2011/0269761 A1 | 11/2011 | Langkopf et al. |
| 2011/0301193 A1 | 12/2011 | Errico et al. |
| 2012/0004198 A1 | 1/2012 | Liao et al. |
| 2013/0157996 A1 | 6/2013 | Biswas et al. |
| 2013/0158034 A1 | 6/2013 | Brown et al. |
| 2013/0324557 A1* | 12/2013 | Priest et al. ............... 514/255.05 |

FOREIGN PATENT DOCUMENTS

| | | |
|---|---|---|
| EP | 528172 A1 | 1/1993 |
| EP | 1099442 A2 | 5/2001 |
| EP | 1099701 A1 | 5/2001 |
| EP | 1500650 A1 | 1/2005 |
| EP | 2272841 A1 | 1/2011 |
| FR | 2692895 A1 | 6/1992 |
| JP | 53141271 A1 | 12/1978 |
| JP | 07285962 A1 | 10/1995 |
| JP | 2001354563 A1 | 12/2001 |
| JP | 2002302439 A1 | 10/2002 |
| JP | 2004115450 A1 | 4/2004 |
| JP | 2004175872 A1 | 6/2004 |
| JP | 2004203871 A1 | 7/2004 |
| JP | 2007091708 A1 | 8/2007 |
| WO | WO 9212973 | 1/1992 |
| WO | WO 9312796 A1 | 7/1993 |
| WO | WO 9701546 A1 | 1/1996 |
| WO | WO 9620173 A1 | 7/1996 |
| WO | WO 9710219 A1 | 3/1997 |
| WO | WO 9715567 A1 | 5/1997 |
| WO | WO 9722588 A1 | 6/1997 |
| WO | WO 9962486 A1 | 12/1999 |
| WO | WO 0035889 A1 | 6/2000 |
| WO | WO 0116271 A1 | 3/2001 |
| WO | WO 0158869 A2 | 8/2001 |
| WO | WO 0181316 A2 | 11/2001 |
| WO | WO 02051396 A1 | 7/2002 |
| WO | WO 02079189 A2 | 10/2002 |
| WO | WO 02088073 A1 | 11/2002 |
| WO | WO 03045385 A1 | 6/2003 |
| WO | WO 03051275 A2 | 6/2003 |
| WO | WO 03082278 A1 | 10/2003 |
| WO | WO 2004013100 A2 | 2/2004 |
| WO | WO 2004/026840 A1 | 4/2004 |
| WO | WO 2004039795 A2 | 5/2004 |
| WO | WO 2004058755 A2 | 7/2004 |
| WO | WO 2005005392 A1 | 1/2005 |
| WO | WO 2005007656 A1 | 1/2005 |
| WO | WO 2005021545 A1 | 3/2005 |
| WO | WO 2005023794 A2 | 3/2005 |
| WO | WO 2005046683 | 5/2005 |
| WO | WO 2005042524 A1 | 5/2005 |
| WO | WO 2005080373 A1 | 9/2005 |
| WO | WO 2005080390 A1 | 9/2005 |
| WO | WO 2005113553 A2 | 12/2005 |
| WO | WO 2005115374 A1 | 12/2005 |
| WO | WO 2006002383 A2 | 1/2006 |
| WO | WO 2006068594 A1 | 6/2006 |
| WO | WO 2006094246 A2 | 9/2006 |
| WO | WO 2007002559 A1 | 1/2007 |
| WO | WO 2007/017093 A1 | 2/2007 |
| WO | WO 2007054215 A1 | 5/2007 |
| WO | WO 2007054302 A1 | 5/2007 |
| WO | WO 2007060028 A1 | 5/2007 |
| WO | WO 2007062314 A2 | 5/2007 |
| WO | WO 2007068381 A1 | 6/2007 |
| WO | WO 2007068383 A1 | 6/2007 |
| WO | WO 2007086799 A1 | 8/2007 |
| WO | WO 2007097470 A2 | 8/2007 |
| WO | WO 2007141504 A1 | 12/2007 |
| WO | WO 2008003746 A1 | 1/2008 |
| WO | WO 2008/022938 | 2/2008 |
| WO | WO 2008014602 A1 | 2/2008 |
| WO | WO 2008056687 A1 | 5/2008 |
| WO | WO 2008063667 A1 | 5/2008 |
| WO | WO 2008063670 A1 | 5/2008 |
| WO | WO 2008073825 A1 | 6/2008 |
| WO | WO 2008080015 A2 | 7/2008 |
| WO | WO 2008112156 A1 | 9/2008 |
| WO | WO 2009023179 A2 | 2/2009 |
| WO | WO 2009117269 A1 | 9/2009 |
| WO | WO 2009156089 A1 | 12/2009 |
| WO | WO 2010027236 A1 | 3/2010 |
| WO | WO 2010046780 A2 | 4/2010 |
| WO | WO 2010114471 A1 | 10/2010 |
| WO | WO 2010137351 A1 | 12/2010 |
| WO | WO 2010141330 A1 | 12/2010 |
| WO | WO 2011014649 A1 | 2/2011 |
| WO | WO 2011023703 A1 | 3/2011 |
| WO | WO 2011/061330 A2 | 5/2011 |
| WO | WO 2011054436 A2 | 5/2011 |
| WO | WO 2011085126 A2 | 7/2011 |
| WO | WO 2011106632 A1 | 9/2011 |
| WO | WO 2011142359 A1 | 11/2011 |
| WO | WO 2011146300 A1 | 11/2011 |

(56) References Cited

FOREIGN PATENT DOCUMENTS

| WO | WO 2011147765 A1 | 12/2011 |
| WO | WO 2012052540 A1 | 4/2012 |
| WO | WO 2012061698 A2 | 5/2012 |
| WO | WO 2012078855 A1 | 6/2012 |
| WO | WO 2012079624 A1 | 6/2012 |
| WO | WO 2012082862 A2 | 6/2012 |
| WO | WO 2012083190 A1 | 6/2012 |
| WO | WO 2012118850 A1 | 9/2012 |
| WO | WO 2012120398 A1 | 9/2012 |

OTHER PUBLICATIONS

Bach, et al., Synlett ".alpha.-Arylation of Cyclic Amines by Aryl Transfer in Lithiated Ureas" 3, pp. 421-424 (2009).
Albrecht, W. L. et al, "3-Substituted imidazo[1,5-a]pyridines," Journal of Heterocyclic Chemistry, 16(7), pp. 1349-1351 (1979).
Bensel, N. et al, "BensenelStraightforward Synthesis of N-Protected Benzylic Amines by Carbamoalkylation of Aromatic Compounds," Tetrahedron Letters, 40, pp. 879-882 (1999).
Boyer, J. H. et al, "Diazotization of 2-Pyridylmethylamine," Journal of Organic Chemistry, 23, pp. 1053-1054 (1958).
Childers, W. E. et al., "Advances in the Development of Novel Analgesics," Expert Opinion on Therapeutic Patents, 18(8), pp. 1027-1067 (2008).
Chung, J.-U. et al, "α-Substituted N-(4-tert-Butylbenzl)-N'-[4-(methylsulfonylamino)-benzyl]thiourea Analogues as Potent and StereospecificTRPV1 Antagonists," Bioorganic & Medicinal Chemistry, 15, pp. 6043-6053 (2007).
DeFalco, J. et al., "TRPM8 Biology and Medicinal Chemistry," Current Topics in Medicinal Chemistry, 11(17), pp. 2237-2252 (2011).
Dou, X.-Y. et al, "Rhodium-Catalyzed Arylation of α-Amido Sulfones with Arylboronic Acids in a Water-Toluene Biphasic System," Inorganica Chimica Acta, 369, pp. 284-287 (2011).
Gomtsyan, A, et al., "α-Methylation at Benzylic Fragment of N-Aryl-N'-benzyl Ureas provides TRPV1 antagonists with better pharmacokinetic properties and higher efficacy in inflammatory pain model," Bioorganic & Medicinal Chemistry Letters, 17, pp. 3894-3899 (2007).
Heymans, F. et al., "Quantitative Structure-Activity Relationships for N-[(N',N'-Disubstituted-amino)acetyl]arylamines for Local Anesthetic Activity and Acute Toxicity," Journal of Medicinal Chemistry, 23(2), pp. 184-193 (1980).
Hou, G. et al., "Iridum,-Monodentate Phophoramidite-Catalyzed Asymmetric Hydrogenation of Substituted Benzophenone N—H Imines," Journal of the American Chemical Society, 132(7) pp. 2124-2125 and S1-S52 (2010).
Kovtun, Y. P. et al, "Improved Method for the Preparation of 3-Aryl- and 3-Styrylimidazo[1,5-a]pyridines," Chemistry of Heterocyclic Compounds (New York) (Translation of Khimiya Geterotsiklicheskikh Soedinenii), 36(5), pp. 557-559 (2000).
Kraznov, V. A. et al., "Synthesis and Anticonvulsive Activity of Fluorine-Substituted Benzyhydrylamides," Pharmaceutical Chemistry Journal, 31(7), pp. 368-369 (1997).
Laurent, M. et al, "A Practical Synthesis of para Di- and Mono-Substituted Benzhydryiamines from Benzhydrol Precursors," Synthesis, 5, pp. 667-672 (2000).
Lespagnol, A. et al, "Amides with a papaverine structure," Bulletin de la Societe Chimique de France, (2), pp. 699-702, (1972).
Liu, Z. et al, "Catalytic Asymmetric Addition of Arylboronic acids to N-Boc Imines Generated in situ using C2-Symmetric Cationic N-Heterocyclic Carbenes (NHCs) Pd2b diaquocomplexes," Tetrahedron, 66, pp. 2619-2623 (2010).
Maki, T. et al., "4,5,6,7-Tetrachlorobenzo[d][1,3,2]dioxaboro]-2-ol as an Effective Catalyst for the Amide Condensation of Sterically Demanding Carboxylic Acids," Organic Letters, 8(7), pp. 1431-1434 and S1-S29 (2006).
Metzger, F. et al. "Sulphonylurea Binding in Rat Isolated Glomerull; Pharmacological Characterization and Dependence on Cell Metabolism and Cytoskeleton," Nauyn-Schmiedberg's Archives of Pharmacology, 355(2), pp. 141-149 (1997).

Muccioli, G.G. et al, "1-Benzhydryl-3-phenylurea and 1-Benzhydryl-3-phenylthiourea Derivatives: New Templates among the CB1 Cannabinoid Receptor Inverse Agonists," Journal of Medicinal Chemistry, 48, pp. 7486-7490 (2005).
Pacchiano, F. et al, "Ureido-Substituted Benzenesulfonamides Potently Inhibit Carbonic Anhydrase IX and Show Antimetastatic Acitivty in a Model of Breast Cancer Metastasis," Journal of Medicinal Chemistry, 54, pp. 1896-1902 (2011).
Raja, E. K. et al., "Superelectrophilic Chemistry of Amino-Nitriles and Related Substrates," Tetrahedron, 67(25), pp. 4494-4497 (2011).
Sasse, A. et al, "(Partial) Agonist/Antagonist Properties of Novel Diarylalkyl Carbamates on Histamine H3 Receptors," Bioorganic & Medicinal Chemistry, 8, pp. 1139-1149 (2000).
Trivedi, B.K. et al, "Inhibitors of Acyl-CoA:Cholesterol Acyltransferase. 4. A Novel Series of Urea ACAT Inhibitors as Potential Hypocholesterolemic Agents," Journal of Medicinal Chemistry, 36(22), pp. 3300-3307 (1993).
Weii, A, "Conservation of Functional and Pharmacological Properties in the Distantly Related Temperature Sensors TRPV1 and TRPM8," Molecular Pharmacology, 68(2), pp. 518-527 (2005).
Wrobleski, S.T. et al., "Rational Design and Synthesis of an Orally Active Indolopyridone as a Novel Conformationally Constrained Cannabinoid Ligand Possessing Antiinflammatory Properties," Journal of Medicinal Chemistry, 46(11), pp. 2110-2116 (2003).
XP002690876, Database PubChem Compound [Online]"ACIM78XL-Compound Summary" Database Accession No. CID2437712 (Jul. 15, 2005) (Cited in International Search Report for PCT Application No. PCT/US2012/043566).
XP002690877, Database Registry [Online] Chemical Abstracts Service, Columbus, Ohio, US "6-Methoxy-N-[phenyl(pryidin-2-yl)methyl]quinoline-2-carboxamide," Database Accession No. 1241062-82-7 (Sep. 15, 2010) (Cited in International Search Report for PCT Application No. PCT/US2012/043566).
XP002691556, Database PubChem Compound [Online] "Zinc58157967—Compound Summary" Database Accession No. CID52501511 (May 20, 2011) (Cited in International Search Report for PCT Application No. PCT/US2012/043566).
XP002690878, Database Registry [Online] Chemical Abstracts Service, Columbus, Ohio, US "1,6-Dihydro-1-methyl-6-oxo-N-(phenyl-2-pyridinylmethyl)-3-pyridinecarboxamide," Database Accession No. 1280882-39-4 (Apr. 17, 2011) (Cited in International Search Report for PCT Application No. PCT/US2012/043566).
XP002690879, Database Registry [Online] Chemical Abstracts Service, Columbus, Ohio, US "2-Methyl-N-(phenyl-3-pyridinylmethyl)-1H-benzimidazole-6-carboxamide," Database Accession No. 1214549-94-6 (Mar. 25, 2010) (Cited in International Search Report for PCT Application No. PCT/US2012/043566).
Shintani, et al., Organic Letters "Rhodium-Catalyzed Asymmetric Addition of Potassium Organotrifluoroborates to N-Sulfonyl Ketimines" 13(12), pp. 2977-2979 (2011).
Shintani, et al., J. Am. Chem. Soc "Rhodium-Catalyzed Asymmetric Arylationof N-Tosyl Ketimines" 132(38), pp. 13168-13169 (2010).
Zaugg, et al., J of Organic Chem "Neighboring Group Reactions. I. Nuclephilic Attack Alkoxide and Hydroxide ion on 3-(.omega.-Haloalkyl)-3-phenyl-2-benzofuranones. A new Synthesis of 1-Benzoxacycloalkanes" 26(12), pp. 4821-4824 (1961).
De la Fuente, et al., Tetrahedron "Synthesis of chromeno[4,3,2-cd]isoindolin-2-ones and chromeno[4,3,2-de]isoquinolin-3-ones. Electrophilic versus anionic cyclization of carbamates" 60(44) pp. 10019-10028 (2004).
Meisenbach, et al., Chemical Communications "New methoxy-substituted 9-phenylxanthen-9-ylamine linkers for the solid phase synthesis of protected peptide amides" 9, pp. 849-850 (1997).
Arbuzov, et al., Trudy Kazan. Khim. Tekhnol. Inst. Im. S. M. Kirova "Reactions of double decomposition of metallic derivatives of acid amides. I. Reaction of sodium and silver salts of benzamide and dibenzamide with chloro and bromo derivatives of the triarylmethane series as well as of phenylxanthene series" 23, pp. 40-53 (1957) with English Abstract.

\* cited by examiner

CHROMAN DERIVATIVES AS TRPM8 INHIBITORS

CROSS REFERENCES TO RELATED APPLICATIONS

This application claims the benefit of U.S. Provisional Application No. 61/680,199, filed on Aug. 6, 2012, which is hereby incorporated by reference in its entirety and for all purposes as if fully set forth herein.

FIELD OF THE INVENTION

The present invention relates to chroman compounds and related derivatives that have TRPM8 antagonist properties and are useful in preparing medicaments and compositions and in treating diseases and conditions such as those mediated by TRPM8. The compounds and compositions may be used to treat various diseases or conditions modulated by TRPM8 such as, but not limited to, migraines and neuropathic pain.

BACKGROUND OF THE INVENTION

Cold sensation is derived from activation of the somatosensory system by a cold stimulus. Calcium imaging and patch clamp experiments in dissociated trigeminal and dorsal root ganglia neurons have revealed cold stimuli induced calcium influx, suggesting the direct opening of a calcium-permeable ion channels by cold (Thut et al., 2003; Reid, 2005). A recently cloned non-selective cation channel, TRPM8 (transient receptor potential melastatin 8) or trp-p8 (identified as a prostate-specific gene, up-regulated in prostate cancer and other malignancies, (Tsavaler et al., 2001)) is activated by cold stimulus of 10 to 24° C. temperature (McKemy et al., 2002; Peier et al., 2002). In addition, TRPM8 is also activated by compounds that elicit cool sensation such as menthol, icilin (AG-3-5) (McKemy et al., 2002), and the endogenous lipid $PIP_2$ (Rohacs et al., 2005). Correlating with the cold sensitivity of both A delta and C-fibers, TRPM8 is highly expressed in sensory neurons of the trigeminal and dorsal root ganglia (McKemy et al., 2002; Peier et al., 2002; Thut et al., 2003). TRPM8 is also expressed in nerve fibers innervating urinary bladder in guinea pigs (Tsukimi et al., 2005) and humans (Mukerji et al., 2006) and believed to contribute to the bladder hypersensitivity.

Activation mechanism of TRPM8 by menthol and icilin appears to differ. Icilin requires calcium for robust activation of TRPM8, whereas menthol and cold do not (Chuang et al., 2004). Typically, activation by all these agonists follows a period of calcium-dependent desensitization. The domain swap analysis of chicken and rat TRPM8 and further mutational studies revealed that determinants of icilin sensitivity map to a region of TRPM8 that corresponds to the capsaicin binding site in TRPV1 transmembrane domain 3 to 4 region (Chuang et al., 2004).

Cold allodynia and mechanical hyperalgesia are associated with neuropathic pain in humans and in rodent models of neuropathic and chemotherapy-induced pain. TRPM8 is shown to mediate the analgesia by agonists such as menthol and icilin (by desensitization of the receptor) during experimental neuropathic pain in rodents (Proudfoot et al., 2006). Further, attenuation of cold sensation and cold allodynia after chronic constriction injury model of neuropathic pain in TRPM8 knockout mice (Colburn et al., 2007; Dhaka et al., 2007) suggests that antagonists of TRPM8 may be considered as pain therapeutics for chemotherapy-induced pain, neuropathic pain and bladder disorders.

Mint oil that contains menthol, an agonist of TRPM8 has been reported to alleviate pain in post-herpetic neuralgia (Davies et al., 2002), a neuropathic pain condition. Furthermore, oral or intracerebroventricular injection of menthol decreased nociceptive responses to hot-plate test and acetic acid-induced writhing in mice (Galeotti et al., 2002). These responses are believed to be mediated by the activation and desensitization of the TRPM8. These observations and the knockout mice studies indicate that TRPM8 modulation by antagonists might be beneficial for patients experiencing neuropathic pain.

A need exists for TRPM8 antagonist compounds that can be used to treat diseases and conditions mediated by TRPM8 such as, but not limited to, migraines and neuropathic pain and those other conditions described herein.

SUMMARY OF THE INVENTION

The present invention comprises a new class of compounds useful in the treatment of diseases, such as TRPM8-mediated diseases and other maladies, such as inflammatory or neuropathic pain and diseases involving sensory nerve function such as asthma, rheumatoid arthritis, osteoarthritis, inflammatory bowel disorders, urinary incontinence, migraine and psoriasis. In particular, the compounds of the invention are useful for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. Accordingly, the invention also comprises pharmaceutical compositions comprising the compounds, methods for the treatment of TRPM8-receptor-mediated diseases, such as inflammatory or neuropathic pain, asthma, rheumatoid arthritis, osteoarthritis, inflammatory bowel disorders, urinary incontinence, migraine and psoriasis diseases, using the compounds and compositions of the invention, and intermediates and processes useful for the preparation of the compounds of the invention.

In one aspect, the invention provides compounds of Formula I or a pharmaceutically-acceptable salt thereof, a tautomer thereof, a pharmaceutically-acceptable salt of the tautomer, a stereoisomer thereof, or a mixture thereof. Compounds of Formula I have the following structure

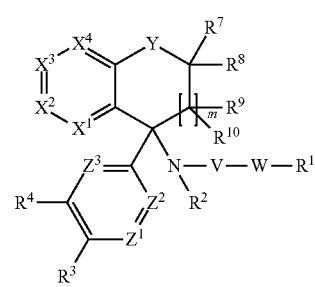

I where
V is selected from —C(=O)— or —S(=O)$_2$—;
W is absent or is selected from —NH—, —NR$^{1a}$—, or O;
X$^1$ is selected from —CR$^5$— or —N—;

$X^2$ is selected from —$CR^5$— or —N—;
$X^3$ is selected from —$CR^5$— or —N—;
$X^4$ is selected from —$CR^5$— or —N—;
Y is selected from —O—, —$CH_2$—, —NH—, —$NR^{1b}$—, —$CF_2$—, —C(=O)—, —C(H)(F)—, or —C(H)(OH)—;
$Z^1$ is selected from —$CR^6$— or —N—;
$Z^2$ is selected from —$CR^6$— or —N—;
$Z^3$ is selected from —$CR^6$— or —N—;
  wherein 0, 1, or 2 of $X^1$, $X^2$, $X^3$, and $X^4$ are N;
  wherein 0, 1, or 2 of $Z^1$, $Z^2$, and $Z^3$ are N;
  m is 0, 1, or 2;
  $R^1$ is $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-6}$alkOH, $C_{1-6}$alk-C(=O)$R^a$, $C_{1-6}$alk-C(=O)O$R^a$, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkO$R^a$, —O$C_{2-6}$alkN$R^aR^a$, —S$R^a$, =S, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the ring is additionally substituted by 0 or 1 directly bonded, $SO_2$ linked, C(=O) linked or $CH_2$ linked saturated, partially-saturated or unsaturated 3-, 4-, 5-, 6- or 7-membered monocyclic ring containing 0, 1, 2, 3 or 4 heteroatoms selected from N, O and S, but containing no more than one O or S atom, and substituted by 0, 1, 2 or 3 groups selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$;
  $R^{1a}$ is $C_{1-6}$alk;
  $R^{1b}$ is $C_{1-6}$alk or —C(=O)$R^b$;
  $R^2$ is H or $C_{1-6}$alk;
  $R^3$ is H, $C_{1-8}$alk, $C_{1-8}$alkOH, $C_{1-4}$haloalk, halo, cyano, $R^b$, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ or —N$R^aC_{2-6}$alkO$R^a$;
  $R^4$ is H, $C_{1-6}$alk, —$C_{1-3}$haloalk, —O$C_{1-6}$alk, —O$C_{1-3}$haloalk, —N($C_{1-6}$alk)$C_{1-6}$alk, —NH$C_{1-6}$alk, —NC(=O)$C_{1-6}$alk, —N($C_{1-6}$alk)$C_{1-6}$alk, F, Cl, Br, CN, OH or $NH_2$; or $R^3$ and $R^4$ together form a four-atom unsaturated bridge containing 0 or 1 N atoms, wherein the bridge is substituted by 0, 1 or 2 $R^5$ substituents;
  $R^5$ is, at each instance, independently selected from H, $C_{1-8}$alk, $C_{1-8}$alkOH, $C_{1-4}$haloalk, halo, cyano, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ or —N$R^aC_{2-6}$alkO$R^a$;
  $R^6$ is, at each instance, independently selected from H, halo, O$R^a$, $C_{1-6}$alk, or $CF_3$;
  $R^7$ and $R^8$ are independently selected from H or $C_{1-6}$alk, or $R^7$ and $R^8$, together with the carbon atom to which they are attached, join to form a 3 to 7 membered cycloalkyl ring or a 3-7 membered heterocyclyl ring that includes 1 or 2 heteroatoms selected from O, N, or S;
  $R^9$ and $R^{10}$ are, at each instance, independently selected from H or $C_{1-6}$alk;
  $R^a$ is independently, at each instance, H or $R^b$; and
  $R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —O$C_{1-4}$alk, —OH, —$NH_2$, —O$C_{1-4}$alk, —O$C_{1-4}$haloalk, —NH$C_{1-4}$alk, and —N($C_{1-4}$alk)$C_{1-4}$alk.

In some such embodiments, the compound is not one of the following compounds and is not a salt of one of the following compounds:

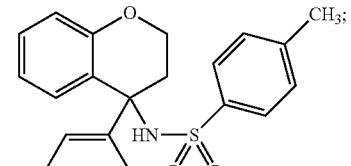

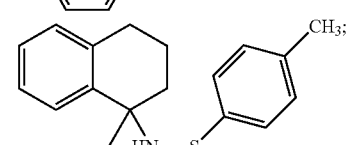

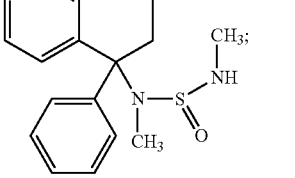

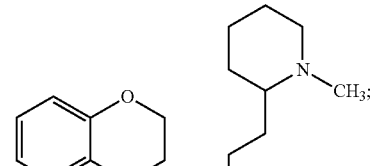

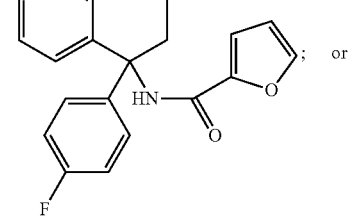

In some embodiments, Y is selected from —O—, —CH$_2$—, —NH—, or —NR$^{1b}$—. In still further such embodiments, Y is selected from —O— or —CH$_2$—.

In some embodiments of the compound of Formula I, the compound of Formula I has the Formula II:

II where:
Y is selected from —O— or —CH$_2$—.
In other embodiments, the compound of Formula II, has the Formula IIA:

IIA

In other embodiments, the compound of Formula I has the Formula III

III where Y is —O— or —CH$_2$—.
In yet other embodiments, the compound of Formula III has the Formula IIIA, IIIB, IIIC, or IIID

IIIA

IIIB

IIIC

IIID

In still other embodiments, the compound of Formula I has the Formula IV

IV where Y is —O— or —CH$_2$—.

In some embodiments, the compound of Formula IV has the Formula IVA, IVB, IVC, or IVD

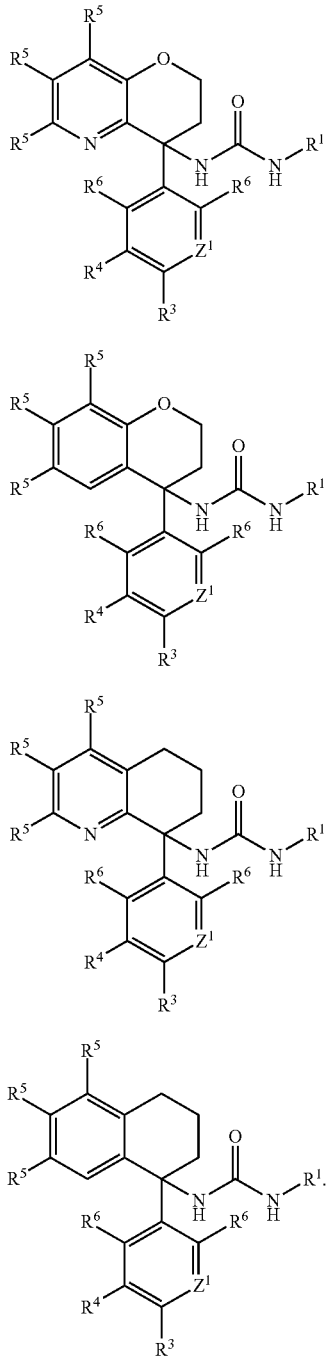

In another aspect, the invention provides pharmaceutical compositions that include the compound of any of the embodiments or the pharmaceutically-acceptable salt thereof, the tautomer thereof, the pharmaceutically-acceptable salt of the tautomer, or the mixture thereof, and a pharmaceutically-acceptable diluent or carrier.

In yet another aspect, the invention provides methods of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject. Such methods typically include administering the compound according to any of the embodiments or the pharmaceutically-acceptable salt thereof, the tautomer thereof, the pharmaceutically-acceptable salt of the tautomer, or the mixture thereof to the subject. In some such embodiments, the subject is suffering from neuropathic pain whereas in other embodiments the subject is suffering from migraines or migraine pain.

The compounds of the invention may also be used to prepare pharmaceutical compositions and medicaments. Therefore, in some embodiments, the invention provides the use of the compound according to any of the embodiments or the pharmaceutically-acceptable salt thereof, the tautomer thereof, the pharmaceutically-acceptable salt of the tautomer, or the mixture thereof in the preparation of a medicament.

In another aspect, the invention provides the use of the compound according to any of the embodiments or the pharmaceutically-acceptable salt thereof, the tautomer thereof, the pharmaceutically-acceptable salt of the tautomer, or the mixture thereof for treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject. In some such embodiments, the compound is used to treat neuropathic pain. In other embodiments, the compound is used to treat migraines or migraine pain The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION OF THE INVENTION

The compounds of this invention may have in general several asymmetric centers and are typically depicted in the form of racemic mixtures. This invention is intended to encompass racemic mixtures, partially racemic mixtures and separate enantiomers and diastereomers.

Unless otherwise specified, the following definitions apply to terms found in the specification and claims:

"$C_{\alpha-\beta}$alk" means an alkyl group comprising a minimum of $\alpha$ and a maximum of $\beta$ carbon atoms in a branched, cyclical or linear relationship or any combination of the three, wherein $\alpha$ and $\beta$ represent integers. The alkyl groups described in this section may also contain one or two double or triple bonds. A designation of $C_0$alk indicates a direct bond. Examples of $C_{1-6}$alkyl include, but are not limited to the following:

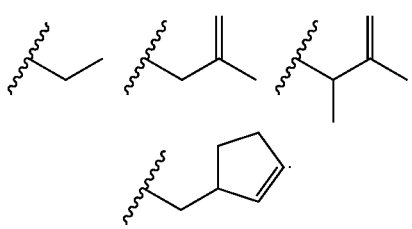

Where the term "$C_{\alpha-\beta}$alkyl" and "$C_{\alpha-\beta}$cycloalkyl" are used, they relate to acyclic saturated alkyls and cyclic saturated alkyls, respectively.

"Benzo group", alone or in combination, means the divalent radical $C_4H_4=$, one representation of which is —CH=CH—CH=CH—, that when vicinally attached to another ring forms a benzene-like ring—for example tetrahydronaphthalene, indole and the like.

The terms "oxo" and "thioxo" represent the groups =O (as in carbonyl) and =S (as in thiocarbonyl), respectively.

The term "cyano" refers to a nitrile group which may be written as —C≡N.

"Halo" or "halogen" means a halogen atoms selected from F, Cl, Br and I.

"$C_{V-W}$haloalk" means an alk group, as described above, wherein any number, but at least one, of the hydrogen atoms attached to the alk chain are replaced by F, Cl, Br or I.

The group $N(R^a)R^a$ and the like include substituents where the two $R^a$ groups together form a ring, optionally including a N, O or S atom, and include groups such as:

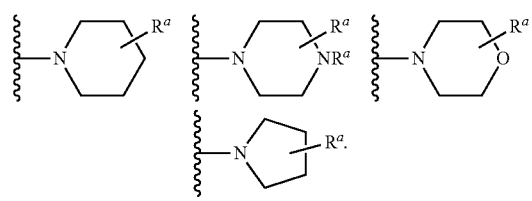

The group $N(C_{\alpha-\beta}alk)C_{\alpha-\beta}alk$, wherein $\alpha$ and $\beta$ are as defined above, include substituents where the two $C_{\alpha-\beta}$alk groups together form a ring, optionally including a N, O or S atom, and include groups such as:

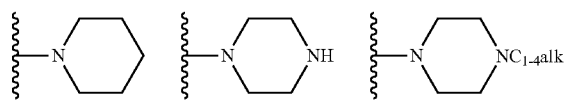

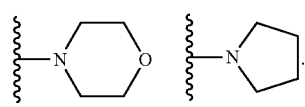

"Heterocycle" means a ring comprising at least one carbon atom and at least one other atom selected from N, O and S. Examples of heterocycles that may be found in the claims include, but are not limited to, the following:

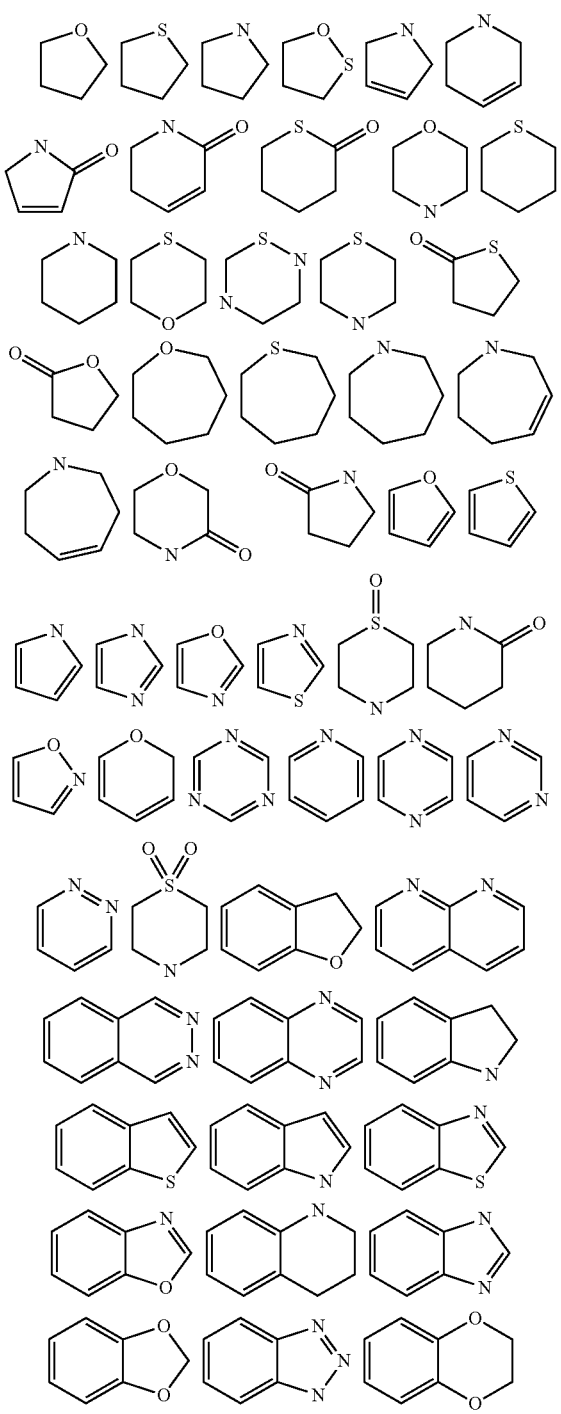

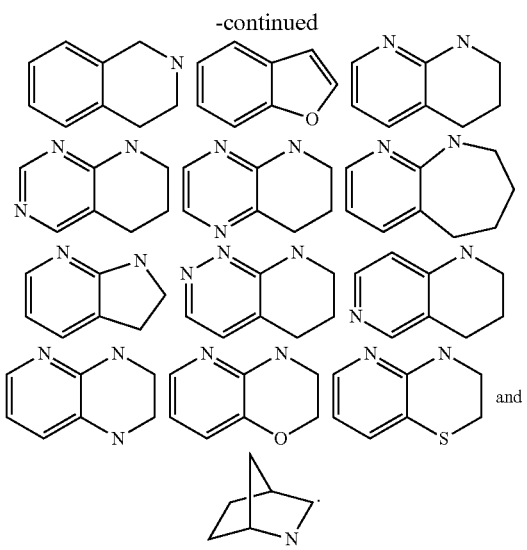

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

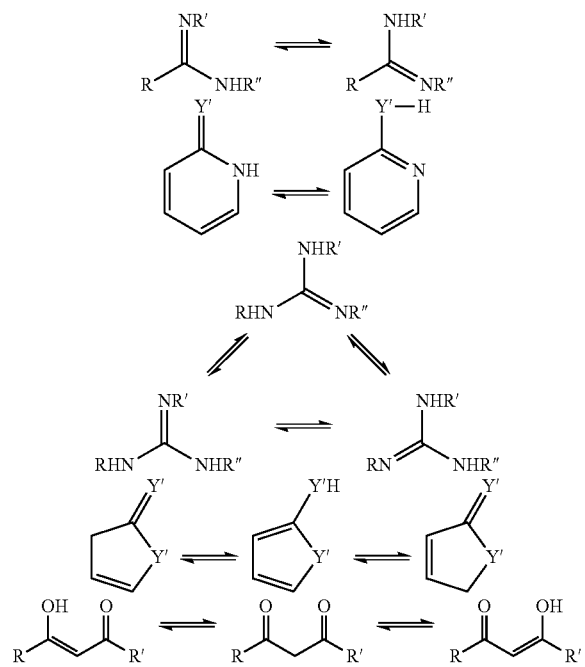

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language like "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Another aspect of the invention relates to a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound as described above.

Another aspect of the invention relates to a pharmaceutical composition comprising a compound according to Claim 1 and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

Embodiments

The embodiments listed below are presented in numbered form for convenience.

1. In a first embodiment, the invention provides a compound of Formula I having the following structure:

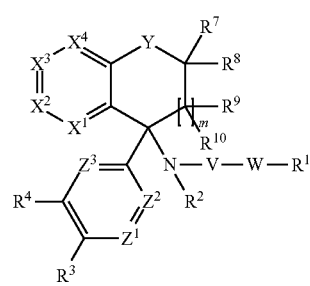

a pharmaceutically-acceptable salt thereof, a tautomer thereof, a pharmaceutically-acceptable salt of the tautomer, a stereoisomer thereof, or a mixture thereof, wherein:

V is selected from —C(═O)— or —S(═O)$_2$—;
W is absent or is selected from —NH—, —NR$^{1a}$—, or O;
X$^1$ is selected from —CR$^5$— or —N—;
X$^2$ is selected from —CR$^5$— or —N—;
X$^3$ is selected from —CR$^5$— or —N—;
X$^4$ is selected from —CR$^5$— or —N—;
Y is selected from —O—, —CH$_2$—, —NH—, —NR$^{1b}$—, —CF$_2$—, —C(═O)—, —C(H)(F)—, or —C(H)(OH)—;
Z$^1$ is selected from —CR$^6$— or —N—;
Z$^2$ is selected from —CR$^6$— or —N—;
Z$^3$ is selected from —CR$^6$— or —N—;
wherein 0, 1, or 2 of X$^1$, X$^2$, X$^3$, and X$^4$ are N;
wherein 0, 1, or 2 of Z$^1$, Z$^2$, and Z$^3$ are N;
m is 0, 1, or 2;
R$^1$ is C$_{1-6}$alk or a direct-bonded, C$_{1-2}$alk-linked, C$_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, but containing no more than one O or S atom, the C$_{1-6}$alk and ring being substituted by 0, 1, 2 or 3 substituents independently selected from halo, oxo, C$_{1-6}$alk, C$_{1-6}$alkOH, C$_{1-6}$alk-C(═O)R$^a$, C$_{1-6}$alk-C(═O)OR$^a$, C$_{1-4}$haloalk, cyano, nitro, —C(═O)R$^a$, —C(═O)OR$^a$, —C(═O)NR$^a$R$^a$, —C(═NR$^a$)NR$^a$R$^a$, —OR$^a$, —OC(═O)R$^a$, —OC(═O)NR$^a$R$^a$, —OC(═O)N(R$^a$)S(═O)$_2$R$^a$, —OC$_{2-6}$alkNR$^a$R$^a$, —OC$_{2-6}$alkOR$^a$, —SR$^a$, ═S, —S(═O)R$^a$, —S(═O)$_2$R$^a$, —S(═O)$_2$NR$^a$R$^a$, —S(═O)$_2$N(R$^a$)C(═O)R$^a$, —S(═O)$_2$N(R$^a$)C(═O)OR$^a$, —S(═O)$_2$N(R$^a$)C(═O)NR$^a$R$^a$, —NR$^a$R$^a$, —N(R$^a$)C(═O)R$^a$, —N(R$^a$)C(═O)OR$^a$, —N(R$^a$)C(═O)NR$^a$R$^a$, —N(R$^a$)C(═NR$^a$)NR$^a$R$^a$, —N(R$^a$)S(═O)$_2$R$^a$, —N(R$^a$)S(═O)$_2$NR$^a$R$^a$, —NR$^a$C$_{2-6}$alkNR$^a$R$^a$ and —NR$^a$C$_{2-6}$alkOR$^a$, wherein the ring is additionally substituted by 0 or 1 directly bonded, SO$_2$ linked, C(═O) linked or CH$_2$ linked saturated, partially-saturated or unsaturated 3-, 4-, 5-, 6- or 7-membered monocyclic ring containing 0, 1, 2, 3 or 4 heteroatoms selected from N, O and S, but containing no more than one O or S atom, and substituted by 0, 1, 2 or 3 groups selected from halo, oxo, C$_{1-6}$alk, C$_{1-4}$haloalk, cyano, nitro, —C(═O)R$^a$, —C(═O)OR$^a$, —C(═O)NR$^a$R$^a$, —C(═NR$^a$)NR$^a$R$^a$, —OR$^a$, —OC(═O)R$^a$, —SR$^a$, —S(═O)R$^a$, —S(═O)$_2$R$^a$, —S(═O)$_2$NR$^a$R$^a$, —NR$^a$R$^a$, and —N(R$^a$)C(═O)R$^a$;

R$^{1a}$ is C$_{1-6}$alk;
R$^{1b}$ is C$_{1-6}$alk or —C(═O)R$^b$;
R$^2$ is H or C$_{1-6}$alk;
R$^3$ is H, C$_{1-8}$alk, C$_{1-8}$alkOH, C$_{1-4}$haloalk, halo, cyano, R$^b$, —C(═O)R$^b$, —C(═O)OR$^b$, —C(═O)NR$^a$R$^a$, —C(═NR$^a$)NR$^a$R$^a$, —OR$^a$, —OC(═O)R$^b$, —OC(═O)NR$^a$R$^a$, —OC$_{2-6}$alkNR$^a$R$^a$, —OC$_{2-6}$alkOR$^a$, —SR$^a$, —S(═O)R$^b$, —S(═O)$_2$R$^b$, —S(═O)$_2$NR$^a$R$^a$, —NR$^a$R$^a$, —N(R$^a$)C(═O)R$^b$, —N(R$^a$)C(═O)OR$^b$, —N(R$^a$)C(═O)NR$^a$R$^a$, —N(R$^a$)C(═NR$^a$)NR$^a$R$^a$, —N(R$^a$)S(═O)$_2$R$^b$, —N(R$^a$)S(═O)$_2$NR$^a$R$^a$, —NR$^a$C$_{2-6}$alkNR$^a$R$^a$ or —NR$^a$C$_{2-6}$alkOR$^a$;

R$^4$ is H, C$_{1-6}$alk, —C$_{1-3}$haloalk, —OC$_{1-6}$alk, —OC$_{1-3}$haloalk, —N(C$_{1-6}$alk)C$_{1-6}$alk, —NHC$_{1-6}$alk, —NC(═O)C$_{1-6}$alk, —N(C$_{1-6}$alk)C$_{1-6}$alk, F, Cl, Br, CN, OH or NH$_2$; or R$^3$ and R$^4$ together form a four-atom unsaturated bridge containing 0 or 1 N atoms, wherein the bridge is substituted by 0, 1 or 2 R$^5$ substituents;

R$^5$ is, at each instance, independently selected from H, C$_{1-8}$alk, C$_{1-8}$alkOH, C$_{1-4}$haloalk, halo, cyano, —C(═O)R$^b$, —C(═O)OR$^b$, —C(═O)NR$^a$R$^a$, —C(═NR$^a$)NR$^a$R$^a$, —OR$^a$, —OC(═O)R$^b$, —OC(═O)NR$^a$R$^a$, —OC$_{2-6}$alkNR$^a$R$^a$, —OC$_{2-6}$alkOR$^a$, —SR$^a$, —S(═O)R$^b$, —S(═O)$_2$R$^b$, —S(═O)$_2$NR$^a$R$^a$, —NR$^a$R$^a$, —N(R$^a$)C(═O)R$^b$, —N(R$^a$)C(═O)OR$^b$, —N(R$^a$)C(═O)NR$^a$R$^a$, —N(R$^a$)C(═NR$^a$)NR$^a$R$^a$, —N(R$^a$)S(═O)$_2$R$^b$, —N(R$^a$)S(═O)$_2$NR$^a$R$^a$, —NR$^a$C$_{2-6}$alkNR$^a$R$^a$ or —NR$^a$C$_{2-6}$alkOR$^a$;

R$^6$ is, at each instance, independently selected from H, halo, ORE, C$_{1-6}$alk, or CF$_3$;

R$^7$ and R$^8$ are independently selected from H or C$_{1-6}$alk, or R$^7$ and R$^8$, together with the carbon atom to which they are attached, join to form a 3 to 7 membered cycloalkyl ring or a 3-7 membered heterocyclyl ring that includes 1 or 2 heteroatoms selected from O, N, or S;

R$^9$ and R$^{10}$ are, at each instance, independently selected from H or C$_{1-6}$alk;

R$^a$ is independently, at each instance, H or R$^b$; and
R$^b$ is independently, at each instance, phenyl, benzyl or C$_{1-6}$alk, the phenyl, benzyl and C$_{1-6}$alk being substituted by 0, 1, 2 or 3 substituents selected from halo, oxo, C$_{1-4}$alk, C$_{1-3}$haloalk, —OC$_{1-4}$alk, —OH, —NH$_2$, —OC$_{1-4}$alk, —OC$_{1-4}$haloalk, —NHC$_{1-4}$alk, and —N(C$_{1-4}$alk)C$_{1-4}$alk;

wherein the compound is not one of the following compounds and is not a salt thereof:

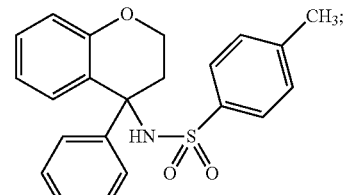

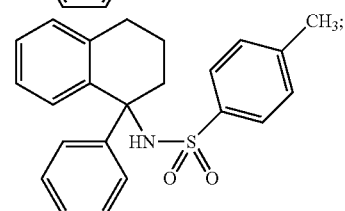

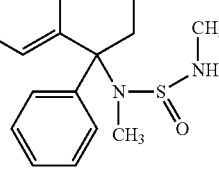

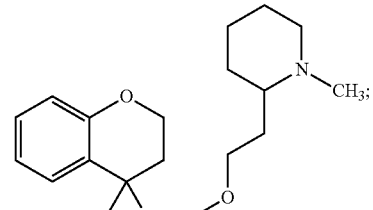

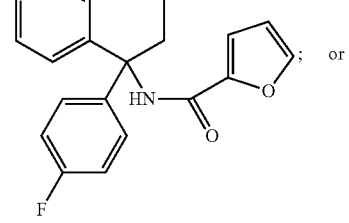

-continued

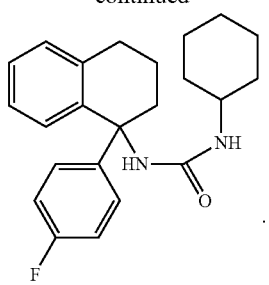

In some versions of embodiment 1, the compound is not one of the following compounds, is not a salt thereof, is not a tautomer thereof, is not a salt of a tautomer, is not a stereoisomer thereof, and is not a salt of a stereoisomer:

-continued

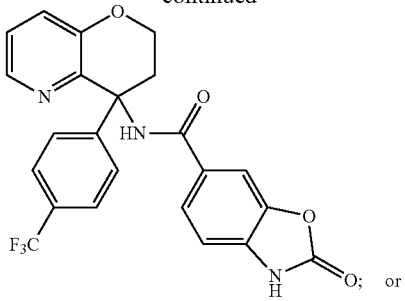

In some embodiments, Y is selected from —O—, —CH$_2$—, —NH—, or —NR$^{1b}$—. In still further such embodiments, Y is selected from —O— or —CH$_2$—.

2. The compound of embodiment 1 or the pharmaceutically-acceptable salt thereof, the tautomer thereof, the pharmaceutically-acceptable salt of the tautomer, the stereoisomer thereof, or the mixture thereof, wherein R$^7$ and R$^8$ are both H.

3. The compound of embodiment 1 or the pharmaceutically-acceptable salt thereof, the tautomer thereof, the pharmaceutically-acceptable salt of the tautomer, the stereoisomer thereof, or the mixture thereof, wherein R$^7$ and R$^8$ are selected from H and —CH$_3$.

4. The compound of embodiment 3 or the pharmaceutically-acceptable salt thereof, the tautomer thereof, the pharmaceutically-acceptable salt of the tautomer, the stereoisomer thereof, or the mixture thereof, wherein R$^7$ and R$^8$ are both —CH$_3$.

5. The compound of embodiment 1 or the pharmaceutically-acceptable salt thereof, the tautomer thereof, the pharmaceutically-acceptable salt of the tautomer, the stereoisomer thereof, or the mixture thereof, wherein R$^7$ and R$^8$, together with the carbon atom to which they are attached, join to form a 3-7 membered cycloalkyl ring.

6. The compound of embodiment 5 or the pharmaceutically-acceptable salt thereof, the tautomer thereof, the pharmaceutically-acceptable salt of the tautomer, the stereoisomer thereof, or the mixture thereof, wherein R$^7$ and R$^8$, together with the carbon atom to which they are attached, join to form a cyclopropyl or cyclobutyl ring.

7. The compound of embodiment 1 or the pharmaceutically-acceptable salt thereof, the tautomer thereof, the pharmaceutically-acceptable salt of the tautomer, the stereoisomer thereof, or the mixture thereof, wherein m is 0.

8. The compound of any one of embodiments 1-6 or the pharmaceutically-acceptable salt thereof, the tautomer thereof, the pharmaceutically-acceptable salt of the tautomer, the stereoisomer thereof, or the mixture thereof, wherein m is 1.

9. The compound of any one of embodiment 1-6 or the pharmaceutically-acceptable salt thereof, the tautomer thereof, the pharmaceutically-acceptable salt of the tautomer, the stereoisomer thereof, or the mixture thereof, wherein m is 2.

10. The compound of any one of embodiments 1-9 or the pharmaceutically-acceptable salt thereof, the tautomer thereof, the pharmaceutically-acceptable salt of the tautomer, the stereoisomer thereof, or the mixture thereof, wherein Y is —NH—.

11. The compound of any one of embodiments 1-9 or the pharmaceutically-acceptable salt thereof, the tautomer thereof, the pharmaceutically-acceptable salt of the tautomer, the stereoisomer thereof, or the mixture thereof, wherein Y is —$NR^{1b}$— and $R^{1b}$ is —$CH_3$.

12. The compound of any one of embodiments 1-9 or the pharmaceutically-acceptable salt thereof, the tautomer thereof, the pharmaceutically-acceptable salt of the tautomer, the stereoisomer thereof, or the mixture thereof, wherein Y is —O—.

13. The compound of any one of embodiments 1-9 or the pharmaceutically-acceptable salt thereof, the tautomer thereof, the pharmaceutically-acceptable salt of the tautomer, the stereoisomer thereof, or the mixture thereof, wherein Y is —$CH_2$—.

14. The compound of any one of embodiments 1-13 or the pharmaceutically-acceptable salt thereof, the tautomer thereof, the pharmaceutically-acceptable salt of the tautomer, the stereoisomer thereof, or the mixture thereof, wherein $R^9$ and $R^{10}$ are H.

15. The compound of embodiment 1 or the pharmaceutically-acceptable salt thereof, the tautomer thereof, the pharmaceutically-acceptable salt of the tautomer, the stereoisomer thereof, or the mixture thereof, wherein the compound of Formula I has the Formula II:

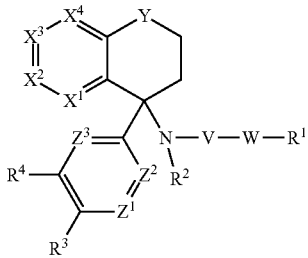

II wherein:
Y is selected from —O— or —$CH_2$—.

16. The compound of embodiment 15 or the pharmaceutically-acceptable salt thereof, the tautomer thereof, the pharmaceutically-acceptable salt of the tautomer, the stereoisomer thereof, or the mixture thereof, wherein the compound of Formula II has the Formula IIA:

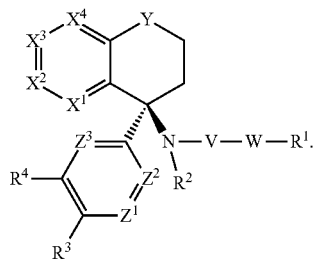

IIA

17. The compound of any one of embodiments 1-16 or the pharmaceutically-acceptable salt thereof, the tautomer thereof, the pharmaceutically-acceptable salt of the tautomer, the stereoisomer thereof, or the mixture thereof, wherein 0 or 1 of $X^1$, $X^2$, $X^3$, and $X^4$ are N.

18. The compound of embodiment 17 or the pharmaceutically-acceptable salt thereof, the tautomer thereof, the pharmaceutically-acceptable salt of the tautomer, the stereoisomer thereof, or the mixture thereof, wherein 1 of $X^1$, $X^2$, $X^3$, and $X^4$ are N.

19. The compound of embodiment 17 or the pharmaceutically-acceptable salt thereof, the tautomer thereof, the pharmaceutically-acceptable salt of the tautomer, the stereoisomer thereof, or the mixture thereof, wherein 0 of $X^1$, $X^2$, $X^3$, and $X^4$ are N.

20. The compound of embodiment 17 or the pharmaceutically-acceptable salt thereof, the tautomer thereof, the pharmaceutically-acceptable salt of the tautomer, the stereoisomer thereof, or the mixture thereof, wherein $X^1$ is N and $X^2$, $X^3$, and $X^4$ are all —$CR^5$—.

21. The compound of embodiment 17 or the pharmaceutically-acceptable salt thereof, the tautomer thereof, the pharmaceutically-acceptable salt of the tautomer, the stereoisomer thereof, or the mixture thereof, wherein $X^2$ is N and $X^1$, $X^3$, and $X^4$ are all —$CR^5$—.

22. The compound of embodiment 17 or the pharmaceutically-acceptable salt thereof, the tautomer thereof, the pharmaceutically-acceptable salt of the tautomer, the stereoisomer thereof, or the mixture thereof, wherein $X^3$ is N and $X^1$, $X^2$, and $X^4$ are all —$CR^5$—.

23. The compound of embodiment 17 or the pharmaceutically-acceptable salt thereof, the tautomer thereof, the pharmaceutically-acceptable salt of the tautomer, the stereoisomer thereof, or the mixture thereof, wherein $X^4$ is N and $X^1$, $X^2$, and $X^3$ are all —$CR^5$—.

24. The compound of any one of embodiments 1-23 or the pharmaceutically-acceptable salt thereof, the tautomer thereof, the pharmaceutically-acceptable salt of the tautomer, the stereoisomer thereof, or the mixture thereof, wherein 0 or 1 of $Z^1$, $Z^2$, and $Z^3$ are N.

25. The compound of embodiment 24 or the pharmaceutically-acceptable salt thereof, the tautomer thereof, the pharmaceutically-acceptable salt of the tautomer, the stereoisomer thereof, or the mixture thereof, wherein 0 of $Z^1$, $Z^2$, and $Z^3$ are N.

26. The compound of embodiment 24 or the pharmaceutically-acceptable salt thereof, the tautomer thereof, the pharmaceutically-acceptable salt of the tautomer, the stereoisomer thereof, or the mixture thereof, wherein 1 of $Z^1$, $Z^2$, and $Z^3$ are N.

27. The compound of embodiment 24 or the pharmaceutically-acceptable salt thereof, the tautomer thereof, the pharmaceutically-acceptable salt of the tautomer, the stereoisomer thereof, or the mixture thereof, wherein $Z^1$ is N and $Z^2$ and $Z^3$ are —$CR^6$—.

28. The compound of embodiment 24 or the pharmaceutically-acceptable salt thereof, the tautomer thereof, the pharmaceutically-acceptable salt of the tautomer, the stereoisomer thereof, or the mixture thereof, wherein $Z^2$ is N and $Z^1$ and $Z^3$ are —$CR^6$—.

29. The compound of embodiment 24 or the pharmaceutically-acceptable salt thereof, the tautomer thereof, the pharmaceutically-acceptable salt of the tautomer, the stereoisomer thereof, or the mixture thereof, wherein $Z^3$ is N and $Z^1$ and $Z^2$ are —$CR^6$—.

30. The compound of any one of embodiments 1-29 or the pharmaceutically-acceptable salt thereof, the tautomer thereof, the pharmaceutically-acceptable salt of the tautomer, the stereoisomer thereof, or the mixture thereof, wherein V is —C(=O)—.

31. The compound of any one of embodiments 1-29 or the pharmaceutically-acceptable salt thereof, the tautomer thereof, the pharmaceutically-acceptable salt of the tautomer, the stereoisomer thereof, or the mixture thereof, wherein V is —S(=O)₂—.

32. The compound of any one of embodiments 1-31 or the pharmaceutically-acceptable salt thereof, the tautomer thereof, the pharmaceutically-acceptable salt of the tautomer, the stereoisomer thereof, or the mixture thereof, wherein W is absent.

33. The compound of any one of embodiments 1-31 or the pharmaceutically-acceptable salt thereof, the tautomer thereof, the pharmaceutically-acceptable salt of the tautomer, the stereoisomer thereof, or the mixture thereof, wherein W is —NH—.

34. The compound of any one of embodiments 1-31 or the pharmaceutically-acceptable salt thereof, the tautomer thereof, the pharmaceutically-acceptable salt of the tautomer, the stereoisomer thereof, or the mixture thereof, wherein W is —O—.

35. The compound of any one of embodiments 1-34 or the pharmaceutically-acceptable salt thereof, the tautomer thereof, the pharmaceutically-acceptable salt of the tautomer, the stereoisomer thereof, or the mixture thereof, wherein R² is H.

36. The compound of embodiment 1 or the pharmaceutically-acceptable salt thereof, the tautomer thereof, the pharmaceutically-acceptable salt of the tautomer, the stereoisomer thereof, or the mixture thereof, wherein the compound of Formula I has the Formula III

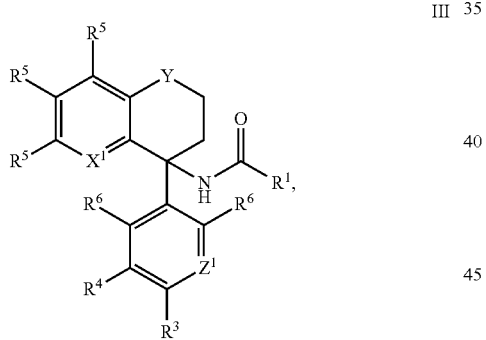

III wherein Y is —O— or —CH₂—. In some such embodiments, the compounds has the Formula III'

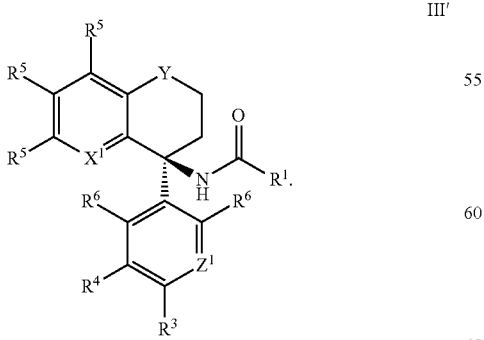

III'

37. The compound of embodiment 36 or the pharmaceutically-acceptable salt thereof, the tautomer thereof, the pharmaceutically-acceptable salt of the tautomer, the stereoisomer thereof, or the mixture thereof, wherein the compound of Formula III has the Formula IIIA, IIIB, IIIC, or IIID

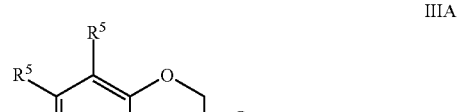

IIIA

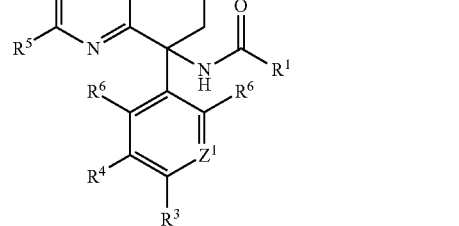

IIIB

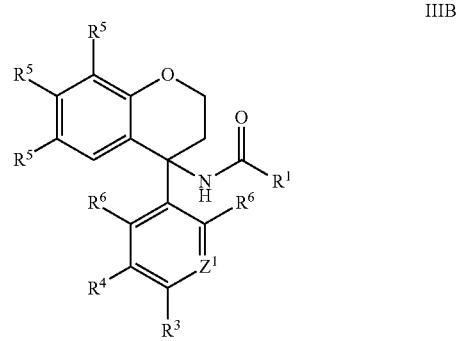

IIIC

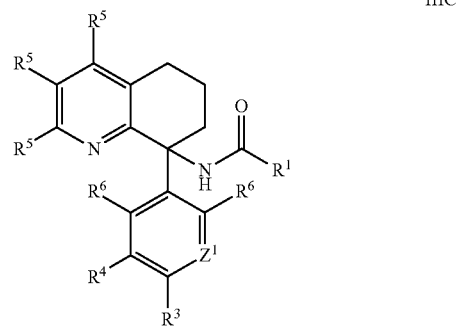

IIID

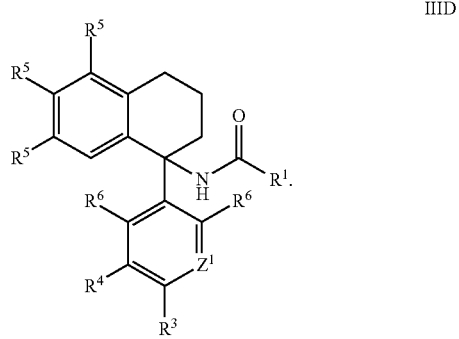

38. The compound of embodiment 37 or the pharmaceutically-acceptable salt thereof, the tautomer thereof, the pharmaceutically-acceptable salt of the tautomer, the stereoisomer thereof, or the mixture thereof, wherein the compound of Formula III has the Formula IIIA. In some such embodiments, the compound has the Formula IIIA'

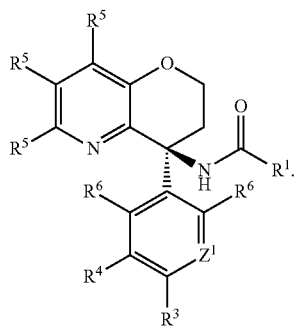
IIIA′

39. The compound of embodiment 37 or the pharmaceutically-acceptable salt thereof, the tautomer thereof, the pharmaceutically-acceptable salt of the tautomer, the stereoisomer thereof, or the mixture thereof, wherein the compound of Formula III has the Formula IIIB. In some such embodiments, the compound has the Formula IIIB′

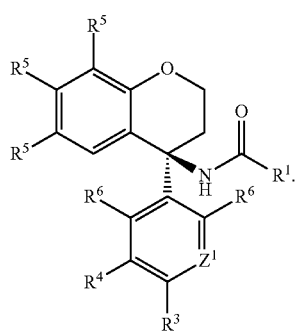
IIIB′

40. The compound of embodiment 37 or the pharmaceutically-acceptable salt thereof, the tautomer thereof, the pharmaceutically-acceptable salt of the tautomer, the stereoisomer thereof, or the mixture thereof, wherein the compound of Formula III has the Formula IIIC. In some such embodiments, the compound has the Formula IIIC′

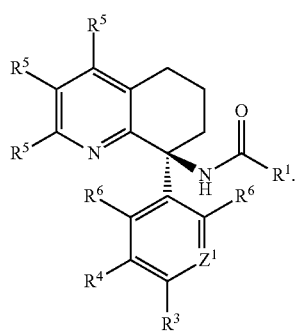
IIIC′

41. The compound of embodiment 37 or the pharmaceutically-acceptable salt thereof, the tautomer thereof, the pharmaceutically-acceptable salt of the tautomer, the stereoisomer thereof, or the mixture thereof, wherein the compound of Formula III has the Formula IIID. In some such embodiments, the compound has the Formula IIID′

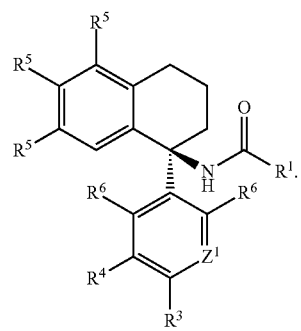
IIID′

42. The compound of embodiment 1 or the pharmaceutically-acceptable salt thereof, the tautomer thereof, the pharmaceutically-acceptable salt of the tautomer, the stereoisomer thereof, or the mixture thereof, wherein the compound of Formula I has the Formula IV

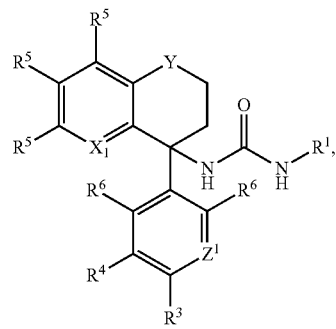
IV wherein Y is —O— or —CH$_2$—. In some embodiments, the compound of Formula IV has the Formula IV′

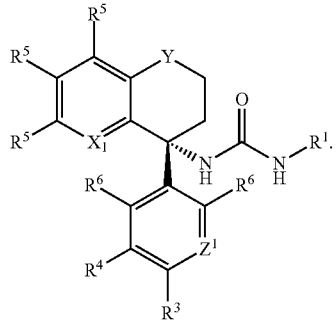
IV′

43. The compound of embodiment 42 or the pharmaceutically-acceptable salt thereof, the tautomer thereof, the pharmaceutically-acceptable salt of the tautomer, the stereoisomer thereof, or the mixture thereof, wherein the compound of Formula IV has the Formula IVA, IVB, IVC, or IVD

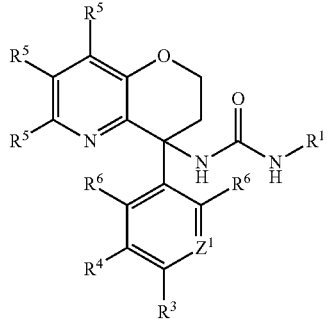
IVA

IVB

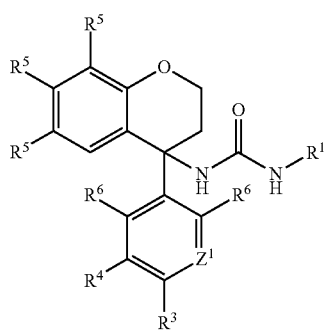

IVC

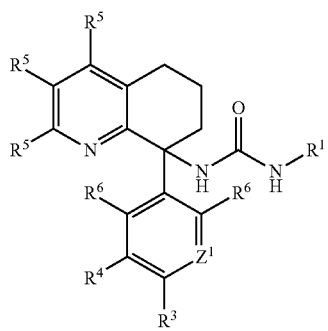

IVD

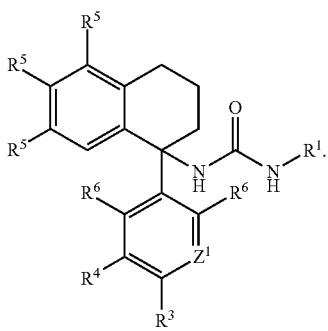

44. The compound of embodiment 43 or the pharmaceutically-acceptable salt thereof, the tautomer thereof, the pharmaceutically-acceptable salt of the tautomer, the stereoisomer thereof, or the mixture thereof, wherein the compound of Formula IV has the Formula IVA. In some such embodiments, the compound has the Formula IVA'

IVA'

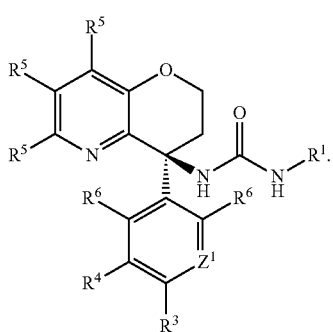

45. The compound of embodiment 43 or the pharmaceutically-acceptable salt thereof, the tautomer thereof, the pharmaceutically-acceptable salt of the tautomer, the stereoisomer thereof, or the mixture thereof, wherein the compound of Formula IV has the Formula IVB. In some such embodiments, the compound has the Formula IVB'

IVB'

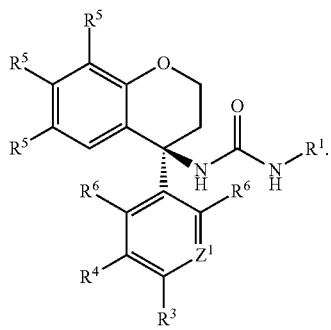

46. The compound of embodiment 43 or the pharmaceutically-acceptable salt thereof, the tautomer thereof, the pharmaceutically-acceptable salt of the tautomer, the stereoisomer thereof, or the mixture thereof, wherein the compound of Formula IV has the Formula IVC. In some such embodiments, the compound has the Formula IVC'

IVC'

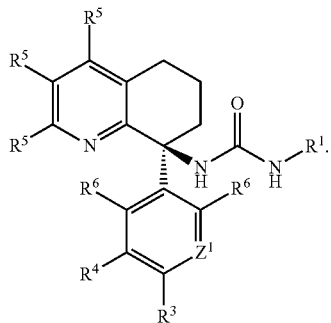

47. The compound of embodiment 43 or the pharmaceutically-acceptable salt thereof, the tautomer thereof, the pharmaceutically-acceptable salt of the tautomer, the stereoisomer thereof, or the mixture thereof, wherein the compound of Formula IV has the Formula IVD. In some such embodiments, the compound has the Formula IVD'

IVD'

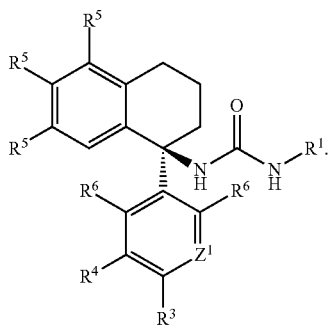

48. The compound of any one of embodiments 1-47 or the pharmaceutically-acceptable salt thereof, the tautomer thereof, the pharmaceutically-acceptable salt of the tautomer, the stereoisomer thereof, or the mixture thereof, wherein $R^3$ is selected from H, $C_{1-8}$alk, $C_{1-8}$ alkOH, $C_{1-4}$ haloalk, halo, or —$OR^a$.

49. The compound of any one of embodiments 1-47 or the pharmaceutically-acceptable salt thereof, the tautomer thereof, the pharmaceutically-acceptable salt of the tautomer, the stereoisomer thereof, or the mixture thereof, wherein $R^3$ is selected from —H, —$CH_3$, —F, —Cl, —$CF_3$, or —$OCF_3$.

50. The compound of embodiment 49 or the pharmaceutically-acceptable salt thereof, the tautomer thereof, the pharmaceutically-acceptable salt of the tautomer, the stereoisomer thereof, or the mixture thereof, wherein $R^3$ is selected from —$CH_3$, —F, —Cl, —$CF_3$, or —$OCF_3$.

51. The compound of embodiment 49 or the pharmaceutically-acceptable salt thereof, the tautomer thereof, the pharmaceutically-acceptable salt of the tautomer, the stereoisomer thereof, or the mixture thereof, wherein $R^3$ is selected from —$CF_3$ or —$OCF_3$.

52. The compound of any one of embodiments 1-47 or the pharmaceutically-acceptable salt thereof, the tautomer thereof, the pharmaceutically-acceptable salt of the tautomer, the stereoisomer thereof, or the mixture thereof, wherein $R^3$ is $R^b$ and $R^b$ is a phenyl substituted by 0, 1, 2 or 3 substituents selected from halo, $C_{1-4}$alk, $C_{1-3}$haloalk, —$OC_{1-4}$alk, —OH, —$NH_2$, —$OC_{1-4}$alk, —$OC_{1-4}$haloalk, —$NHC_{1-4}$alk, and —$N(C_{1-4}$alk$)C_{1-4}$alk.

53. The compound of any one of embodiments 1-52 or the pharmaceutically-acceptable salt thereof, the tautomer thereof, the pharmaceutically-acceptable salt of the tautomer, the stereoisomer thereof, or the mixture thereof, wherein $R^4$ is H.

54. The compound of any one of embodiments 1-52 or the pharmaceutically-acceptable salt thereof, the tautomer thereof, the pharmaceutically-acceptable salt of the tautomer, the stereoisomer thereof, or the mixture thereof, wherein $R^4$ is selected from F, Cl, $C_{1-6}$alk, —$OC_{1-6}$alk, —$OC_{1-3}$haloalk, or —$C_{1-3}$haloalk.

55. The compound of embodiment 54 or the pharmaceutically-acceptable salt thereof, the tautomer thereof, the pharmaceutically-acceptable salt of the tautomer, the stereoisomer thereof, or the mixture thereof, wherein $R^4$ is selected from —F, —Cl, or —$OCF_3$.

56. The compound of embodiment 55 or the pharmaceutically-acceptable salt thereof, the tautomer thereof, the pharmaceutically-acceptable salt of the tautomer, the stereoisomer thereof, or the mixture thereof, wherein $R^4$ is —F.

57. The compound of any one of embodiments 1-47 or the pharmaceutically-acceptable salt thereof, the tautomer thereof, the pharmaceutically-acceptable salt of the tautomer, the stereoisomer thereof, or the mixture thereof, wherein —$R^3$ is —$OCF_3$ and $R^4$ is —F.

58. The compound of any one of embodiments 1-47 or the pharmaceutically-acceptable salt thereof, the tautomer thereof, the pharmaceutically-acceptable salt of the tautomer, the stereoisomer thereof, or the mixture thereof, wherein $R^3$ and $R^4$ together form a four-atom unsaturated bridge containing 0 or 1 N atoms, wherein the bridge is substituted by 0, 1 or 2 $R^5$ substituents.

59. The compound of any one of embodiments 1-58 or the pharmaceutically-acceptable salt thereof, the tautomer thereof, the pharmaceutically-acceptable salt of the tautomer, the stereoisomer thereof, or the mixture thereof, wherein each instance of $R^5$ is H.

60. The compound of any one of embodiments 1-58 or the pharmaceutically-acceptable salt thereof, the tautomer thereof, the pharmaceutically-acceptable salt of the tautomer, the stereoisomer thereof, or the mixture thereof, wherein in at least one instance, $R^5$ is selected from $C_{1-8}$alk, halo, or —$OR^a$.

61. The compound of any one of embodiments 1-58 or the pharmaceutically-acceptable salt thereof, the tautomer thereof, the pharmaceutically-acceptable salt of the tautomer, the stereoisomer thereof, or the mixture thereof, wherein in at least one instance, $R^5$ is selected from —$CH_3$, —Cl, —F, or —OMe.

62. The compound of any one of embodiments 1-61 or the pharmaceutically-acceptable salt thereof, the tautomer thereof, the pharmaceutically-acceptable salt of the tautomer, the stereoisomer thereof, or the mixture thereof, wherein each instance of $R^6$ is H.

63. The compound of any one of embodiments 1-61 or the pharmaceutically-acceptable salt thereof, the tautomer thereof, the pharmaceutically-acceptable salt of the tautomer, the stereoisomer thereof, or the mixture thereof, wherein at least one instance of $R^6$ is halo or $C_{1-6}$alk.

64. The compound of any one of embodiments 1-61 or the pharmaceutically-acceptable salt thereof, the tautomer thereof, the pharmaceutically-acceptable salt of the tautomer, the stereoisomer thereof, or the mixture thereof, wherein at least one instance of $R^6$ is —F, —Cl, or —$CH_3$.

65. The compound of any one of embodiments 1-64 or the pharmaceutically-acceptable salt thereof, the tautomer thereof, the pharmaceutically-acceptable salt of the tautomer, the stereoisomer thereof, or the mixture thereof, wherein $R^1$ is the saturated, partially-saturated or unsaturated 3-, 4-, 5-, 6- or 7-membered monocyclic or 7-, 8-, 9-, 10- or 11-membered bicyclic ring and the monocyclic or bicyclic ring is substituted by 0, 1, 2, or 3 substituents, wherein the substituents are selected from F, Cl, Br, I, oxo, cyano, —$CH_3$, —$CH_2CH_3$, —$CH_2CH_2CH_3$, —$C(H)(CH_3)_2$, —$CH_2C(H)(CH_3)_2$, —$CH_2C(H)$=$CH_2$, —$CH_2CO_2H$, —$CH_2CF_3$, —C(OH)($CH_3)_2$, —$SO_2N(H)CH_3$, —$N(H)SO_2CH_3$, —$OCH_3$, —$OCF_3$, —OH, —$OCH_2CO_2H$, —$CH_2OH$, —$CH_2CH_2OH$, —$CH_2C(H)(CH_3)OH$, —$CO_2H$, —$CO_2CH_3$, —$CO_2CH_2CH_3$, —$CO_2C(CH_3)_3$, —$CO_2NH_2$, —$CO_2N(H)CH_3$, —$SO_2CH_3$, —OC(=O)$CH_3$, —$NH_2$, —NHC(=O)$CH_3$, —$N(CH_3)_2$, —$N(H)CH_2CH_3$, —$CF_3$, —$CHF_2$, —$CH_2C(H)(CF_3)OH$, —$CH_2C(CH_3)_2OH$, —$CH_2$-phenyl, —C(=O)-phenyl, tetrazolyl, oxadiazolonyl, pyridyl, oxetanyl,

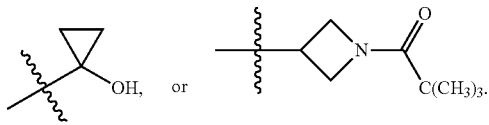 [SMILES: *C1(O)CC1 ; "or" ; *C1CN(C(=O)C(C)(C)C)C1]

66. The compound of any one of embodiments 1-64 or the pharmaceutically-acceptable salt thereof, the tautomer thereof, the pharmaceutically-acceptable salt of the tautomer, the stereoisomer thereof, or the mixture thereof, wherein $R^1$ is a phenyl, pyridyl, pyridinonyl, piperidinonyl, pyridazinonyl, pyrazinonyl, pyridazinyl, pyrimidinyl, pyrazinyl, tetradyrofuranyl, tetrahydropyranyl, thiazolyl, isothiazolyl, furanyl, thiophenyl, pyrazolyl, isoxazolyl, triazolyl, oxazolyl, imidazolyl, pyrrolidinonyl, piperidinyl, cyclohexyl, cyclohexanonyl, quinolinyl, isoquinolinyl, naphthyridinyl, pyrrolopyridinyl, pyrrolopyrimidinyl, benzothiophenyl, pyrazolopyrimidinyl, triazolopyrimidinyl, indazolyl, tetrahydroindazolyl, tetrahydrocyclopentapyrazolyl, dihydropyrazolooxazinyl, indolinonyl, isoindolinonyl, benzooxazolonyl, oxazolopyridinonyl, benzoimidazolonyl, isoindolindionyl, tetrahydroquinolinyl, dihydroquinolinonyl, benzooxazinonyl, dihydrobenzooxazinonyl, dihydroindenonyl, benzothiazolyl, benzimidazolyl, imidazopyridinyl, tetrazolopyridinyl, quinolinonyl, quinoxalinyl, indolyl, or quinoxalindionyl substituted by 0, 1, 2, or 3 substituents.

67. The compound of any one of embodiments 1-64 or the pharmaceutically-acceptable salt thereof, the tautomer thereof, the pharmaceutically-acceptable salt of the tautomer, the stereoisomer thereof, or the mixture thereof, wherein $R^1$ is a phenyl, pyridyl, pyridinonyl, pyrazinonyl, pyridazinyl, pyrimidinyl, tetrahydropyranyl, thiazolyl, isothiazolyl, imidazolyl, piperidinyl, quinolinyl, isoquinolinyl, indazolyl, indolinonyl, isoindolinonyl, benzooxazolonyl, dihydroquinolinonyl, imidazopyridinyl, quinolinonyl, indolyl substituted by 0, 1, 2, or 3 substituents.

68. The compound of embodiment 67 or the pharmaceutically-acceptable salt thereof, the tautomer thereof, the pharmaceutically-acceptable salt of the tautomer, the stereoisomer thereof, or the mixture thereof, wherein $R^1$ is a phenyl substituted by 0, or 1 substituent.

69. The compound of embodiment 67 or the pharmaceutically-acceptable salt thereof, the tautomer thereof, the pharmaceutically-acceptable salt of the tautomer, the stereoisomer thereof, or the mixture thereof, wherein $R^1$ is a pyridinonyl substituted by 0, or 1 substituent.

70. The compound of embodiment 67 or the pharmaceutically-acceptable salt thereof, the tautomer thereof, the pharmaceutically-acceptable salt of the tautomer, the stereoisomer thereof, or the mixture thereof, wherein $R^1$ is a pyridyl substituted by 0, or 1 substituent.

71. The compound of embodiment 67 or the pharmaceutically-acceptable salt thereof, the tautomer thereof, the pharmaceutically-acceptable salt of the tautomer, the stereoisomer thereof, or the mixture thereof, wherein $R^1$ is a benzooxazolonyl substituted by 0, or 1 substituent.

72. The compound of embodiment 67 or the pharmaceutically-acceptable salt thereof, the tautomer thereof, the pharmaceutically-acceptable salt of the tautomer, the stereoisomer thereof, or the mixture thereof, wherein $R^1$ is a quinolinyl substituted by 0, or 1 substituent.

73. The compound of any one of embodiments 1-64 or the pharmaceutically-acceptable salt thereof, the tautomer thereof, the pharmaceutically-acceptable salt of the tautomer, the stereoisomer thereof, or the mixture thereof, wherein $R^1$ is a group of formula

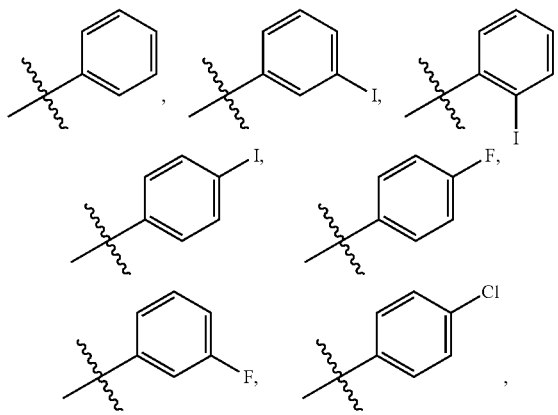

-continued

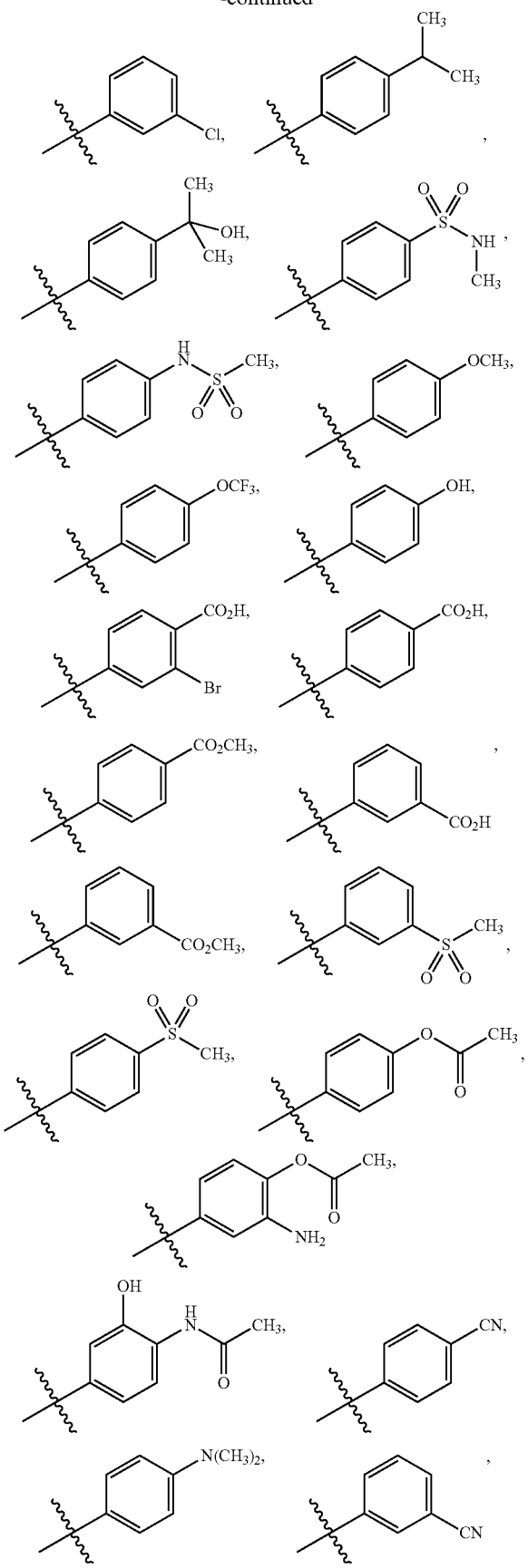

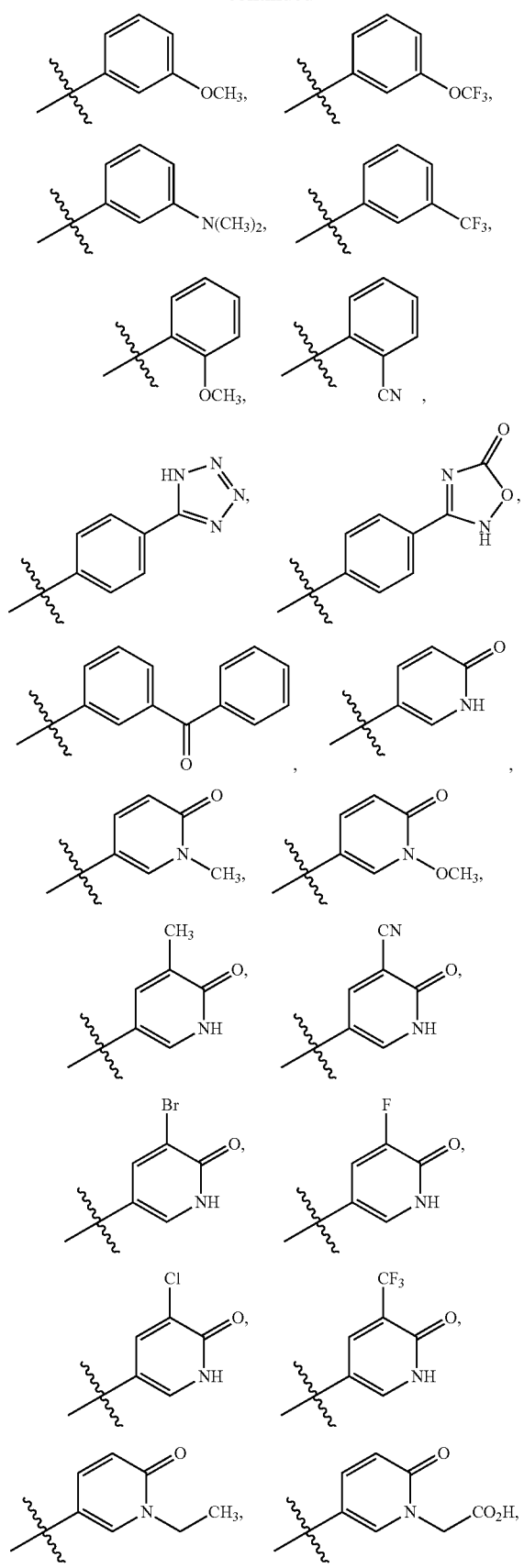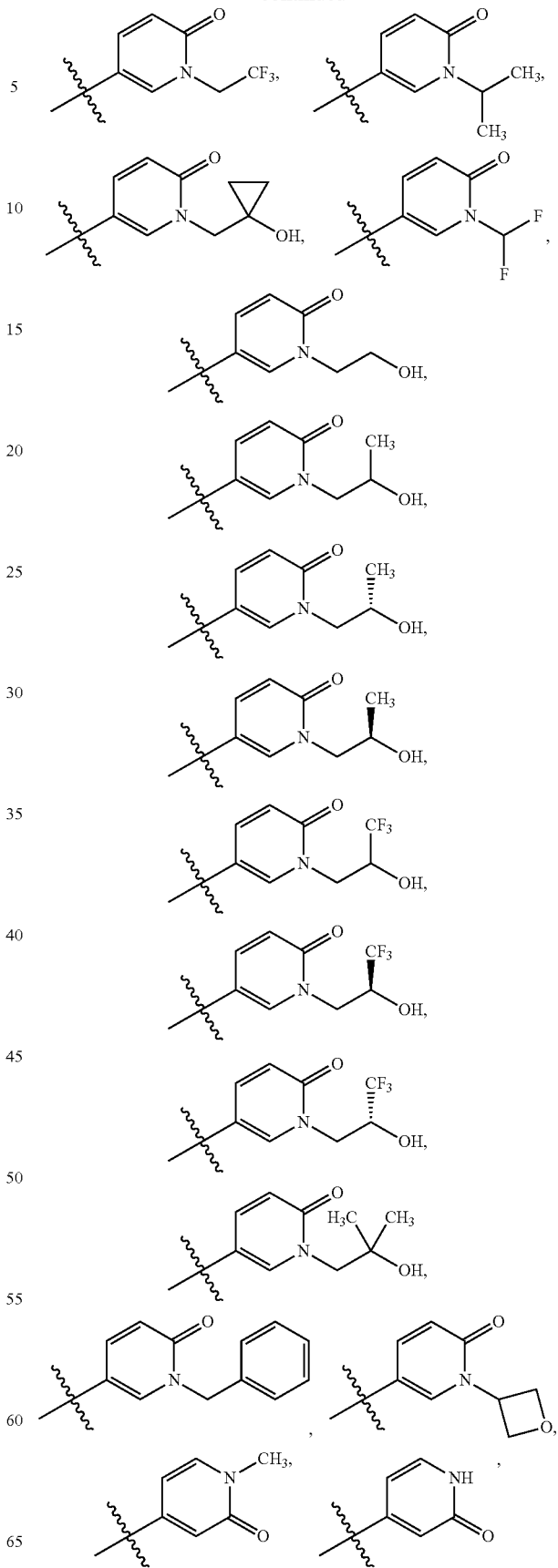

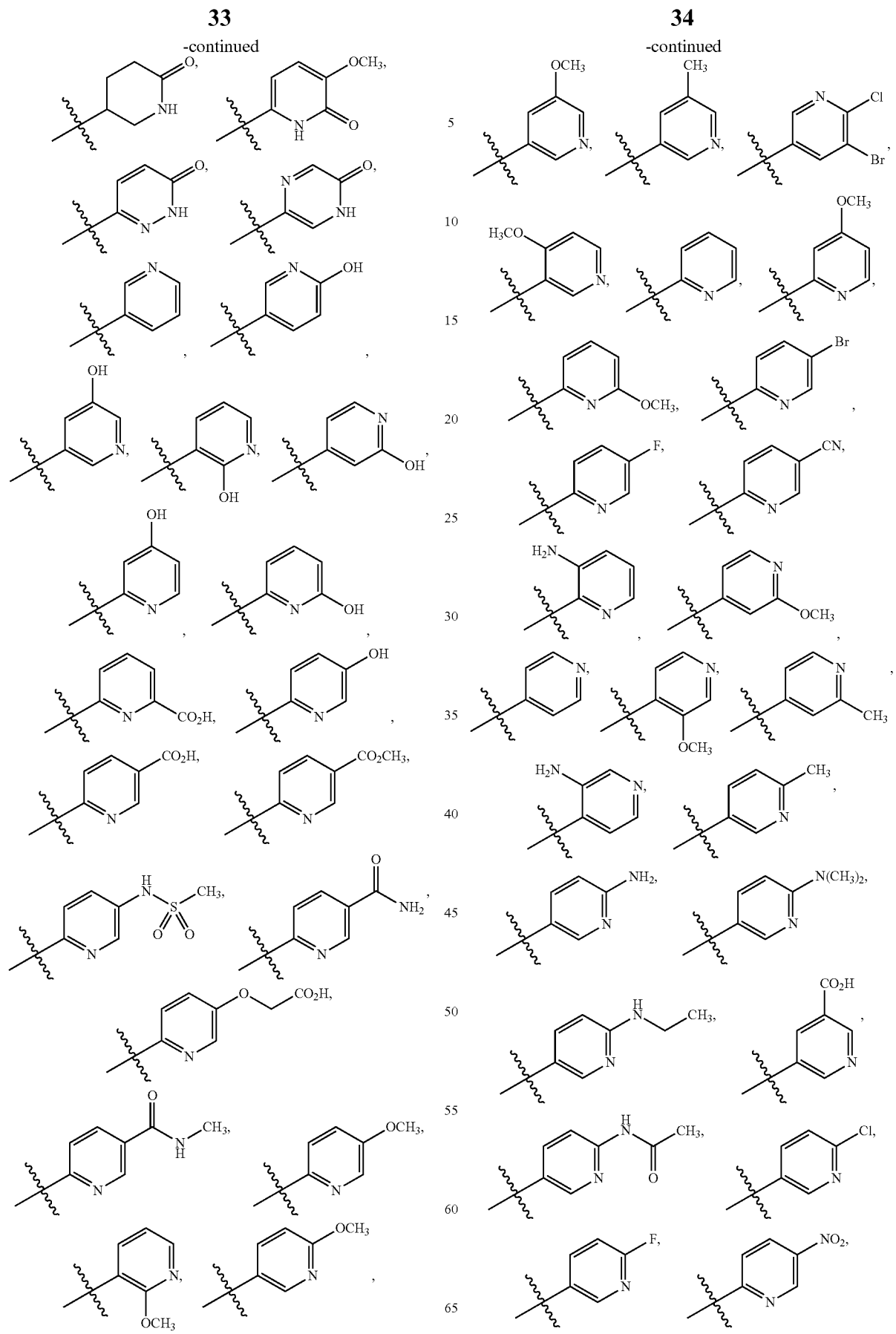

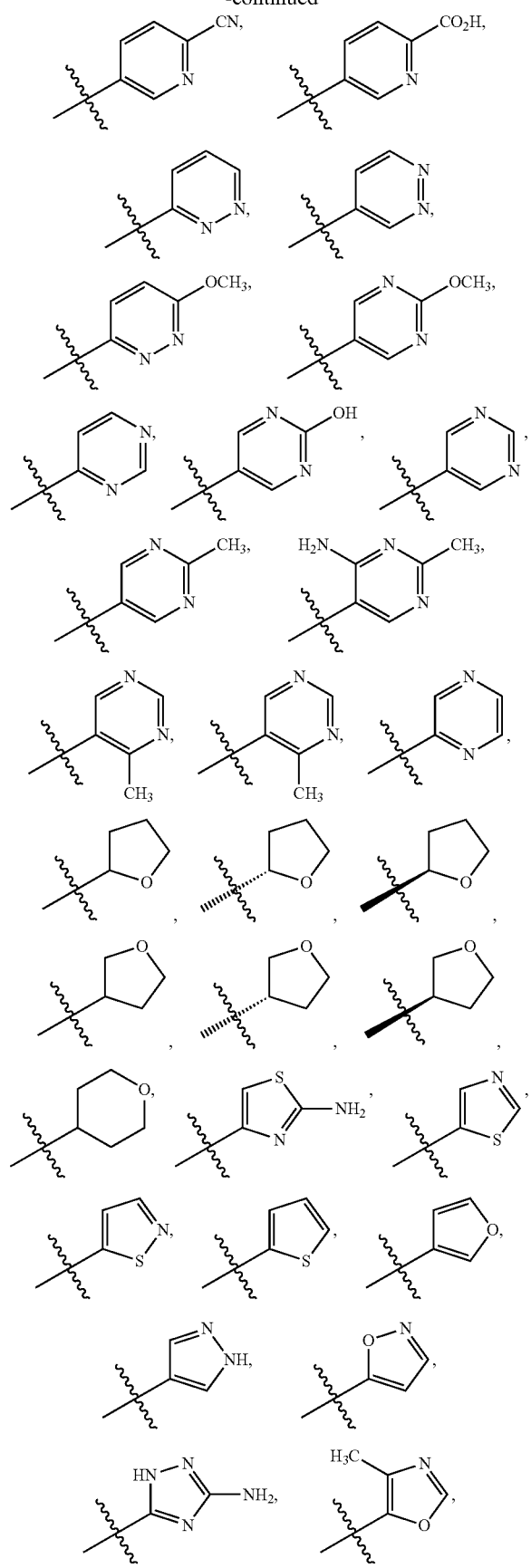
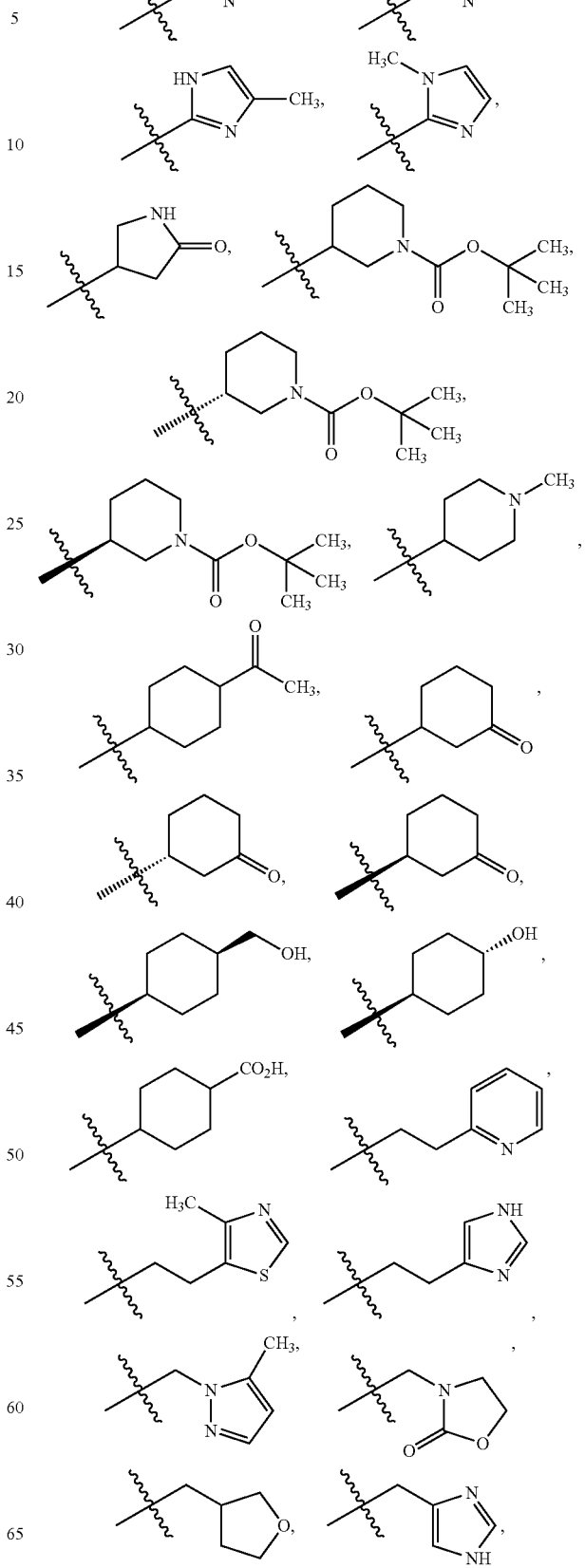

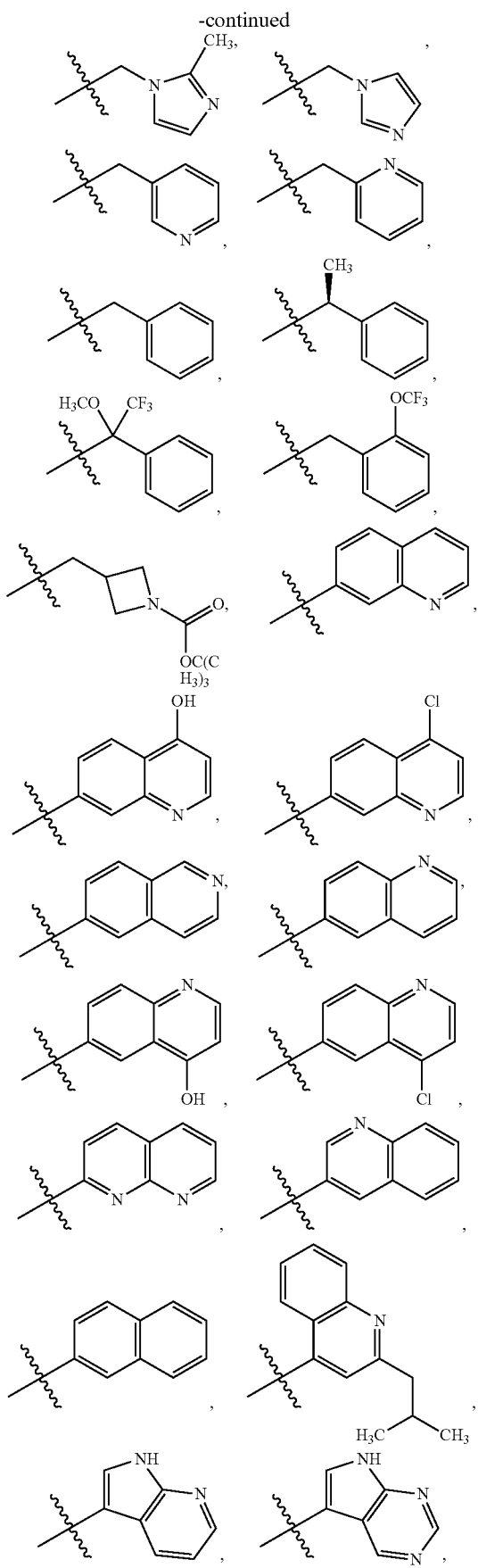
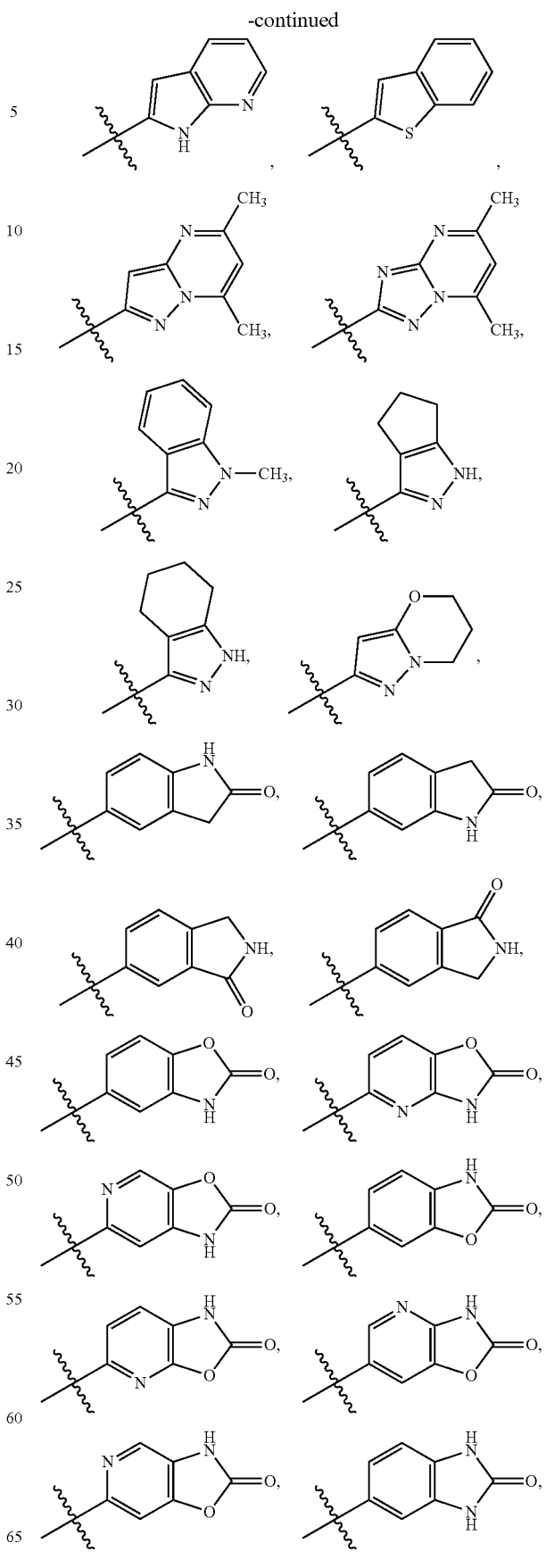

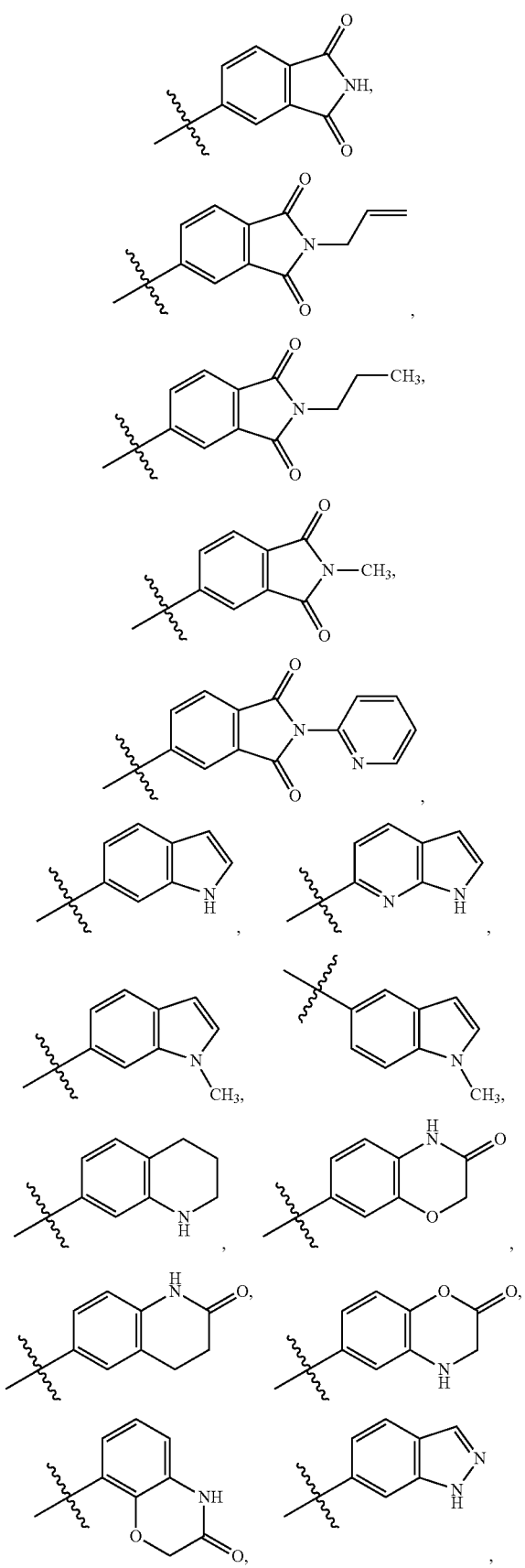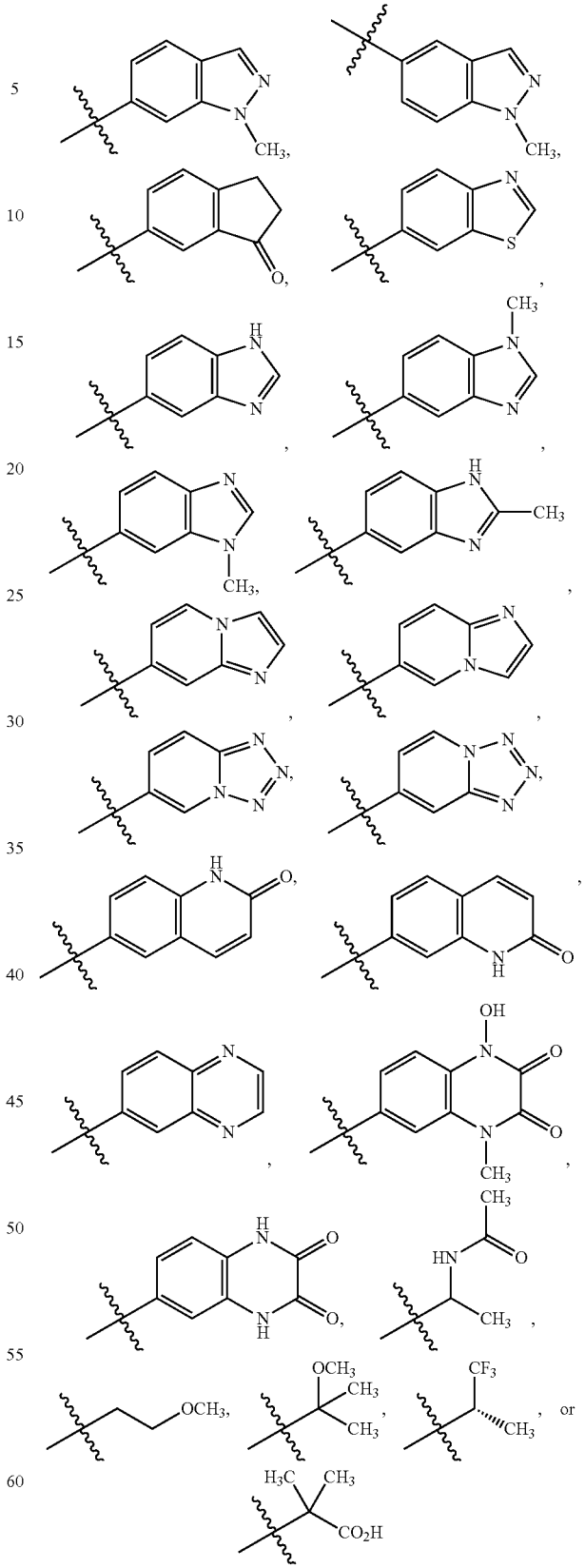
and the symbol ⁓, when drawn across a bond, indicates the point of attachment to the rest of the molecule.

74. The compound of any one of embodiments 1-64 or the pharmaceutically-acceptable salt thereof, the tautomer thereof, the pharmaceutically-acceptable salt of the tautomer, the stereoisomer thereof, or the mixture thereof, wherein $R^1$ is a group of formula
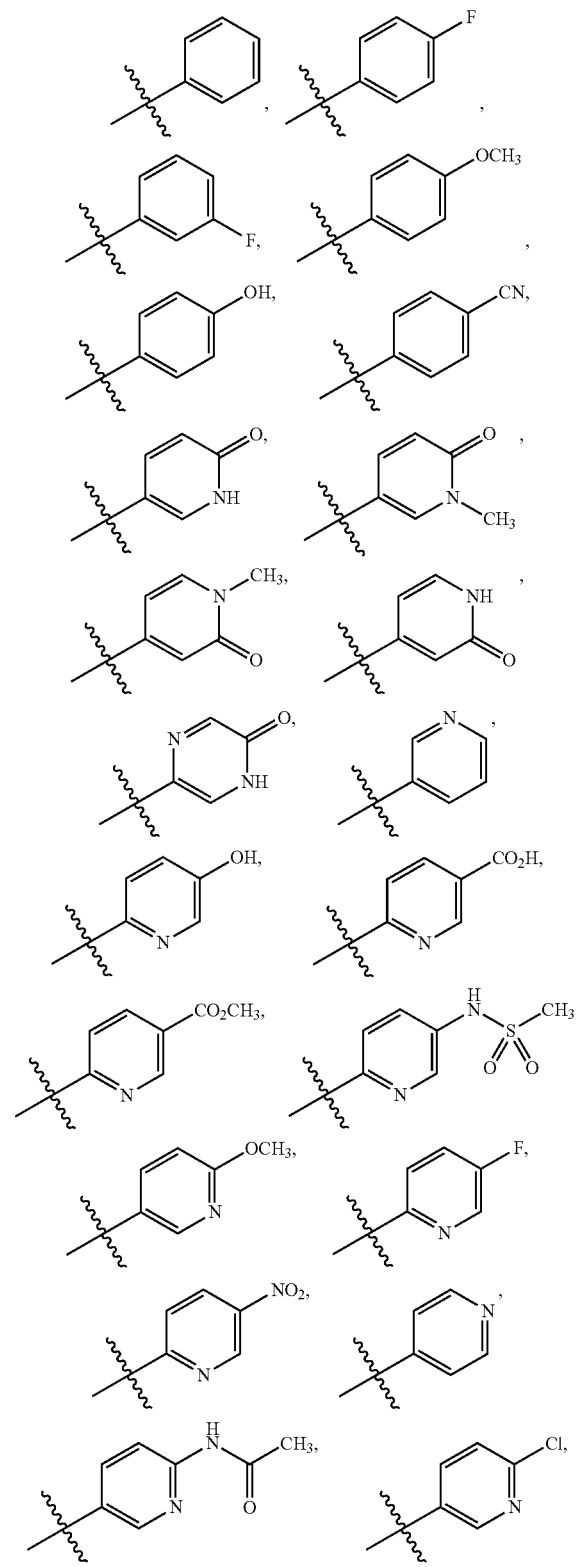
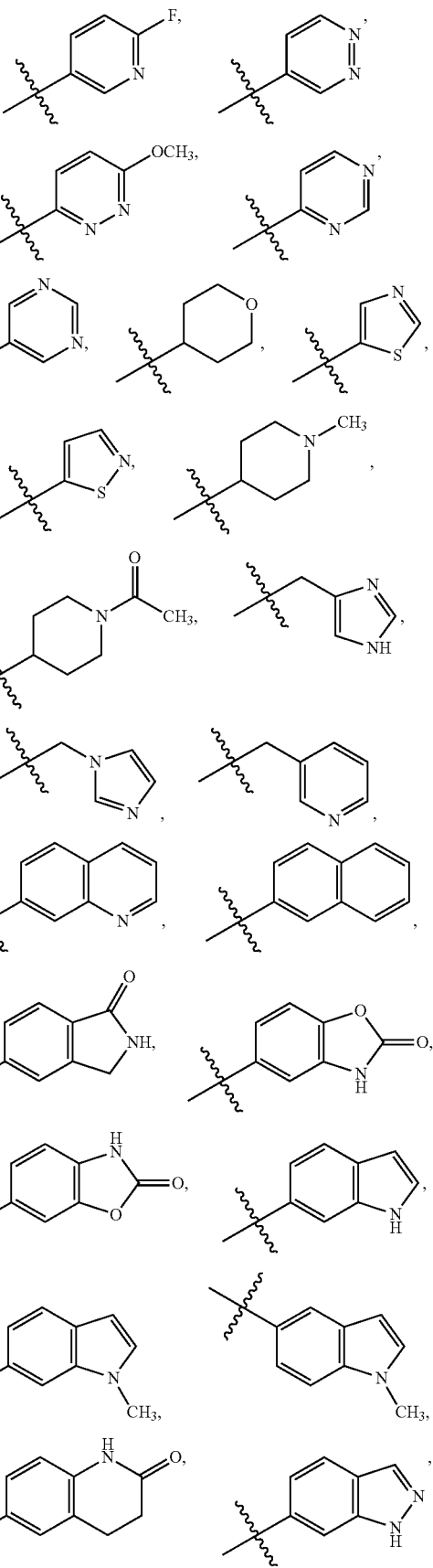

-continued

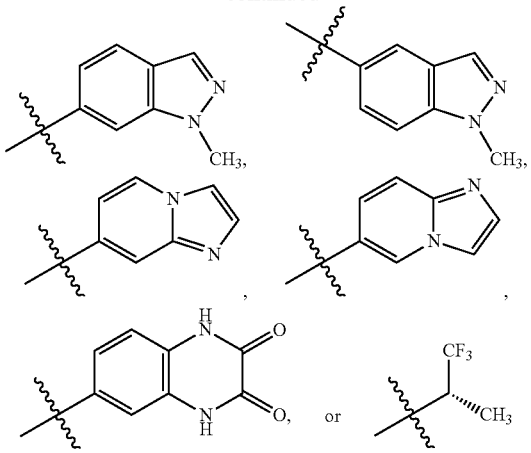

and the symbol ⌇, when drawn across a bond, indicates the point of attachment to the rest of the molecule.

75. The compound of any one of embodiments 1-64 or the pharmaceutically-acceptable salt hereof, the tautomer thereof, the pharmaceutically-acceptable salt of the tautomer, the stereoisomer thereof, or the mixture thereof, wherein $R^1$ is a group of formula

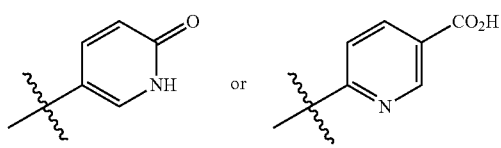 [SMILES: *c1ccc(=O)[nH]c1 ; "or" ; *c1ccc(C(=O)O)cn1]

and the symbol ⌇, when drawn across a bond, indicates the point of attachment to the rest of the molecule.

76. The compound of any one of embodiments 1-64 or the pharmaceutically-acceptable salt thereof, the tautomer thereof, the pharmaceutically-acceptable salt of the tautomer, the stereoisomer thereof, or the mixture thereof, wherein $R^1$ is

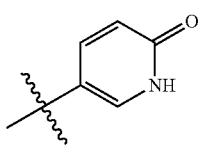 [SMILES: *c1ccc(=O)[nH]c1]

and the symbol ⌇, when drawn across a bond, indicates the point of attachment to the rest of the molecule.

77. The compound of any one of embodiments 1-64 or the pharmaceutically-acceptable salt thereof, the tautomer thereof, the pharmaceutically-acceptable salt of the tautomer, the stereoisomer thereof, or the mixture thereof, wherein $R^1$ is

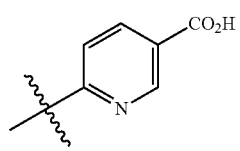 [SMILES: *c1ccc(C(=O)O)cn1]

and the symbol ⌇, when drawn across a bond, indicates the point of attachment to the rest of the molecule.

78. The compound of embodiment 1, wherein the compound is
(S)-N-(4-(4-(trifluoromethyl)phenyl)-3,4-dihydro-2H-pyrano[3,2-b]pyridin-4-yl)benzamide;
(S)-4-fluoro-N-(4-(4-(trifluoromethyl)phenyl)-3,4-dihydro-2H-pyrano[3,2-b]pyridin-4-yl)benzamide;
(S)-N-(4-(3,4-dichlorophenyl)-3,4-dihydro-2H-pyrano[3,2-b]pyridin-4-yl)benzamide;
(S)-4-hydroxy-N-(4-(4-(trifluoromethyl)phenyl)-3,4-dihydro-2H-pyrano[3,2-b]pyridin-4-yl)benzamide;
(S)-4-methoxy-N-(4-(4-(trifluoromethyl)phenyl)-3,4-dihydro-2H-pyrano[3,2-b]pyridin-4-yl)benzamide;
4-fluoro-N-(4-(3-fluoro-4-(trifluoromethoxy)phenyl)-3,4-dihydro-2H-pyrano[3,2-b]pyridin-4-yl)benzamide;
N-(4-(3-fluoro-4-(trifluoromethoxy)phenyl)-3,4-dihydro-2H-pyrano[3,2-b]pyridin-4-yl)benzamide;
4-fluoro-N-(4-(4-(trifluoromethoxy)phenyl)-3,4-dihydro-2H-pyrano[3,2-b]pyridin-4-yl)benzamide;
N-(4-(4-(trifluoromethoxy)phenyl)-3,4-dihydro-2H-pyrano[3,2-b]pyridin-4-yl)benzamide;
N-(4-(3,4-dichlorophenyl)-3,4-dihydro-2H-pyrano[3,2-b]pyridin-4-yl)-4-fluorobenzamide;
4-fluoro-N-(4-phenyl-3,4-dihydro-2H-pyrano[3,2-b]pyridin-4-yl)benzamide;
N-(4-phenyl-3,4-dihydro-2H-pyrano[3,2-b]pyridin-4-yl)benzamide;
N-(4-(6-(trifluoromethyl)pyridin-3-yl)-3,4-dihydro-2H-pyrano[3,2-b]pyridin-4-yl)benzamide;
(S)-N-(4-(4-chlorophenyl)-3,4-dihydro-2H-pyrano[3,2-b]pyridin-4-yl)benzamide;
(S)-N-(4-(4-chloro-3-fluorophenyl)-3,4-dihydro-2H-pyrano[3,2-b]pyridin-4-yl)benzamide;
(S)-N-(4-(4-fluorophenyl)-3,4-dihydro-2H-pyrano[3,2-b]pyridin-4-yl)benzamide;
(S)-N-(4-(3-(trifluoromethoxy)phenyl)-3,4-dihydro-2H-pyrano[3,2-b]pyridin-4-yl)benzamide;
(S)-N-(4-(p-tolyl)-3,4-dihydro-2H-pyrano[3,2-b]pyridin-4-yl)benzamide;
(S)-N-(4-(3-fluoro-4-(trifluoromethyl)phenyl)-3,4-dihydro-2H-pyrano[3,2-b]pyridin-4-yl)benzamide;
(S)-2-oxo-N-(4-(4-(trifluoromethyl)phenyl)-3,4-dihydro-2H-pyrano[3,2-b]pyridin-4-yl)-2,3-dihydrobenzo[d]oxazole-6-carboxamide;
(S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-6-carboxamide;
2-oxo-N-(4-(4-(trifluoromethoxy)phenyl)-3,4-dihydro-2H-pyrano[3,2-b]pyridin-4-yl)-2,3-dihydrobenzo[d]oxazole-6-carboxamide;
2-oxo-N-(4-(4-(trifluoromethoxy)phenyl)-3,4-dihydro-2H-pyrano[3,2-b]pyridin-4-yl)-2,3-dihydrobenzo[d]oxazole-5-carboxamide;
N-(4-(3,4-dichlorophenyl)-3,4-dihydro-2H-pyrano[3,2-b]pyridin-4-yl)-2-oxo-2,3-dihydrobenzo[d]oxazole-6-carboxamide;
N-(4-(3,4-dichlorophenyl)-3,4-dihydro-2H-pyrano[3,2-b]pyridin-4-yl)-2-oxo-2,3-dihydrobenzo[d]oxazole-5-carboxamide;
2-oxo-N-(4-phenyl-3,4-dihydro-2H-pyrano[3,2-b]pyridin-4-yl)-2,3-dihydrobenzo[d]oxazole-6-carboxamide;
2-oxo-N-(4-(6-(trifluoromethyl)pyridin-3-yl)-3,4-dihydro-2H-pyrano[3,2-b]pyridin-4-yl)-2,3-dihydrobenzo[d]oxazole-5-carboxamide;
(S)-N-(4-(4-(trifluoromethyl)phenyl)chroman-4-yl)benzamide;
N-(8-(4-(trifluoromethyl)phenyl)-5,6,7,8-tetrahydroquinolin-8-yl)benzamide;

methyl 6-((4-(3-fluoro-4-(trifluoromethoxy)phenyl)-3,4-dihydro-2H-pyrano[3,2-b]pyridin-4-yl)carbamoyl)nicotinate;

6-oxo-N-(8-(4-(trifluoromethyl)phenyl)-5,6,7,8-tetrahydroquinolin-8-yl)-1,6-dihydropyridine-3-carboxamide;

(S)-6-methoxy-N-(4-(4-(trifluoromethyl)phenyl)-3,4-dihydro-2H-pyrano[3,2-b]pyridin-4-yl)nicotinamide;

(S)-2-oxo-N-(4-(4-(trifluoromethyl)phenyl)-3,4-dihydro-2H-pyrano[3,2-b]pyridin-4-yl)-1,2,3,4-tetrahydroquinoline-6-carboxamide;

(S)-N-(4-(4-(trifluoromethyl)phenyl)-3,4-dihydro-2H-pyrano[3,2-b]pyridin-4-yl)-1H-indazole-6-carboxamide;

(S)-N-(4-(4-(trifluoromethyl)phenyl)-3,4-dihydro-2H-pyrano[3,2-b]pyridin-4-yl)pyrimidine-4-carboxamide;

(S)-N-(4-(4-(trifluoromethyl)phenyl)-3,4-dihydro-2H-pyrano[3,2-b]pyridin-4-yl)-1H-indole-6-carboxamide;

(S)-N-(4-(4-(trifluoromethyl)phenyl)-3,4-dihydro-2H-pyrano[3,2-b]pyridin-4-yl)pyridazine-4-carboxamide;

(S)-1-methyl-N-(4-(4-(trifluoromethyl)phenyl)-3,4-dihydro-2H-pyrano[3,2-b]pyridin-4-yl)-1H-indazole-6-carboxamide;

(S)-N-(4-(4-(trifluoromethyl)phenyl)-3,4-dihydro-2H-pyrano[3,2-b]pyridin-4-yl)thiazole-5-carboxamide;

(S)-5-hydroxy-N-(4-(4-(trifluoromethyl)phenyl)-3,4-dihydro-2H-pyrano[3,2-b]pyridin-4-yl)picolinamide;

(S)-N-(4-(4-(trifluoromethyl)phenyl)-3,4-dihydro-2H-pyrano[3,2-b]pyridin-4-yl)isothiazole-5-carboxamide;

(S)-1-methyl-N-(4-(4-(trifluoromethyl)phenyl)-3,4-dihydro-2H-pyrano[3,2-b]pyridin-4-yl)-1H-indole-5-carboxamide;

(S)-5-acetamido-N-(4-(4-(trifluoromethyl)phenyl)-3,4-dihydro-2H-pyrano[3,2-b]pyridin-4-yl)picolinamide;

(S)-1-methyl-N-(4-(4-(trifluoromethyl)phenyl)-3,4-dihydro-2H-pyrano[3,2-b]pyridin-4-yl)-1H-indazole-5-carboxamide;

(S)-5-oxo-N-(4-(4-(trifluoromethyl)phenyl)-3,4-dihydro-2H-pyrano[3,2-b]pyridin-4-yl)-4,5-dihydropyrazine-2-carboxamide;

(S)-N-(4-(4-(trifluoromethyl)phenyl)-3,4-dihydro-2H-pyrano[3,2-b]pyridin-4-yl)isonicotinamide;

(S)-6-methoxy-N-(4-(4-(trifluoromethyl)phenyl)-3,4-dihydro-2H-pyrano[3,2-b]pyridin-4-yl)pyridazine-3-carboxamide;

(S)-N-(4-(4-(trifluoromethyl)phenyl)-3,4-dihydro-2H-pyrano[3,2-b]pyridin-4-yl)nicotinamide;

(S)-N-(4-(4-(trifluoromethyl)phenyl)-3,4-dihydro-2H-pyrano[3,2-b]pyridin-4-yl)imidazo[1,2-a]pyridine-7-carboxamide;

(S)-N-(4-(3-fluoro-4-(trifluoromethoxy)phenyl)-3,4-dihydro-2H-pyrano[3,2-b]pyridin-4-yl)-5-oxo-4,5-dihydropyrazine-2-carboxamide;

(S)-N-(4-(3-fluoro-4-(trifluoromethoxy)phenyl)-3,4-dihydro-2H-pyrano[3,2-b]pyridin-4-yl)-5-hydroxypicolinamide;

(S)-N-(4-(3-fluoro-4-(trifluoromethoxy)phenyl)-3,4-dihydro-2H-pyrano[3,2-b]pyridin-4-yl)imidazo[1,2-a]pyridine-6-carboxamide;

(S)-N-(4-(3-fluoro-4-(trifluoromethoxy)phenyl)-3,4-dihydro-2H-pyrano[3,2-b]pyridin-4-yl)-1-methyl-1H-indazole-5-carboxamide;

(S)-N-(4-(3-fluoro-4-(trifluoromethoxy)phenyl)-3,4-dihydro-2H-pyrano[3,2-b]pyridin-4-yl)-2-oxo-1,2,3,4-tetrahydroquinoline-6-carboxamide;

(S)-5-fluoro-N-(4-(3-fluoro-4-(trifluoromethoxy)phenyl)-3,4-dihydro-2H-pyrano[3,2-b]pyridin-4-yl)picolinamide;

(S)-N-(4-(4-(trifluoromethyl)phenyl)-3,4-dihydro-2H-pyrano[3,2-b]pyridin-4-yl)quinoline-7-carboxamide;

(S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-5-carboxamide;

(S)-6-oxo-N-(4-(4-(trifluoromethoxy)phenyl)-3,4-dihydro-2H-pyrano[3,2-b]pyridin-4-yl)-1,6-dihydropyridine-3-carboxamide;

(S)-N-(4-(3-fluoro-4-(trifluoromethoxy)phenyl)-3,4-dihydro-2H-pyrano[3,2-b]pyridin-4-yl)-6-oxo-1,6-dihydropyridine-3-carboxamide;

(S)-6-oxo-N-(4-(4-(trifluoromethyl)phenyl)-3,4-dihydro-2H-pyrano[3,2-b]pyridin-4-yl)-1,6-dihydropyridine-3-carboxamide;

(S)-2-oxo-N-(4-(4-(trifluoromethyl)phenyl)-3,4-dihydro-2H-pyrano[3,2-b]pyridin-4-yl)-2,3-dihydrobenzo[d]oxazole-5-carboxamide;

(S)-N-(4-(3-fluoro-4-(trifluoromethoxy)phenyl)-3,4-dihydro-2H-pyrano[3,2-b]pyridin-4-yl)-5-nitropicolinamide;

(S)-N5-(4-(3-fluoro-4-(trifluoromethoxy)phenyl)-3,4-dihydro-2H-pyrano[3,2-b]pyridin-4-yl)-N2-methylpyridine-2,5-dicarboxamide;

(S)-N-(4-(3-fluoro-4-(trifluoromethoxy)phenyl)-3,4-dihydro-2H-pyrano[3,2-b]pyridin-4-yl)-2,3-dioxo-1,2,3,4-tetrahydroquinoxaline-6-carboxamide;

(S)-N-(4-(3-fluoro-4-(trifluoromethoxy)phenyl)-3,4-dihydro-2H-pyrano[3,2-b]pyridin-4-yl)-5-(methylsulfonamido)picolinamide;

(S)-1-(4-(3-fluoro-4-(trifluoromethoxy)phenyl)-3,4-dihydro-2H-pyrano[3,2-b]pyridin-4-yl)-3-(6-fluoropyridin-3-yl)urea;

1-((S)-4-(4-(trifluoromethyl)phenyl)-3,4-dihydro-2H-pyrano[3,2-b]pyridin-4-yl)-3-((S)-1,1,1-trifluoropropan-2-yl)urea;

(S)-1-(4-cyanophenyl)-3-(4-(3-fluoro-4-(trifluoromethoxy)phenyl)-3,4-dihydro-2H-pyrano[3,2-b]pyridin-4-yl)urea;

(S)-1-(6-chloropyridin-3-yl)-3-(4-(3-fluoro-4-(trifluoromethoxy)phenyl)-3,4-dihydro-2H-pyrano[3,2-b]pyridin-4-yl)urea;

1-(pyridin-3-yl)-3-(4-(4-(trifluoromethyl)phenyl)chroman-4-yl)urea;

1-(pyridin-3-yl)-3-(8-(4-(trifluoromethyl)phenyl)-5,6,7,8-tetrahydroquinolin-8-yl)urea;

(S)-1-(3-fluorophenyl)-3-(4-(4-(trifluoromethyl)phenyl)-3,4-dihydro-2H-pyrano[3,2-b]pyridin-4-yl)urea;

(S)-1-(pyridin-3-yl)-3-(4-(4-(trifluoromethyl)phenyl)-3,4-dihydro-2H-pyrano[3,2-b]pyridin-4-yl)urea;

(S)-1-(4-fluorophenyl)-3-(4-(4-(trifluoromethyl)phenyl)-3,4-dihydro-2H-pyrano[3,2-b]pyridin-4-yl)urea;

(S)-6-((4-(3-fluoro-4-(trifluoromethoxy)phenyl)-3,4-dihydro-2H-pyrano[3,2-b]pyridin-4-yl)carbamoyl)nicotinic acid;

(S)-N-(4-(3-fluoro-4-(trifluoromethoxy)phenyl)-3,4-dihydro-2H-pyrano[3,2-b]pyridin-4-yl)benzenesulfonamide;

(S)-N-(4-(3-fluoro-4-(trifluoromethoxy)phenyl)-3,4-dihydro-2H-pyrano[3,2-b]pyridin-4-yl)pyridine-3-sulfonamide;

(S)-tert-butyl (4-(3-fluoro-4-(trifluoromethoxy)phenyl)-3,4-dihydro-2H-pyrano[3,2-b]pyridin-4-yl)carbamate;

1-methyl-6-oxo-N-(4-(4-(trifluoromethyl)phenyl)-3,4-dihydro-2H-pyrano[3,2-b]pyridin-4-yl)-1,6-dihydropyridine-3-carboxamide;

1-oxo-N-(4-(4-(trifluoromethyl)phenyl)-3,4-dihydro-2H-pyrano[3,2-b]pyridin-4-yl)isoindoline-5-carboxamide; or (S)-N-(4-(naphthalen-2-yl)-3,4-dihydro-2H-pyrano[3,2-b]pyridin-4-yl)-6-oxo-1,6-dihydropyridine-3-carboxamide; or the pharmaceutically-acceptable salt thereof, the tautomer thereof, the pharmaceutically-acceptable salt of the tautomer, the stereoisomer thereof, or the mixture thereof 79. The compound of embodiment 1, wherein the compound is (S)-N-(4-(4-(trifluoromethyl)phenyl)-3,4-dihydro-2H-pyrano[3,2-b]pyridin-4-yl)benzamide;
(S)-4-fluoro-N-(4-(4-(trifluoromethyl)phenyl)-3,4-dihydro-2H-pyrano[3,2-b]pyridin-4-yl)benzamide;
(S)-N-(4-(3,4-dichlorophenyl)-3,4-dihydro-2H-pyrano[3,2-b]pyridin-4-yl)benzamide;
(S)-4-hydroxy-N-(4-(4-(trifluoromethyl)phenyl)-3,4-dihydro-2H-pyrano[3,2-b]pyridin-4-yl)benzamide;
(S)-4-methoxy-N-(4-(4-(trifluoromethyl)phenyl)-3,4-dihydro-2H-pyrano[3,2-b]pyridin-4-yl)benzamide;
4-fluoro-N-(4-(3-fluoro-4-(trifluoromethoxy)phenyl)-3,4-dihydro-2H-pyrano[3,2-b]pyridin-4-yl)benzamide;
N-(4-(3-fluoro-4-(trifluoromethoxy)phenyl)-3,4-dihydro-2H-pyrano[3,2-b]pyridin-4-yl)benzamide;
4-fluoro-N-(4-(4-(trifluoromethoxy)phenyl)-3,4-dihydro-2H-pyrano[3,2-b]pyridin-4-yl)benzamide;
N-(4-(4-(trifluoromethoxy)phenyl)-3,4-dihydro-2H-pyrano[3,2-b]pyridin-4-yl)benzamide;
N-(4-(3,4-dichlorophenyl)-3,4-dihydro-2H-pyrano[3,2-b]pyridin-4-yl)-4-fluorobenzamide;
4-fluoro-N-(4-phenyl-3,4-dihydro-2H-pyrano[3,2-b]pyridin-4-yl)benzamide;
N-(4-phenyl-3,4-dihydro-2H-pyrano[3,2-b]pyridin-4-yl)benzamide;
N-(4-(6-(trifluoromethyl)pyridin-3-yl)-3,4-dihydro-2H-pyrano[3,2-b]pyridin-4-yl)benzamide;
(S)-N-(4-(4-chlorophenyl)-3,4-dihydro-2H-pyrano[3,2-b]pyridin-4-yl)benzamide;
(S)-N-(4-(4-chloro-3-fluorophenyl)-3,4-dihydro-2H-pyrano[3,2-b]pyridin-4-yl)benzamide;
(S)-N-(4-(4-fluorophenyl)-3,4-dihydro-2H-pyrano[3,2-b]pyridin-4-yl)benzamide;
(S)-N-(4-(3-(trifluoromethoxy)phenyl)-3,4-dihydro-2H-pyrano[3,2-b]pyridin-4-yl)benzamide;
(S)-N-(4-(p-tolyl)-3,4-dihydro-2H-pyrano[3,2-b]pyridin-4-yl)benzamide;
(S)-N-(4-(3-fluoro-4-(trifluoromethyl)phenyl)-3,4-dihydro-2H-pyrano[3,2-b]pyridin-4-yl)benzamide;
(S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-6-carboxamide;
2-oxo-N-(4-(4-(trifluoromethoxy)phenyl)-3,4-dihydro-2H-pyrano[3,2-b]pyridin-4-yl)-2,3-dihydrobenzo[d]oxazole-6-carboxamide;
2-oxo-N-(4-(4-(trifluoromethoxy)phenyl)-3,4-dihydro-2H-pyrano[3,2-b]pyridin-4-yl)-2,3-dihydrobenzo[d]oxazole-5-carboxamide;
N-(4-(3,4-dichlorophenyl)-3,4-dihydro-2H-pyrano[3,2-b]pyridin-4-yl)-2-oxo-2,3-dihydrobenzo[d]oxazole-6-carboxamide;
N-(4-(3,4-dichlorophenyl)-3,4-dihydro-2H-pyrano[3,2-b]pyridin-4-yl)-2-oxo-2,3-dihydrobenzo[d]oxazole-5-carboxamide;
2-oxo-N-(4-phenyl-3,4-dihydro-2H-pyrano[3,2-b]pyridin-4-yl)-2,3-dihydrobenzo[d]oxazole-6-carboxamide;
2-oxo-N-(4-(6-(trifluoromethyl)pyridin-3-yl)-3,4-dihydro-2H-pyrano[3,2-b]pyridin-4-yl)-2,3-dihydrobenzo[d]oxazole-5-carboxamide;
(S)-N-(4-(4-(trifluoromethyl)phenyl)chroman-4-yl)benzamide;
N-(8-(4-(trifluoromethyl)phenyl)-5,6,7,8-tetrahydroquinolin-8-yl)benzamide;
methyl 6-((4-(3-fluoro-4-(trifluoromethoxy)phenyl)-3,4-dihydro-2H-pyrano[3,2-b]pyridin-4-yl)carbamoyl)nicotinate;
6-oxo-N-(8-(4-(trifluoromethyl)phenyl)-5,6,7,8-tetrahydroquinolin-8-yl)-1,6-dihydropyridine-3-carboxamide;
(S)-6-methoxy-N-(4-(4-(trifluoromethyl)phenyl)-3,4-dihydro-2H-pyrano[3,2-b]pyridin-4-yl)nicotinamide;
(S)-2-oxo-N-(4-(4-(trifluoromethyl)phenyl)-3,4-dihydro-2H-pyrano[3,2-b]pyridin-4-yl)-1,2,3,4-tetrahydroquinoline-6-carboxamide;
(S)-N-(4-(4-(trifluoromethyl)phenyl)-3,4-dihydro-2H-pyrano[3,2-b]pyridin-4-yl)-1H-indazole-6-carboxamide;
(S)-N-(4-(4-(trifluoromethyl)phenyl)-3,4-dihydro-2H-pyrano[3,2-b]pyridin-4-yl)pyrimidine-4-carboxamide;
(S)-N-(4-(4-(trifluoromethyl)phenyl)-3,4-dihydro-2H-pyrano[3,2-b]pyridin-4-yl)-1H-indole-6-carboxamide;
(S)-N-(4-(4-(trifluoromethyl)phenyl)-3,4-dihydro-2H-pyrano[3,2-b]pyridin-4-yl)pyridazine-4-carboxamide;
(S)-1-methyl-N-(4-(4-(trifluoromethyl)phenyl)-3,4-dihydro-2H-pyrano[3,2-b]pyridin-4-yl)-1H-indazole-6-carboxamide;
(S)-N-(4-(4-(trifluoromethyl)phenyl)-3,4-dihydro-2H-pyrano[3,2-b]pyridin-4-yl)thiazole-5-carboxamide;
(S)-5-hydroxy-N-(4-(4-(trifluoromethyl)phenyl)-3,4-dihydro-2H-pyrano[3,2-b]pyridin-4-yl)picolinamide;
(S)-N-(4-(4-(trifluoromethyl)phenyl)-3,4-dihydro-2H-pyrano[3,2-b]pyridin-4-yl)isothiazole-5-carboxamide;
(S)-1-methyl-N-(4-(4-(trifluoromethyl)phenyl)-3,4-dihydro-2H-pyrano[3,2-b]pyridin-4-yl)-1H-indole-5-carboxamide;
(S)-5-acetamido-N-(4-(4-(trifluoromethyl)phenyl)-3,4-dihydro-2H-pyrano[3,2-b]pyridin-4-yl)picolinamide;
(S)-1-methyl-N-(4-(4-(trifluoromethyl)phenyl)-3,4-dihydro-2H-pyrano[3,2-b]pyridin-4-yl)-1H-indazole-5-carboxamide;
(S)-5-oxo-N-(4-(4-(trifluoromethyl)phenyl)-3,4-dihydro-2H-pyrano[3,2-b]pyridin-4-yl)-4,5-dihydropyrazine-2-carboxamide;
(S)-N-(4-(4-(trifluoromethyl)phenyl)-3,4-dihydro-2H-pyrano[3,2-b]pyridin-4-yl)isonicotinamide;
(S)-6-methoxy-N-(4-(4-(trifluoromethyl)phenyl)-3,4-dihydro-2H-pyrano[3,2-b]pyridin-4-yl)pyridazine-3-carboxamide;
(S)-N-(4-(4-(trifluoromethyl)phenyl)-3,4-dihydro-2H-pyrano[3,2-b]pyridin-4-yl)nicotinamide;
(S)-N-(4-(4-(trifluoromethyl)phenyl)-3,4-dihydro-2H-pyrano[3,2-b]pyridin-4-yl)imidazo[1,2-a]pyridine-7-carboxamide;
(S)-N-(4-(3-fluoro-4-(trifluoromethoxy)phenyl)-3,4-dihydro-2H-pyrano[3,2-b]pyridin-4-yl)-5-oxo-4,5-dihydropyrazine-2-carboxamide;
(S)-N-(4-(3-fluoro-4-(trifluoromethoxy)phenyl)-3,4-dihydro-2H-pyrano[3,2-b]pyridin-4-yl)-5-hydroxypicolinamide;
(S)-N-(4-(3-fluoro-4-(trifluoromethoxy)phenyl)-3,4-dihydro-2H-pyrano[3,2-b]pyridin-4-yl)imidazo[1,2-a]pyridine-6-carboxamide;
(S)-N-(4-(3-fluoro-4-(trifluoromethoxy)phenyl)-3,4-dihydro-2H-pyrano[3,2-b]pyridin-4-yl)-1-methyl-1H-indazole-5-carboxamide;
(S)-N-(4-(3-fluoro-4-(trifluoromethoxy)phenyl)-3,4-dihydro-2H-pyrano[3,2-b]pyridin-4-yl)-2-oxo-1,2,3,4-tetrahydroquinoline-6-carboxamide;
(S)-5-fluoro-N-(4-(3-fluoro-4-(trifluoromethoxy)phenyl)-3,4-dihydro-2H-pyrano[3,2-b]pyridin-4-yl)picolinamide;
(S)-N-(4-(4-(trifluoromethyl)phenyl)-3,4-dihydro-2H-pyrano[3,2-b]pyridin-4-yl)quinoline-7-carboxamide;

(S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-5-carboxamide;

(S)-6-oxo-N-(4-(4-(trifluoromethoxy)phenyl)-3,4-dihydro-2H-pyrano[3,2-b]pyridin-4-yl)-1,6-dihydropyridine-3-carboxamide;

(S)-N-(4-(3-fluoro-4-(trifluoromethoxy)phenyl)-3,4-dihydro-2H-pyrano[3,2-b]pyridin-4-yl)-6-oxo-1,6-dihydropyridine-3-carboxamide;

(S)-6-oxo-N-(4-(4-(trifluoromethyl)phenyl)-3,4-dihydro-2H-pyrano[3,2-b]pyridin-4-yl)-1,6-dihydropyridine-3-carboxamide;

(S)-N-(4-(3-fluoro-4-(trifluoromethoxy)phenyl)-3,4-dihydro-2H-pyrano[3,2-b]pyridin-4-yl)-5-nitropicolinamide;

(S)-N5-(4-(3-fluoro-4-(trifluoromethoxy)phenyl)-3,4-dihydro-2H-pyrano[3,2-b]pyridin-4-yl)-N2-methylpyridine-2,5-dicarboxamide;

(S)-N-(4-(3-fluoro-4-(trifluoromethoxy)phenyl)-3,4-dihydro-2H-pyrano[3,2-b]pyridin-4-yl)-2,3-dioxo-1,2,3,4-tetrahydroquinoxaline-6-carboxamide;

(S)-N-(4-(3-fluoro-4-(trifluoromethoxy)phenyl)-3,4-dihydro-2H-pyrano[3,2-b]pyridin-4-yl)-5-(methylsulfonamido)picolinamide;

(S)-1-(4-(3-fluoro-4-(trifluoromethoxy)phenyl)-3,4-dihydro-2H-pyrano[3,2-b]pyridin-4-yl)-3-(6-fluoropyridin-3-yl)urea;

1-((S)-4-(4-(trifluoromethyl)phenyl)-3,4-dihydro-2H-pyrano[3,2-b]pyridin-4-yl)-3-((S)-1,1,1-trifluoropropan-2-yl)urea;

(S)-1-(4-cyanophenyl)-3-(4-(3-fluoro-4-(trifluoromethoxy)phenyl)-3,4-dihydro-2H-pyrano[3,2-b]pyridin-4-yl)urea;

(S)-1-(6-chloropyridin-3-yl)-3-(4-(3-fluoro-4-(trifluoromethoxy)phenyl)-3,4-dihydro-2H-pyrano[3,2-b]pyridin-4-yl)urea;

1-(pyridin-3-yl)-3-(4-(4-(trifluoromethyl)phenyl)chroman-4-yl)urea;

1-(pyridin-3-yl)-3-(8-(4-(trifluoromethyl)phenyl)-5,6,7,8-tetrahydroquinolin-8-yl)urea;

(S)-1-(3-fluorophenyl)-3-(4-(4-(trifluoromethyl)phenyl)-3,4-dihydro-2H-pyrano[3,2-b]pyridin-4-yl)urea;

(S)-1-(pyridin-3-yl)-3-(4-(4-(trifluoromethyl)phenyl)-3,4-dihydro-2H-pyrano[3,2-b]pyridin-4-yl)urea;

(S)-1-(4-fluorophenyl)-3-(4-(4-(trifluoromethyl)phenyl)-3,4-dihydro-2H-pyrano[3,2-b]pyridin-4-yl)urea;

(S)-6-((4-(3-fluoro-4-(trifluoromethoxy)phenyl)-3,4-dihydro-2H-pyrano[3,2-b]pyridin-4-yl)carbamoyl)nicotinic acid;

(S)-N-(4-(3-fluoro-4-(trifluoromethoxy)phenyl)-3,4-dihydro-2H-pyrano[3,2-b]pyridin-4-yl)benzenesulfonamide;

(S)-N-(4-(3-fluoro-4-(trifluoromethoxy)phenyl)-3,4-dihydro-2H-pyrano[3,2-b]pyridin-4-yl)pyridine-3-sulfonamide; or (S)-tert-butyl (4-(3-fluoro-4-(trifluoromethoxy)phenyl)-3,4-dihydro-2H-pyrano[3,2-b]pyridin-4-yl)carbamate; or the pharmaceutically-acceptable salt thereof, the tautomer thereof, the pharmaceutically-acceptable salt of the tautomer, the stereoisomer thereof, or the mixture thereof.

80. The compound of embodiment 1, wherein the compound is (S)-N-(4-(4-(trifluoromethyl)phenyl)-3,4-dihydro-2H-pyrano[3,2-b]pyridin-4-yl)benzamide;

(S)-N-(4-(3,4-dichlorophenyl)-3,4-dihydro-2H-pyrano[3,2-b]pyridin-4-yl)benzamide;

(S)-4-hydroxy-N-(4-(4-(trifluoromethyl)phenyl)-3,4-dihydro-2H-pyrano[3,2-b]pyridin-4-yl)benzamide;

(S)-4-methoxy-N-(4-(4-(trifluoromethyl)phenyl)-3,4-dihydro-2H-pyrano[3,2-b]pyridin-4-yl)benzamide;

4-fluoro-N-(4-(3-fluoro-4-(trifluoromethoxy)phenyl)-3,4-dihydro-2H-pyrano[3,2-b]pyridin-4-yl)benzamide;

N-(4-(3-fluoro-4-(trifluoromethoxy)phenyl)-3,4-dihydro-2H-pyrano[3,2-b]pyridin-4-yl)benzamide;

N-(4-(4-(trifluoromethoxy)phenyl)-3,4-dihydro-2H-pyrano[3,2-b]pyridin-4-yl)benzamide;

(S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-6-carboxamide;

2-oxo-N-(4-(4-(trifluoromethoxy)phenyl)-3,4-dihydro-2H-pyrano[3,2-b]pyridin-4-yl)-2,3-dihydrobenzo[d]oxazole-6-carboxamide;

2-oxo-N-(4-(4-(trifluoromethoxy)phenyl)-3,4-dihydro-2H-pyrano[3,2-b]pyridin-4-yl)-2,3-dihydrobenzo[d]oxazole-5-carboxamide;

N-(4-(3,4-dichlorophenyl)-3,4-dihydro-2H-pyrano[3,2-b]pyridin-4-yl)-2-oxo-2,3-dihydrobenzo[d]oxazole-6-carboxamide;

N-(4-(3,4-dichlorophenyl)-3,4-dihydro-2H-pyrano[3,2-b]pyridin-4-yl)-2-oxo-2,3-dihydrobenzo[d]oxazole-5-carboxamide;

2-oxo-N-(4-phenyl-3,4-dihydro-2H-pyrano[3,2-b]pyridin-4-yl)-2,3-dihydrobenzo[d]oxazole-6-carboxamide;

methyl 6-((4-(3-fluoro-4-(trifluoromethyl)phenyl)-3,4-dihydro-2H-pyrano[3,2-b]pyridin-4-yl)carbamoyl)nicotinate;

(S)-N-(4-(4-(trifluoromethyl)phenyl)-3,4-dihydro-2H-pyrano[3,2-b]pyridin-4-yl)-1H-indazole-6-carboxamide;

(S)-N-(4-(4-(trifluoromethyl)phenyl)-3,4-dihydro-2H-pyrano[3,2-b]pyridin-4-yl)-1H-indole-6-carboxamide;

(S)-1-methyl-N-(4-(4-(trifluoromethyl)phenyl)-3,4-dihydro-2H-pyrano[3,2-b]pyridin-4-yl)-1H-indazole-6-carboxamide;

(S)-N-(4-(4-(trifluoromethyl)phenyl)-3,4-dihydro-2H-pyrano[3,2-b]pyridin-4-yl)thiazole-5-carboxamide;

(S)-5-hydroxy-N-(4-(4-(trifluoromethyl)phenyl)-3,4-dihydro-2H-pyrano[3,2-b]pyridin-4-yl)picolinamide;

(S)-1-methyl-N-(4-(4-(trifluoromethyl)phenyl)-3,4-dihydro-2H-pyrano[3,2-b]pyridin-4-yl)-1H-indole-5-carboxamide;

(S)-5-oxo-N-(4-(4-(trifluoromethyl)phenyl)-3,4-dihydro-2H-pyrano[3,2-b]pyridin-4-yl)-4,5-dihydropyrazine-2-carboxamide;

(S)-N-(4-(3-fluoro-4-(trifluoromethoxy)phenyl)-3,4-dihydro-2H-pyrano[3,2-b]pyridin-4-yl)imidazo[1,2-a]pyridine-6-carboxamide;

(S)-N-(4-(3-fluoro-4-(trifluoromethoxy)phenyl)-3,4-dihydro-2H-pyrano[3,2-b]pyridin-4-yl)-1-methyl-1H-indazole-5-carboxamide;

(S)-N-(4-(3-fluoro-4-(trifluoromethoxy)phenyl)-3,4-dihydro-2H-pyrano[3,2-b]pyridin-4-yl)-2-oxo-1,2,3,4-tetrahydroquinoline-6-carboxamide;

(S)-5-fluoro-N-(4-(3-fluoro-4-(trifluoromethoxy)phenyl)-3,4-dihydro-2H-pyrano[3,2-b]pyridin-4-yl)picolinamide;

(S)-N-(4-(4-(trifluoromethyl)phenyl)-3,4-dihydro-2H-pyrano[3,2-b]pyridin-4-yl)quinoline-7-carboxamide;

(S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-5-carboxamide;

(S)-6-oxo-N-(4-(4-(trifluoromethoxy)phenyl)-3,4-dihydro-2H-pyrano[3,2-b]pyridin-4-yl)-1,6-dihydropyridine-3-carboxamide;

(S)-N-(4-(3-fluoro-4-(trifluoromethoxy)phenyl)-3,4-dihydro-2H-pyrano[3,2-b]pyridin-4-yl)-6-oxo-1,6-dihydropyridine-3-carboxamide;

(S)-N5-(4-(3-fluoro-4-(trifluoromethoxy)phenyl)-3,4-dihydro-2H-pyrano[3,2-b]pyridin-4-yl)-N2-methylpyridine-2,5-dicarboxamide;

(S)-N-(4-(3-fluoro-4-(trifluoromethoxy)phenyl)-3,4-dihydro-2H-pyrano[3,2-b]pyridin-4-yl)-5-(methylsulfonamido)picolinamide;

(S)-1-(4-(3-fluoro-4-(trifluoromethoxy)phenyl)-3,4-dihydro-2H-pyrano[3,2-b]pyridin-4-yl)-3-(6-fluoropyridin-3-yl)urea;

(S)-1-(4-cyanophenyl)-3-(4-(3-fluoro-4-(trifluoromethoxy)phenyl)-3,4-dihydro-2H-pyrano[3,2-b]pyridin-4-yl)urea;

(S)-1-(6-chloropyridin-3-yl)-3-(4-(3-fluoro-4-(trifluoromethoxy)phenyl)-3,4-dihydro-2H-pyrano[3,2-b]pyridin-4-yl)urea;

(S)-1-(pyridin-3-yl)-3-(4-(4-(trifluoromethyl)phenyl)-3,4-dihydro-2H-pyrano[3,2-b]pyridin-4-yl)urea;

(S)-1-(4-fluorophenyl)-3-(4-(4-(trifluoromethyl)phenyl)-3,4-dihydro-2H-pyrano[3,2-b]pyridin-4-yl)urea; or (S)-6-((4-(3-fluoro-4-(trifluoromethoxy)phenyl)-3,4-dihydro-2H-pyrano[3,2-b]pyridin-4-yl)carbamoyl)nicotinic acid; or the pharmaceutically-acceptable salt thereof, the tautomer thereof, the pharmaceutically-acceptable salt of the tautomer, the stereoisomer thereof, or the mixture thereof.

81. The compound of embodiment 1, wherein the compound is (S)-N-(4-(4-(trifluoromethyl)phenyl)-3,4-dihydro-2H-pyrano[3,2-b]pyridin-4-yl)benzamide or the pharmaceutically-acceptable salt thereof, the tautomer thereof, the pharmaceutically-acceptable salt of the tautomer, the stereoisomer thereof, or the mixture thereof.

82. The compound of embodiment 1, wherein the compound is (S)-4-hydroxy-N-(4-(4-(trifluoromethyl)phenyl)-3,4-dihydro-2H-pyrano[3,2-b]pyridin-4-yl)benzamide or the pharmaceutically-acceptable salt thereof, the tautomer thereof, the pharmaceutically-acceptable salt of the tautomer, the stereoisomer thereof, or the mixture thereof.

83. The compound of embodiment 1, wherein the compound is (S)-6-((4-(3-fluoro-4-(trifluoromethoxy)phenyl)-3,4-dihydro-2H-pyrano[3,2-b]pyridin-4-yl)carbamoyl)nicotinic acid or the pharmaceutically-acceptable salt thereof, the tautomer thereof, the pharmaceutically-acceptable salt of the tautomer, the stereoisomer thereof, or the mixture thereof.

84. The compound of embodiment 1, wherein the compound is (S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-6-carboxamide or the pharmaceutically-acceptable salt thereof, the tautomer thereof, the pharmaceutically-acceptable salt of the tautomer, the stereoisomer thereof, or the mixture thereof.

85. The compound of embodiment 1, wherein the compound is 2-oxo-N-(4-(4-(trifluoromethoxy)phenyl)-3,4-dihydro-2H-pyrano[3,2-b]pyridin-4-yl)-2,3-dihydrobenzo[d]oxazole-6-carboxamide or the pharmaceutically-acceptable salt thereof, the tautomer thereof, the pharmaceutically-acceptable salt of the tautomer, the stereoisomer thereof, or the mixture thereof.

86. The compound of embodiment 1, wherein the compound is 2-oxo-N-(4-(4-(trifluoromethoxy)phenyl)-3,4-dihydro-2H-pyrano[3,2-b]pyridin-4-yl)-2,3-dihydrobenzo[d]oxazole-5-carboxamide or the pharmaceutically-acceptable salt thereof, the tautomer thereof, the pharmaceutically-acceptable salt of the tautomer, the stereoisomer thereof, or the mixture thereof.

87. The compound of embodiment 1, wherein the compound is (S)-N-(4-(3-fluoro-4-(trifluoromethoxy)phenyl)-3,4-dihydro-2H-pyrano[3,2-b]pyridin-4-yl)-6-oxo-1,6-dihydropyridine-3-carboxamide or the pharmaceutically-acceptable salt thereof, the tautomer thereof, the pharmaceutically-acceptable salt of the tautomer, the stereoisomer thereof, or the mixture thereof.

88. The compound of embodiment 1, wherein the compound is N-(4-(3,4-dichlorophenyl)-3,4-dihydro-2H-pyrano[3,2-b]pyridin-4-yl)-2-oxo-2,3-dihydrobenzo[d]oxazole-5-carboxamide or the pharmaceutically-acceptable salt thereof, the tautomer thereof, the pharmaceutically-acceptable salt of the tautomer, the stereoisomer thereof, or the mixture thereof.

89. The compound of embodiment 1, wherein the compound is 2-oxo-N-(4-phenyl-3,4-dihydro-2H-pyrano[3,2-b]pyridin-4-yl)-2,3-dihydrobenzo[d]oxazole-6-carboxamide or the pharmaceutically-acceptable salt thereof, the tautomer thereof, the pharmaceutically-acceptable salt of the tautomer, the stereoisomer thereof, or the mixture thereof.

90. The compound of embodiment 1, wherein the compound is (S)-1-(pyridin-3-yl)-3-(4-(4-(trifluoromethyl)phenyl)-3,4-dihydro-2H-pyrano[3,2-b]pyridin-4-yl)urea or the pharmaceutically-acceptable salt thereof, the tautomer thereof, the pharmaceutically-acceptable salt of the tautomer, the stereoisomer thereof, or the mixture thereof.

91. The compound of embodiment 1, wherein the compound is (S)-N-(4-(3-fluoro-4-(trifluoromethoxy)phenyl)-3,4-dihydro-2H-pyrano[3,2-b]pyridin-4-yl)-5-(methylsulfonamido)picolinamide or the pharmaceutically-acceptable salt thereof, the tautomer thereof, the pharmaceutically-acceptable salt of the tautomer, the stereoisomer thereof, or the mixture thereof.

92. The compound of embodiment 1, wherein the compound is (S)-N5-(4-(3-fluoro-4-(trifluoromethoxy)phenyl)-3,4-dihydro-2H-pyrano[3,2-b]pyridin-4-yl)-N2-methylpyridine-2,5-dicarboxamide or the pharmaceutically-acceptable salt thereof, the tautomer thereof, the pharmaceutically-acceptable salt of the tautomer, the stereoisomer thereof, or the mixture thereof.

93. The compound of embodiment 1, wherein the compound is (S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-5-carboxamide or the pharmaceutically-acceptable salt thereof, the tautomer thereof, the pharmaceutically-acceptable salt of the tautomer, the stereoisomer thereof, or the mixture thereof.

94. The compound of embodiment 1, wherein the compound is (S)-5-hydroxy-N-(4-(4-(trifluoromethyl)phenyl)-3,4-dihydro-2H-pyrano[3,2-b]pyridin-4-yl)picolinamide or the pharmaceutically-acceptable salt thereof, the tautomer thereof, the pharmaceutically-acceptable salt of the tautomer, the stereoisomer thereof, or the mixture thereof.

95. The compound of embodiment 1, wherein the compound is (S)-2-oxo-N-(4-(4-(trifluoromethyl)phenyl)-3,4-dihydro-2H-pyrano[3,2-b]pyridin-4-yl)-1,2,3,4-tetrahydroquinoline-6-carboxamide or the pharmaceutically-acceptable salt thereof, the tautomer thereof, the pharmaceutically-acceptable salt of the tautomer, the stereoisomer thereof, or the mixture thereof.

96. The compound of embodiment 1, wherein the compound is methyl 6-((4-(3-fluoro-4-(trifluoromethoxy)phenyl)-3,4-dihydro-2H-pyrano[3,2-b]pyridin-4-yl)carbamoyl)nicotinate or the pharmaceutically-acceptable salt thereof, the tautomer thereof, the pharmaceutically-acceptable salt of the tautomer, the stereoisomer thereof, or the mixture thereof.

97. The compound of embodiment 1, wherein the compound is (S)-N-(4-(3,4-dichlorophenyl)-3,4-dihydro-2H-pyrano[3,2-b]pyridin-4-yl)-6-oxo-1,6-dihydropyridine-3-carboxamide;

(S)-N-(4-(2-fluoro-4-(trifluoromethoxy)phenyl)-3,4-dihydro-2H-pyrano[3,2-b]pyridin-4-yl)-6-oxo-1,6-dihydropyridine-3-carboxamide;

(S)-N-(4-(2-chloro-4-(trifluoromethoxy)phenyl)-3,4-dihydro-2H-pyrano[3,2-b]pyridin-4-yl)-6-oxo-1,6-dihydropyridine-3-carboxamide;

(S)-N-(4-(2-methyl-4-(trifluoromethoxy)phenyl)-3,4-dihydro-2H-pyrano[3,2-b]pyridin-4-yl)-6-oxo-1,6-dihydropyridine-3-carboxamide;

(S)-N-(4-(3-chloro-4-(trifluoromethyl)phenyl)-3,4-dihydro-2H-pyrano[3,2-b]pyridin-4-yl)-6-oxo-1,6-dihydropyridine-3-carboxamide;

(S)-N-(4-(3-chloro-4-(trifluoromethoxy)phenyl)-3,4-dihydro-2H-pyrano[3,2-b]pyridin-4-yl)-6-oxo-1,6-dihydropyridine-3-carboxamide;

(S)-N-(4-(3-fluoro-4-(trifluoromethyl)phenyl)-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-6-methyl-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-7-methyl-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-8-methyl-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-6-chloro-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-7-chloro-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-8-chloro-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-6-fluoro-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-7-fluoro-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-8-fluoro-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-6-methoxy-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-7-methoxy-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-8-methoxy-3,4-dihydro-2H-pyrano[3,2-b]pyridin-4-yl)-6-oxo-1,6-dihydropyridine-3-carboxamide;

(S)-N-(4-([1,1'-biphenyl]-4-yl)-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-2,2-dimethyl-3,4-dihydro-2H-pyrano[3,2-b]pyridin-4-yl)-6-oxo-1,6-dihydropyridine-3-carboxamide;

(S)-N-(4'-(3-fluoro-4-(trifluoromethoxy)phenyl)-3',4'-dihydrospiro[cyclobutane-1,2'-pyrano[3,2-b]pyridin]-4'-yl)-6-oxo-1,6-dihydropyridine-3-carboxamide;

(S)-N-(4-(3-fluoro-4-(trifluoromethoxy)phenyl)chroman-4-yl)-6-oxo-1,6-dihydropyridine-3-carboxamide;

(S)-N-(8-(3-fluoro-4-(trifluoromethoxy)phenyl)-5,6,7,8-tetrahydroquinolin-8-yl)-6-oxo-1,6-dihydropyridine-3-carboxamide;

(S)-N-(4-(3-fluoro-4-(trifluoromethoxy)phenyl)-1-methyl-1,2,3,4-tetrahydro-1,5-naphthyridin-4-yl)-6-oxo-1,6-dihydropyridine-3-carboxamide;

(S)-N-(1-acetyl-4-(3-fluoro-4-(trifluoromethoxy)phenyl)-1,2,3,4-tetrahydro-1,5-naphthyridin-4-yl)-6-oxo-1,6-dihydropyridine-3-carboxamide;

(S)-N-(9-(3-fluoro-4-(trifluoromethoxy)phenyl)-6,7,8,9-tetrahydrooxepino[3,2-b]pyridin-9-yl)-6-oxo-1,6-dihydropyridine-3-carboxamide;

(S)-N-(3-(3-fluoro-4-(trifluoromethoxy)phenyl)-2,3-dihydrofuro[3,2-b]pyridin-3-yl)-6-oxo-1,6-dihydropyridine-3-carboxamide;

(S)-N-(4-(5-fluoro-6-(trifluoromethoxy)pyridin-3-yl)-3,4-dihydro-2H-pyrano[3,2-b]pyridin-4-yl)-6-oxo-1,6-dihydropyridine-3-carboxamide;

(S)-6-((4-(3,4-dichlorophenyl)-3,4-dihydro-2H-pyrano[3,2-b]pyridin-4-yl)carbamoyl)nicotinic acid;

(S)-6-((4-(4-(trifluoromethoxy)phenyl)-3,4-dihydro-2H-pyrano[3,2-b]pyridin-4-yl)carbamoyl)nicotinic acid;

(S)-6-((4-(4-(trifluoromethyl)phenyl)-3,4-dihydro-2H-pyrano[3,2-b]pyridin-4-yl)carbamoyl)nicotinic acid;

(S)-6-((4-(3-fluoro-4-(trifluoromethyl)phenyl)-3,4-dihydro-2H-pyrano[3,2-b]pyridin-4-yl)carbamoyl)nicotinic acid;

(S)-6-((4-(3-chloro-4-(trifluoromethyl)phenyl)-3,4-dihydro-2H-pyrano[3,2-b]pyridin-4-yl)carbamoyl)nicotinic acid;

(S)-6-((4-(2-fluoro-4-(trifluoromethoxy)phenyl)-3,4-dihydro-2H-pyrano[3,2-b]pyridin-4-yl)carbamoyl)nicotinic acid;

(S)-6-((4-(3-chloro-4-(trifluoromethoxy)phenyl)-3,4-dihydro-2H-pyrano[3,2-b]pyridin-4-yl)carbamoyl)nicotinic acid;

(S)-6-((4-(3-fluoro-4-(trifluoromethoxy)phenyl)chroman-4-yl)carbamoyl)nicotinic acid;

(S)-6-((8-(3-fluoro-4-(trifluoromethoxy)phenyl)-5,6,7,8-tetrahydroquinolin-8-yl)carbamoyl)nicotinic acid;

(S)-N-(4-(3-fluoro-4-(trifluoromethoxy)phenyl)-1,2,3,4-tetrahydro-1,5-naphthyridin-4-yl)-6-oxo-1,6-dihydropyridine-3-carboxamide;

(S)-N-(9-(3-fluoro-4-(trifluoromethoxy)phenyl)-6,7,8,9-tetrahydro-5H-pyrido[3,2-b]azepin-9-yl)-6-oxo-1,6-dihydropyridine-3-carboxamide; or (R)—N-(3-(3-fluoro-4-(trifluoromethoxy)phenyl)-2,3-dihydro-1H-pyrrolo[3,2-b]pyridin-3-yl)-6-oxo-1,6-dihydropyridine-3-carboxamide; or the pharmaceutically-acceptable salt thereof, the tautomer thereof, the pharmaceutically-acceptable salt of the tautomer, the stereoisomer thereof, or the mixture thereof.

98. The compound or tautomer of any one of embodiments 1-97 in a neutral form.

99. The compound of any one of embodiments 1-97 in a neutral form.

100. The pharmaceutically-acceptably salt of the compound or the pharmaceutically acceptable salt of the tautomer of any one of embodiments 1-97.

101. The pharmaceutically-acceptably salt of the compound of any one of embodiments 1-97.

102. A pharmaceutical composition comprising the compound according to any one of embodiments 1-97 or the pharmaceutically-acceptable salt thereof, the tautomer thereof, the pharmaceutically-acceptable salt of the tautomer, the stereoisomer thereof, or the mixture thereof, and a pharmaceutically-acceptable diluent or carrier.

103. A method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject, the method comprising administering the compound according to any one of embodiments 1-96 or the pharmaceutically-acceptable salt thereof, the tautomer thereof, the pharmaceutically-acceptable salt of the tautomer, the stereoisomer thereof, or the mixture thereof to the subject.

104. The method of embodiment 103, wherein the subject is suffering from neuropathic pain.

105. The method of embodiment 103, wherein the subject is suffering from migraine pain.

106. The use of the compound according to any one of embodiments 1-97 or the pharmaceutically-acceptable salt thereof, the tautomer thereof, the pharmaceutically-acceptable salt of the tautomer, the stereoisomer thereof, or the mixture thereof in the preparation of a medicament.

107. The use of the compound according to any one of embodiments 1-97 or the pharmaceutically-acceptable salt thereof, the tautomer thereof, the pharmaceutically-acceptable salt of the tautomer, the stereoisomer thereof, or the mixture thereof for treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject.

108. The use of embodiment 107, wherein the use is for treating neuropathic pain.

109. The use of embodiment 107, wherein the use is for treating migraine.

110. The compound according to any one of embodiments 1-97 or the pharmaceutically-acceptable salt thereof, the tautomer thereof, the pharmaceutically-acceptable salt of the tautomer, the stereoisomer thereof, or the mixture thereof for treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject.

111. The compound of embodiment 110 or the pharmaceutically-acceptable salt thereof, the tautomer thereof, the pharmaceutically-acceptable salt of the tautomer, the stereoisomer thereof, or the mixture thereof for treating neuropathic pain in a subject.

112. The compound of embodiment 110 or the pharmaceutically-acceptable salt thereof, the tautomer thereof, the pharmaceutically-acceptable salt of the tautomer, the stereoisomer thereof, or the mixture thereof for treating migraine in a subject.

EXAMPLES

Unless otherwise noted, all materials were obtained from commercial suppliers and used without further purification. All parts are by weight and temperatures are in degrees centigrade unless otherwise indicated. All microwave assisted reactions were conducted with a Smith Synthesizer from Biotage. Mass spectral data was determined by electrospray ionization technique. All examples were purified to >90% purity as determined by high-performance liquid chromatography. Unless otherwise stated, reactions were run at room temperature.

The following abbreviations are used:
DABCO—1,4-diazabicyclo[2.2.2]octane
DCM—dichloromethane
DIPEA—diisopropyl ethylamine
DMSO—dimethyl sulfoxide
DMF—N,N-dimethylformamide
THF—tetrahydrofuran
EDCI—1-ethyl-3-(3-dimethylaminopropyl)carbodiimide
$Et_2O$—diethyl ether EtOAc—ethyl acetate
EtOH—ethyl alcohol
HATU—2-(7-Aza-1H-benzotriazole-1-yl)-1,1,3,3-tetramethyluronium hexafluorophosphate
MeCN—acetonitrile
MeOH—methyl alcohol
n-BuLi—n-butyllithium
SFC—supercritical fluid chromatography
TEA—triethylamine
TFA—trifluoroacetic acid
h—hour
min—min
rt—room temperature (22-25° C.)
mL milliliters
μL microliters
g grams
ng micrograms
mg milligrams
μmoL micromolar General Method of Preparation The compounds described herein are prepared using techniques known to one skilled in the art through the reaction sequences depicted in Schemes 1-4 as well as by other methods. Furthermore, in the following schemes, where specific acids, bases, reagents, coupling agents, solvents, etc. are mentioned, it is understood that other suitable acids, bases, reagents, coupling agents, solvents, etc. may be used and are included within the scope of the present invention.

Amines used for the synthesis of compounds of the present invention were prepared as described in Scheme 1. Ketones of the Formula (1) were treated with aryl or heteroaryl metal halides of Formula (2) at low temperature to give alcohols of the Formula (3). The alcohol of Formula (4) was treated with substituted cyanides (4) and sulfuric acid to give amides of Formula (5). Amides of Formula (5) could be hydrolized with acid or base to give amines of Formula (6c).

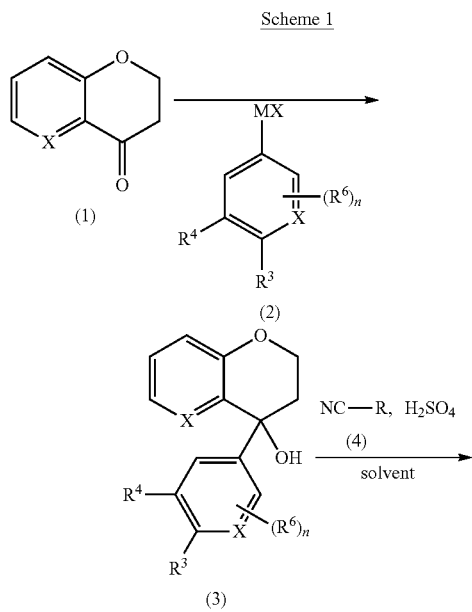

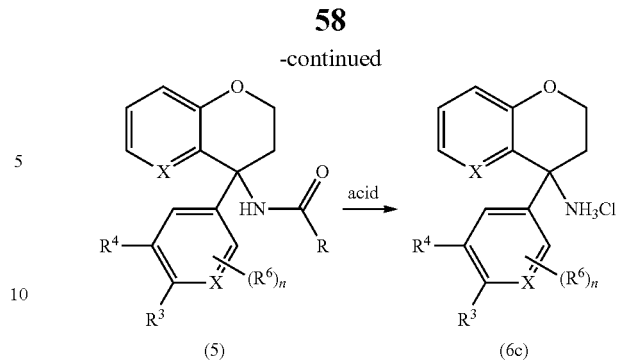

An alternative approach to amines of Formula (6c) is shown in Scheme 2. Ketones of the Formula (7) were treated with 2-methylpropane-2-sulfinamide and titanium ethoxide in 2-MeTHF to give sulfinimines of the Formula (8). The compounds of Formula (8) were treated with aryl or heteroaryl metal halides of Formula (9) at low temperature to give sulfinamides of the Formula (10). Hydrolysis of sulfinamides (10) with hydrochloric acid in MeOH gives diaryl amines of Formula (6c).

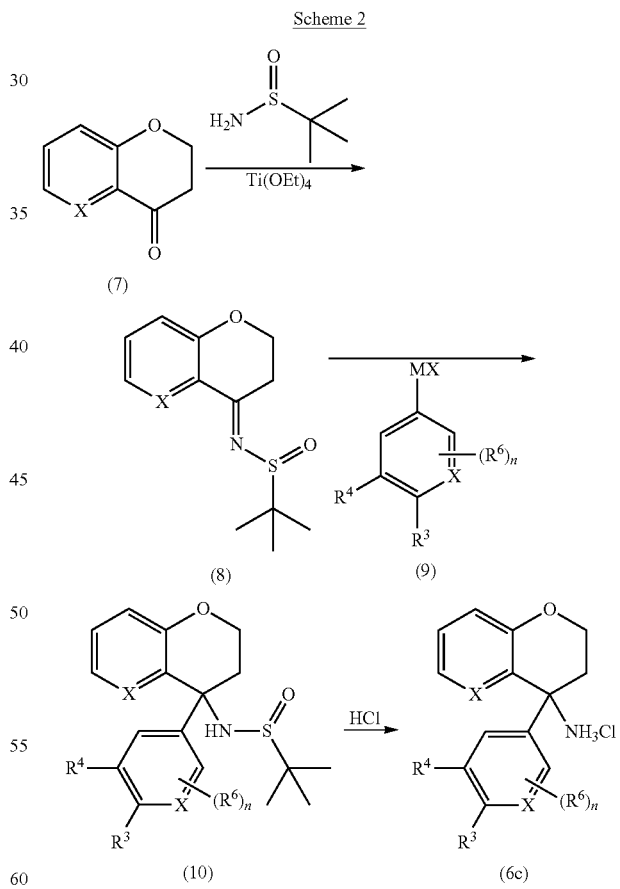

The method described in Scheme 2 can be adapted to a asymmetric syntheses using the appropriate (R)- or (S)-2-methylpropane-2-sulfinamides to give sulfinimines of the Formula (10a) or (10b). Subsequent aryl metal addition and hydrolysis provides chiral amines of Formula (6a) or (6b).

Scheme 3

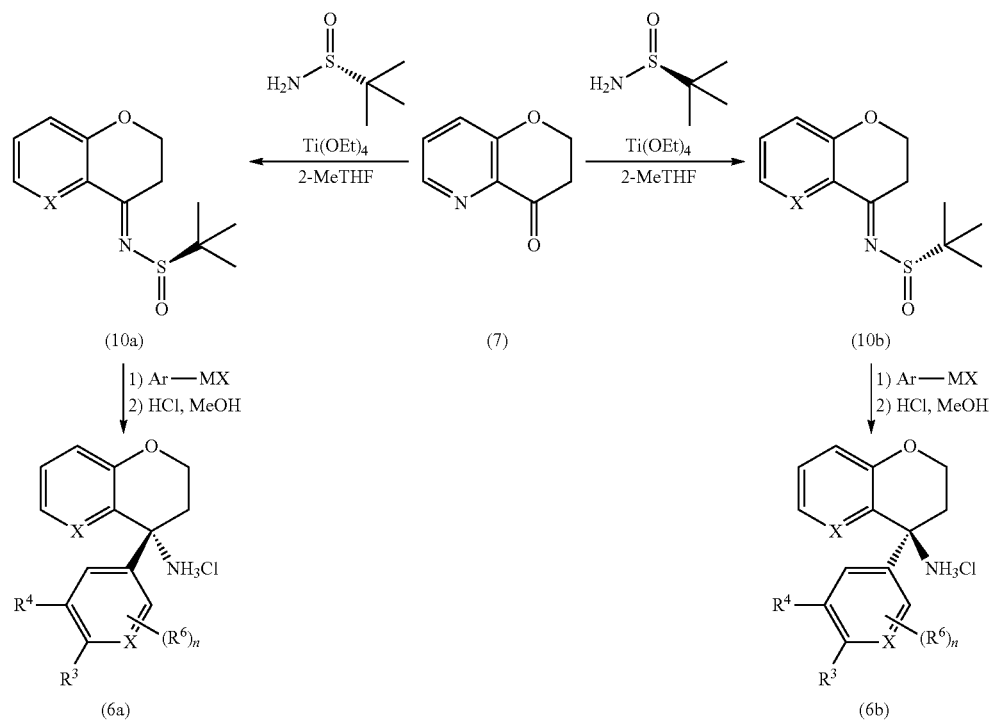

The coupling reaction of chromanamines of Formula (6a-c) with various carboxylic acids of Formula (11) provides amides of Formula (Ia), and the coupling can be performed as shown in Scheme 4. The coupling reaction can be mediated by a suitable coupling agent such as HATU in the presence of a base in a suitable solvent to afford compounds of the present invention. Alternatively, ureas, carbamates, or sulfonamides, can also be prepared utilizing the appropriate partner and coupling conditions.

Scheme 4

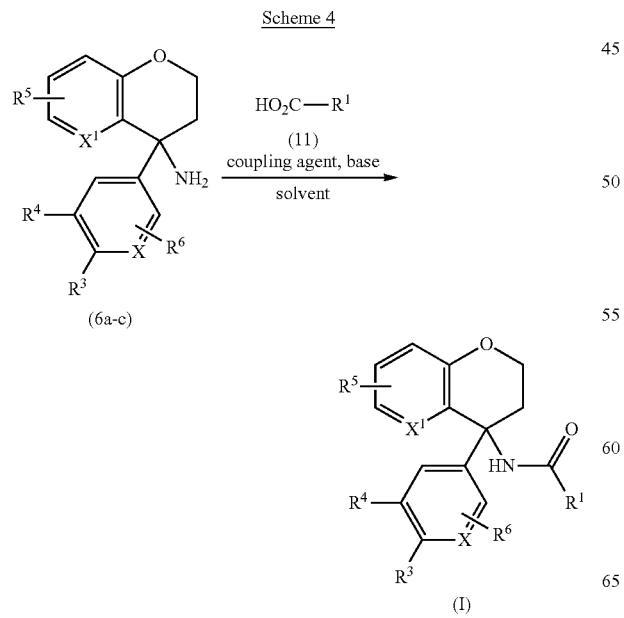

EXPERIMENTALS FOR INTERMEDIATES

Scheme 5

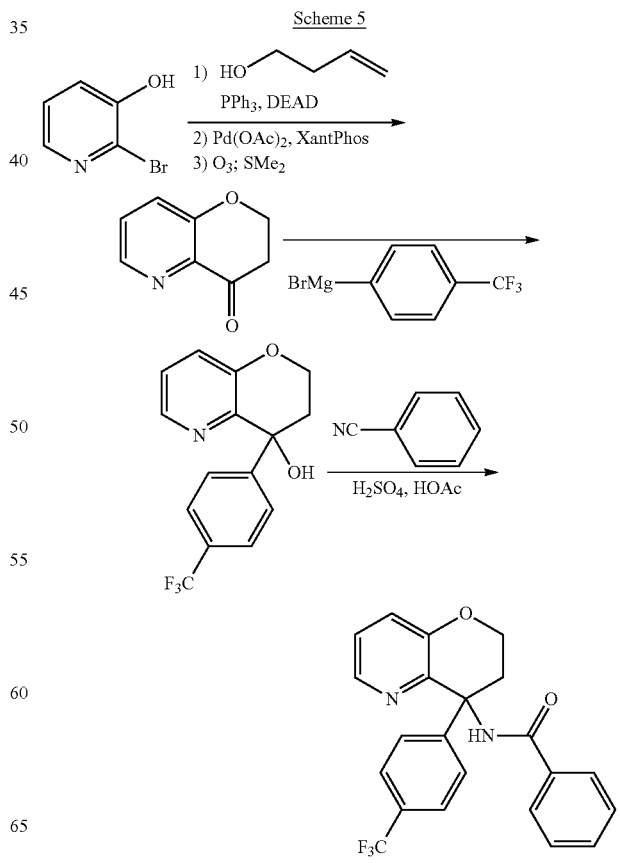

Intermediate 1

4-(4-(trifluoromethyl)phenyl)-3,4-dihydro-2H-pyrano[3,2-b]pyridin-4-ol

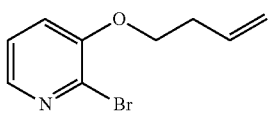

Step 1. 2-bromo-3-(but-3-en-1-yloxy)pyridine. Diethyl azodicarboxylate (95 mL, 0.6 mol) was added dropwise to a stirred mixture of 2-bromo-3-hydroxypyridine (97 g, 0.55 mol), 3-buten-1-ol (47.7 mL, 0.55 mol), and PPh$_3$ (175.3 g, 0.66 mol) in THF (970 mL) at 0° C. under a N$_2$ atmosphere. The reaction mixture was warmed to 50° C. in an oil bath and stirred for 17.5 h. Reaction progress was monitored by TLC (15% EtOAc in hexane, UV active). The reaction mixture was cooled to ambient temperature and diluted with saturated NaHCO$_3$ solution (500 mL). The aqueous solution was extracted with EtOAc (1 L). The organic layer was dried over Na$_2$SO$_4$ (200 g), and concentrated. The residual product was purified by column chromatography using 60-120 mesh, eluting with 5% EtOAc in hexane to afford the title compound as a pale yellow oil. $^1$H NMR (400 MHz, CDCl$_3$): δ 7.97-7.98 (m, 1H), 7.13-7.22 (m, 1H), 7.11 (d, J=8 Hz, 1H), 5.89-5.99 (m, 1H), 5.13-5.23 (m, 2H), 4.06-4.11 (m, 2H), 2.59-2.64 (m, 2H).

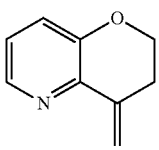

Step 2. 4-methylene-3,4-dihydro-2H-pyrano[3,2-b]pyridine. To a solution of 2-bromo-3-(but-3-en-1-yloxy)pyridine (130 g, 0.567 mol) in DMF (1.3 L), PPh$_3$ (59.5 g, 0.22 mol), Pd(OAc)$_2$ (19.9 g, 85 mol), KOAc (278.25 g, 2.835 mol), and tetraethyl ammonium chloride hydrate (187.9 g, 1.134 mol) were added under argon atmosphere. The flask was purged with argon for 15 min, and then the resulting reaction mixture was stirred at 110° C. for 16 h. Reaction progress was monitored by TLC (10% EtOAc in hexane, UV active). The reaction mixture was diluted with EtOAc and saturated NaHCO$_3$ solution. The organic layer was separated and dried over Na$_2$SO$_4$ (200 g), and concentrated. The product thus obtained was purified by column chromatography using 60-120 mesh, eluting with 5% EtOAc in hexane to afford the title compound as a pale yellow oil. MS (ESI pos. ion) m/z: 148 (MH+).

Step 3. 2H-pyrano[3,2-b]pyridin-4(3H)-one. To a solution of 4-methylene-3,4-dihydro-2H-pyrano[3,2-b]pyridine (175 g, 1.19 mol) in a mixture of solvents (MeOH:CHCl$_3$) was added a catalytic amount of NaHCO$_3$ (1 g). The reaction mixture was cooled to −78° C. and purged with O$_3$. Reaction progress was monitored by TLC (50% EtOAc in hexane, UV active). After 16 h, the reaction mixture was quenched with dimethyl sulfide (50 mL) at −78° C. The resulting mixture was stirred for 12 h at ambient temperature. The reaction mixture was then diluted with EtOAc and water. The organic layer was washed with water (3×500 mL), dried over Na$_2$SO$_4$ (200 g), and concentrated under reduced pressure. The residue thus obtained was recrystallized with diethyl ether to give the title compound as a colorless solid. MS (ESI pos. ion) m/z: 150.2 (MH+).

Grignard Procedure A:

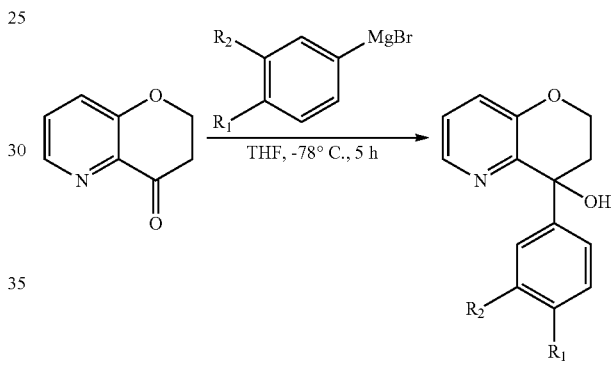

To a stirred suspension of magnesium (402 mmol) in THF (10 times), was added the corresponding aryl bromide (201 mmol). The reaction was stirred for 5 h (cautious: slightly exothermic, cooled with water bath if needed). The Grignard solution was cannulated into a stirred solution of the 2H-pyrano[3,2-b]pyridin-4(3H)-one (67.1 mmol) in THF (10 times) at −78° C. in a drop wise fashion. The stirring was continued for 1 h. The reaction mixture was quenched with saturated NH$_4$Cl (250 mL), and the product was extracted with EtOAc (2×500 mL). The combined organic layers were dried over Na$_2$SO$_4$, concentrated, and purified by column chromatography using silica (100-200 mesh silica) with 25-30% EtOAc in petroleum ether as eluent to give the desired alcohol.

Grignard Procedure B:

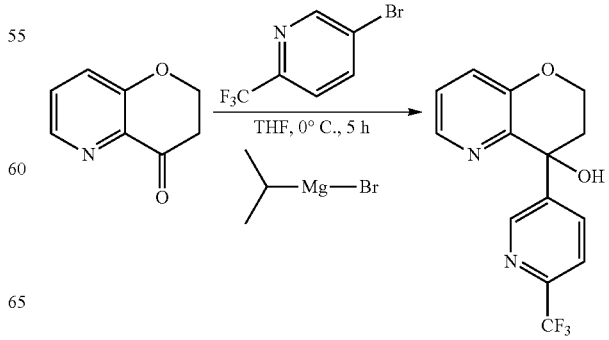

To a 0° C. solution of 5-bromo-2-(trifluoromethyl)pyridine (0.604 g, 2.68 mmol) in THF (10 mL) was added isopropyl magnesium bromide (1 mL, 2.68 mmol) in a drop-wise fashion. The reaction mixture was stirred in a cooling bath for 1 h and was then treated with 2H-pyrano[3,2-b]pyridin-4(3H)-one (200 mg, 1.34 mmol) in THF (5 mL). After stirring for 1 h, saturated NH₄Cl (50 mL) was added to the reaction mixture, and the aqueous solution was extracted with EtOAc (3×10 mL). The combined organic layers were dried over Na₂SO₄, and concentrated. The residue was purified by column chromatography to give the desired alcohol.

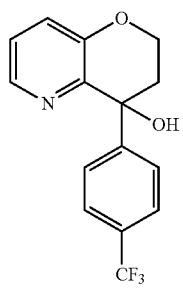

Intermediate 1: 4-(4-(trifluoromethyl)phenyl)-3,4-dihydro-2H-pyrano[3,2-b]pyridin-4-ol. MS (ESI pos. ion) m/z: 295.9 (MH+); ¹H NMR (400 MHz, CDCl₃): δ 8.2 (d, J=3.6 Hz, 1H), 7.6 (d, J=8.0 Hz, 2H), 7.4 (d, J=8.0 Hz, 2H) 7.3 (d, J=6.4 Hz, 1H), 7.2 (m, 1H), 4.4 (m, 1H), 4.3 (m, 1H), 4.0 (s, 1H), 2.5 (m, 1H), 2.3 (m, 1H).

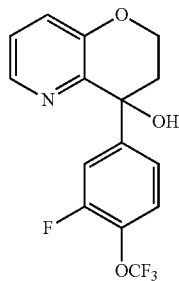

Intermediate 2: 4-(3-fluoro-4-(trifluoromethoxy)phenyl)-3,4-dihydro-2H-pyrano[3,2-b]pyridin-4-ol. MS (ESI pos. ion) m/z: 330.2 (MH+); ¹H NMR (300 MHz, DMSO-d₆): δ 8.06 (dd, J=1.5, 2.7 Hz, 1H), 7.40-7.49 (m, 2H), 7.23-7.33 (m, 2H), 7.12 (d, J=8.7 Hz, 1H), 6.34 (s, 1H), 4.24-4.41 (m, 2H), 2.35-2.45 (m, 1H), 2.09-2.15 (m, 1H).

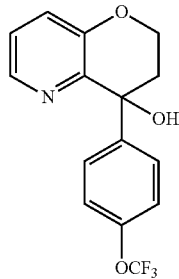 [SMILES: OC1(c2ccc(OC(F)(F)F)cc2)CCOc2cccnc21]

Intermediate 3: 4-(4-(trifluoromethoxy)phenyl)-3,4-dihydro-2H-pyrano[3,2-b]pyridin-4-ol. MS (ESI pos. ion) m/z: 312.0 (MH+); ¹H NMR (400 MHz, CDCl₃): δ 8.2 (d, J=3.6 Hz, 1H), 7.6 (d, J=8.0 Hz, 2H), 7.4 (d, J=8.0 Hz, 2H) 7.3 (d, J=6.4 Hz, 1H), 7.2 (m, 1H), 4.4 (m, 1H), 4.3 (m, 1H), 4.0 (s, 1H), 2.5 (m, 1H), 2.3 (m, 1H).

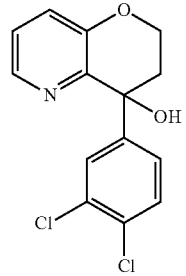 [SMILES: OC1(c2ccc(Cl)c(Cl)c2)CCOc2cccnc21]

Intermediate 4: 4-(3,4-dichlorophenyl)-3,4-dihydro-2H-pyrano[3,2-b]pyridin-4-ol. MS (ESI pos. ion) m/z: 296.1 (MH+); ¹H NMR (400 MHz, CDCl₃): δ 8.2 (q, J=1.2, 4.0 Hz, 1H), 7.4 (m, 2H), 7.2 (m, 2H) 7.0 (dd, J=2.4, 8.4 Hz, 1H), 4.3 (m, 1H), 4.1 (m, 2H), 3.9 (s, 1H), 2.5 (m, 1H), 2.3 (m, 1H).

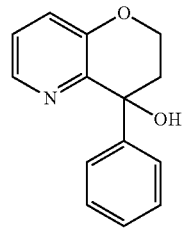 [SMILES: OC1(c2ccccc2)CCOc2cccnc21]

Intermediate 5: 4-phenyl-3,4-dihydro-2H-pyrano[3,2-b]pyridin-4-ol. MS (ESI pos. ion) m/z: 228.1 (MH+); ¹H NMR (300 MHz, CDCl₃): δ 8.20-8.18 (m, 1H), 7.34-7.16 (m, 6H), 4.35-4.28 (m, 1H), 4.15-4.03 (m, 1H), 2.55-2.46 (m, 1H), 2.40-2.33 (m, 1H).

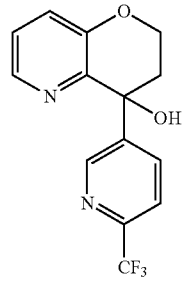

Intermediate 6: 4-(6-(trifluoromethyl)pyridin-3-yl)-3,4-dihydro-2H-pyrano[3,2-b]pyridin-4-ol. MS (ESI pos. ion) m/z: 297.0 (MH+).

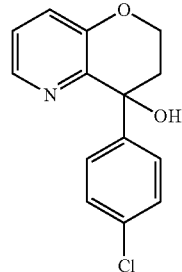 [SMILES: OC1(c2ccc(Cl)cc2)CCOc2cccnc21]

Intermediate 7: 4-(4-chlorophenyl)-3,4-dihydro-2H-pyrano[3,2-b]pyridin-4-ol. MS (ESI pos. ion) m/z: 262.1 (MH+). ¹H NMR (DMSO-d₆) δ: 8.05 (dd, J=4.3, 1.4 Hz, 1H), 7.30-7.36 (m, 2H), 7.19-7.30 (m, 4H), 6.09 (s, 1H), 4.35 (td, J=11.0, 2.3 Hz, 1H), 4.21 (dt, J=11.0, 4.1 Hz, 1H), 2.31 (ddd, J=14.3, 10.9, 3.7 Hz, 1H), 2.05-2.18 (m, 1H).

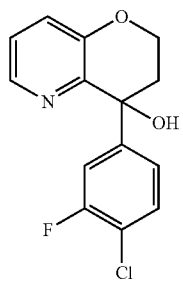 [SMILES: OC1(c2ccc(Cl)c(F)c2)CCOc2cccnc21]

Intermediate 8: 4-(4-chloro-3-fluorophenyl)-3,4-dihydro-2H-pyrano[3,2-b]pyridin-4-ol. MS (ESI pos. ion) m/z: 280.0 (MH+). $^1$H NMR (DMSO-$d_6$) δ: 8.07 (dd, J=4.3, 1.4 Hz, 1H), 7.49 (t, J=8.1 Hz, 1H), 7.35 (dd, J=11.0, 2.0 Hz, 1H), 7.31 (dd, J=8.3, 1.5 Hz, 1H), 7.25 (dd, J=8.2, 4.3 Hz, 1H), 7.06 (dd, J=8.4, 1.6 Hz, 1H), 6.27 (s, 1H), 4.38 (td, J=11.2, 2.2 Hz, 1H), 4.28 (dt, J=11.1, 3.9 Hz, 1H), 2.33-2.46 (m, 1H), 2.06-2.20 (m, 1H).

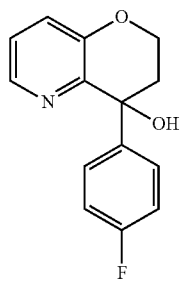 [SMILES: OC1(c2ccc(F)cc2)CCOc2cccnc21]

Intermediate 9: 4-(4-fluorophenyl)-3,4-dihydro-2H-pyrano[3,2-b]pyridin-4-ol. MS (ESI pos. ion) m/z: 246.2 (MH+). $^1$H NMR (DMSO-$d_6$) δ: 8.06 (dd, J=4.3, 1.4 Hz, 1H), 7.18-7.33 (m, 4H), 7.04-7.13 (m, 2H), 6.03 (s, 1H), 4.34 (td, J=10.8, 2.4 Hz, 1H), 4.19 (dt, J=11.1, 4.2 Hz, 1H), 2.24-2.38 (m, 1H), 2.07-2.18 (m, 1H).

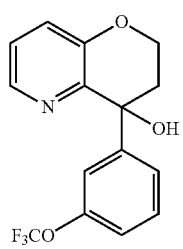

Intermediate 10: 4-(3-(trifluoromethoxy)phenyl)-3,4-dihydro-2H-pyrano[3,2-b]pyridin-4-ol. MS (ESI pos. ion) m/z: 312.0 (MH+).

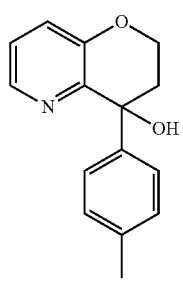 [SMILES: Cc1ccc(C2(O)CCOc3cccnc32)cc1]

Intermediate 11: 4-(p-tolyl)-3,4-dihydro-2H-pyrano[3,2-b]pyridin-4-ol. MS (ESI pos. ion) m/z: 242.1 (MH+).

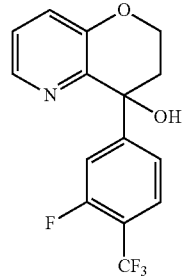 [SMILES: OC1(c2ccc(C(F)(F)F)c(F)c2)CCOc2cccnc21]

Intermediate 12: 4-(3-fluoro-4-(trifluoromethyl)phenyl)-3,4-dihydro-2H-pyrano[3,2-b]pyridin-4-ol. MS (ESI pos. ion) m/z: 314.1 (MH+). $^1$H NMR (DMSO-$d_6$) δ: 8.05 (dd, J=4.3, 1.4 Hz, 1H), 7.69 (t, J=8.0 Hz, 1H), 7.43 (d, J=12.5 Hz, 1H), 7.28-7.36 (m, 1H), 7.20-7.28 (m, 2H), 6.41 (s, 1H), 4.25-4.44 (m, 2H), 2.36-2.47 (m, 1H), 2.12 (dt, J=14.3, 2.5 Hz, 1H).

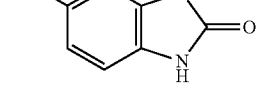

Intermediate 13: 2-oxo-2,3-dihydrobenzo[d]oxazole-6-carbonitrile. To a solution of 6-bromo benzoxazolinone (2 g, 9.4 mmol) in DMF (20 mL) was added CuCN (16.79 g, 188 mmol), and the reaction was stirred at 175° C. for 6 h. The reaction progress was monitored by TLC (100% EtOAc). The reaction was diluted with EtOAc (10 mL) and filtered through Celite® brand filter agent. The organic layer was concentrated and purified by column chromatography (silica gel, 0-50% EtOAc in hexanes) to give the title compound. MS (ESI pos. ion) m/z: 158.9 (MH−).

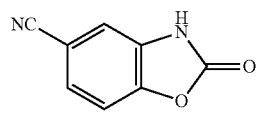

Intermediate 14: 2-oxo-2,3-dihydrobenzo[d]oxazole-5-carbonitrile. To a solution of 5-bromo benzoxazolinone (1 g, 4.7 mmol) in DMF (15 mL), were added Zn(CN)$_2$ (1 g, 9.4 mmol) and Pd(PPh$_3$)$_4$. The reaction was stirred at 150° C. for 24 h. The reaction progress was monitored by TLC (100% EtOAc). The reaction was diluted with EtOAc (10 mL) and filtered through Celite® brand filter agent. The organic layer was concentrated and purified by column chromatography (silica gel, 0-50% EtOAc in hexanes) to give the title compound. $^1$H NMR (400 MHz, CDCl$_3$): δ 8.6 (br s, 1H), 7.5 (dd, J=1.8, 8.4 Hz, 1H), 7.3-7.4 (m, 2H).

Ritter Reaction Procedure A:

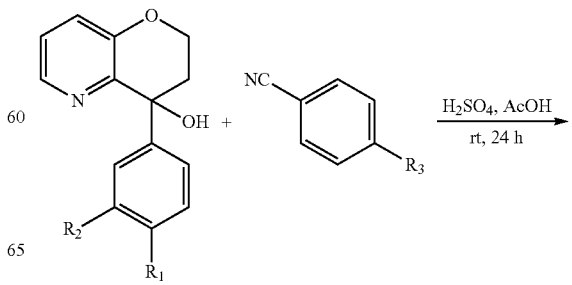

-continued

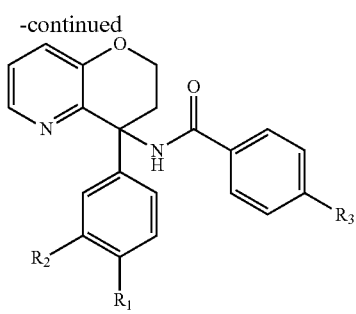

To a stirred mixture of 4-(substituted) phenyl)-3,4-dihydro-2H-pyrano[3,2-b]pyridin-4-ol (1.5 mmol) and 4-substituted benzonitrile (9.1 mmol) at 0° C. were added acetic acid (23.3 mmol) and conc. $H_2SO_4$ (15.9 mmol). The ice bath was removed, and the reaction was stirred at ambient temperature for 24 h. The reaction mixture was diluted with water (20 mL) and EtOAc (40 mL) and quenched slowly with saturated NaHCO$_3$ solution (125 mL). The aqueous layer was subsequently extracted with EtOAc (2×50 mL). The combined organic layers were washed with brine (50 mL), dried over Na$_2$SO$_4$, concentrated, and purified by column chromatography to give the desired product.

Ritter Reaction Procedure B:

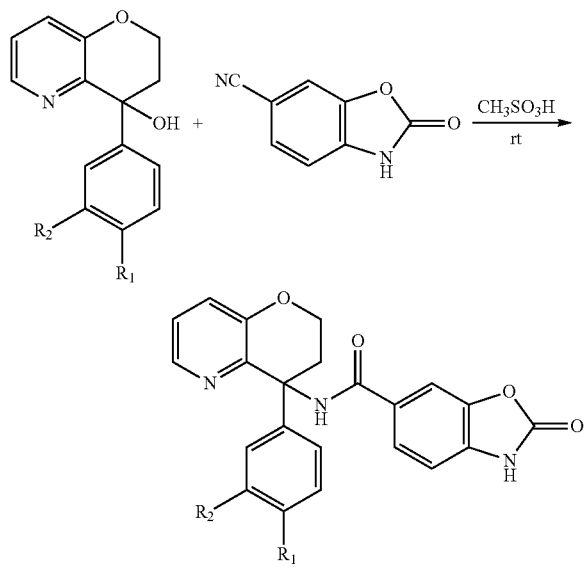

To a stirred mixture of 4-(substituted) phenyl)-3,4-dihydro-2H-pyrano[3,2-b]pyridin-4-ol (1.5 mmol) and 2-oxo-2,3-dihydrobenzo[d]oxazole-6-carbonitrile (1.5 mmol) at 0° C. was added methanesulfonic acid (10 mL). The ice bath was removed, and the reaction was stirred at ambient temperature for 24 h. The reaction mixture was diluted with water (20 mL) and EtOAc (40 mL) and quenched slowly with saturated NaHCO$_3$ solution (125 mL). The organic layer was separated, and the aqueous layer extracted with EtOAc (2×50 mL). The combined organic layers were washed with brine (50 mL), dried over Na$_2$SO$_4$, concentrated, and purified by column chromatography to give the desired products.

Ritter Reaction Procedure C:

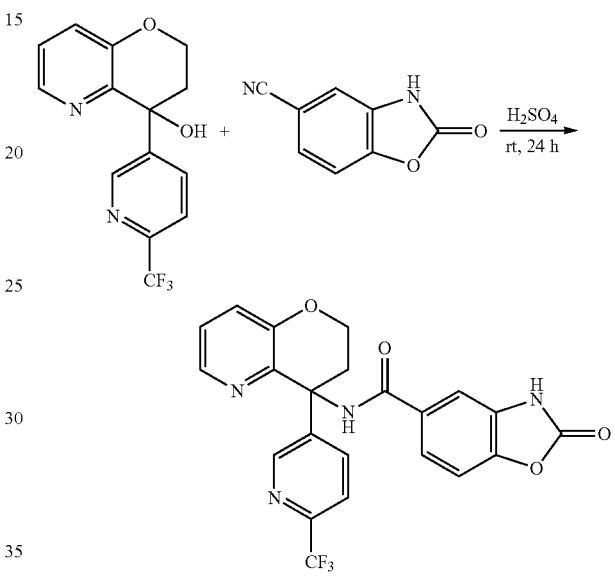

To a cooled mixture at 0° C. of 4-(6-(trifluoromethyl) pyridin-3-yl)-3,4-dihydro-2H-pyrano[3,2-b]pyridin-4-ol (1 g, 3 mmol) and 2-oxo-2,3-dihydrobenzo-[d]oxazole-5-carbonitrile (810 mg, 5 mmol) was added conc. $H_2SO_4$ (20 mL). The ice bath was removed and the reaction was stirred at ambient temperature for 24 h. The reaction mixture was diluted with water (20 mL) and EtOAc (40 mL), then slowly quenched with saturated NaHCO$_3$ solution (125 mL). The organic layer was separated and the aqueous layer extracted with EtOAc (2×50 mL). The combined organic layers were washed with brine (50 mL), dried over Na$_2$SO$_4$, concentrated, and purified by column chromatography to give the desired product.

TABLE 1

Examples 1-27 were prepared in a manner analagous to that shown in Scheme 5 and described above.

| Ex. # | Alcohol Intermediate | Grignard procedure | Ritter procedure | Nitrile Intermediate | Structure | Compound Name | MS MH+ |
|---|---|---|---|---|---|---|---|
| 1[1] | 1 | A | A | CN-phenyl | (see structure) | (S)-N-(4-(4-(trifluoromethyl)phenyl)-3,4-dihydro-2H-pyrano[3,2-b]pyridin-4-yl)benzamide | 398.9 |

TABLE 1-continued

Examples 1-27 were prepared in a manner analagous to that shown in Scheme 5 and described above.

| Ex. # | Alcohol Intermediate | Grignard procedure | Ritter procedure | Nitrile Intermediate | Structure | Compound Name | MS MH+ |
|---|---|---|---|---|---|---|---|
| 2[2] | 1 | A | A | 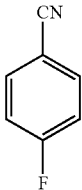 | 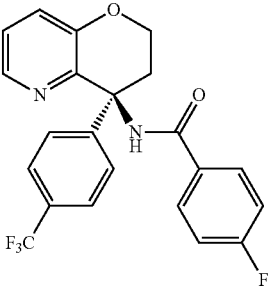 | (S)-4-fluoro-N-(4-(4-(trifluoromethyl)phenyl)-3,4-dihydro-2H-pyrano[3,2-b]pyridin-4-yl)benzamide | 416.7 |
| 3[3] | 4 | A | A | 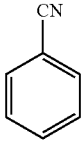 | 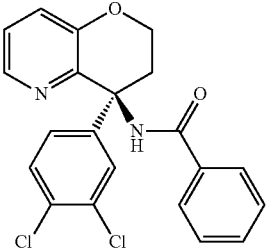 [SMILES: O=C(N[C@]1(c2ccc(Cl)c(Cl)c2)CCOc2cccnc21)c1ccccc1] | (S)-N-(4-(3,4-dichlorophenyl)-3,4-dihydro-2H-pyrano[3,2-b]pyridin-4-yl)benzamide | 399.0 |
| 4[4] | 1 | A | A | 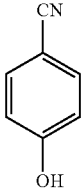 | 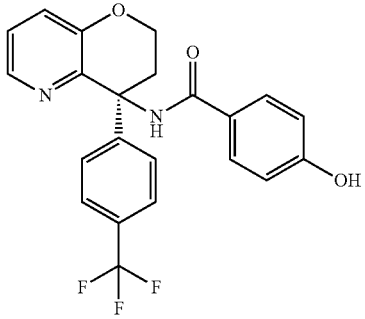 [SMILES: O=C(N[C@]1(c2ccc(C(F)(F)F)cc2)CCOc2cccnc21)c1ccc(O)cc1] | (S)-4-hydroxy-N-(4-(4-(trifluoromethyl)phenyl)-3,4-dihydro-2H-pyrano[3,2-b]pyridin-4-yl)benzamide | 415.0 |
| 5[5] | 1 | A | A | 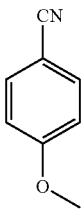 | 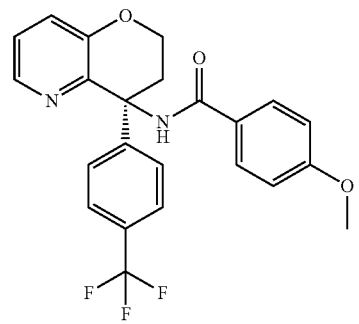 [SMILES: COc1ccc(C(=O)N[C@]2(c3ccc(C(F)(F)F)cc3)CCOc3cccnc32)cc1] | (S)-4-methoxy-N-(4-(4-(trifluoromethyl)phenyl)-3,4-dihydro-2H-pyrano[3,2-b]pyridin-4-yl)benzamide | 429.2 |
| 6 | 2 | A | A | 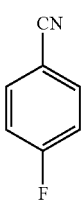 | 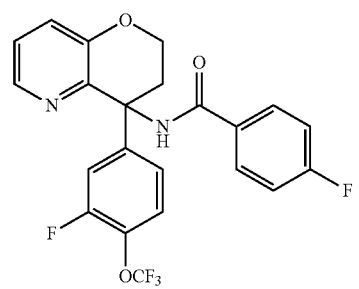 | 4-fluoro-N-(4-(3-fluoro-4-(trifluoromethoxy)phenyl)-3,4-dihydro-2H-pyrano[3,2-b]pyridin-4-yl)benzamide | 451.3 |

TABLE 1-continued

Examples 1-27 were prepared in a manner analagous to that shown in Scheme 5 and described above.

| Ex. # | Alcohol Inter- mediate | Grignard procedure | Ritter procedure | Nitrile Inter- mediate | Structure | Compound Name | MS MH+ |
|---|---|---|---|---|---|---|---|
| 7 | 2 | A | A | 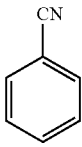 | 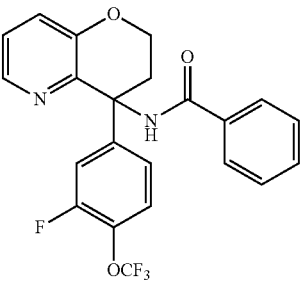 [SMILES: O=C(NC1(c2ccc(OC(F)(F)F)c(F)c2)CCOc2cccnc21)c1ccccc1] | N-(4-(3-fluoro-4-(trifluoromethoxy)phenyl)-3,4-dihydro-2H-pyrano[3,2-b]pyridin-4-yl)benzamide | 433.0 |
| 8 | 3 | A | A | 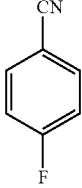 | 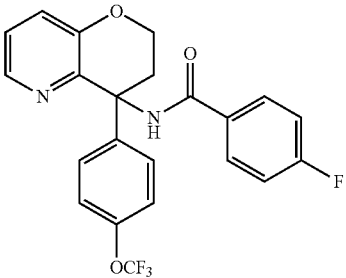 [SMILES: O=C(NC1(c2ccc(OC(F)(F)F)cc2)CCOc2cccnc21)c1ccc(F)cc1] | 4-fluoro-N-(4-(4-(trifluoromethoxy)phenyl)-3,4-dihydro-2H-pyrano[3,2-b]pyridin-4-yl)benzamide | 433.1 |
| 9 | 3 | A | A | 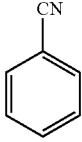 | 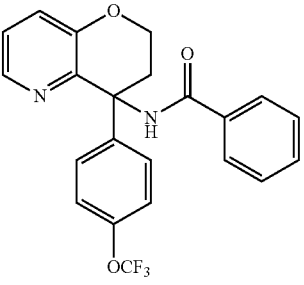 [SMILES: O=C(NC1(c2ccc(OC(F)(F)F)cc2)CCOc2cccnc21)c1ccccc1] | N-(4-(4-(trifluoromethoxy)phenyl)-3,4-dihydro-2H-pyrano[3,2-b]pyridin-4-yl)benzamide | 415.1 |
| 10 | 4 | A | A | 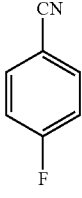 | 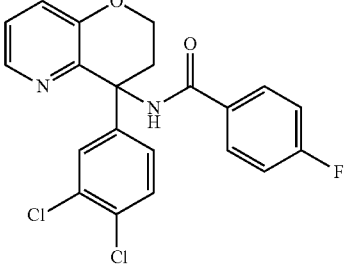 | N-(4-(3,4-dichlorophenyl)-3,4-dihydro-2H-pyrano[3,2-b]pyridin-4-yl)-4-fluorobenzamide | 416.9 |
| 11 | 5 | A | A | 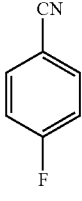 | 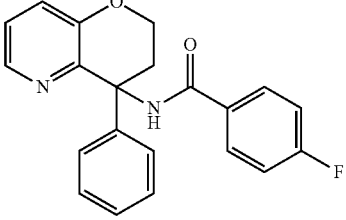 | 4-fluoro-N-(4-phenyl-3,4-dihydro-2H-pyrano[3,2-b]pyridin-4-yl)benzamide | 348.9 |

TABLE 1-continued

Examples 1-27 were prepared in a manner analagous to that shown in Scheme 5 and described above.

| Ex. # | Alcohol Intermediate | Grignard procedure | Ritter procedure | Nitrile Intermediate | Structure | Compound Name | MS MH+ |
|---|---|---|---|---|---|---|---|
| 12 | 5 | A | A | | 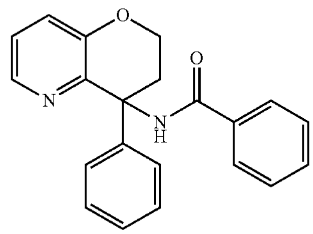 [SMILES: O=C(NC1(c2ccccc2)CCOc2cccnc21)c1ccccc1] | N-(4-phenyl-3,4-dihydro-2H-pyrano[3,2-b]pyridin-4-yl)benzamide | 331.0 |
| 13 | 6 | B | A | | 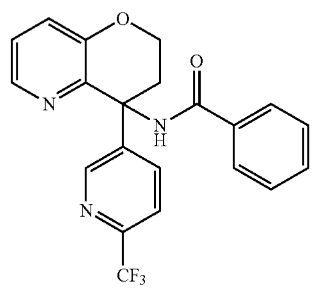 [SMILES: O=C(NC1(c2ccc(C(F)(F)F)nc2)CCOc2cccnc21)c1ccccc1] | N-(4-(6-(trifluoromethyl)pyridin-3-yl)-3,4-dihydro-2H-pyrano[3,2-b]pyridin-4-yl)benzamide | 400.3 |
| 14[6] | 7 | A | A | | 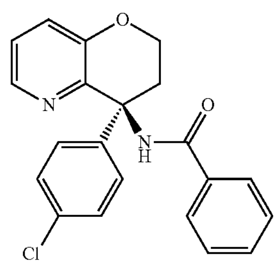 [SMILES: O=C(N[C@]1(c2ccc(Cl)cc2)CCOc2cccnc21)c1ccccc1] | (S)-N-(4-(4-chlorophenyl)-3,4-dihydro-2H-pyrano[3,2-b]pyridin-4-yl)benzamide | 365.1 |
| 15[7] | 8 | A | A | | 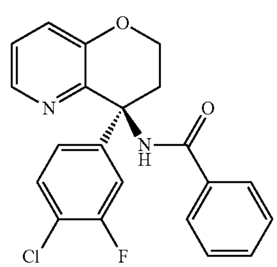 [SMILES: O=C(N[C@]1(c2ccc(Cl)c(F)c2)CCOc2cccnc21)c1ccccc1] | (S)-N-(4-(4-chloro-3-fluorophenyl)-3,4-dihydro-2H-pyrano[3,2-b]pyridin-4-yl)benzamide | 383.1 |
| 16[8] | 9 | A | A | | 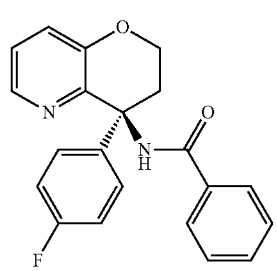 [SMILES: O=C(N[C@]1(c2ccc(F)cc2)CCOc2cccnc21)c1ccccc1] | (S)-N-(4-(4-fluorophenyl)-3,4-dihydro-2H-pyrano[3,2-b]pyridin-4-yl)benzamide | 349.1 |

TABLE 1-continued

Examples 1-27 were prepared in a manner analagous to that shown in Scheme 5 and described above.

| Ex. # | Alcohol Intermediate | Grignard procedure | Ritter procedure | Nitrile Intermediate | Structure | Compound Name | MS MH+ |
|---|---|---|---|---|---|---|---|
| 17[9] | 10 | A | A | 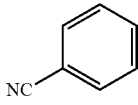 | 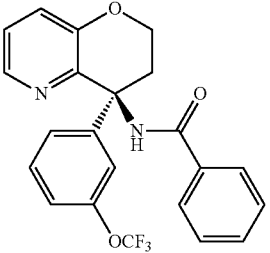 [SMILES: O=C(N[C@]1(c2cccc(OC(F)(F)F)c2)CCOc2cccnc21)c1ccccc1] | (S)-N-(4-(3-(trifluoromethoxy)phenyl)-3,4-dihydro-2H-pyrano[3,2-b]pyridin-4-yl)benzamide | 415.2 |
| 18[10] | 11 | A | A | 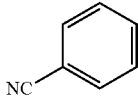 | 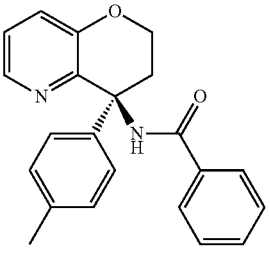 [SMILES: Cc1ccc([C@@]2(NC(=O)c3ccccc3)CCOc3cccnc32)cc1] | (S)-N-(4-(p-tolyl)-3,4-dihydro-2H-pyrano[3,2-b]pyridin-4-yl)benzamide | 345.2 |
| 19[11] | 12 | A | A | 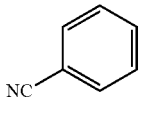 | 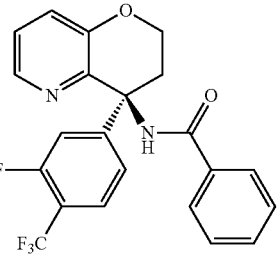 | (S)-N-(4-(3-fluoro-4-(trifluoromethyl)phenyl)-3,4-dihydro-2H-pyrano[3,2-b]pyridin-4-yl)benzamide | 417.0 |
| 20[12] | 1 | A | B | 12 | 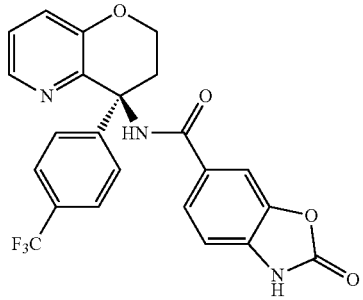 [SMILES: O=C(N[C@]1(c2ccc(C(F)(F)F)cc2)CCOc2cccnc21)c1ccc2[nH]c(=O)oc2c1] | (S)-2-oxo-N-(4-(4-(trifluoromethyl)phenyl)-3,4-dihydro-2H-pyrano[3,2-b]pyridin-4-yl)-2,3-dihydrobenzo[d]oxazole-6-carboxamide | 456.0 |
| 21[13] | 1 | A | B | 12 | 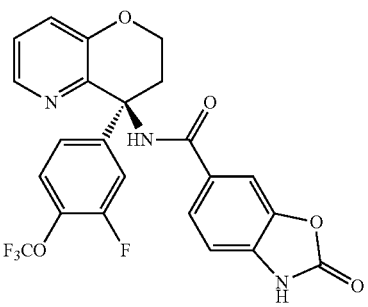 [SMILES: O=C(N[C@]1(c2ccc(OC(F)(F)F)c(F)c2)CCOc2cccnc21)c1ccc2[nH]c(=O)oc2c1] | (S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-6-carboxamide | 490.0 |

TABLE 1-continued

Examples 1-27 were prepared in a manner analagous to that shown in Scheme 5 and described above.

| Ex. # | Alcohol Intermediate | Grignard procedure | Ritter procedure | Nitrile Intermediate | Structure | Compound Name | MS MH+ |
|---|---|---|---|---|---|---|---|
| 22 | 3 | A | B | 7 | 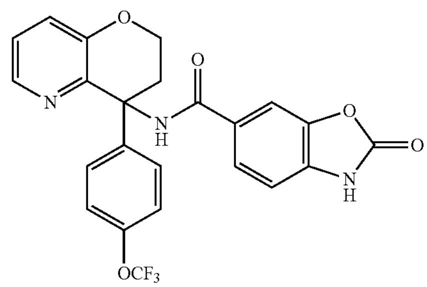 [SMILES: O=C(NC1(c2ccc(OC(F)(F)F)cc2)CCOc2cccnc21)c1ccc2[nH]c(=O)oc2c1] | 2-oxo-N-(4-(4-(trifluoromethoxy)phenyl)-3,4-dihydro-2H-pyrano[3,2-b]pyridin-4-yl)-2,3-dihydrobenzo[d]oxazole-6-carboxamide | 471.9 |
| 23 | 3 | A | B | 8 | 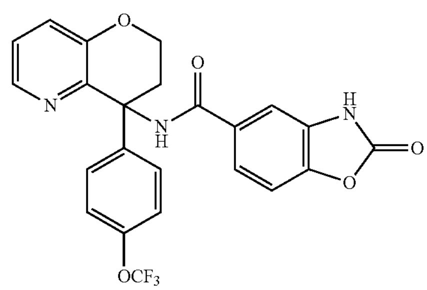 | 2-oxo-N-(4-(4-(trifluoromethoxy)phenyl)-3,4-dihydro-2H-pyrano[3,2-b]pyridin-4-yl)-2,3-dihydrobenzo[d]oxazole-5-carboxamide | 472.0 |
| 24 | 4 | A | B | 7 | 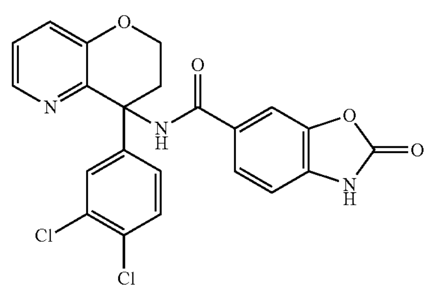 [SMILES: O=C(NC1(c2ccc(Cl)c(Cl)c2)CCOc2cccnc21)c1ccc2[nH]c(=O)oc2c1] | N-(4-(3,4-dichlorophenyl)-3,4-dihydro-2H-pyrano[3,2-b]pyridin-4-yl)-2-oxo-2,3-dihydrobenzo[d]oxazole-6-carboxamide | 456.0 |
| 25 | 4 | A | B | 8 | 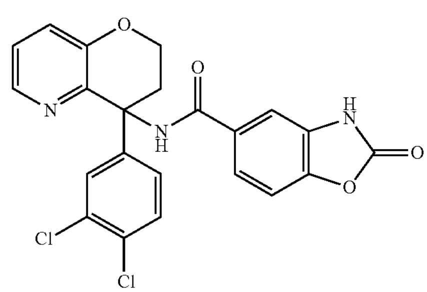 [SMILES: O=C(NC1(c2ccc(Cl)c(Cl)c2)CCOc2cccnc21)c1ccc2oc(=O)[nH]c2c1] | N-(4-(3,4-dichlorophenyl)-3,4-dihydro-2H-pyrano[3,2-b]pyridin-4-yl)-2-oxo-2,3-dihydrobenzo[d]oxazole-5-carboxamide | 456.0 |
| 26 | 5 | A | A | 7 | 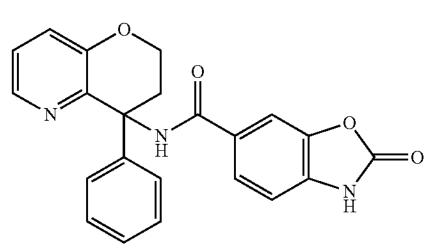 [SMILES: O=C(NC1(c2ccccc2)CCOc2cccnc21)c1ccc2[nH]c(=O)oc2c1] | 2-oxo-N-(4-phenyl-3,4-dihydro-2H-pyrano[3,2-b]pyridin-4-yl)-2,3-dihydrobenzo[d]oxazole-6-carboxamide | 388.3 |

TABLE 1-continued

Examples 1-27 were prepared in a manner analagous to that shown in Scheme 5 and described above.

| Ex. # | Alcohol Intermediate | Grignard procedure | Ritter procedure | Nitrile Intermediate | Structure | Compound Name | MS MH+ |
|---|---|---|---|---|---|---|---|
| 27 | 6 | A | C | 8 | 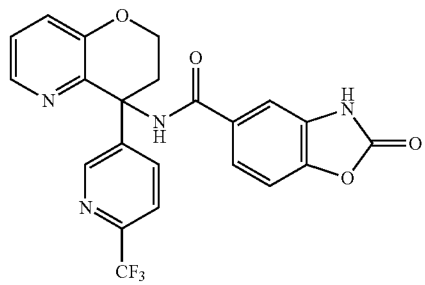 [SMILES: O=C(NC1(c2ccc(C(F)(F)F)nc2)CCOc2cccnc21)c1ccc2oc(=O)[nH]c2c1] | 2-oxo-N-(4-(6-(trifluoromethyl)pyridin-3-yl)-3,4-dihydro-2H-pyrano[3,2-b]pyridin-4-yl)-2,3-dihydrobenzo[d]oxazole-5-carboxamide | 457.1 |

[1]Purified via preparative SFC [using a AD-H (2 x 15 cm); mobile phase: 20% methanol (0.1% NH4OH)/liquid CO$_2$, at a flow rate of 70 mL/min] resulting in Peak 1 and 2 fractions with enantiomeric excess >99%. Peak 2 correlates with the (S) enantiomer.
[2]Purified via preparative SFC [using a Chiralpak ADH(21 x 250 mm, 5 um); mobile phase: 20% methanol (40 mM NH$_3$)/liquid CO$_2$, at a flow rate of 70 mL/min] resulting in Peak 1 and 2 fractions with enantiomeric excess >99%. Peak 2 correlates with the (S) enantiomer.
[3]Purified via preparative SFC [using a AD-H (2 x 15 cm); mobile phase: 20% methanol/liquid CO$_2$, at a flow rate of 60 mL/min] resulting in Peak 1 and 2 fractions with enantiomeric excess >99%. Peak 2 correlates with the (S) enantiomer.
[4]Purified via preparative SFC [using a AD-H (21 x 250 mm, 5 um); mobile phase: 12% methanol (40 mM NH$_3$)/liquid CO$_2$, at a flow rate of 70 mL/min] resulting in Peak 1 and 2 fractions with enantiomeric excess >99%. Peak 2 correlates with the (S) enantiomer.
[5]Purified via preparative SFC [using a Chiralcel OJH (21 x 250 mm, 5 um); mobile phase: 20% ethanol (20 mM NH$_3$)/liquid CO$_2$, at a flow rate of 75 mL/min] resulting in Peak 1 and 2 fractions with enantiomeric excess >98%. Peak 2 correlates with the (S) enantiomer.
[6]Purified via preparative SFC [using a AD-H column (250 x 20 mm); mobile phase: 20% methanol (20 mM NH$_3$)/liquid CO$_2$, at a flow rate of 75 mL/min] resulting in Peak 1 and 2 fractions with enantiomeric excess >98%. Peak 2 correlates with the (S) enantiomer.
[7]Purified via preparative SFC [using a AD-H column (250 x 20 mm); mobile phase: 20% methanol (20 mM NH$_3$)/liquid CO$_2$, at a flow rate of 75 mL/min] resulting in Peak 1 and 2 fractions with enantiomeric excess >98%. Peak 2 correlates with the (S) enantiomer.
[8]Purified via preparative SFC [using a AD-H column (250 x 20 mm); mobile phase: 20% methanol (20 mM NH$_3$)/liquid CO$_2$, at a flow rate of 75 mL/min] resulting in Peak 1 and 2 fractions with enantiomeric excess >98%. Peak 2 correlates with the (S) enantiomer.
[9]Purified via preparative SFC [using a AD-H column (250 x 20 mm); mobile phase: 10% methanol (20 mM NH$_3$)/liquid CO$_2$, at a flow rate of 75 mL/min] resulting in Peak 1 and 2 fractions with enantiomeric excess >98%. Peak 2 correlates with the (S) enantiomer.
[10]Purified via preparative SFC [using a AD-H column (250 x 20 mm); mobile phase: 20% methanol (20 mM NH$_3$)/liquid CO$_2$, at a flow rate of 75 mL/min] resulting in Peak 1 and 2 fractions with enantiomeric excess >98%. Peak 2 correlates with the (S) enantiomer.
[11]Purified via preparative SFC [using a ODH column (21 x 250 mm, 5 um); mobile phase: 30% methanol (20 mM NH$_3$)/liquid CO$_2$, at a flow rate of 65 mL/min] resulting in Peak 1 and 2 fractions with enantiomeric excess >98%. Peak 2 correlates with the (S) enantiomer.
[12]Purified via preparative SFC [using a AD-H column (250 x 20 mm); mobile phase: 20% methanol/liquid CO$_2$, at a flow rate of 75 mL/min] resulting in Peak 1 and 2 fractions with enantiomeric excess >99%. Peak 2 correlates with the (S) enantiomer.
[13]Purified via preparative SFC [using a Chiralcel OJH (21 x 250 mm, 5 um); mobile phase: 20% ethanol (20 mM NH$_3$)/liquid CO$_2$, at a flow rate of 70 mL/min] resulting in Peak 1 and 2 fractions with enantiomeric excess >99%. Peak 2 correlates with the (S) enantiomer.

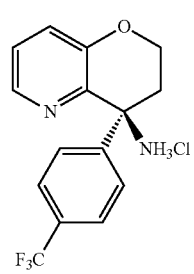

40

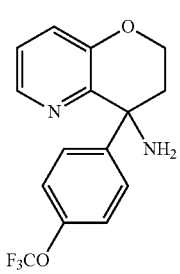 [SMILES: NC1(c2ccc(OC(F)(F)F)cc2)CCOc2cccnc21]

45

Intermediate 15: (S)-4-(4-(trifluoromethyl)phenyl)-3,4-dihydro-2H-pyrano[3,2-b]pyridin-4-amine. To a microwave vial with 4-methoxy-N-(4-(4-(trifluoromethyl)phenyl)-3,4-dihydro-2H-pyrano[3,2-b]pyridin-4-yl)benzamide (2 g, 4.67 mmol) was added HCl (5 M aqueous, 20 mL, 100 mmol). The vial was sealed and heated by microwave at 150° C. for 80 min. The reaction was then concentrated in vacuo and the residue dissolved in half saturated aqueous NaHCO$_3$ (75 mL) and DCM (50 mL). The organic layer was separated, and the aqueous layer was extracted with DCM (2×50 mL). The combined organic layers were washed with brine, dried over MgSO$_4$, and concentrated to give a green oil. Purification by ISCO (40 g SiO$_2$, 10-100% acetone in hexanes) gave racemic title compound. 4-(4-(trifluoromethyl)phenyl)-3,4-dihydro-2H-pyrano[3,2-b]pyridin-4-amine ( ) was separated by preparative SFC (using a AD-H (2×15 cm); mobile phase: 12% isopropanol (DEA)/CO$_2$, at a flow rate of 60 mL/min] resulting in Peak 1 and 2 fractions with enantiomeric excess >99%).

Intermediate 16

4-(4-(trifluoromethoxy)phenyl)-3,4-dihydro-2H-pyrano[3,2-b]pyridin-4-amine

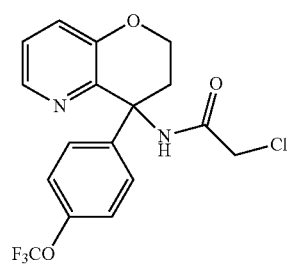 [SMILES: O=C(CCl)NC1(c2ccc(OC(F)(F)F)cc2)CCOc2cccnc21]

Step 1: 2-chloro-N-(4-(4-(trifluoromethoxy)phenyl)-3,4-dihydro-2H-pyrano[3,2-b]pyridin-4-yl)acetamide. To a stirred mixture of 4-(4-(trifluoromethoxy)phenyl)-3,4-dihydro-2H-pyrano[3,2-b]pyridin-4-ol (3 g. 9.6 mmol, Intermediate 3) and 2-chloroacetonitrile (7.2 mL, 128.5 mmol) at 0° C., were added acetic acid (8.68 mL) and conc. H₂SO₄ (9.45 mL). The ice bath was then removed, and the reaction was stirred at room temperature for 12 h. The progress of reaction was monitored by TLC (50% EtOAc in petroleum ether). The reaction was diluted with H₂O (20 mL) and EtOAc (40 mL) and quenched slowly with saturated NaHCO₃ (125 mL). The organic layer was separated and the aqueous layer extracted with EtOAc (2×50 mL). The combined organic layers were washed with brine (50 mL), dried over MgSO₄, and concentrated to give the product as a residue. Purification by column chromatography (60-120 mesh silica, 0-50% EtOAc in hexanes) gives the title compound as a white solid. MS (ESI pos. ion) m/z: 387.0 (MH+).

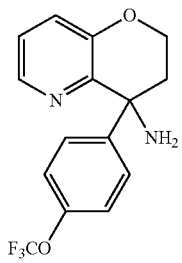

Step 2: 4-(4-(trifluoromethoxy)phenyl)-3,4-dihydro-2H-pyrano[3,2-b]pyridin-4-amine. To a stirred solution of 2-chloro-N-(4-(4-(trifluoromethoxy)phenyl)-3,4-dihydro-2H-pyrano[3,2-b]pyridin-4-yl)acetamide (1.5 g, 3.8 mmol) in EtOH (5 times) and AcOH (cat.), was added thiourea (0.3 g, 4.2 mmol). The reaction was stirred at 60° C. for 12 h. The progress of reaction was monitored by TLC (50% EtOAc in petroleum ether). The reaction was diluted with EtOAc (10 mL) and quenched slowly with saturated NaHCO₃ (25 mL). The aqueous layer was extracted with EtOAc (10 mL). The combined organic layers were washed with brine (10 mL), dried over MgSO₄, and concentrated to give the product as a residue. Purification by column chromatography (60-120 mesh silica, 0-50% EtOAc/hexanes) gives the title compound as a brown oil. MS (ESI pos. ion) m/z: 294.1 (M-NH₂). ¹H NMR (300 MHz, CDCl₃): δ 8.2 (d, J=4.0 Hz, 1H), 7.3 (m, 2H), 7.1-7.2 (m, 4H), 4.3 (m, 1H), 4.0 (m, 1H), 2.35-2.45 (m, 2H).

Scheme 6

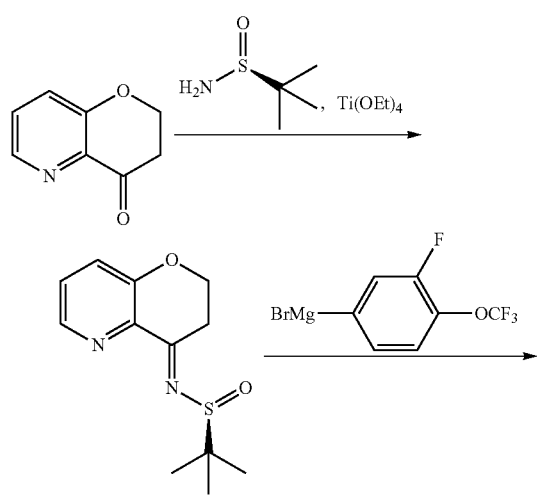

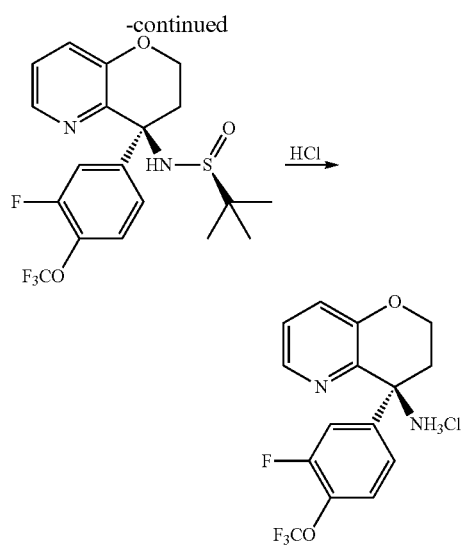

Intermediate 17

(S)-4-(3-fluoro-4-(trifluoromethoxy)phenyl)-3,4-dihydro-2H-pyrano[3,2-b]pyridin-4-amine hydrochloride

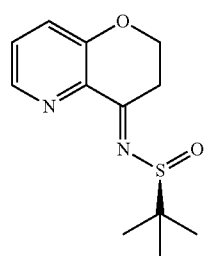 [SMILES: CC(C)(C)[S@](=O)/N=C1\CCOc2cccnc21]

Step 1. (S)-2-methyl-N-(2H-pyrano[3,2-b]pyridin-4(3H)-ylidene)propane-2-sulfinamide. To a solution of 2H-pyrano[3,2-b]pyridin-4(3H)-one (20.28 g, 136 mmol) and 2-MeTHF (200 mL) was added (S)-2-methylpropane-2-sulfinamide (24.72 g, 204 mmol) and titanium ethoxide (65 mL, 264 mmol). The solution was stirred at room temperature. After 4 h, the reaction was poured into rapidly stirring brine (500 mL). The suspension was stirred for 5 min and then EtOAc (200 mL) was poured into the stirring suspension. After stirring for a further 15 min, the suspension was filtered through a pad of Celite® brand filter agent. The solids were suspended again in water:EtOAc (1:1, 400 mL total). After stirring for 20 min, the suspension was filtered through a pad of Celite® brand filter agent. The solids were treated once more with EtOAc:water as previously described and filtered. The filtrate was separated, and the aqueous solution extracted with EtOAc (100 mL). The combined organic layers were concentrated in vacuo and adsorbed onto a plug of silica gel and chromatographed through a Redi-Sep® pre-packed silica gel column (330 g), eluting with 0-40% EtOAc in DCM, to provide the title compound as a golden oil. MS (ESI pos. ion) m/z: 253.1 (MH+).

and EtOH (30 mL) was added 4M HCl in dioxane (6 mL, 24.00 mmol). After 2 h, the reaction was concentrated in vacuo and triturated with ether (~60 mL) and filtered. The solids were rinsed with more ether and dried in the funnel to give the title compound as an off-white solid. MS (ESI pos. ion) m/z: 329.0 (MH+). $^1$H NMR (DMSO-$d_6$) δ: 9.33 (br. s., 3H), 8.35 (dd, J=3.8, 2.0 Hz, 1H), 7.59-7.75 (m, 2H), 7.42-7.54 (m, 2H), 7.00-7.13 (m, 1H), 4.34-4.51 (m, 1H), 3.77-3.85 (m, 1H), 2.70-2.88 (m, 1H), 2.65 (dd, J=11.8, 3.9 Hz, 1H).

Scheme 7

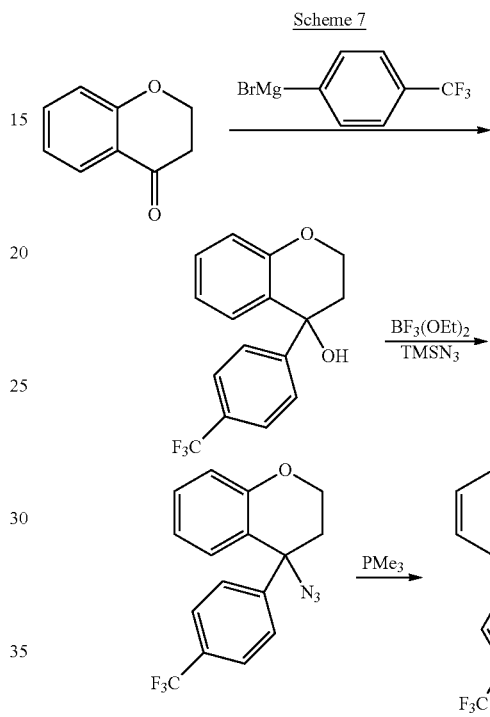

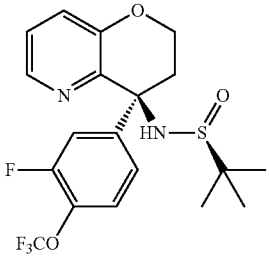 [SMILES: CC(C)(C)[S@](=O)N[C@]1(c2ccc(OC(F)(F)F)c(F)c2)CCOc2cccnc21]

Step 2. (S)-N—((S)-4-(3-fluoro-4-(trifluoromethoxy)phenyl)-3,4-dihydro-2H-pyrano[3,2-b]pyridin-4-yl)-2-methylpropane-2-sulfonamide. To an oven-dried round bottom flask was added magnesium (2.58 g, 106 mmol), iodine (~25 mg), and 2-MeTHF (100 mL). The flask was placed in a water bath. The solution was treated with 10% 4-bromo-2-fluoro-1-(trifluoromethoxy)benzene (20.63 g, 80 mmol) and upon initiation was treated with the remaining bromide at a rate such that the temperature did not exceed 35° C. After stirring for 30 min. the Grignard solution was transferred dropwise to a solution of (S,E)-2-methyl-N-(2H-pyrano[3,2-b]pyridin-4(3H)-ylidene)propane-2-sulfinamide in 2-MeTHF (50 mL) that was cooled in a dry ice/acetone bath. The solution was stirred in the cooling bath and then the cooling bath was removed and the reaction was allowed to warm to room temperature. The reaction was quenched with MeOH (5 mL) and diluted with water (50 mL). After stirring for 30 minutes, the suspension was filtered through a pad of Celite® brand filter agent and the solids rinsed with EtOAc (3×20 mL). The filtrate was separated and the organic layers were concentrated in vacuo. The product thus obtained was adsorbed onto a plug of silica gel and chromatographed through a Redi-Sep® pre-packed silica gel column (80 g), eluting with 0-50% EtOAc in hexane, to provide the title compound as a golden oil. MS (ESI pos. ion) m/z: 433.0 (MH+).

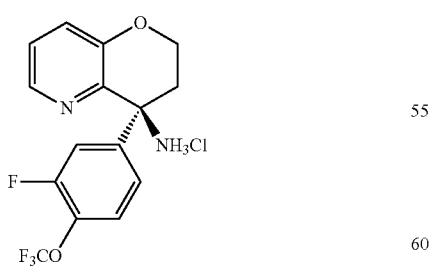

Step 3. (S)-4-(3-fluoro-4-(trifluoromethoxy)phenyl)-3,4-dihydro-2H-pyrano[3,2-b]pyridin-4-amine hydrochloride. To a solution of (S)-N—((S)-4-(3-fluoro-4-(trifluoromethoxy)phenyl)-3,4-dihydro-2H-pyrano[3,2-b]pyridin-4-yl)-2-methylpropane-2-sulfonamide (5.1 g, 11.79 mmol)

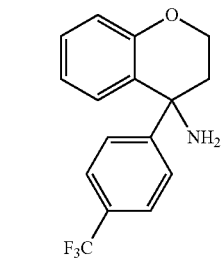 [SMILES: NC1(c2ccc(C(F)(F)F)cc2)CCOc2ccccc21]

Intermediate 18

4-(4-(trifluoromethyl)phenyl)chroman-4-amine

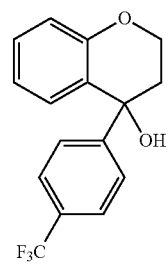 [SMILES: OC1(c2ccc(C(F)(F)F)cc2)CCOc2ccccc21]

Step 1. 4-(4-(trifluoromethyl)phenyl)chroman-4-ol. A round bottom flask with magnesium turnings (1.311 g, 54.0 mmol) and a crystal of $I_2$ was flame dried under $N_2$ until a purple gas was generated. The flask was cooled to room temperature and THF (30 mL) was added followed by 1-bromo-4-(trifluoromethyl)benzene (3.78 mL, 27.0 mmol). The reaction mixture turned dark brown after 15 min, and the resulting mixture was stirred under $N_2$ at room temperature for 2 h. The reaction mixture was cooled to 0° C. in a ice bath and then chroman-4-one (2.66 g, 17.98 mmol) in THF (20 mL) was added dropwise. The cooling bath was then removed and the solution allowed to warm to room temperature and stirred for 2.5 h. The reaction was quenched with saturated $NH_4Cl$ (10 mL) and $H_2O$ (10 mL). The mixture was then extracted with EtOAc (2×10 mL). The combined organic layers were dried ($MgSO_4$), and concentrated. Purification by ISCO (120 g $SiO_2$, 0-40% EtOAc/hexanes) gave the title compound as a yellow oil. MS (ESI pos. ion) m/z: 277.0 (M–OH). $^1$H NMR ($CDCl_3$) δ: 7.47-7.65 (m, 4H), 7.23 (td, J=5.6, 2.6 Hz, 1H), 6.93 (d, J=8.2 Hz, 1H), 6.79-6.90 (m, 2H), 4.40 (td, J=11.1, 2.6 Hz, 1H), 4.27 (dt, J=11.3, 4.0 Hz, 1H), 2.25-2.38 (m, 2H), 2.12-2.23 (m, 1H).

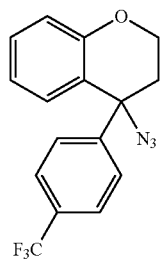 [SMILES: [N-]=[N+]=NC1(c2ccc(C(F)(F)F)cc2)CCOc2ccccc21]

Step 2. 4-azido-4-(4-(trifluoromethyl)phenyl)chroman. To a solution of 4-(4-(trifluoromethyl)phenyl)chroman-4-ol (112 mg, 0.381 mmol) in toluene (4 mL), was added an ice bath and TMS azide (0.101 mL, 0.761 mmol). After 5 min., the solution was treated with $BF_3$.$OEt_2$ (0.048 mL, 0.381 mmol) dropwise. The solution turned from clear to light yellow during the addition. After 20 min, the reaction was quenched with MeOH (2 mL) and diluted with EtOAc (20 mL). The organic solution was washed with water (2×10 mL) and the organic layer concentrated in vacuo to give the title compound as a light yellow oil. MS (ESI pos. ion) m/z: 277.0 (M–$N_3$). $^1$H NMR ($CDCl_3$) δ: 7.57-7.65 (m, J=8.3 Hz, 2H), 7.41-7.52 (m, J=8.2 Hz, 2H), 7.26-7.33 (m, 1H), 6.81-7.03 (m, 3H), 4.30-4.44 (m, 1H), 4.21-4.30 (m, 1H), 2.23-2.34 (m, 1H), 2.12-2.23 (m, 1H).

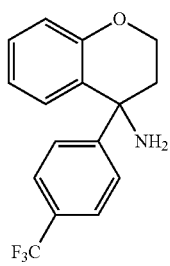 [SMILES: NC1(c2ccc(C(F)(F)F)cc2)CCOc2ccccc21]

Step 3. 4-(4-(trifluoromethyl)phenyl)chroman-4-amine. A solution of 4-azido-4-(4-(trifluoromethyl)phenyl)chroman (110 mg, 0.345 mmol) in THF (4 mL) was cooled in an ice bath. After 5 min., the solution was treated with 1 M trimethylphosphine (0.362 mL, 0.362 mmol) dropwise. After stirring for 20 min., the solution was diluted with MeOH (2 mL). The mixture was washed with water (5 mL). The organic layer was concentrated in vacuo to give the title compound in an unpurified form. MS (ESI pos. ion) m/z: 277.0 (M–$NH_2$).

Scheme 8

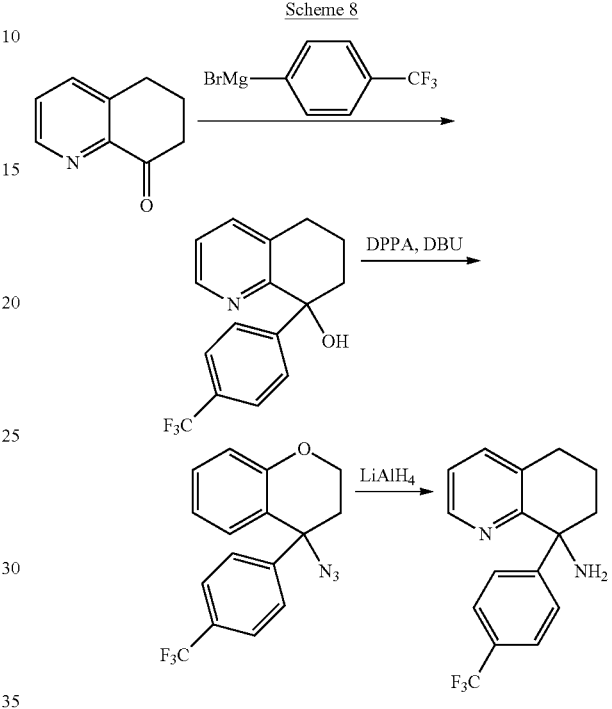

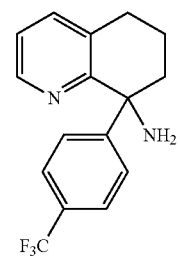 [SMILES: NC1(c2ccc(C(F)(F)F)cc2)CCCc2cccnc21]

Intermediate 19

8-(4-(trifluoromethyl)phenyl)-5,6,7,8-tetrahydroquinolin-8-amine

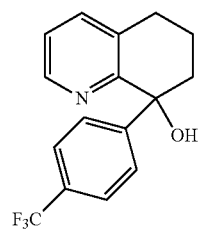

Step 1. 8-(4-(trifluoromethyl)phenyl)-5,6,7,8-tetrahydroquinolin-8-ol. To a solution of magnesium (515 mg, 21.19 mmol) in THF (50 mL) was added 1M diisobutylaluminum hydride in hexanes (0.14 mL, 0.140 mmol). The solution was stirred at room temperature. After 20 min., the reaction was treated with a 20% portion of 1-bromo-4-(trifluoromethyl)benzene (1.9 mL, 13.57 mmol). After stirring for 20 min., the solution went from clear to light brown. The remaining 1-bromo-4-(trifluoromethyl)benzene was added dropwise. The solution was stirred for 0.5 h and then cooled in a dry ice/acetone bath. After cooling for 1 h, the reaction was treated with a solution of 6,7-dihydroquinolin-8(5H)-one (1.0 g, 6.79 mmol) in THF (7 mL) dropwise over 10 min. The solution was allowed to warm to room temperature as the cooling bath expires. After stirring for 16 h, the reaction was quenched with sat'd $NH_4Cl$. The reaction was poured into water and EtOAc. The aqueous layer was extracted with EtOAc (25 mL). The combined EtOAc layers were concentrated in vacuo and adsorbed onto a plug of silica gel and chromatographed through a Redi-Sep® pre-packed silica gel column (40 g), eluting with 0-20% EtOAc in hexane, to provide the title compound as a colorless oil. MS (ESI pos. ion) m/z: 293.9 (MH+). $^1$H NMR (CDCl$_3$) δ: 8.36-8.51 (m, 1H), 7.44-7.60 (m, 3H), 7.27 (s, 1H), 7.15-7.26 (m, 2H), 4.19 (s, 1H), 2.82-3.01 (m, 2H), 2.14-2.36 (m, 2H), 1.90 (dt, J=14.2, 4.5 Hz, 1H), 1.57-1.78 (m, 1H).

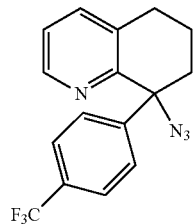 [SMILES: [N-]=[N+]=NC1(c2ccc(C(F)(F)F)cc2)CCCc2cccnc21]

Step 2. 8-azido-8-(4-(trifluoromethyl)phenyl)-5,6,7,8-tetrahydroquinoline. To a solution of 8-(4-(trifluoromethyl)phenyl)-5,6,7,8-tetrahydroquinolin-8-ol (1.2 g, 4.09 mmol) and toluene (2.5 mL) was added DPPA (2.7 mL, 12.53 mmol) and DBU (0.77 mL, 5.11 mmol). The reaction was then treated with sodium azide (780 mg, 12.00 mmol) and stirred for 2 days. The reaction was poured into a separatory funnel containing water and EtOAc. The aqueous layer was extracted with EtOAc (2×25 mL). The combined EtOAc layers were concentrated in vacuo and adsorbed onto a plug of silica gel and chromatographed through a Redi-Sep® pre-packed silica gel column (40 g), eluting with 0-40% EtOAc in hexane, to provide the title compound as a colorless oil. MS (ESI pos. ion) m/z: 319.0 (MH+).

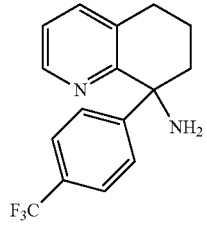 [SMILES: NC1(c2ccc(C(F)(F)F)cc2)CCCc2cccnc21]

Step 3. 8-(4-(trifluoromethyl)phenyl)-5,6,7,8-tetrahydroquinolin-8-amine. To a 0° C. solution of 8-azido-8-(4-(trifluoromethyl)phenyl)-5,6,7,8-tetrahydroquinoline (90 mg, 0.283 mmol) and THF (1 mL) was added 1M LiAlH$_4$ in THF (0.3 mL, 0.300 mmol) dropwise. After 30 min., the reaction was quenched with saturated Rochelle's salt. The reaction was diluted with EtOAc and the aqueous layer extracted with EtOAc (5 mL). The combined EtOAc layers were concentrated in vacuo to give the title compound as a yellow solid. MS (ESI pos. ion) m/z: 293.0 (MH+).

Example 28

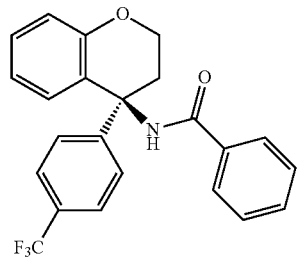 [SMILES: O=C(N[C@]1(c2ccc(C(F)(F)F)cc2)CCOc2ccccc21)c1ccccc1]

(S)-N-(4-(4-(trifluoromethyl)phenyl)chroman-4-yl)benzamide. To a solution of 4-(4-(trifluoromethyl)phenyl)chroman-4-amine (0.345 mmol) (in an unpurified form) and DCM (8 mL) were added DIEA (0.060 mL, 0.345 mmol) and benzoyl chloride (0.040 mL, 0.345 mmol). After stirring for 2 h, LC-MS showed ~40% conversion. The reaction was treated with more benzoyl chloride (0.04 mL). After a further 1 h, the reaction was washed with water (5 mL). The organic layer was concentrated in vacuo, taken up in DCM (1.5 mL) and adsorbed onto a plug of silica gel and chromatographed through a Redi-Sep® pre-packed silica gel column (12 g), eluting with 0-10% EtOAc in hexane, to provide racemic compound as a white solid. The product was separated by preparative SFC (using a ASH (21×250 mm, 5um); mobile phase: 15% isopropanol (20 mM NH3)/liquid CO$_2$, at a flow rate of 70 mL/min] resulting in Peak 1 and 2 fractions with enantiomeric excess >99%). Peak 2 correlates with the (S) enantiomer. MS (ESI, positive ion) m/z: 419.9 (MH+). $^1$H NMR (300 MHz, CDCl$_3$) δ: 7.74-7.85 (m, 2H), 7.60 (d, J=8.3 Hz, 2H), 7.50-7.58 (m, 1H), 7.41-7.50 (m, 4H), 7.18-7.24 (m, 1H), 6.93 (dd, J=8.3, 0.9 Hz, 1H), 6.71-6.88 (m, 2H), 6.50 (s, 1H), 4.23-4.47 (m, 2H), 3.54-3.70 (m, 1H), 2.58 (ddd, J=14.5, 10.5, 4.2 Hz, 1H).

Example 29

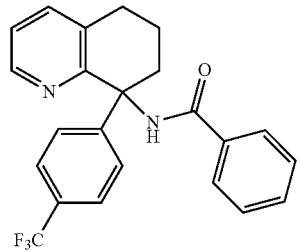 [SMILES: O=C(NC1(c2ccc(C(F)(F)F)cc2)CCCc2cccnc21)c1ccccc1]

N-(8-(4-(trifluoromethyl)phenyl)-5,6,7,8-tetrahydroquinolin-8-yl)benzamide. To a 0° C. solution of 8-(4-(trifluoromethyl)phenyl)-5,6,7,8-tetrahydroquinolin-8-amine (62 mg, 0.136 mmol) and DCM (1 mL) was added DIEA (0.035 mL, 0.201 mmol) and then benzoyl chloride (0.0175 mL, 0.151 mmol) dropwise. After 1 h, the reaction was poured into water and the aqueous layer back extracted with DCM (5 mL). The combined DCM layers were concentrated in vacuo and adsorbed onto a plug of silica gel and chromatographed through a Redi-Sep® pre-packed silica gel column (12 g), eluting with 0-30% EtOAc in hexane, to provide the title compound as a white solid. MS (ESI, positive ion) m/z: 397.0 (MH+). $^1$H NMR (300MHz, CDCl$_3$) δ: 8.46-8.63 (m, 2H), 7.74-7.88 (m, 2H), 7.33-7.66 (m, 8H), 7.24-7.28 (m, 1H), 3.55 (dt, J=14.0, 4.2 Hz, 1H), 2.89 (dd, J=9.6, 6.8 Hz, 1H), 2.54-2.82 (m, 2H), 1.86-2.01 (m, 1H), 1.65-1.83 (m, 1H).

General Amide Formation Procedure for Examples (30-63)

To a solution of (S)-4-(3-fluoro-4-(trifluoromethoxy)phenyl)-3,4-dihydro-2H-pyrano[3,2-b]pyridin-4-amine hydrochloride, the corresponding carboxylic acid (1.2 eq), and DIPEA (2 eq) in DCM or DMF (1 mL) at room temperature was added an amide coupling reagent such as (HATU, TBTU, or EDCI) (1.2 eq.). The reaction was stirred for 1-16 h at room temperature. The reaction was diluted with DMF (1 mL), filtered through a syringe filter, and then purified by preperative reverse phase HPLC (gradient elution 10-100% MeCN/ 0.1% TFA in H$_2$O). The product containing fractions were then combined and the solvent removed by lyophilzation to provide the target compound as the TFA salt; or the product was dissolved in MeOH (1 mL) and washed through PL-HCO$_3$ MP-resin and the resin was further washed with MeOH (2×0.4 mL). The combined filtrates were then concentrated and dried in vacuo to give the title compounds as free bases; or the product containing fractions were concentrated, the solids dissolved in DCM and the organic layer extracted with saturated aqueous NaHCO$_3$, dried, and concentrated to provide the title compounds as free bases.

TABLE 2

Examples 30-63 were prepared via amide formation analogous to the procedures described above

| Ex # | Amine Intermediate | Acid Structure | Product Structure | Product Name | MS M + H |
|---|---|---|---|---|---|
| 30 | | | | methyl 6-((4-(3-fluoro-4-(trifluoromethoxy)phenyl)-3,4-dihydro-2H-pyrano[3,2-b]pyridin-4-yl)carbamoyl)nicotinate | 492.0 |
| 31 | | | | 6-oxo-N-(8-(4-(trifluoromethyl)phenyl)-5,6,7,8-tetrahydroquinolin-8-yl)-1,6-dihydropyridine-3-carboxamide | 414.0 |
| 32 | | | | (S)-6-methoxy-N-(4-(4-(trifluoromethyl)phenyl)-3,4-dihydro-2H-pyrano[3,2-b]pyridin-4-yl)nicotinamide | 430.1 |

TABLE 2-continued

Examples 30-63 were prepared via amide formation analogous to the procedures described above

| Ex # | Amine Intermediate | Acid Structure | Product Structure | Product Name | MS M + H |
|---|---|---|---|---|---|
| 33 | | | | (S)-2-oxo-N-(4-(4-(trifluoromethyl)phenyl)-3,4-dihydro-2H-pyrano[3,2-b]pyridin-4-yl)-1,2,3,4-tetrahydroquinoline-6-carboxamide | 468.0 |
| 34 | | | | (S)-N-(4-(4-(trifluoromethyl)phenyl)-3,4-dihydro-2H-pyrano[3,2-b]pyridin-4-yl)-1H-indazole-6-carboxamide | 439.1 |
| 35 | | | | (S)-N-(4-(4-(trifluoromethyl)phenyl)-3,4-dihydro-2H-pyrano[3,2-b]pyridin-4-yl)pyrimidine-4-carboxamide | 401.0 |
| 36 | | | | (S)-N-(4-(4-(trifluoromethyl)phenyl)-3,4-dihydro-2H-pyrano[3,2-b]pyridin-4-yl)-1H-indole-6-carboxamide | 438.0 |
| 37 | | | | (S)-N-(4-(4-(trifluoromethyl)phenyl)-3,4-dihydro-2H-pyrano[3,2-b]pyridin-4-yl)pyridazine-4-carboxamide | 401.1 |

TABLE 2-continued

Examples 30-63 were prepared via amide formation analogous to
the procedures described above

| Ex # | Amine Intermediate | Acid Structure | Product Structure | Product Name | MS M + H |
|---|---|---|---|---|---|
| 38 | | | | (S)-1-methyl-N-(4-(4-(trifluoromethyl)phenyl)-3,4-dihydro-2H-pyrano[3,2-b]pyridin-4-yl)-1H-indazole-6-carboxamide | 453.0 |
| 39 | | | | (S)-N-(4-(4-(trifluoromethyl)phenyl)-3,4-dihydro-2H-pyrano[3,2-b]pyridin-4-yl)thiazole-5-carboxamide | 406.0 |
| 40 | | | | (S)-5-hydroxy-N-(4-(4-(trifluoromethyl)phenyl)-3,4-dihydro-2H-pyrano[3,2-b]pyridin-4-yl)picolinamide | 416.0 |
| 41 | | | | (S)-N-(4-(4-(trifluoromethyl)phenyl)-3,4-dihydro-2H-pyrano[3,2-b]pyridin-4-yl)isothiazole-5-carboxamide | 406.0 |
| 42 | | | | (S)-1-methyl-N-(4-(4-(trifluoromethyl)phenyl)-3,4-dihydro-2H-pyrano[3,2-b]pyridin-4-yl)-1H-indole-5-carboxamide | 452.1 |

TABLE 2-continued

Examples 30-63 were prepared via amide formation analogous to the procedures described above

| Ex # | Amine Intermediate | Acid Structure | Product Structure | Product Name | MS M + H |
|---|---|---|---|---|---|
| 43 | | | | (S)-5-acetamido-N-(4-(4-(trifluoromethyl)phenyl)-3,4-dihydro-2H-pyrano[3,2-b]pyridin-4-yl)picolinamide | 457.1 |
| 44 | | | | (S)-1-methyl-N-(4-(4-(trifluoromethyl)phenyl)-3,4-dihydro-2H-pyrano[3,2-b]pyridin-4-yl)-1H-indazole-5-carboxamide | 453.0 |
| 45 | | | | (S)-5-oxo-N-(4-(4-(trifluoromethyl)phenyl)-3,4-dihydro-2H-pyrano[3,2-b]pyridin-4-yl)-4,5-dihydropyrazine-2-carboxamide | 417.0 |
| 46 | | | | (S)-N-(4-(4-(trifluoromethyl)phenyl)-3,4-dihydro-2H-pyrano[3,2-b]pyridin-4-yl)isonicotinamide | 400.1 |
| 47 | | | | (S)-6-methoxy-N-(4-(4-(trifluoromethyl)phenyl)-3,4-dihydro-2H-pyrano[3,2-b]pyridin-4-yl)pyridazine-3-carboxamide | 431.1 |

TABLE 2-continued

Examples 30-63 were prepared via amide formation analogous to the procedures described above

| Ex # | Amine Intermediate | Acid Structure | Product Structure | Product Name | MS M + H |
|---|---|---|---|---|---|
| 48 | | | | (S)-N-(4-(4-(trifluoromethyl)phenyl)-3,4-dihydro-2H-pyrano[3,2-b]pyridin-4-yl)nicotinamide | 400.1 |
| 49 | | | | (S)-N-(4-(4-(trifluoromethyl)phenyl)-3,4-dihydro-2H-pyrano[3,2-b]pyridin-4-yl)imidazo[1,2-a]pyridine-7-carboxamide | 439.1 |
| 50 | | | | (S)-N-(4-(3-fluoro-4-(trifluoromethoxy)phenyl)-3,4-dihydro-2H-pyrano[3,2-b]pyridin-4-yl)-5-oxo-4,5-dihydropyrazine-2-carboxamide | 451.0 |
| 51 | | | | (S)-N-(4-(3-fluoro-4-(trifluoromethoxy)phenyl)-3,4-dihydro-2H-pyrano[3,2-b]pyridin-4-yl)-5-hydroxypicolinamide | 450.0 |
| 52 | | | | (S)-N-(4-(3-fluoro-4-(trifluoromethoxy)phenyl)-3,4-dihydro-2H-pyrano[3,2-b]pyridin-4-yl)imidazo[1,2-a]pyridine-6-carboxamide | 473.0 |

TABLE 2-continued

Examples 30-63 were prepared via amide formation analogous to the procedures described above

| Ex # | Amine Intermediate | Acid Structure | Product Structure | Product Name | MS M + H |
|---|---|---|---|---|---|
| 53 | | | | (S)-N-(4-(3-fluoro-4-(trifluoromethoxy)phenyl)-3,4-dihydro-2H-pyrano[3,2-b]pyridin-4-yl)-1-methyl-1H-indazole-5-carboxamide | 487.1 |
| 54 | | | | (S)-N-(4-(3-fluoro-4-(trifluoromethoxy)phenyl)-3,4-dihydro-2H-pyrano[3,2-b]pyridin-4-yl)-2-oxo-1,2,3,4-tetrahydroquinoline-6-carboxamide | 502.0 |
| 55 | | | | (S)-5-fluoro-N-(4-(3-fluoro-4-(trifluoromethoxy)phenyl)-3,4-dihydro-2H-pyrano[3,2-b]pyridin-4-yl)picolinamide | 452.0 |
| 56 | | | | (S)-N-(4-(4-(trifluoromethyl)phenyl)-3,4-dihydro-2H-pyrano[3,2-b]pyridin-4-yl)qumoline-7-carboxamide | 449.8 |

TABLE 2-continued

Examples 30-63 were prepared via amide formation analogous to the procedures described above

| Ex # | Amine Intermediate | Acid Structure | Product Structure | Product Name | MS M + H |
|---|---|---|---|---|---|
| 57 | | | | (S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-5-carboxamide | 489.6 |
| 58 | | | | (S)-6-oxo-N-(4-(4-(trifluoromethoxy)phenyl)-3,4-dihydro-2H-pyrano[3,2-b]pyridin-4-yl)-1,6-dihydropyridine-3-carboxamide | 431.7 |
| 59 | | | | (S)-N-(4-(3-fluoro-4-(trifluoromethoxy)phenyl)-3,4-dihydro-2H-pyrano[3,2-b]pyridin-4-yl)-6-oxo-1,6-dihydropyridine-3-carboxamide | 449.8 |
| 60 | | | | (S)-6-oxo-N-(4-(4-(trifluoromethyl)phenyl)-3,4-dihydro-2H-pyrano[3,2-b]pyridin-4-yl)-1,6-dihydropyridine-3-carboxamide | 416.1 |
| 61 | | | | (S)-2-oxo-N-(4-(4-(trifluoromethyl)phenyl)-3,4-dihydro-2H-pyrano[3,2-b]pyridin-4-yl)-2,3-dihydrobenzo[d]oxazole-5-carboxamide | 456.0 |

TABLE 2-continued

Examples 30-63 were prepared via amide formation analogous to the procedures described above

| Ex # | Amine Intermediate | Acid Structure | Product Structure | Product Name | MS M + H |
|---|---|---|---|---|---|
| 62 | | | | (S)-N-(4-(3-fluoro-4-(trifluoromethoxy)phenyl)-3,4-dihydro-2H-pyrano[3,2-b]pyridin-4-yl)-5-nitropicolinamide | 479.0 |
| 63 | | | | (S)-N5-(4-(3-fluoro-4-(trifluoromethoxy)phenyl)-3,4-dihydro-2H-pyrano[3,2-b]pyridin-4-yl)-N2-methylpyridine-2,5-dicarboxamide | 491.0 |

[1]Purified via preparative SFC [using a ChiralpakAD-H (250 x 30 mm, 5 um); mobile phase: 30% methanol/liquid CO$_2$, at a flow rate of 120 mL/min] resulting in Peak 1 and Peak 2 fractions with enantiomeric excess >99%. Peak 2 correlates with the (S) enantiomer.

Example 64

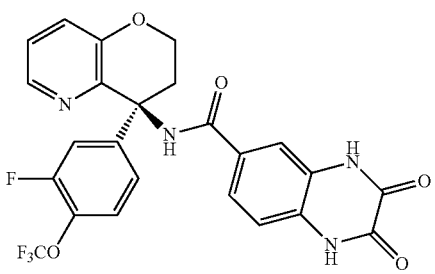 [SMILES: O=C(N[C@]1(c2ccc(OC(F)(F)F)c(F)c2)CCOc2cccnc21)c1ccc2[nH]c(=O)c(=O)[nH]c2c1]

(S)-N-(4-(3-fluoro-4-(trifluoromethoxy)phenyl)-3,4-dihydro-2H-pyrano[3,2-b]pyridin-4-yl)-2,3-dioxo-1,2,3,4-tetrahydroquinoxaline-6-carboxamide. To a solution of 2,3-dioxo-1,2,3,4-tetrahydroquinoxaline-6-carboxylic acid (0.300 g, 1.455 mmol) in DCM (3 mL) was added oxalyl chloride (0.387 mL, 4.37 mmol) and a drop of DMF (anhydrous). The resulting mixture was then stirred at room temperature for 2 h, then the mixture was concentrated in vacuo to give 2,3-dioxo-1,2,3,4-tetrahydroquinoxaline-6-carbonyl chloride. A solution of (S)-4-(3-fluoro-4-(trifluoromethoxy)phenyl)-3,4-dihydro-2H-pyrano[3,2-b]pyridin-4-amine hydrochloride (50 mg, 0.137 mmol) in DCM (1 mL) at 0° C. was added 2,3-dioxo-1,2,3,4-tetrahydroquinoxaline-6-carbonyl chloride (326 mg, 1.453 mmol), and DIEA (0.072 mL, 0.411 mmol). The resulting mixture was stirred at 0° C. for 30 min and then at room temperature for overnight. The reaction was diluted with H2O (5 mL) and EtOAc (7 mL). The mixture was then stirred at room temperature for 30 min. The mixture was then filtered and the organic layer was dried over MgSO$_4$, and concentrated in vacuo. The residue was dissolved in DMSO (2 mL) and solution was purified by preparative HPLC (0-100% MeCN 0.1% TFA/H$_2$O 0.1% TFA) to give the title compound as a white solid. MS (ESI, positive ion) m/z: 517.0 (MH+). $^1$H NMR (400 MHz, d$_4$-MeOH) δ: 8.27 (dd, J=4.8, 1.3 Hz, 1H), 7.60-7.69 (m, 3H), 7.51-7.58 (m, 1H), 7.42-7.48 (m, 2H), 7.24 (d, J=8.4 Hz, 2H), 4.45-4.59 (m, 1H), 4.16-4.35 (m, 1H), 3.07-3.27 (m, 1H), 2.84-3.05 (m, 1H).

Example 65

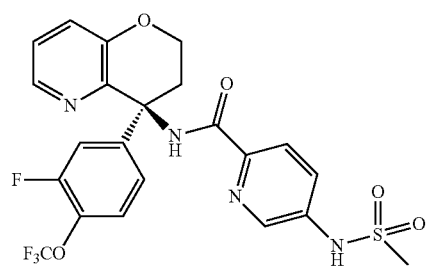 [SMILES: CS(=O)(=O)Nc1ccc(C(=O)N[C@]2(c3ccc(OC(F)(F)F)c(F)c3)CCOc3cccnc32)nc1]

(S)-N-(4-(3-fluoro-4-(trifluoromethoxy)phenyl)-3,4-dihydro-2H-pyrano[3,2-b]pyridin-4-yl)-5-(methylsulfonamido)picolinamide

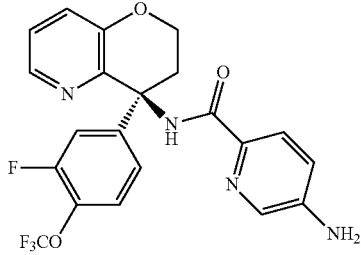 [SMILES: Nc1ccc(C(=O)N[C@]2(c3ccc(OC(F)(F)F)c(F)c3)CCOc3cccnc32)nc1]

Step 1: (S)-5-amino-N-(4-(3-fluoro-4-(trifluoromethoxy)phenyl)-3,4-dihydro-2H-pyrano[3,2-b]pyridin-4-yl)picolinamide. To a solution of (S)-N-(4-(3-fluoro-4-(trifluoromethoxy)phenyl)-3,4-dihydro-2H-pyrano[3,2-b]pyridin-4-yl)-5-nitropicolinamide (105 mg, 0.220 mmol, Example 62) in MeOH (1.3 mL) was added a solution of Pd on carbon (0.012 mL, 0.110 mmol) in EtOAc (0.3 mL). The resulting mixture was stirred at room temperature under H$_2$ (balloon) for 2 h. The mixture was filtered through Celite® brand filter agent t and the Celite® brand filter agent was washed with MeOH (2×2 mL). The filtrate was concentrated in vacuo and the residue purified by silica gel column chromatography using ISCO instrument (70-100% EtOAc/hexane) to give the title compound as a yellow solid. MS (ESI, positive ion) m/z: 449.0 (MH+).

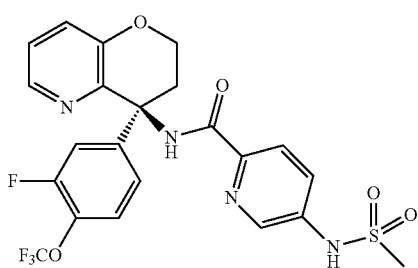 [SMILES: CS(=O)(=O)Nc1ccc(C(=O)N[C@]2(c3ccc(OC(F)(F)F)c(F)c3)CCOc3cccnc32)nc1]

Step 2: (S)-N-(4-(3-fluoro-4-(trifluoromethoxy)phenyl)-3,4-dihydro-2H-pyrano[3,2-b]pyridin-4-yl)-5-(methylsulfonamido)picolinamide. To a solution of (S)-5-amino-N-(4-(3-fluoro-4-(trifluoromethoxy)phenyl)-3,4-dihydro-2H-pyrano[3,2-b]pyridin-4-yl)picolinamide (44 mg, 0.098 mmol) in DCM (0.6 mL) were added methanesulfonyl chloride (8.40 µl, 0.128 mmol) and DIEA (0.022 mL, 0.128 mmol). The resulting mixture was stirred at room temperature overnight. A solution of NaOH (10 N, 2 drops) was added, and the resulting mixture was stirred at room temperature for 2 h. The reaction mixture was filtered and the filtrate concentrated in vacuo. The residue was purified by prep HPLC (0-100% MeCN 0.1% TFA/H$_2$O 0.1% TFA) to give the title compound as a white solid. MS (ESI, positive ion) m/z: 527.0 (MH+). $^1$H NMR (400MHz, d$_4$-MeOH) δ: 8.48 (d, J=2.3 Hz, 1H), 8.30 (dd, J=4.5, 1.4 Hz, 1H), 8.05 (d, J=8.6 Hz, 1H), 7.83 (dd, J=8.6, 2.5 Hz, 1H), 7.37-7.62 (m, 4H), 7.25 (d, J=8.6 Hz, 1H), 4.47 (dt, J=11.9, 4.4 Hz, 1H), 4.05-4.26 (m, 1H), 3.12-3.25 (m, 2H), 3.10 (s, 3H).

Example 66

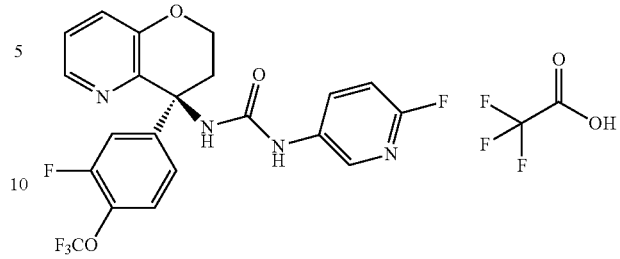

(S)-1-(4-(3-fluoro-4-(trifluoromethoxy)phenyl)-3,4-dihydro-2H-pyrano[3,2-b]pyridin-4-yl)-3-(6-fluoropyridin-3-yl)urea 2,2,2-trifluoroacetate. To a solution of (S)-4-(3-fluoro-4-(trifluoromethoxy)phenyl)-3,4-dihydro-2H-pyrano[3,2-b]pyridin-4-amine hydrochloride (0.030 g, 0.082 mmol) in DCM (0.5 mL) were added 5-amino-2-fluoropyridine (0.014 g, 0.123 mmol), CDI (0.027 g, 0.165 mmol), and TEA (0.046 mL, 0.329 mmol). The resulting mixture was then stirred at room temperature for 18 h. The mixture was filtered and the filtrate was purified by preparative HPLC (0-100% MeCN 0.1% TFA/H2O 0.1% TFA) to give the title compound as a yellow solid. MS (ESI, positive ion) m/z: 467 (MH+). $^1$H NMR (400 MHz, d$_4$-MeOH) δ: 8.29 (dd, J=4.8, 1.3 Hz, 1H), 8.15 (s, 1H), 7.97 (ddd, J=9.1, 6.7, 2.7 Hz, 1H), 7.60-7.67 (m, 1H), 7.52-7.58 (m, 1H), 7.35-7.49 (m, 2H), 7.20 (d, J=8.6 Hz, 1H), 6.99 (dd, J=9.0, 2.9 Hz, 1H), 4.48 (ddd, J=11.8, 6.2, 3.5 Hz, 1H), 4.18 (ddd, J=11.9, 9.5, 2.6 Hz, 1H), 3.04-3.20 (m, 1H), 2.78-2.90 (m, 1H).

Example 67

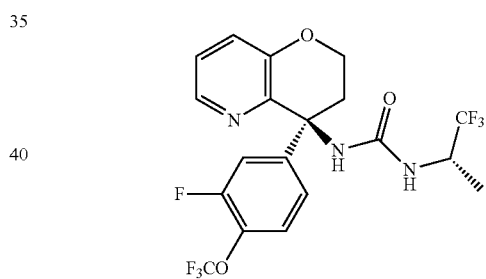

1-((S)-4-(4-(trifluoromethyl)phenyl)-3,4-dihydro-2H-pyrano[3,2-b]pyridin-4-yl)-3-((S)-1,1,1-trifluoropropan-2-yl)urea 2,2,2-trifluoroacetate. To a solution of CDI (41.3 mg, 0.255 mmol) in DCM (0.25 mL) was added (S)-1,1,1-trifluoropropan-2-amine (0.026 mL, 0.255 mmol). The round bottom flask was then sealed, and the mixture was stirred at room temperature for 2.5 h. A solution of 4-(4-(trifluoromethyl)phenyl)-3,4-dihydro-2H-pyrano[3,2-b]pyridin-4-amine (50.0 mg, 0.170 mmol) and DIEA (0.058 mL, 0.340 mmol) in DCM (1 mL) was then added, and the reaction was stirred at room temperature for 20 h. The reaction was diluted with DMF, filtered through a syringe filter, and the reaction purified by RPHPLC (Gemini Axia C18 50×150 mm column, gradient elution 10-100% MeCN/0.1% TFA in H$_2$O). The product containing fractions were combined and the solvent removed by lyophilization to give the title compound as a white solid. MS (ESI, positive ion) m/z: 433.9 (MH+). $^1$H NMR (300 MHz, d$_4$-MeOH) δ: 8.18-8.29 (m, 1H), 7.64-7.71 (m, J=8.2 Hz, 2H), 7.59 (br. s., 1H), 7.47-7.56 (m, 1H), 7.34-7.47 (m, J=8.3 Hz, 2H), 4.25-4.46 (m, 2H), 4.06 (ddd, J=11.9, 9.6, 2.6 Hz, 1H), 3.02-3.20 (m, 1H), 2.54-2.72 (m, 1H), 1.19-1.30 (m, 3H).

General Urea Formation Procedure for Examples (68-74)

To a solution of chromane amine (1 eq.) in DCM was added the desired isocyanate (1.2 eq) and DIEA (1 eq). The resulting mixture was then stirred at room temperature for 18 h. The mixture was then concentrated in vacuo and the product thus obtained was dissolved in DMSO (1 mL). The solution mixture was then purified by preparative HPLC (0%-100% MeCN 0.1% TFA/H2O 0.1% TFA) to give the title compound.

TABLE 3

Examples 68-74 were prepared via urea formation analogous to the procedures described above

| Ex # | Amine Intermediate | Isocyanate Structure | Product Structure | Product Name | MS M + H |
|---|---|---|---|---|---|
| 68 | | | | (S)-1-(4-cyanophenyl)-3-(4-(3-fluoro-4-(trifluoromethoxy)phenyl)-3,4-dihydro-2H-pyrano[3,2-b]pyridin-4-yl)urea | 473.0 |
| 69 | | | | (S)-1-(6-chloropyridin-3-yl)-3-(4-(3-fluoro-4-(trifluoromethoxy)phenyl)-3,4-dihydro-2H-pyrano[3,2-b]pyridin-4-yl)urea | 483.0 |
| 70 | | | | 1-(pyridin-3-yl)-3-(4-(4-(trifluoromethyl)phenyl)chroman-4-yl)urea | 414.0 |
| 71 | | | | 1-(pyridin-3-yl)-3-(8-(4-(trifluoromethyl)phenyl)-5,6,7,8-tetrahydroquinolin-8-yl)urea | 413.0 |
| 72 | | | | (S)-1-(3-fluorophenyl)-3-(4-(4-(trifluoromethyl)phenyl)-3,4-dihydro-2H-pyrano[3,2-b]pyridin-4-yl)urea | 431.7 |

TABLE 3-continued

Examples 68-74 were prepared via urea formation analogous to the procedures described above

| Ex # | Amine Intermediate | Isocyanate Structure | Product Structure | Product Name | MS M + H |
|---|---|---|---|---|---|
| 73 | | | | (S)-1-(pyridin-3-yl)-3-(4-(4-(trifluoro-methyl)phenyl)-3,4-dihydro-2H-pyrano[3,2-b]pyridin-4-yl)urea | 414.8 |
| 74 | | | | (S)-1-(4-fluorophenyl)-3-(4-(4-(trifluoro-methyl)phenyl)-3,4-dihydro-2H-pyrano[3,2-b]pyridin-4-yl)urea | 431.9 |

Example 75

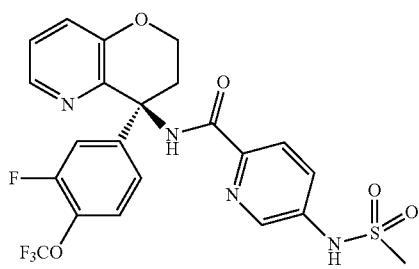 [SMILES: CS(=O)(=O)Nc1ccc(C(=O)N[C@]2(c3ccc(OC(F)(F)F)c(F)c3)CCOc3cccnc32)nc1]

(S)-6-(4-(3-fluoro-4-(trifluoromethoxy)phenyl)-3,4-dihydro-2H-pyrano[3,2-b]pyridin-4-yl)carbamoyl)nicotinic acid. To a solution of (S)-methyl 6-((4-(3-fluoro-4-(trifluoromethoxy)phenyl)-3,4-dihydro-2H-pyrano[3,2-b]pyridin-4-yl)carbamoyl)nicotinate (7.6 g, 15.47 mmol) and THF (30 mL):MeOH (10 mL), was added 5M NaOH (6 mL, 30.0 mmol) dropwise. The solution was stirred at room temperature. After 20 min, LC-MS indicated complete conversion. The reaction was poured into water (30 mL) and treated with 5N HCl (6 mL). The aqueous solution was extracted with EtOAc (3×25 mL). The combined organic layers were washed with brine, dried over $MgSO_4$, and concentrated in vacuo to give the title compound. MS (ESI, positive ion) m/z: 478.0 (MH+). $^1$H NMR (400 MHz, DMSO-$d_6$) δ: 13.72 (br. s., 1H), 9.61 (s, 1H), 9.10 (dd, J=2.0, 0.8 Hz, 1H), 8.47 (dd, J=8.0, 2.2 Hz, 1H), 8.33 (dd, J=3.6, 2.2 Hz, 1H), 8.10-8.23 (m, 1H), 7.48-7.69 (m, 2H), 7.36-7.48 (m, 2H), 7.29 (dt, J=8.8, 1.1 Hz, 1H), 4.42 (dt, J=11.9, 4.1 Hz, 1H), 4.07 (td, J=11.3, 2.2 Hz, 1H), 3.50 (dt, J=12.2, 2.3 Hz, 1H), 2.95 (ddd, J=14.6, 10.9, 3.6 Hz, 1H).

Example 76

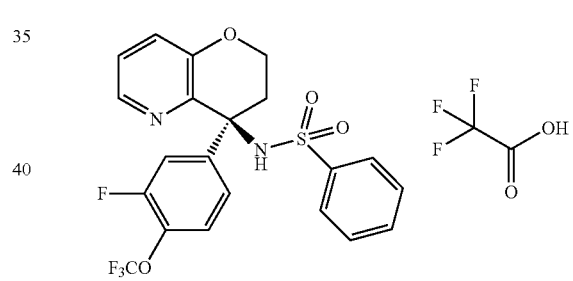

(S)-N-(4-(3-fluoro-4-(trifluoromethoxy)phenyl)-3,4-dihydro-2H-pyrano[3,2-b]pyridin-4-yl)benzenesulfonamide 2,2,2-trifluoroacetate. To a solution of (S)-4-(3-fluoro-4-(trifluoromethoxy)phenyl)-3,4-dihydro-2H-pyrano[3,2-b]pyridin-4-amine hydrochloride (0.030 g, 0.082 mmol) in DCM (0.5 mL) was added benzenesulfonic chloride (0.012 mL, 0.099 mmol) and TEA (0.017 mL, 0.123 mmol). The resulting mixture was then stirred at room temperature for 18 h. The mixture was filtered and the filtrate was purified by preparative HPLC (0-100% MeCN 0.1% TFA/H2O 0.1% TFA) to give the title compound as a yellow solid. MS (ESI, positive ion) m/z: 469 (MH+). $^1$H NMR (400 MHz, $d_4$-MeOH) δ: 8.10 (dd, J=4.5, 1.4 Hz, 1H), 7.56-7.65 (m, 2H), 7.43-7.51 (m, 1H), 7.25-7.40 (m, 4H), 7.20-7.25 (m, 1H), 7.10-7.19 (m, 2H), 4.19-4.46 (m, 1H), 3.87-4.10 (m, 1H), 2.70-2.98 (m, 2H).

Example 77

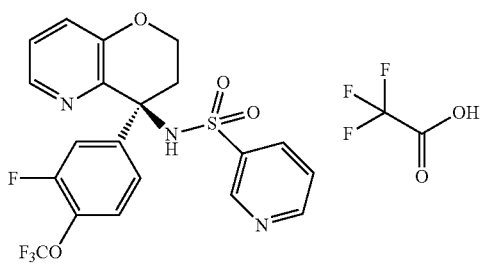

(S)-N-(4-(3-fluoro-4-(trifluoromethoxy)phenyl)-3,4-dihydro-2H-pyrano[3,2-b]pyridin-4-yl)pyridine-3-sulfonamide 2,2,2-trifluoroacetate. To a solution of (S)-4-(3-fluoro-4-(trifluoromethoxy)phenyl)-3,4-dihydro-2H-pyrano[3,2-b]pyridin-4-amine hydrochloride (0.030 g, 0.082 mmol) in DCM (0.5 mL) were added 3-pyridinesulfonylchloride HCl (0.015 mL, 0.099 mmol) and TEA (0.034 mL, 0.247 mmol). The resulting mixture was stirred at room temperature for 18 h. The mixture was filtered and the filtrate was purified by preparative HPLC (0-100% MeCN 0.1% TFA/H2O 0.1% TFA) to give the title compound as a yellow solid. MS (ESI, positive ion) m/z: 470 (MH+). $^1$H NMR (400MHz, $d_4$-MeOH) δ: 8.70 (d, J=1.8 Hz, 1H), 8.62 (dd, J=5.0, 1.5 Hz, 1H), 7.97-8.07 (m, 2H), 7.44 (dd, J=8.0, 4.9 Hz, 1H), 7.30-7.38 (m, 2H), 7.16-7.29 (m, 3H), 4.34-4.46 (m, 1H), 3.97-4.13 (m, 1H), 2.73-3.01 (m, 2H).

Example 78

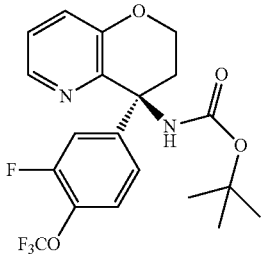 [SMILES: CC(C)(C)OC(=O)N[C@]1(c2ccc(OC(F)(F)F)c(F)c2)CCOc2cccnc21]

(S)-tert-butyl (4-(3-fluoro-4-(trifluoromethoxy)phenyl)-3,4-dihydro-2H-pyrano[3,2-b]pyridin-4-yl)carbamate. To a solution of (S)-4-(3-fluoro-4-(trifluoromethoxy)phenyl)-3,4-dihydro-2H-pyrano[3,2-b]pyridin-4-amine HCl (41.8 mg, 0.115 mmol) and DCM (2 mL) were added TEA (0.032 mL, 0.229 mmol) and di-tert-butyl dicarbonate (0.032 mL, 0.138 mmol). After 72 h, the reaction was washed with water (5 mL) and concentrated in vacuo. The product thus obtained was adsorbed onto a plug of silica gel and chromatographed through a Redi-Sep® pre-packed silica gel column (4 g), eluting with DCM, to provide the title compound as a colorless oil. MS (ESI, positive ion) m/z: 429.0 (MH+). $^1$H NMR (300MHz, CDCl$_3$) δ: 8.22 (t, J=3.0 Hz, 1H), 7.15-7.25 (m, 4H), 7.04-7.14 (m, 1H), 6.32 (br. s., 1H), 4.34 (dt, J=11.7, 4.1 Hz, 1H), 4.00 (td, J=11.4, 2.4 Hz, 1H), 3.13 (d, J=14.6 Hz, 1H), 2.97 (ddd, J=14.7, 11.1, 3.8 Hz, 1H), 1.33-1.49 (m, 9H).

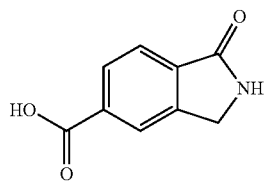 [SMILES: O=C(O)c1ccc2c(c1)CNC2=O]

Intermediate 20

1-oxoisoindoline-5-carboxylic acid

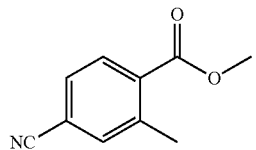

Step 1. methyl 4-cyano-2-methylbenzoate. To a stirred solution of methyl 4-bromo-2-methylbenzoate (2 g, 8.7 mmol) in DMF (20 mL), was added CuCN (1.9 g, 12.2 mmol). The reaction was then stirred at 175° C. for 6 h. The progress of the reaction was monitored by TLC (10% EtOAc in hexanes). The reaction was diluted with EtOAc (10 mL) and filtered through Celite® brand filtering agent. The filtrate was concentrated in vacuo and the material was purified by column chromatography (SiO$_2$, 0-50% EtOAc in hexanes) to give the title compound. MS (ESI pos. ion) m/z: 177.1 (MH+).

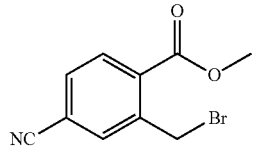

Step 2. methyl 2-(bromomethyl)-4-cyanobenzoate. To a stirred solution of methyl 4-cyano-2-methylbenzoate (1 g, 5.7 mmol) in CCl$_4$ (30 mL), was added NBS (1.4 g, 6.2 mmol), and catalytic AIBN. The reaction mixture was stirred for 48 h at 80° C. The reaction progress was monitored by TLC (10% EtOAc in hexanes). The reaction was cooled to room temperature and diluted with water (25 mL). The organic layer was separated and the aqueous layer extracted with EtOAc (2×50 mL). The combined organic layers were washed with brine (50 mL), dried over Na$_2$SO$_4$, concentrated, and purified by column chromatography silica (60-120 mesh silica with 80-100% EtOAc in petroleum ether) as eluent to give the title compound as a colorless solid. $^1$H NMR (400 MHz, CDCl$_3$): δ 8.05 (d, J=8.0 Hz, 1H), 7.78 (s, 1H), 7.6 (d, J=8.0 Hz, 1H), 4.9 (s, 2H), 4.0 (s, 3H).

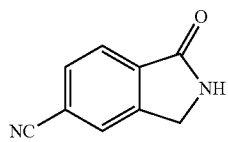

Step 3. 1-oxoisoindoline-5-carbonitrile. To methyl 2-(bromomethyl)-4-cyanobenzoate (0.3 g, 1.18 mmol) in a sealed tube, was added 7N NH$_3$ in MeOH (10 mL). The tube was then sealed and the reaction stirred at 40° C. for 18 h. The reaction progress was monitored by TLC (90% EtOAc in hexanes). The reaction was filtered to give the title compound as a white solid. $^1$H NMR (400MHz, DMSO-d$_6$): δ 8.95 (s, 1H), 8.1 (s, 1H), 7.9 (d, J=8.0 Hz, 1H), 7.8 (d, J=8.0 Hz, 1H), 4.4 (s, 2H).

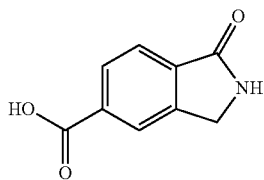

Step 4. 1-oxoisoindoline-5-carboxylic acid. To a stirred solution of 1-oxoisoindoline-5-carbonitrile (0.15 g, 1.1 mmol) in H$_2$O (0.15 mL), were added H$_2$SO$_4$ (0.15 mL) and AcOH (0.15 mL). The reaction was then stirred at 100° C. for 24 h. The reaction progress was monitored by TLC (80% EtOAc in hexanes). The reaction was diluted with water (25 mL) and the organic layer separated. The aqueous layer was then extracted with EtOAc (2×50 mL). The combined organic layers were washed with brine (50 mL), dried over Na$_2$SO$_4$, and concentrated in vacuo to give the title compound as a colorless solid. MS (ESI pos. ion) m/z: 178.2 (MH+).

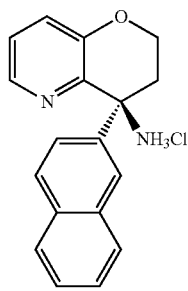

Intermediate 21

(S)-4-(naphthalen-2-yl)-3,4-dihydro-2H-pyrano[3,2-b]pyridin-4-amine hydrochloride

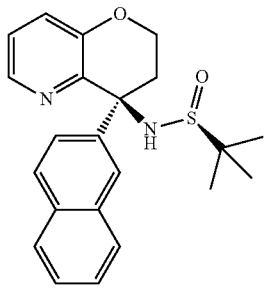 [SMILES: CC(C)(C)[S@](=O)N[C@]1(c2ccc3ccccc3c2)CCOc2cccnc21]

Step 1: (S)-2-methyl-N—((S)-4-(naphthalen-2-yl)-3,4-dihydro-2H-pyrano[3,2-b]pyridin-4-yl)propane-2-sulfinamide. To a solution of magnesium turnings (0.083 mL, 5.80 mmol) and iodine (10 mg) in 2-MeTHF (6 mL) under N$_2$ at room temperature was slowly added a solution of 2-bromonaphthalene (1.0 g, 4.83 mmol) in 2-MeTHF (4 mL). After addition, the mixture was stirred at room temperature for 18 h. The mixture was cooled to −78° C., and a solution of (S,E)-2-methyl-N-(2H-pyrano[3,2-b]pyridin-4(3H)-ylidene)propane-2-sulfinamide (0.490 g, 1.942 mmol) in 2-MeTHF (3 mL) was added dropwise. The mixture was then stirred at −78° C. for 1 h and at room temperature for 5 h. The mixture was quenched with saturated NH$_4$Cl (1.5 mL). The mixture was then extracted with EtOAc (2×5 mL). The combined organic extracts were dried over MgSO$_4$, concentrated, and purified by silica gel column chromatography using ISCO (30-60% EtOAc/hexanes) to give the title compound as a yellow solid. MS (ESI, positive ion) m/z: 381.0 (M+H)

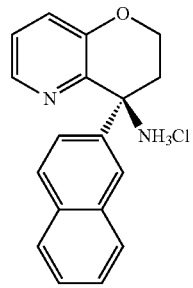

Step 2: (S)-4-(naphthalen-2-yl)-3,4-dihydro-2H-pyrano[3,2-b]pyridin-4-amine hydrochloride. To a solution of (S)-2-methyl-N—((S)-4-(naphthalen-2-yl)-3,4-dihydro-2H-pyrano[3,2-b]pyridin-4-yl)propane-2-sulfinamide (45 mg, 0.118 mmol) in EtOH (0.4 mL) was added 4M HCl in 1,4-dioxane (0.059 mL, 0.237 mmol). The mixture was stirred at room temperature for 1 h. The mixture was concentrated and dried in vacuo to give the title compound, which was used in the next step without further purification. MS (ESI, positive ion) m/z: 277.1 (M+H).

TABLE 4

Examples 79-81 were prepared via amide formation analogous to the procedures described above

| Ex # | Amine Intermediate | Acid Structure | Product Structure | Product Name | MS M + H |
|---|---|---|---|---|---|
| 79 | | | | 1-methyl-6-oxo-N-(4-(4-(trifluoromethyl)phenyl)-3,4-dihydro-2H-pyrano[3,2-b]pyridin-4-yl)-1,6-dihydropyridine-3-carboxamide | 429.8 |
| 80 | | | | 1-oxo-N-(4-(4-(trifluoromethyl)phenyl)-3,4-dihydro-2H-pyrano[3,2-b]pyridin-4-yl)isoindoline-5-carboxamide | 454.3 |
| 81 | | | | (S)-N-(4-(naphthalen-2-yl)-3,4-dihydro-2H-pyrano[3,2-b]pyridin-4-yl)-6-oxo-1,6-dihydropyridine-3-carboxamide | 398.0 |

TABLE 5

$^1$H NMR Data of Examples 1-81.

| Ex. # | Freq., Solvent | $^1$HNMR Data (δ ppm) |
|---|---|---|
| 1 | 300 MHz, d$_4$-MeOH | 8.19 (dd, J = 4.0, 2.0 Hz, 1H), 7.74-7.86 (m, 2H), 7.65 (d, J = 8.6 Hz, 2H), 7.58 (d, J = 8.5 Hz, 2H), 7.52 (d, J = 7.3 Hz, 1H), 7.40-7.49 (m, 2H), 7.28-7.38 (m, 2H), 4.33-4.47 (m, 1H), 4.07 (td, J = 11.1, 2.5 Hz, 1H), 3.33-3.40 (m, 1H), 3.01-3.16 (m, 1H) |
| 2 | 300 MHz, d$_4$-MeOH | 8.18 (dd, J = 4.1, 1.9 Hz, 1H), 7.77-7.92 (m, 2H), 7.61-7.71 (m, J = 8.5 Hz, 2H), 7.51-7.61 (m, J = 8.6 Hz, 2H), 7.26-7.39 (m, 2H), 7.10-7.25 (m, 2H), 4.31-4.47 (m, 1H), 3.99-4.14 (m, 1H), 3.33-3.42 (m, 1H), 2.94-3.10 (m, 1H) |
| 3 | 400 MHz, CDCl$_3$ | 8.9 (s, 1H), 8.3 (m, 1H), 7.81 (d, J = 7.2 Hz, 1H), 7.6 (s, 1H), 7.5-7.6 (m, 2H), 7.45 (t, J = 7.2 Hz, 3H), 7.2-7.4 (m, 3H), 4.3 (m, 1H), 4.01-4.15 (m, 1H), 3.2 (m, 1H), 2.91 (m, 1H) |
| 4 | 300 MHz, CDCl$_3$ | 8.28 (t, J = 2.9 Hz, 1H), 8.05 (s, 1H), 7.40-7.70 (m, 6H), 7.29 (d, J = 3.1 Hz, 2H), 6.68 (d, J = 8.6 Hz, 2H), 4.38 (dt, J = 11.6, 3.6 Hz, 1H), 3.99 (td, J = 12.1, 2.0 Hz, 1H), 3.36-3.47 (m, 1H), 2.97-3.27 (m, 1H) |
| 5 | 300 MHz, CDCl$_3$ | 8.37 (s, 1H), 8.30 (dd, J = 3.6, 2.3 Hz, 1H), 7.70-7.89 (m, 2H), 7.48-7.63 (m, 4H), 7.27 (d, J = 1.9 Hz, 1H), 6.84-6.99 (m, 2H), 4.40 (dt, J = 11.7, 3.8 Hz, 1H), 4.04 (td, J = 12.1, 2.2 Hz, 1H), 3.84 (s, 3H), 3.73-3.82 (m, 1H), 2.89 (ddd, J = 14.7, 12.5, 4.2 Hz, 1H) |

TABLE 5-continued

¹H NMR Data of Examples 1-81.

| Ex. # | Freq., Solvent | ¹HNMR Data (δ ppm) |
|---|---|---|
| 6 | 400 MHz, DMSO-$d_6$ | 8.92 (s, 1H), 8.11-8.12 (m, 1H), 7.88-7.91 (m, 2H), 7.46-7.55 (m, 2H), 7.20-7.31 (m, 5H), 4.30-4.33 (m, 1H), 4.11-4.13 (m, 1H), 3.25-3.34 (m, 1H), 2.84-2.86 (m, 1H). |
| 7 | 400 MHz, DMSO-$d_6$ | 8.89 (s, 1H), 8.12-8.13 (m, 1H), 7.81 (d, J = 7.6 Hz, 1H), 7.42-7.54 (m, 5H), 7.22-7.31 (m, 3H), 4.31-4.36 (m, 1H), 4.11-4.15 (m, 1H), 3.23-3.27 (m, 1H), 2.88-2.91 (m, 1H). |
| 8 | 400 MHz, CDCl$_3$ | δ 8.5 (s, 1H), 8.3 (dd, J = 2.0, 4.0 Hz, 1H), 7.88-7.91 (q, d, J = 5.2, 8.8 Hz, 2H), 7.4 (d, J = 8.8 Hz, 2H), 7.1 (m, 4H), 4.4 (m, 1H), 4.0 (m, 1H), 3.8(m, 1H), 2.84-2.86 (m, 1H). |
| 9 | 400 MHz, CDCl$_3$ | 8.5 (s, 1H), 8.3 (m, 1H), 7.81 (d, J = 7.2 Hz, 1H), 7.42-7.54 (m, 5H), 7.1 (d, J = 7.2 Hz, 3H), 4.4-4.42 (m, 1H), 4.01-4.15 (m, 1H), 3.7-3.8 (m, 1H), 2.88-2.91 (m, 1H). |
| 10 | 400 MHz, DMSO-$d_6$ | 8.9 (s, 1H), 8.1 (dd, J = 2.0, 4.0 Hz, 1H), 7.88-7.91 (q, J = 5.2, 8.8 Hz, 2H), 7.6 (m, 2H), 7.3 (m, 5H), 4.3 (m, 1H), 4.1 (m, 1H), 3.2 (m, 1H), 2.86 (m, 1H). |
| 11 | 400 MHz, DMSO-$d_6$ | 8.73 (s, 1H), 8.14 (dd, J = 0.8, 1.6 Hz, 1H), 7.89 (dd, J = 0.8, 1.6 Hz 2H), 7.32-7.23 (m, 8H), 4.3 (m, 1H), 3.94 (m, 1H), 3.31 (m, 1H), 2.8 (m, 1H). |
| 12 | 400 MHz, DMSO-$d_6$ | 8.67 (s, 1H), 8.16 (dd, J = 1.6, 4 Hz, 1H), 7.80 (dd, J = 5.2, 7.2 Hz, 2H), 7.52 (dd, J = 6.4, 7.6 Hz, 1H), 7.45 (t, J = 8, 15.2 Hz, 2H), 7.34-7.25 (m, 7H), 4.32 (m, 1H), 3.96 (m, 1H), 3.26 (m, 1H), 2.89 (m, 1H). |
| 13 | 400 MHz, DMSO-$d_6$ | 9.14 (s, 1H), 8.84 (d, J = 2 Hz, 1H), 8.09-8.04 (m, 2H), 7.85 (t, J = 6, 7.6 Hz, 3H), 7.55 (t, J = 7.2, 2.8 Hz, 1H), 7.46 (t, J = 8, 15.2 Hz, 2H), 7.33-7.24 (m, 2H), 4.40-4.35 (m, 1H), 4.33-4.29 (m, 1H), 3.25-3.20 (m, 1H), 3.03-2.97 (m, 1H). |
| 14 | 400 MHz, DMSO-$d_6$ | 8.47 (s, 1H), 8.29 (dd, J = 3.8, 2.1 Hz, 1H), 7.73-7.86 (m, 2H), 7.33-7.53 (m, 5H), 7.21-7.30 (m, 4H), 4.39 (dt, J = 11.5, 3.7 Hz, 1H), 3.97-4.09 (m, 1H), 3.75 (dt, J = 14.5, 2.6 Hz, 1H), 2.85 (ddd, J = 14.5, 12.9, 4.1 Hz, 1H) |
| 15 | 400 MHz, CDCl$_3$ | 8.48 (s, 1H), 8.30 (dd, J = 4.1, 1.8 Hz, 1H), 7.74-7.87 (m, 2H), 7.46-7.52 (m, 1H), 7.42 (t, J = 7.3 Hz, 2H), 7.26-7.34 (m, 3H), 7.18-7.25 (m, 1H), 4.41 (dt, J = 11.7, 3.6 Hz, 1H), 3.98-4.11 (m, 1H), 3.79 (dt, J = 14.8, 2.7 Hz, 1H), 2.81 (ddd, J = 14.7, 12.8, 4.2 Hz, 1H) |
| 16 | 400 MHz, CDCl$_3$ | 8.49 (s, 1H), 8.29 (dd, J = 3.7, 2.2 Hz, 1H), 7.72-7.89 (m, 2H), 7.32-7.54 (m, 5H), 7.17-7.32 (m, 3H), 6.89-7.04 (m, 2H), 4.39 (dt, J = 11.2, 3.8 Hz, 1H), 3.95-4.12 (m, 1H), 3.74 (dt, J = 14.6, 2.5 Hz, 1H), 2.86 (ddd, J = 14.5, 13.0, 4.2 Hz, 1H) |
| 17 | 400 MHz, CDCl$_3$ | 8.46 (s, 1H), 8.30 (dd, J = 3.7, 2.2 Hz, 1H), 7.72-7.88 (m, 2H), 7.36-7.54 (m, 4H), 7.32 (t, J = 8.0 Hz, 1H), 7.27-7.30 (m, 2H), 7.11 (d, J = 8.2 Hz, 1H), 4.40 (dt, J = 11.6, 3.7 Hz, 1H), 3.95-4.10 (m, 1H), 3.76 (dt, J = 14.7, 2.5 Hz, 1H), 2.88 (ddd, J = 14.5, 13.0, 4.2 Hz, 1H) |
| 18 | 400 MHz, CDCl$_3$ | 8.40 (s, 1H), 8.27 (t, J = 2.9 Hz, 1H), 7.72-7.87 (m, 2H), 7.43-7.50 (m, 1H), 7.36-7.43 (m, 2H), 7.28 (d, J = 8.4 Hz, 2H), 7.23 (d, J = 2.9 Hz, 2H), 7.09 (d, J = 8.0 Hz, 2H), 4.36 (dt, J = 11.4, 3.6 Hz, 1H), 3.98-4.13 (m, 1H), 3.65 (dt, J = 14.4, 2.5 Hz, 1H), 2.93 (ddd, J = 14.3, 13.0, 4.2 Hz, 1H), 2.29 (s, 3H) |
| 19 | 400 MHz, CDCl$_3$ | 8.46 (s, 1H), 8.31 (dd, J = 4.1, 1.8 Hz, 1H), 7.76-7.83 (m, 2H), 7.47-7.56 (m, 2H), 7.43 (t, J = 7.3 Hz, 2H), 7.33-7.40 (m, 2H), 7.27-7.33 (m, 2H), 4.43 (dt, J = 11.8, 3.9 Hz, 1H), 4.06 (td, J = 12.2, 2.2 Hz, 1H), 3.76-3.89 (m, 1H), 2.85 (ddd, J = 14.7, 12.5, 4.1 Hz, 1H) |
| 20 | 400 MHz, DMSO-$d_6$ | 8.79 (s, 1H), 8.10 (dd, J = 1.57, 4.30 Hz, 1H), 7.78 (d, J = 1.37 Hz, 1H), 7.60-7.71 (m, 3H), 7.57 (d, J = 8.41 Hz, 2H), 7.19-7.35 (m, 2H), 7.12 (d, J = 8.22 Hz, 1H), 4.34 (ddd, J = 2.84, 8.02, 11.25 Hz, 1H), 4.13 (ddd, J = 2.73, 11.15 Hz, 1H), 3.20-3.27 (m, 1H), 2.86 (ddd, J = 2.74, 7.87, 14.23 Hz, 1H). |
| 21 | 400 MHz, DMSO-$d_6$ | 8.81 (s, 1H), 8.12 (dd, J = 1.56, 4.11 Hz, 1H), 7.78 (s, 1H), 7.68 (dd, J = 1.17, 8.22 Hz, 1H), 7.41-7.60 (m, 2H), 7.17-7.36 (m, 3H), 7.11 (d, J = 8.22 Hz, 1H), 4.28-4.38 (m, 1H), 4.07-4.17 (m, 1H), 3.22-3.27 (m, 1H), 2.71-2.91 (m, 1H). |
| 22 | 400 MHz, DMSO-$d_6$ | 11.95 (br s, 1H), 8.83 (s, 1H), 8.11 (d, J = 2.4 Hz, 1H), 7.79 (s, 1H), 7.68 (d, J = 8.4 Hz, 1H), 7.4 (d, J = 8.8 Hz, 2H), 7.2-7.4 (m, 4H), 7.11 (d, J = 8.4 Hz, 1H), 4.30-4.34 (m, 1H), 4.10-4.14 (m, 1H), 2.81-2.86 (m, 1H). |
| 23 | 400 MHz, DMSO-$d_6$ | 11.95 (br s, 1H), 8.82 (s, 1H), 8.11 (dd, J = 1.6, 4.4 Hz, 1H), 7.53-7.60 (dd, J = 1.2, 8.4 Hz, 1H), 7.5 (s, 1H), 7.4 (d, J = 8.8 Hz, 1H), 7.2-7.35 (m, 5H), 4.31-4.38 (m, 1H), 4.09-4.15 (m, 1H), 2.82-2.89 (m, 1H). |
| 24 | 400 MHz, DMSO-$d_6$ | 11.95 (br s, 1H), 8.82 (s, 1H), 8.11 (s, 1H), 7.79 (s, 1H), 7.68 (d, J = 8.0 Hz, 1H), 7.5-7.6 (m, 2H), 7.3 (m, 3H), 7.11 (d, J = 8.4 Hz, 1H), 4.30-4.34 (m, 1H), 4.10-4.14 (m, 1H), 3.2 (m, 1H), 2.81-2.86 (m, 1H). |
| 25 | 400 MHz, DMSO-$d_6$ | 11.80 (br s, 1H), 8.9 (s, 1H), 8.11 (d, J = 4.4 Hz, 1H), 7.53-7.65 (m, 4H), 7.2-7.4 (m, 4H), 4.31-4.38 (t, J = 8.8 Hz, 1H), 4.1-4.8 (t, J = 8.4 Hz, 1H), 3.2 (m, 1H), 2.82-2.89 (m, 1H). |
| 26 | 400 MHz, DMSO-$d_6$ | 11.95 (br s, 1H), 8.57 (s, 1H), 8.13 (s, 1H), 7.72 (s, 1H), 7.66 (d, J = 8.0 Hz, 1H), 7.33-7.32 (m, 2H), 7.29-7.27 (m, 5H), 7.15 (d, J = 8.0 Hz, 1H), 4.33-4.30 (m, 1H), 3.97-3.92 (m, 1H), 3.28 (m, 1H), 2.80-2.77 (m, 1H). |

TABLE 5-continued

¹H NMR Data of Examples 1-81.

| Ex. # | Freq., Solvent | ¹HNMR Data (δ ppm) |
|---|---|---|
| 27 | 400 MHz, DMSO-$d_6$ | 11.99 (s, 1H), 9.16 (s, 1H), 8.83 (s, 1H), 8.09 (dd, J = 2.8, 13.6 Hz 2H), 7.85 (d, J = 8.4 Hz, 1H), 7.64 (d, J = 8.4 Hz, 1H), 7.55 (s, 1H) 7.34-7.25 (m, 3H), 4.36-4.30 (m, 2H), 3.24-3.20 (m, 1H), 3.00-2.98 (m, 1H). |
| 28 | 300 MHz, CDCl$_3$ | 7.74-7.85 (m, 2H), 7.60 (d, J = 8.3 Hz, 2H), 7.50-7.58 (m, 1H), 7.41-7.50 (m, 4H), 7.18-7.24 (m, 1H), 6.93 (dd, J = 8.3, 0.9 Hz, 1H), 6.71-6.88 (m, 2H), 6.50 (s, 1H), 4.23-4.47 (m, 2H), 3.54-3.70 (m, 1H), 2.58 (ddd, J = 14.5, 10.5, 4.2 Hz, 1H) |
| 29 | 300 MHz, CDCl$_3$ | 8.46-8.63 (m, 2H), 7.74-7.88 (m, 2H), 7.33-7.66 (m, 8H), 7.24-7.28 (m, 1H), 3.55 (dt, J = 14.0, 4.2 Hz, 1H), 2.89 (dd, J = 9.6, 6.8 Hz, 1H), 2.54-2.82 (m, 2H), 1.86-2.01 (m, 1H), 1.65-1.83 (m, 1H) |
| 30 | 400 MHz, $d_4$-MeOH | 9.18 (br. s., 1H), 8.51 (d, J = 8.0 Hz, 1H), 8.29 (br. s., 1H), 8.18 (d, J = 7.6 Hz, 1H), 7.36-7.56 (m, 4H), 7.25 (d, J = 8.4 Hz, 1H), 4.46 (d, J = 11.1 Hz, 1H), 4.13 (t, J = 11.1 Hz, 1H), 3.97 (br. s., 3H), 3.18-3.28 (m, 1H), 3.13 (d, J = 10.4 Hz, 1H) |
| 31 | 300 MHz, $d_4$-MeOH | 8.34-8.44 (m, 1H), 8.04 (d, J = 2.2 Hz, 1H), 7.92 (dd, J = 9.6, 2.7 Hz, 1H), 7.57-7.74 (m, 3H), 7.25-7.40 (m, 3H), 6.50 (d, J = 9.5 Hz, 1H), 3.16 (td, J = 12.9, 3.4 Hz, 1H), 2.94-3.09 (m, 1H), 2.80-2.93 (m, 1H), 2.54-2.66 (m, 1H), 1.81-1.95 (m, 1H), 1.50-1.70 (m, 1H) |
| 32 | 300 MHz, CDCl$_3$ | 9.42 (s, 1H), 8.70 (d, J = 2.3 Hz, 1H), 8.33 (dd, J = 5.2, 1.2 Hz, 1H), 8.09 (dd, J = 8.8, 2.5 Hz, 1H), 7.76 (dd, J = 8.6, 1.2 Hz, 1H), 7.56-7.71 (m, 3H), 7.34 (d, J = 8.3 Hz, 2H), 6.75 (d, J = 8.8 Hz, 1H), 4.43-4.56 (m, 1H), 3.91-4.06 (m, 4H), 3.61-3.80 (m, 1H), 2.60 (d, J = 14.2 Hz, 1H) |
| 33 | 300 MHz, CDCl$_3$ | 8.41 (s, 1H), 8.31 (dd, J = 3.7, 2.1 Hz, 1H), 7.74 (s, 1H), 7.66 (s, 1H), 7.50-7.64 (m, 5H), 7.27-7.30 (m, 2H), 6.75 (d, J = 8.2 Hz, 1H), 4.41 (dt, J = 11.7, 3.7 Hz, 1H), 4.03 (td, J = 12.2, 2.2 Hz, 1H), 3.79 (dt, J = 14.8, 2.6 Hz, 1H), 2.94-3.08 (m, 2H), 2.87 (ddd, J = 14.6, 12.7, 4.2 Hz, 1H), 2.54-2.73 (m, 2H) |
| 34 | 300 MHz, $d_4$-MeOH | 9.42 (s, 1H), 8.34 (d, J = 4.1 Hz, 1H), 8.16 (s, 2H), 7.77-7.87 (m, 1H), 7.51-7.77 (m, 5H), 7.40 (d, J = 8.3 Hz, 2H), 4.51 (d, J = 12.0 Hz, 1H), 4.01 (t, J = 11.9 Hz, 1H), 3.68 (d, J = 4.5 Hz, 1H), 2.78 (d, J = 14.2 Hz, 1H) |
| 35 | 300 MHz, CDCl$_3$ | 9.27 (d, J = 1.3 Hz, 1H), 9.02 (d, J = 5.1 Hz, 1H), 8.26 (dd, J = 4.0, 2.0 Hz, 1H), 8.07 (dd, J = 5.0, 1.4 Hz, 1H), 7.63-7.74 (m, J = 8.5 Hz, 2H), 7.52-7.63 (m, J = 8.5 Hz, 2H), 7.36-7.48 (m, 2H), 4.43 (d, J = 11.8 Hz, 1H), 4.00-4.15 (m, 1H), 3.24 (dd, J = 4.3, 2.9 Hz, 1H), 3.17 (dd, J = 10.8, 3.9 Hz, 1H) |
| 36 | 300 MHz, $d_4$-MeOH | 8.31 (d, J = 5.0 Hz, 1H), 7.94-8.01 (m, 1H), 7.75-7.81 (m, 1H), 7.71 (d, J = 8.5 Hz, 2H), 7.60-7.68 (m, 2H), 7.51-7.59 (m, 3H), 7.42 (d, J = 3.1 Hz, 1H), 6.52 (d, J = 3.1 Hz, 1H), 4.49-4.63 (m, 1H), 4.26 (ddd, J = 11.7, 8.6, 2.9 Hz, 1H), 3.17 (ddd, J = 14.5, 8.4, 3.4 Hz, 1H), 2.90 (ddd, J = 14.7, 7.0, 2.9 Hz, 1H) |
| 37 | 300 MHz, $d_4$-MeOH | 9.49-9.56 (m, 1H), 9.37 (dd, J = 5.4, 1.2 Hz, 1H), 8.24 (dd, J = 4.8, 1.5 Hz, 1H), 8.07 (dd, J = 5.3, 2.3 Hz, 1H), 7.72 (d, J = 8.3 Hz, 2H), 7.58-7.67 (m, 1H), 7.54 (d, J = 8.2 Hz, 3H), 4.44-4.56 (m, 1H), 4.11-4.24 (m, 1H), 3.26 (m, 1H), 2.75-2.88 (m, 1H) |
| 38 | 300 MHz, $d_4$-MeOH | 8.30 (dd, J = 4.8, 1.2 Hz, 1H), 8.16 (s, 1H), 8.07 (s, 1H), 7.84 (d, J = 8.6 Hz, 1H), 7.69-7.81 (m, 3H), 7.52-7.69 (m, 4H), 4.51-4.66 (m, 1H), 4.27 (ddd, J = 11.6, 8.4, 2.8 Hz, 1H), 4.13 (s, 3H), 3.19-3.28 (m, 1H), 2.86 (ddd, J = 14.5, 7.2, 2.9 Hz, 1H) |
| 39 | 300 MHz, $d_4$-MeOH | 9.16 (s, 1H), 8.58 (s, 1H), 8.15-8.33 (m, 1H), 7.72 (t, J = 7.9 Hz, 3H), 7.47-7.66 (m, 3H), 4.44-4.60 (m, 1H), 4.22 (ddd, J = 11.6, 8.5, 2.9 Hz, 1H), 3.23 (ddd, J = 14.5, 8.4, 3.1 Hz, 1H), 2.75-2.91 (m, 1H) |
| 40 | 300 MHz, $d_4$-MeOH | 8.27 (dd, J = 4.8, 1.3 Hz, 1H), 8.16 (d, J = 2.6 Hz, 1H), 7.91 (d, J = 8.6 Hz, 1H), 7.61-7.78 (m, 3H), 7.49-7.61 (m, 3H), 7.26 (dd, J = 8.6, 2.8 Hz, 1H), 4.47 (ddd, J = 11.8, 5.6, 3.6 Hz, 1H), 4.09-4.23 (m, 1H), 3.16-3.28 (m, 1H), 2.89-3.03 (m, 1H) |
| 41 | 300 MHz, $d_4$-MeOH | 8.56 (d, J = 1.8 Hz, 1H), 8.24 (dd, J = 4.7, 1.5 Hz, 1H), 7.91 (d, J = 1.8 Hz, 1H), 7.72 (d, J = 8.5 Hz, 2H), 7.46-7.64 (m, 4H), 4.48 (ddd, J = 11.7, 6.5, 3.4 Hz, 1H), 4.16 (ddd, J = 11.8, 9.1, 2.9 Hz, 1H), 3.21-3.30 (m, 1H), 2.88 (ddd, J = 14.5, 6.5, 2.9 Hz, 1H) |
| 42 | 300 MHz, $d_4$-MeOH | 8.32 (dd, J = 5.0, 1.3 Hz, 1H), 8.18 (d, J = 1.5 Hz, 1H), 7.80 (dd, J = 8.5, 1.3 Hz, 1H), 7.62-7.76 (m, 4H), 7.55 (d, J = 8.3 Hz, 2H), 7.45 (d, J = 8.6 Hz, 1H), 7.27 (d, J = 3.2 Hz, 1H), 6.56 (d, J = 2.8 Hz, 1H), 4.50-4.67 (m, 1H), 4.26 (ddd, J = 11.8, 8.6, 2.9 Hz, 1H), 3.84 (s, 3H), 3.17 (ddd, J = 14.6, 8.5, 3.2 Hz, 1H), 2.87 (ddd, J = 14.7, 7.1, 2.9 Hz, 1H) |
| 43 | 300 MHz, $d_4$-MeOH | 8.72-8.82 (m, 1H), 8.19-8.34 (m, 2H), 8.08-8.19 (m, 1H), 7.68-7.83 (m, 3H), 7.64 (dd, J = 8.5, 5.0 Hz, 1H), 7.52 (d, J = 8.2 Hz, 2H), 4.54 (td, J = 7.7, 3.5 Hz, 1H), 4.16-4.32 (m, 1H), 3.19 (ddd, J = 14.4, 8.1, 2.8 Hz, 1H), 2.79 (td, J = 7.2, 4.5 Hz, 1H), 2.20 (s, 3H) |
| 44 | 300 MHz, $d_4$-MeOH | 8.39 (s, 1H), 8.30 (d, J = 4.1 Hz, 1H), 8.13 (s, 1H), 7.86-7.97 (m, 1H), 7.79 (d, J = 7.7 Hz, 1H), 7.59-7.76 (m, 4H), 7.56 (d, J = 8.3 Hz, 2H), 4.51-4.66 (m, 1H), 4.27 (ddd, J = 11.6, 8.4, 2.8 Hz, 1H), 4.10 (s, 3H), 3.19 (ddd, J = 14.5, 8.2, 3.0 Hz, 1H), 2.85 (ddd, J = 14.6, 7.3, 2.9 Hz, 1H) |
| 45 | 300 MHz, $d_4$-MeOH | 8.26 (dd, J = 4.5, 1.5 Hz, 1H), 8.01 (dd, J = 6.5, 1.1 Hz, 2H), 7.68 (d, J = 8.5 Hz, 2H), 7.45-7.61 (m, 4H), 4.45 (dt, J = 11.9, 4.4 Hz, 1H), 4.03-4.20 (m, 1H), 3.01-3.22 (m, 2H) |

TABLE 5-continued

¹H NMR Data of Examples 1-81.

| Ex. # | Freq., Solvent | ¹HNMR Data (δ ppm) |
|---|---|---|
| 46 | 300 MHz, $d_4$-MeOH | 8.74-8.85 (m, 2H), 8.23 (dd, J = 4.6, 1.5 Hz, 1H), 7.97-8.07 (m, 2H), 7.70 (d, J = 8.3 Hz, 2H), 7.52-7.60 (m, 3H), 7.42-7.52 (m, 1H), 4.47 (ddd, J = 11.8, 6.0, 3.5 Hz, 1H), 4.12 (ddd, J = 11.9, 9.5, 2.7 Hz, 1H), 3.23-3.39 (m, 1H), 2.89 (ddd, J = 14.4, 6.0, 2.7 Hz, 1H) |
| 47 | 300 MHz, $d_4$-MeOH | 8.28 (dd, J = 4.6, 1.5 Hz, 1H), 8.10 (d, J = 9.2 Hz, 1H), 7.64-7.76 (m, 2H), 7.55-7.64 (m, 3H), 7.47-7.55 (m, 1H), 7.27 (d, J = 9.2 Hz, 1H), 4.49 (dt, J = 12.1, 4.5 Hz, 1H), 4.06-4.24 (m, 4H), 3.10-3.21 (m, 2H) |
| 48 | 300 MHz, $d_4$-MeOH | 9.13 (d, J = 1.6 Hz, 1H), 8.82 (d, J = 5.3, 1.5 Hz, 1H), 8.56 (dt, J = 8.2, 1.8 Hz, 1H), 8.27 (dd, J = 4.9, 1.4 Hz, 1H), 7.79 (dd, J = 7.8, 5.6 Hz, 1H), 7.67-7.76 (m, 3H), 7.60 (dd, J = 8.6, 4.9 Hz, 1H), 7.54 (d, J = 8.3 Hz, 2H), 4.53 (ddd, J = 11.9, 6.8, 3.4 Hz, 1H), 4.19 (ddd, J = 11.9, 8.9, 2.8 Hz, 1H), 3.19-3.29 (m, 1H), 2.69-2.88 (m, 1H) |
| 49 | 300 MHz, $d_4$-MeOH | 8.49 (dd, J = 7.1, 0.8 Hz, 1H), 8.19 (dd, J = 4.1, 1.9 Hz, 1H), 8.07 (s, 1H), 7.95 (s, 1H), 7.63-7.75 (m, 3H), 7.54-7.63 (m, 2H), 7.30-7.39 (m, 2H), 7.23-7.30 (m, 1H), 4.33-4.48 (m, 1H), 4.06 (td, J = 11.1, 2.6 Hz, 1H), 3.40 (ddd, J = 14.3, 10.5, 3.6 Hz, 1H), 2.94-3.07 (m, 1H) |
| 50 | 300 MHz, $d_4$-MeOH | 8.29 (dd, J = 4.7, 1.5 Hz, 1H), 8.02 (dd, J = 5.3, 1.1 Hz, 2H), 7.61-7.69 (m, 1H), 7.57 (dd, J = 8.6, 4.8 Hz, 1H), 7.35-7.48 (m, 2H), 7.14-7.26 (m, 1H), 4.48 (dt, J = 12.0, 4.7 Hz, 1H), 4.17 (dt, J = 12.4, 6.1 Hz, 1H), 3.07 (t, J = 5.5 Hz, 2H) |
| 51 | 300 MHz, $d_4$-MeOH | 8.30 (dd, J = 4.8, 1.5 Hz, 1H), 8.17 (d, J = 2.6 Hz, 1H), 7.92 (d, J = 8.6 Hz, 1H), 7.71 (dd, J = 8.5, 1.5 Hz, 1H), 7.61 (dd, J = 8.5, 4.8 Hz, 1H), 7.36-7.50 (m, 2H), 7.16-7.33 (m, 2H), 4.50 (ddd, J = 11.9, 6.2, 3.5 Hz, 1H), 4.20 (ddd, J = 12.0, 9.2, 2.9 Hz, 1H), 3.15 (ddd, J = 14.5, 9.4, 3.4 Hz, 1H), 2.91-3.03 (m, 1H) |
| 52 | 300 MHz, $d_4$-MeOH | 9.29-9.39 (m, 1H), 8.24-8.32 (m, 2H), 8.22 (dd, J = 4.1, 1.9 Hz, 1H), 8.12 (d, J = 2.2 Hz, 1H), 7.97 (d, J = 9.4 Hz, 1H), 7.50 (dd, J = 11.8, 2.3 Hz, 1H), 7.36-7.47 (m, 4H), 7.17-7.27 (m, 1H), 4.39-4.49 (m, 1H), 4.02-4.17 (m, 1H), 3.38-3.48 (m, 1H), 2.88-3.03 (m, 1H) |
| 53 | 300 MHz, $d_4$-MeOH | 8.31 (d, J = 0.9 Hz, 1H), 8.22 (dd, J = 3.8, 2.0 Hz, 1H), 8.13 (d, J = 0.7 Hz, 1H), 7.86 (dd, J = 8.9, 1.6 Hz, 1H), 7.61 (d, J = 8.9 Hz, 1H), 7.48 (dd, J = 12.0, 2.3 Hz, 1H), 7.31-7.44 (m, 3H), 7.24-7.31 (m, 1H), 4.35-4.51 (m, 1H), 4.03-4.22 (m, 4H), 3.34-3.40 (m, 1H), 3.05-3.17 (m, 1H) |
| 54 | 300 MHz, DMSO-$d_6$ | 10.28 (s, 1H), 8.67 (s, 1H), 8.13 (dd, J = 4.2, 1.8 Hz, 1H), 7.69 (s, 1H), 7.64 (dd, J = 8.3, 2.0 Hz, 1H), 7.43-7.55 (m, 2H), 7.26-7.36 (m, 2H), 7.22 (d, J = 8.8 Hz, 1H), 6.86 (d, J = 8.2 Hz, 1H), 4.30-4.38 (m, 1H), 4.10-4.19 (m, 1H), 3.15-3.31 (m, 1H), 2.84-2.98 (m, 3H), 2.41-2.46 (m, 2H) |
| 55 | 400 MHz, $d_4$-MeOH | 8.50 (d, J = 2.7 Hz, 1H), 8.25 (t, J = 2.9 Hz, 1H), 8.14 (dd, J = 8.9, 4.4 Hz, 1H), 7.74 (td, J = 8.6, 2.8 Hz, 1H), 7.44 (dd, J = 11.9, 2.3 Hz, 1H), 7.33-7.41 (m, 3H), 7.21-7.27 (m, 1H), 4.40 (dt, J = 11.9, 4.1 Hz, 1H), 4.06 (td, J = 11.6, 2.3 Hz, 1H), 3.35 (m, 1H), 3.10 (ddd, J = 14.7, 11.2, 3.8 Hz, 1H) |
| 56 | 300 MHz, $d_4$-MeOH | 9.07 (dd, J = 4.7, 1.5 Hz, 1H), 8.70 (d, J = 8.3 Hz, 1H), 8.57 (s, 1H), 8.28 (dd, J = 4.8, 1.4 Hz, 1H), 8.18 (d, J = 8.6 Hz, 1H), 8.08-8.15 (m, 1H), 7.81 (dd, J = 8.3, 4.7 Hz, 1H), 7.69-7.78 (m, 2H), 7.50-7.69 (m, 4H), 4.55 (ddd, J = 11.8, 6.6, 3.4 Hz, 1H), 4.22 (ddd, J = 11.9, 9.0, 2.8 Hz, 1H), 3.21-3.28 (m, 1H), 2.88-3.02 (m, 1H) |
| 57 | 300 MHz, $d_4$-MeOH | 8.19 (dd, J = 3.7, 2.2 Hz, 1H), 7.58 (d, J = 8.3 Hz, 1H), 7.50 (br. s., 1H), 7.43 (dd, J = 12.1, 2.3 Hz, 1H), 7.36 (d, J = 7.6 Hz, 1H), 7.30-7.34 (m, 2H), 7.23 (t, J = 7.7 Hz, 2H), 4.33-4.48 (m, 1H), 4.01-4.16 (m, 1H), 3.19-3.29 (m, 1H), 2.99-3.13 (m, 1H) |
| 58 | 300 MHz, $d_4$-MeOH | 8.16 (dd, J = 4.0, 2.0 Hz, 1H), 8.04 (d, J = 2.3 Hz, 1H), 7.91 (dd, J = 9.6, 2.5 Hz, 1H), 7.37-7.46 (m, 2H), 7.21-7.35 (m, 4H), 6.49 (d, J = 9.5 Hz, 1H), 4.34 (dt, J = 11.8, 4.1 Hz, 1H), 3.97 (td, J = 11.4, 2.3 Hz, 1H), 3.41 (ddd, J = 14.4, 11.0, 3.6 Hz, 1H), 2.76-2.88 (m, 1H) |
| 59 | 300 MHz, $d_4$-MeOH | 8.18 (dd, J = 3.9, 1.9 Hz, 1H), 8.04-8.11 (m, 1H), 7.93 (dd, J = 9.6, 2.7 Hz, 1H), 7.35-7.45 (m, 2H), 7.28-7.35 (m, 2H), 7.14-7.24 (m, 1H), 6.51 (dd, J = 9.6, 0.6 Hz, 1H), 4.31-4.44 (m, 1H), 4.07 (td, J = 10.9, 2.6 Hz, 1H), 3.35-3.43 (m, 1H), 2.84-2.96 (m, 1H) |
| 60 | 300 MHz, CDCl$_3$ | 8.27-8.40 (m, 2H), 7.92-8.06 (m, 1H), 7.82 (d, J = 9.6, 2.3 Hz, 1H), 7.43-7.63 (m, 4H), 7.17-7.38 (m, 3H), 6.54 (d, J = 9.6 Hz, 1H), 4.39 (dt, J = 11.5, 3.5 Hz, 1H), 3.90-4.11 (m, 1H), 3.61-3.79 (m, 1H), 2.72-2.96 (m, 1H) |
| 61 | 400 MHz, DMSO-$d_6$ | 8.83 (s, 1H), 8.11 (dd, J = 1.47, 4.21 Hz, 1H), 7.62-7.72 (m, 2H), 7.49-7.60 (m, 3H), 7.47 (d, J = 1.37 Hz, 1H), 7.04-7.36 (m, 3H), 4.34 (ddd, J = 2.74, 8.02, 11.15 Hz, 1H), 4.13 (ddd, J = 2.74, 7.73, 11.05 Hz, 1H), 3.23-3.25 (m, 1H), 2.89 (ddd, J = 2.64, 7.78, 14.23 Hz, 1H). |
| 62 | 400 MHz, $d_4$-MeOH | 8.99 (d, J = 1.6 Hz, 1H), 8.32 (dd, J = 8.0, 2.2 Hz, 1H), 8.21 (dd, J = 4.1, 1.8 Hz, 1H), 8.15 (d, J = 8.0 Hz, 1H), 7.30-7.52 (m, 4H), 7.24 (d, J = 8.6 Hz, 1H), 4.34-4.53 (m, 1H), 3.98-4.17 (m, 1H), 3.36-3.49 (m, 1H), 2.88-3.06 (m, 4H) |
| 63 | 400 MHz, $d_4$-MeOH | 8.27 (dd, J = 4.8, 1.3 Hz, 1H), 7.60-7.69 (m, 3H), 7.51-7.58 (m, 1H), 7.42-7.48 (m, 2H), 7.24 (d, J = 8.4 Hz, 2H), 4.45-4.59 (m, 1H), 4.16-4.35 (m, 1H), 3.07-3.27 (m, 1H), 2.84-3.05 (m, 1H) |

TABLE 5-continued

¹H NMR Data of Examples 1-81.

| Ex. # | Freq., Solvent | ¹HNMR Data (δ ppm) |
|---|---|---|
| 64 | 400 MHz, d₄-MeOH | 8.48 (d, J = 2.3 Hz, 1H), 8.30 (dd, J = 4.5, 1.4 Hz, 1H), 8.05 (d, J = 8.6 Hz, 1H), 7.83 (dd, J = 8.6, 2.5 Hz, 1H), 7.37-7.62 (m, 4H), 7.25 (d, J = 8.6 Hz, 1H), 4.47 (dt, J = 11.9, 4.4 Hz, 1H), 4.05-4.26 (m, 1H), 3.12-3.25 (m, 2H), 3.10 (s, 3H) |
| 65 | 400 MHz, DMSO-d₆ | 9.61 (s, 1H), 9.42 (d, J = 2.2 Hz, 1H), 8.78 (dd, J = 8.6, 2.5 Hz, 1H), 8.32 (dd, J = 3.6, 2.2 Hz, 1H), 8.28 (d, J = 8.8 Hz, 1H), 7.61 (dd, J = 12.0, 2.2 Hz, 1H), 7.54 (t, J = 8.2 Hz, 1H), 7.36-7.45 (m, 2H), 7.28 (d, J = 8.8 Hz, 1H), 4.36-4.53 (m, 1H), 3.98-4.16 (m, 1H), 3.50 (d, J = 16.4 Hz, 1H), 2.84-3.02 (m, 1H) |
| 66 | 400 MHz, d₄-MeOH | 8.29 (dd, J = 4.8, 1.3 Hz, 1H), 8.15 (s, 1H), 7.97 (ddd, J = 9.1, 6.7, 2.7 Hz, 1H), 7.60-7.67 (m, 1H), 7.52-7.58 (m, 1H), 7.35-7.49 (m, 2H), 7.20 (d, J = 8.6 Hz, 1H), 6.99 (dd, J = 9.0, 2.9 Hz, 1H), 4.48 (ddd, J = 11.8, 6.2, 3.5 Hz, 1H), 4.18 (ddd, J = 11.9, 9.5, 2.6 Hz, 1H), 3.04-3.20 (m, 1H), 2.78-2.90 (m, 1H). |
| 67 | 300 MHz, d₄-MeOH | 8.18-8.29 (m, 1H), 7.64-7.71 (m, J = 8.2 Hz, 2H), 7.59 (br. s., 1H), 7.47-7.56 (m, 1H), 7.34-7.47 (m, J = 8.3 Hz, 2H), 4.25-4.46 (m, 1H), 4.06 (ddd, J = 11.9, 9.6, 2.6 Hz, 1H), 3.02-3.20 (m, 1H), 2.54-2.72 (m, 1H), 1.19-1.30 (m, 3H) |
| 68 | 400 MHz, d₄-MeOH | 8.28 (dd, J = 4.7, 1.4 Hz, 1H), 7.56-7.64 (m, 3H), 7.49-7.55 (m, 3H), 7.35-7.48 (m, 2H), 7.19 (d, J = 8.8 Hz, 1H), 4.40-4.54 (m, 1H), 4.09-4.23 (m, 1H), 3.13 (d, J = 3.7 Hz, 1H), 2.86 (dd, J = 5.9, 2.5 Hz, 1H) |
| 69 | 400 MHz, d₄-MeOH | 8.34 (d, J = 2.5 Hz, 1H), 8.26 (dd, J = 4.7, 1.6 Hz, 1H), 7.87 (dd, J = 8.7, 2.8 Hz, 1H), 7.55-7.62 (m, 1H), 7.47-7.54 (m, 1H), 7.36-7.46 (m, 2H), 7.32 (d, J = 8.8 Hz, 1H), 7.14-7.22 (m, 1H), 4.45 (ddd, J = 11.7, 6.1, 3.5 Hz, 1H), 4.14 (ddd, J = 12.0, 9.5, 2.7 Hz, 1H), 3.03-3.19 (m, 1H), 2.78-2.93 (m, 1H) |
| 70 | 300 MHz, d₄-MeOH | 8.48 (d, J = 2.5 Hz, 1H), 8.13 (dd, J = 4.8, 1.3 Hz, 1H), 7.91 (ddd, J = 8.4, 2.6, 1.4 Hz, 1H), 7.61-7.71 (m, J = 8.5 Hz, 2H), 7.50-7.61 (m, J = 8.3 Hz, 2H), 7.31 (dd, J = 8.2, 5.0 Hz, 1H), 7.19 (ddd, J = 8.4, 6.8, 2.0 Hz, 1H), 6.75-6.94 (m, 3H), 4.35 (dd, J = 9.4, 2.4 Hz, 1H), 4.13-4.25 (m, 1H), 3.34-3.39 (m, 1H), 2.40-2.59 (m, 1H) |
| 71 | 300 MHz, CDCl₃ | 11.35 (br. s., 1H), 9.71 (s, 1H), 9.55 (s, 1H), 8.78 (d, J = 5.1 Hz, 1H), 8.28-8.45 (m, 2H), 8.18 (d, J = 8.8 Hz, 1H), 7.91 (dd, J = 7.9, 5.6 Hz, 1H), 7.74 (dd, J = 8.5, 5.6 Hz, 1H), 7.53-7.67 (m, J = 8.3 Hz, 2H), 6.96-7.09 (m, J = 8.0 Hz, 2H), 3.01-3.30 (m, 2H), 2.72-2.94 (m, 1H), 2.27-2.46 (m, 1H), 1.95-2.15 (m, 1H), 1.62 (d, J = 8.9 Hz, 1H) |
| 72 | 300 MHz, d₄-MeOH | 8.12-8.24 (m, 1H), 7.59-7.72 (m, J = 8.3 Hz, 2H), 7.43-7.56 (m, J = 8.3 Hz, 2H), 7.28-7.38 (m, 2H), 7.12-7.28 (m, 2H), 6.94 (d, J = 7.9 Hz, 1H), 6.57-6.72 (m, 1H), 4.29-4.43 (m, 1H), 3.92-4.13 (m, 1H), 3.24-3.30 (m, 1 H), 2.74-2.88 (m, 1H) |
| 73 | 300 MHz, d₄-MeOH | 8.47 (br. s., 1H), 8.19 (dd, J = 3.9, 2.0 Hz, 1H), 8.11 (d, J = 3.9 Hz, 1H), 7.81-7.91 (m, 1H), 7.61-7.70 (m, J = 8.3 Hz, 2H), 7.47-7.55 (m, J = 8.5 Hz, 2H), 7.23-7.39 (m, 3H), 4.31-4.43 (m, 1H), 4.03 (t, J = 9.8 Hz, 1H), 3.25 (s, 1H), 2.77-2.93 (m, 1H) |
| 74 | 300 MHz, d₄-MeOH | 8.17 (dd, J = 4.1, 1.9 Hz, 1H), 7.59-7.71 (m, J = 8.3 Hz, 2H), 7.45-7.55 (m, J = 8.3 Hz, 2H), 7.29-7.37 (m, 2H), 7.21-7.29 (m, 2H), 6.89-7.01 (m, 2H), 4.30-4.44 (m, 1H), 4.04 (t, J = 9.6 Hz, 1H), 3.24-3.30 (m, 1 H), 2.81 (d, J = 5.4 Hz, 1H) |
| 75 | 400 MHz, DMSO-d₆ | 13.72 (br. s., 1H), 9.61 (s, 1H), 9.10 (dd, J = 2.0, 0.8 Hz, 1H), 8.47 (dd, J = 8.0, 2.2 Hz, 1H), 8.33 (dd, J = 3.6, 2.2 Hz, 1H), 8.10-8.23 (m, 1H), 7.48-7.69 (m, 2H), 7.36-7.48 (m, 2H), 7.29 (dt, J = 8.8, 1.1 Hz, 1H), 4.42 (dt, J = 11.9, 4.1 Hz, 1H), 4.07 (td, J = 11.3, 2.2 Hz, 1H), 3.50 (dt, J = 12.2, 2.3 Hz, 1H), 2.95 (ddd, J = 14.6, 10.9, 3.6 Hz, 1H) |
| 76 | 400 MHz, d₄-MeOH | 8.10 (dd, J = 4.5, 1.4 Hz, 1H), 7.56-7.65 (m, 2H), 7.43-7.51 (m, 2H), 7.25-7.40 (m, 4H), 7.20-7.25 (m, 1H), 7.10-7.19 (m, 2H), 4.19-4.46 (m, 1H), 3.87-4.10 (m, 1H), 2.70-2.98 (m, 2H) |
| 77 | 400 MHz, d₄-MeOH | 8.70 (d, J = 1.8 Hz, 1H), 8.62 (dd, J = 5.0, 1.5 Hz, 1H), 7.97-8.07 (m, 2H), 7.44 (dd, J = 8.0, 4.9 Hz, 1H), 7.30-7.38 (m, 2H), 7.16-7.29 (m, 3H), 4.34-4.46 (m, 1H), 3.97-4.13 (m, 1H), 2.73-3.01 (m, 2H) |
| 78 | 300 MHz, CDCl₃ | 8.22 (t, J = 3.0 Hz, 1H), 7.15-7.25 (m, 4H), 7.04-7.14 (m, 1H), 6.32 (br. s., 1H), 4.34 (dt, J = 11.7, 4.1 Hz, 1H), 4.00 (td, J = 11.4, 2.4 Hz, 1H), 3.13 (d, J = 14.6 Hz, 1H), 2.97 (ddd, J = 14.7, 11.1, 3.8 Hz, 1H), 1.33-1.49 (m, 9H) |
| 79 | 400 MHz, CDCl₃ | 8.33 (m, 2H), 8.1 (s, 1H), 7.60 (dd, J = 5.2, 8.8 Hz, 1H), 7.5-7.6 (s, 4H), 7.3 (m, 2H), 6.85 (s, 1H), 6.6-6.5 (d, J = 5.6 Hz, 1H), 4.4 (m, 1H), 4.07-4.11 (m, 1H), 3.8 (m, 1H), 3.6 (s, 1H), 2.8 (m, 1H) |
| 80 | 400 MHz, CDCl₃ | 8.6 (s, 1H), 8.3 (m, 1H), 7.8-8.0 (m, 3H), 7.5 (s, 3H), 7.3 (m, 2H), 6.45 (s, 1H), 4.5 (s, 2H), 4.4 (m, 1H), 4.0 (m, 1H), 3.8 (m, 1H), 2.8-2.9 (m, 1H) |
| 81 | 400 MHz, d₄-MeOH | 8.33 (dd, J = 5.2, 1.3 Hz, 1H), 8.18 (d, J = 2.5 Hz, 1H), 7.96-8.06 (m, 2H), 7.86-7.94 (m, 2H), 7.79-7.84 (m, 1H), 7.74 (dd, J = 8.4, 5.1 Hz, 1H), 7.51-7.59 (m, 4H), 6.55 (d, J = 9.6 Hz, 1H), 4.43-4.66 (m, 1H), 4.19 (ddd, J = 11.9, 9.4, 2.7 Hz, 1H), 3.21-3.30 (m, 1H), 2.71-2.87 (m, 1H) |

Prophetic Examples

The following examples can be made as shown in Scheme 2. The synthesis may be further adapted into an asymmetric synthesis as shown in Scheme 3.

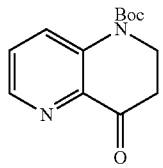

Intermediate 22 tert-butyl 4-oxo-3,4-dihydro-1,5-naphthyridine-1(2H)-carboxylate

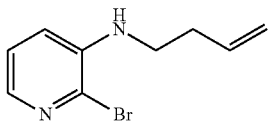

Step 1. 2-bromo-N-(but-3-en-1-yl)pyridin-3-amine. To a solution of 3-amino-2-bromo-pyridine (1 eq, Apollo Scientific Ltd., CAS#39856-58-1) and DMF (0.2 M) is added 60% NaH (1.2 eq). After stirring at room temperature for 30 minutes, the reaction is treated with 4-bromobut-1-ene (1 eq.). Reaction progress is monitored by TLC until judged complete. The reaction mixture is diluted with water and the aqueous solution is extracted with EtOAc. The organic layer is dried over $Na_2SO_4$, and concentrated. The product thus obtained is purified by column chromatography to afford the title compound.

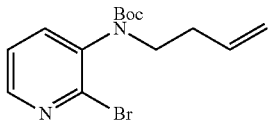 [SMILES: C=CCCN(C(=O)OC(C)(C)C)c1cccnc1Br]

Step 2. tert-butyl (2-bromopyridin-3-yl)(but-3-en-1-yl)carbamate. To a solution of 2-bromo-N-(but-3-en-1-yl)pyridin-3-amine (1 eq.) and DCM (0.2 M) is added $(Boc)_2O$ (1.5 eq.). The solution is stirred at room temperature until judged complete by TLC. The solution is concentrated in vacuo and purified by column chromatography to give the title compound.

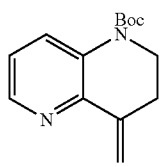 [SMILES: C=C1CCN(C(=O)OC(C)(C)C)c2cccnc21]

Step 3. tert-butyl 4-methylene-3,4-dihydro-1,5-naphthyridine-1(2H)-carboxylate. To a solution of tert-butyl (2-bromopyridin-3-yl)(but-3-en-1-yl)carbamate (1 eq.) in DMF (0.2 M), $PPh_3$ (0.25 eq.), $Pd(OAc)_2$ (0.1 eq), and KOAc (5 eq.), is added, under an argon atmosphere, tetraethyl ammonium chloride hydrate (2 eq.). The flask is purged with argon for 15 min, and the resulting reaction mixture is stirred at 110° C. for 16 h. The reaction progress is monitored by TLC. The reaction mixture is diluted with EtOAc and saturated $NaHCO_3$ solution. The organic layer is separated and dried over $Na_2SO_4$, and concentrated. The compound that may be thus obtained is purified by column chromatography to afford the title compound.

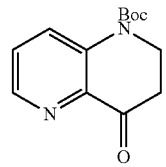 [SMILES: CC(C)(C)OC(=O)N1CCC(=O)c2ncccc21]

Step 4. tert-butyl 4-oxo-3,4-dihydro-1,5-naphthyridine-1(2H)-carboxylate. To a solution of tert-butyl 4-methylene-3,4-dihydro-1,5-naphthyridine-1(2H)-carboxylate (1 eq.) in a mixture of solvents ($MeOH:CHCl_3$) is added a catalytic amount of $NaHCO_3$. The reaction mixture is cooled to −78° C. and purged with $O_3$. Reaction progress is monitored by TLC. After the reaction is judged complete, the reaction mixture is quenched with dimethyl sulfide (5 eq.) at −78° C. The resulting mixture is then stirred for 12 h at ambient temperature. The reaction mixture is diluted with EtOAc and water. The organic layer is washed with water, dried over $Na_2SO_4$, and concentrated in vacuo. The product that may be thus obtained is purified by column chromatography to give the title compound.

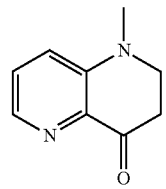

Intermediate 23

1-methyl-2,3-dihydro-1,5-naphthyridin-4(1H)-one

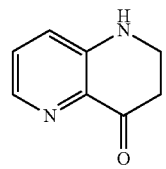 [SMILES: O=C1CCNc2cccnc21]

Step 1: 2,3-dihydro-1,5-naphthyridin-4(1H)-one. To a solution of tert-butyl 4-oxo-3,4-dihydro-1,5-naphthyridine-1(2H)-carboxylate (1 eq.) and 2-MeTHF (0.2 M) is added 4M HCl in dioxane (5 eq.). The reaction is monitored by TLC. The reaction is diluted with EtOAc and washed with saturated $NaHCO_3$. The organic solution is dried over $MgSO_4$ and concentrated in vacuo. The compound that may be thus obtained is purified by column chromatography to give the title compound.

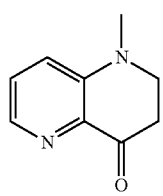

Step 2. 1-methyl-2,3-dihydro-1,5-naphthyridin-4(1H)-one. To a solution of 2,3-dihydro-1,5-naphthyridin-4(1H)-one (1 eq.) and DMF (0.2 M) is added NaH (60%, 1.25 eq). The reaction is stirred for 1 h, and is then treated with iodomethane (1.3 eq.). The reaction is monitored by TLC. The reaction is quenched with water and extracted with EtOAc. The combined organic layers are then dried over MgSO$_4$, concentrated in vacuo, and purified by column chromatography to give the title compound.

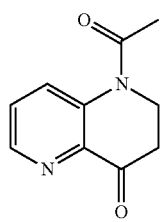

Intermediate 24: 1-acetyl-2,3-dihydro-1,5-naphthyridin-4 (1H)-one. To a solution of 2,3-dihydro-1,5-naphthyridin-4 (1H)-one (1 eq.) and DCM (0.2 eq.) is added DIEA (2.2 eq.) and acetyl chloride (1.2 eq.). The reaction is monitored by TLC. The reaction is washed with water, brine, dried over MgSO$_4$, concentrated in vacuo, and purified by column chromatography to give the title compound.

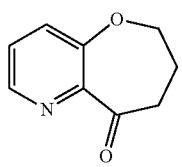 [SMILES: O=C1CCCOc2cccnc21]

Intermediate 25 tert-butyl
7,8-dihydrooxepino[3,2-b]pyridin-9(6H)-one

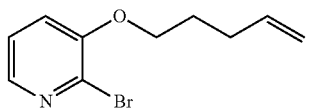

Step 1. 2-bromo-3-(pent-4-en-1-yloxy)pyridine. Diethyl azodicarboxylate (1 eq.) is added dropwise to a stirring mixture of 2-bromo-3-hydroxypyridine (0.92 eq,), pent-4-en-1-ol (0.92 eq), and PPh$_3$ (1.1 eq) in THF (0.2 M) at 0° C. under a N$_2$ atmosphere. The reaction mixture is warmed to 50° C. in an oil bath. Reaction progress is monitored by TLC until judged complete. The reaction mixture is cooled to ambient temperature and diluted with saturated NaHCO$_3$ solution. The aqueous solution is extracted with EtOAc, and the organic layer is dried over Na$_2$SO$_4$ and concentrated. The compound that may be thus obtained is purified by column chromatography to afford the title compound.

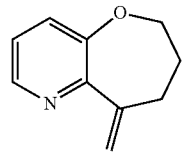

Step 2. 9-methylene-6,7,8,9-tetrahydrooxepino[3,2-b]pyridine. To a solution of 2-bromo-3-(pent-4-en-1-yloxy)pyridine (1 eq.) in DMF (0.2 M), PPh$_3$ (0.25 eq.), Pd(OAc)$_2$ (0.1 eq), and KOAc (5 eq.), is added, under an argon atmosphere, tetraethyl ammonium chloride hydrate (2 eq.). The flask is purged with argon for 15 min, and the resulting reaction mixture is stirred at 110° C. for 16 h. The reaction progress is monitored by TLC. The reaction mixture is diluted with EtOAc and saturated NaHCO$_3$ solution. The organic layer is separated, dried over Na$_2$SO$_4$, and concentrated. The compound that may be thus obtained is purified by column chromatography to afford the title compound.

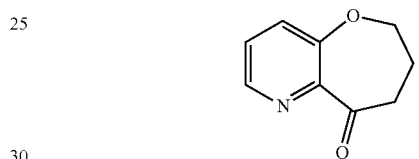

Step 3. tert-butyl 4-oxo-3,4-dihydro-1,5-naphthyridine-1 (2H)-carboxylate. To a solution of 9-methylene-6,7,8,9-tetrahydrooxepino[3,2-b]pyridine (1 eq.) in a mixture of solvents (MeOH:CHCl$_3$) is added a catalytic amount of NaHCO$_3$. The reaction mixture is cooled to –78° C. and purged with O$_3$. Reaction progress is monitored by TLC. After the reaction is judged complete, the reaction mixture is quenched with dimethyl sulfide (5 eq.) at –78° C. The resulting mixture is stirred for 12 h at ambient temperature. The reaction mixture is diluted with EtOAc and water. The organic layer is washed with water, dried over Na$_2$SO$_4$, and concentrated in vacuo. The compound that may be thus obtained is purified by column chromatography to give the title compound.

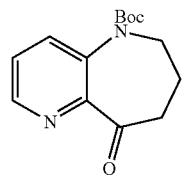 [SMILES: CC(C)(C)OC(=O)N1CCCC(=O)c2ncccc21]

Intermediate 26 tert-butyl 9-oxo-6,7,8,9-tetrahydro-5H-pyrido[3,2-b] azepine-5-carboxylate

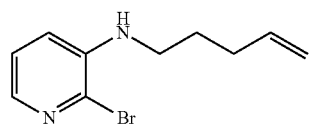

Step 1. 2-bromo-N-(pent-4-en-1-yl)pyridin-3-amine. To a solution of 3-amino-2-bromo-pyridine (1 eq, Apollo Scientific Ltd., CAS#39856-58-1) and DMF (0.2 M) is added 60% NaH (1.2 eq). After stirring at room temperature for 30 minutes, the reaction is treated with 5-bromopent-1-ene (1 eq.). Reaction progress is monitored by TLC until judged complete. The reaction mixture is diluted with water and the aqueous solution is extracted with EtOAc. The organic layer is dried over Na$_2$SO$_4$, and concentrated. The product thus obtained is purified by column chromatography to afford the title compound.

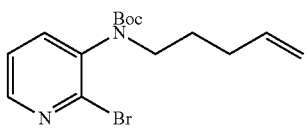 [SMILES: C=CCCCN(C(=O)OC(C)(C)C)c1cccnc1Br]

Step 2. tert-butyl (2-bromopyridin-3-yl)(pent-4-en-1-yl)carbamate. To a solution of 2-bromo-N-(pent-4-en-1-yl)pyridin-3-amine (1 eq.) and DCM (0.2 M) is added (Boc)$_2$O (1.5 eq.). The solution is stirred at room temperature until judged complete by TLC. The solution is concentrated in vacuo and purified by column chromatography to give the title compound.

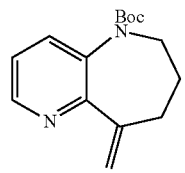 [SMILES: C=C1CCCN(C(=O)OC(C)(C)C)c2cccnc21]

Step 3. tert-butyl 9-methylene-6,7,8,9-tetrahydro-5H-pyrido[3,2-b]azepine-5-carboxylate. To a solution of tert-butyl (2-bromopyridin-3-yl)(pent-4-en-1-yl)carbamate (1 eq.) in DMF (0.2 M), PPh$_3$ (0.25 eq.), Pd(OAc)$_2$ (0.1 eq), and KOAc (5 eq.), is added, under an argon atmosphere, tetraethyl ammonium chloride hydrate (2 eq.). The flask is purged with argon for 15 min, and the resulting reaction mixture is stirred at 110° C. for 16 h. The reaction progress is monitored by TLC. The reaction mixture is diluted with EtOAc and saturated NaHCO$_3$ solution. The organic layer is separated, dried over Na$_2$SO$_4$, and concentrated. The product thus obtained is purified by column chromatography to afford the title compound.

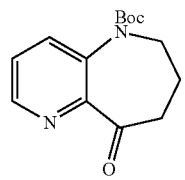

Step 4. tert-butyl 9-oxo-6,7,8,9-tetrahydro-5H-pyrido[3,2-b]azepine-5-carboxylate. To a solution of tert-butyl 9-methylene-6,7,8,9-tetrahydro-5H-pyrido[3,2-b]azepine-5-carboxylate (1 eq.) in a mixture of solvents (MeOH:CHCl$_3$) is added a catalytic amount of NaHCO$_3$. The reaction mixture is cooled to −78° C. and purged with O$_3$. Reaction progress is monitored by TLC. After the reaction is judged complete, the reaction mixture is quenched with dimethyl sulfide (5 eq.) at −78° C. The resulting mixture is stirred for 12 h at ambient temperature. The reaction mixture is diluted with EtOAc and water. The organic layer is washed with water, dried over Na$_2$SO$_4$, and concentrated in vacuo. The compound that may be thus obtained is purified by column chromatography to give the title compound.

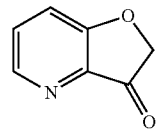

Intermediate 27 furo[3,2-b]pyridin-3(2H)-one

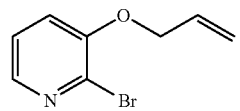

Step 1. 3-(allyloxy)-2-bromopyridine. Diethyl azodicarboxylate (1 eq.) is added dropwise to a stirring mixture of 2-bromo-3-hydroxypyridine (0.92 eq,), allyl alcohol (0.92 eq), and PPh$_3$ (1.1 eq) in THF (0.2 M) at 0° C. under a N$_2$ atmosphere. The reaction mixture is warmed to 50° C. in an oil bath. Reaction progress is monitored by TLC until judged complete. The reaction mixture is cooled to ambient temperature and diluted with saturated NaHCO$_3$ solution. The aqueous solution is extracted with EtOAc, and the organic layer is dried over Na$_2$SO$_4$ and concentrated. The product that may be thus obtained is purified by column chromatography to afford the title compound.

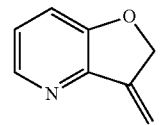

Step 2. 3-methylene-2,3-dihydrofuro[3,2-b]pyridine. To a solution of 3-(allyloxy)-2-bromopyridine (1 eq.) in DMF (0.2 M), PPh$_3$ (0.25 eq.), Pd(OAc)$_2$ (0.1 eq), and KOAc (5 eq.), is added, under an argon atmosphere, tetraethyl ammonium chloride hydrate (2 eq.). The flask is purged with argon for 15 min, and the resulting reaction mixture is stirred at 110° C. for 16 h. The reaction progress is monitored by TLC. The reaction mixture is diluted with EtOAc and saturated NaHCO$_3$ solution. The organic layer is separated and dried over Na$_2$SO$_4$, and concentrated. The product that may be thus obtained is purified by column chromatography to afford the title compound.

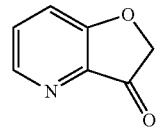

Step 3. furo[3,2-b]pyridin-3(2H)-one. To a solution of 3-methylene-2,3-dihydrofuro[3,2-b]pyridine (1 eq.) in a mixture of solvents (MeOH:CHCl$_3$) is added a catalytic amount of NaHCO$_3$. The reaction mixture is cooled to −78° C. and purged with O₃. Reaction progress is monitored by TLC. After the reaction is judged complete, the reaction mixture is quenched with dimethyl sulfide (5 eq.) at −78° C. The resulting mixture is stirred for 12 h at ambient temperature. The reaction mixture is diluted with EtOAc and water. The organic layer is washed with water, dried over Na₂SO₄, and concentrated in vacuo. The compound that may be thus obtained is purified by column chromatography to give the title compound.

Intermediate 28 tert-butyl 3-oxo-2,3-dihydro-1H-pyrrolo[3,2-b]pyridine-1-carboxylate

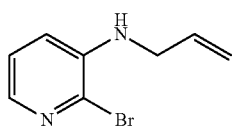

Step 1. N-allyl-2-bromopyridin-3-amine. To a solution of 3-amino-2-bromopyridine (1 eq, Apollo Scientific Ltd., CAS#39856-58-1) and DMF (0.2 M) is added 60% NaH (1.2 eq). After stirring at room temperature for 30 minutes, the reaction is treated with allyl bromide (1 eq.). Reaction progress is monitored by TLC until judged complete. The reaction mixture is diluted with water and the aqueous solution is extracted with EtOAc. The organic layer is dried over Na₂SO₄, and concentrated. The product thus obtained is purified by column chromatography to afford the title compound.

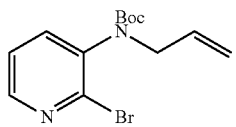 [SMILES: C=CCN(C(=O)OC(C)(C)C)c1cccnc1Br]

Step 2. tert-butyl allyl(2-bromopyridin-3-yl)carbamate. To a solution of N-allyl-2-bromopyridin-3-amine (1 eq.) and DCM (0.2 M) is added (Boc)₂O (1.5 eq.). The solution is stirred at room temperature until judged complete by TLC. The solution is concentrated in vacuo and purified by column chromatography to give the title compound.

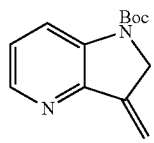

Step 3. tert-butyl 3-methylene-2,3-dihydro-1H-pyrrolo[3,2-b]pyridine-1-carboxylate. To a solution of tert-butyl allyl (2-bromopyridin-3-yl)carbamate (1 eq.) in DMF (0.2 M), PPh₃ (0.25 eq.), Pd(OAc)₂ (0.1 eq), and KOAc (5 eq.), is added, under an argon atmosphere, tetraethyl ammonium chloride hydrate (2 eq.). The flask is purged with argon for 15 min, and the resulting reaction mixture is stirred at 110° C. for 16 h. The reaction progress is monitored by TLC. The reaction mixture is diluted with EtOAc and saturated NaHCO₃ solution. The organic layer is separated and dried over Na₂SO₄, and concentrated. The product that may be thus obtained is purified by column chromatography to afford the title compound.

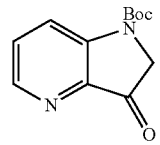 [SMILES: CC(C)(C)OC(=O)N1CC(=O)c2ncccc21]

Step 4. tert-butyl 3-oxo-2,3-dihydro-1H-pyrrolo[3,2-b]pyridine-1-carboxylate. To a solution of tert-butyl 3-methylene-2,3-dihydro-1H-pyrrolo[3,2-b]pyridine-1-carboxylate (1 eq.) in a mixture of solvents (MeOH:CHCl₃) is added a catalytic amount of NaHCO₃. The reaction mixture is cooled to −78° C. and purged with O₃. Reaction progress may be monitored by TLC. After the reaction is judged complete, the reaction mixture is quenched with dimethyl sulfide (5 eq.) at −78° C. The resulting mixture is stirred for 12 h at ambient temperature. The reaction mixture is diluted with EtOAc and water. The organic layer is washed with water, dried over Na₂SO₄, and concentrated in vacuo. The resulting compound is purified by column chromatography to give the title compound.

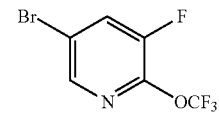

Intermediate 29: 5-bromo-3-fluoro-2-(trifluoromethoxy)pyridine. Reference: Eur. J. Org. Chem. 2010, 6043-6066.

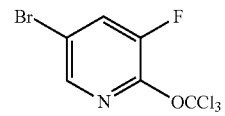

Step 1. 5-bromo-3-fluoro-2-(trichloromethoxy)pyridine. Thiophosgene (1 eq.) in chloroform is added dropwise at 0° C. to a solution of 5-bromo-3-fluoro-2-hydroxypyridine (1 eq.) in aqueous NaOH (5%). The reaction mixture is vigorously stirred for 2 h at 0° C. before being extracted with chloroform. The combined organic layers are washed with dilute hydrochloric acid, water, and dried with Na₂SO₄ before being filtered. The filtrate is saturated with chlorine at 25° C. until the reaction mixture begins to warm up. After 2 h at 25° C., excess chlorine is again added until a yellow solution is obtained. After 24 h at 25° C., excess chlorine is removed with a stream of Ar gas and the solution is concentrated. The pale yellow oil that may be thus obtained may be distilled under vacuum to afford the title compound.

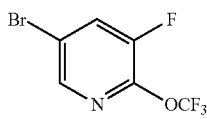

Step 2. 5-bromo-3-fluoro-2-(trifluoromethoxy)pyridine. 5-Bromo-3-fluoro-2-(trichloromethoxy)pyridine (1 eq.) is added dropwise at 120° C. to a mixture of SbF$_3$ (2.0 eq.) and SbCl$_5$ (0.15 eq.). The resulting mixture is stirred for 3 h at 140° C. CC monitoring indicates 100% conversion and disappearance of the OCF$_2$Cl byproduct. The mixture is then cooled to 0° C. and dissolved in DCM. The solution is neutralized with saturated NaHCO$_3$ and potassium fluoride and the aqueous layer is extracted with DCM. The combined organic layers may be dried over Na$_2$SO$_4$ and the solvent distilled off. The product that may be thus obtained is distilled under vacuum to afford the title compound.

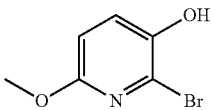

Intermediate 30: 2-bromo-6-methoxypyridin-3-ol. To a 0° C. solution of 2-bromo-6-chloropyridin-3-ol (1 eq.) and DMF (0.2 M) is added NaOMe (2.2 eq.). The solution is allowed to warm to room temperature as the cooling bath expires and allowed to stir at room temperature for 24 h. The reaction is quenched with saturated NH$_4$Cl and diluted with water. The aqueous solution is extracted with EtOAc. The combined EtOAc layers are dried over MgSO$_4$, concentrated in vacuo, and purified by column chromatography to give the title compound.

Intermediate 31

2-bromo-4-chloropyridin-3-ol

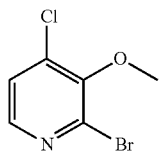

Step 1. 2-bromo-4-chloro-3-methoxypyridine. Phosphorus oxychloride (10 eq.) and 3-methoxy-2-bromo-4(1H)-pyridone (1 eq.) are stirred at 90° C. for 18 h, concentrated in vacuo, and cooled to 20° C. The residue is treated with ice water and adjusted to pH 12 with 40% NaOH, and the product is extracted into DCM. The residue obtained on evaporation of the combined extracts is distilled at reduced pressure to afford the title compound.

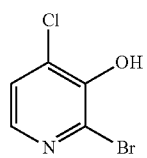

Step 2. 2-bromo-4-chloropyridin-3-ol. To a 0° C. solution of 2-bromo-4-chloro-3-methoxypyridine (1 eq.) and DCM (0.2 M) is added BBr$_3$ (1.2 eq.) dropwise. The reaction is allowed to warm to room temperature as the cooling bath expires. The reaction is stirred at room temperature until judged complete by TLC. The reaction is washed with water, brine, dried over MgSO$_4$, and concentrated in vacuo. The material is purified by column chromatography to give the title compound.

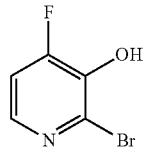

Intermediate 32

2-bromo-4-fluoropyridin-3-ol

Step 1. 4-fluoro-3-methoxypyridin-2-amine. To a solution of 2-amino-4-fluoropyridin-3-ol (1 eq.) and DCM (1 M) is added iodomethane (1.1 eq.), Adogen® 464 (methyltrialkyl (C$_8$-C$_{10}$)ammonium chloride (0.1 eq.), and 40% NaOH (same volume as DCM). The reaction is stirred at room temperature until judged complete by TLC. The DCM layer is separated and the aqueous layer is extracted with DCM. The combined DCM layers are dried over MgSO$_4$, and concentrated in vacuo. The material is purified by column chromatography to give the title compound.

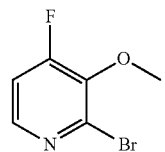

Step 2. 2-bromo-4-fluoro-3-methoxypyridine. To a 0° C. solution of 4-fluoro-3-methoxypyridin-2-amine (1 eq.) and 48% HBr (10 eq.) is added bromine (3 eq.) dropwise, followed by the addition of 40% NaNO$_2$ (5.5 eq.). The reaction is stirred at 0° C. until judged complete by TLC. The reaction mixture is adjusted to pH 13 with 50% NaOH (aq). The aqueous solution is extracted with EtOAc. The combined EtOAc layers are dried over MgSO$_4$, concentrated in vacuo, and purified by column chromatography to give the title compound.

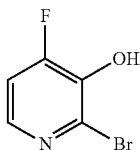

Step 3. 2-bromo-4-fluoropyridin-3-ol. To a 0° C. solution of 2-bromo-4-fluoro-3-methoxypyridine (1 eq.) and DCM (0.2 M) is added BBr$_3$ (1.2 eq.) dropwise. The reaction is allowed to warm to room temperature as the cooling bath expires. The reaction is then stirred at room temperature until judged complete by TLC. The reaction is washed with water, brine, dried over MgSO$_4$, and concentrated in vacuo. The material is purified by column chromatography to give the title compound.

TABLE 6

Prophetic Examples.

| Intermediate # | Starting Pyridine | Ketone Intermediate | Grignard | Grignard Procedure | Intermediate Structure | Intermediate Name |
|---|---|---|---|---|---|---|
| 33 | | | | A | | (S)-4-(3,4-dichlorophenyl)-3,4-dihydro-2H-pyrano[3,2-b]pyridin-4-amine |
| 34 | | | | A | | (S)-4-(2-fluoro-4-(trifluoromethoxy)phenyl)-3,4-dihydro-2H-pyrano[3,2-b]pyridin-4-amine |
| 35 | | | | A | | (S)-4-(2-chloro-4-(trifluoromethoxy)phenyl)-3,4-dihydro-2H-pyrano[3,2-b]pyridin-4-amine |
| 36 | | | | A | | (S)-4-(2-methyl-4-(trifluoromethoxy)phenyl)-3,4-dihydro-2H-pyrano[3,2-b]pyridin-4-amine |
| 37 | | | | A | | (S)-4-(3-chloro-4-(trifluoromethyl)phenyl)-3,4-dihydro-2H-pyrano[3,2-b]pyridin-4-amine |
| 38 | | | | A | | (S)-4-(3-chloro-4-(trifluoromethoxy)phenyl)-3,4-dihydro-2H-pyrano[3,2-b]pyridin-4-amine |

TABLE 6-continued

Prophetic Examples.

| Intermediate # | Starting Pyridine | Ketone Intermediate | Grignard | Grignard Procedure | Intermediate Structure | Intermediate Name |
|---|---|---|---|---|---|---|
| 39 | 2-bromo-3-hydroxypyridine | 2,3-dihydro-4H-pyrano[3,2-b]pyridin-4-one | 3-fluoro-4-(trifluoromethyl)phenylmagnesium bromide | A | (S)-4-(3-fluoro-4-(trifluoromethyl)phenyl)-3,4-dihydro-2H-pyrano[3,2-b]pyridin-4-amine structure | (S)-4-(3-fluoro-4-(trifluoromethyl)phenyl)-3,4-dihydro-2H-pyrano[3,2-b]pyridin-4-amine |
| 40[1] | 2-bromo-6-methyl-3-hydroxypyridine | 6-methyl ketone | 3-fluoro-4-(trifluoromethoxy)phenylmagnesium bromide | A | structure | (S)-4-(3-fluoro-4-(trifluoromethoxy)phenyl)-6-methyl-3,4-dihydro-2H-pyrano[3,2-b]pyridin-4-amine |
| 41[2] | 2-bromo-5-methyl-3-hydroxypyridine | 7-methyl ketone | 3-fluoro-4-(trifluoromethoxy)phenylmagnesium bromide | A | structure | (S)-4-(3-fluoro-4-(trifluoromethoxy)phenyl)-7-methyl-3,4-dihydro-2H-pyrano[3,2-b]pyridin-4-amine |
| 42[3] | 2-bromo-4-methyl-3-hydroxypyridine | 8-methyl ketone | 3-fluoro-4-(trifluoromethoxy)phenylmagnesium bromide | A | structure | (S)-4-(3-fluoro-4-(trifluoromethoxy)phenyl)-8-methyl-3,4-dihydro-2H-pyrano[3,2-b]pyridin-4-amine |
| 43[4] | 2-bromo-6-chloro-3-hydroxypyridine | 6-chloro ketone | 3-fluoro-4-(trifluoromethoxy)phenylmagnesium bromide | A | structure | (S)-6-chloro-4-(3-fluoro-4-(trifluoromethoxy)phenyl)-3,4-dihydro-2H-pyrano[3,2-b]pyridin-4-amine |
| 44[5] | 2-bromo-5-chloro-3-hydroxypyridine | 7-chloro ketone | 3-fluoro-4-(trifluoromethoxy)phenylmagnesium bromide | A | structure | (S)-7-chloro-4-(3-fluoro-4-(trifluoromethoxy)phenyl)-3,4-dihydro-2H-pyrano[3,2-b]pyridin-4-amine |
| 45 | Intermediate 31 | 8-chloro ketone | 3-fluoro-4-(trifluoromethoxy)phenylmagnesium bromide | A | structure | (S)-8-chloro-4-(3-fluoro-4-(trifluoromethoxy)phenyl)-3,4-dihydro-2H-pyrano[3,2-b]pyridin-4-amine |

TABLE 6-continued

Prophetic Examples.

| Intermediate # | Starting Pyridine | Ketone Intermediate | Grignard | Grignard Procedure | Intermediate Structure | Intermediate Name |
| --- | --- | --- | --- | --- | --- | --- |
| 46 | | | | A | | (S)-6-fluoro-4-(3-fluoro-4-(trifluoromethoxy)phenyl)-3,4-dihydro-2H-pyrano[3,2-b]pyridin-4-amine |
| 47[6] | | | | A | | (S)-7-fluoro-4-(3-fluoro-4-(trifluoromethoxy)phenyl)-3,4-dihydro-2H-pyrano[3,2-b]pyridin-4-amine |
| 48 | Intermediate 32 | | | A | | (S)-8-fluoro-4-(3-fluoro-4-(trifluoromethoxy)phenyl)-3,4-dihydro-2H-pyrano[3,2-b]pyridin-4-amine |
| 49 | Intermediate 30 | | | A | | (S)-4-(3-fluoro-4-(trifluoromethoxy)phenyl)-6-methoxy-3,4-dihydro-2H-pyrano[3,2-b]pyridin-4-amine |
| 50[7] | | | | A | | (S)-4-(3-fluoro-4-(trifluoromethoxy)phenyl)-7-methoxy-3,4-dihydro-2H-pyrano[3,2-b]pyridin-4-amine |
| 51[8] | | | | A | | (S)-4-(3-fluoro-4-(trifluoromethoxy)phenyl)-8-methoxy-3,4-dihydro-2H-pyrano[3,2-b]pyridin-4-amine |

TABLE 6-continued

Prophetic Examples.

| Intermediate # | Starting Pyridine | Ketone Intermediate | Grignard | Grignard Procedure | Intermediate Structure | Intermediate Name |
| --- | --- | --- | --- | --- | --- | --- |
| 52 | | | | A | | (S)-4-([1,1'-biphenyl]-4-yl)-3,4-dihydro-2H-pyrano[3,2-b]pyridin-4-amine |
| 53[9] | | | | A | | (S)-4-(3-fluoro-4-(trifluoromethoxy)phenyl)-2,2-dimethyl-3,4-dihydro-2H-pyrano[3,2-b]pyridin-4-amine |
| 54[9] | | | | A | | (S)-4'-(3-fluoro-4-(trifluoromethoxy)phenyl)-3',4'-dihydrospiro[cyclobutane-1,2'-pyrano[3,2-b]pyridin]-4'-amine |
| 55 | | Intermediate 22 | | A | | (S)-tert-butyl 4-amino-4-(3-fluoro-4-(trifluoromethoxy)phenyl)-3,4-dihydro-1,5-naphthyridine-1(2H)-carboxylate |
| 56 | | Intermediate 23 | | A | | (S)-4-(3-fluoro-4-(trifluoromethoxy)phenyl)-1-methyl-1,2,3,4-tetrahydro-1,5-naphthyridin-4-amine |
| 57 | | Intermediate 24 | | A | | (S)-1-(4-amino-4-(3-fluoro-4-(trifluoromethoxy)phenyl)-3,4-dihydro-1,5-naphthyridin-1(2H)-yl)ethanone |

TABLE 6-continued

Prophetic Examples.

| Intermediate # | Starting Pyridine | Ketone Intermediate | Grignard | Grignard Procedure | Intermediate Structure | Intermediate Name |
|---|---|---|---|---|---|---|
| 58 | | Intermediate 25 | 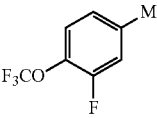 | A | 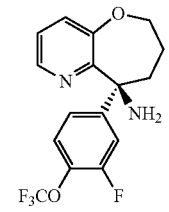 | (S)-9-(3-fluoro-4-(trifluoromethoxy)phenyl)-6,7,8,9-tetrahydrooxepino[3,2-b]pyridin-9-amine |
| 59 | | Intermediate 26 | 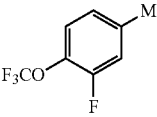 | A | 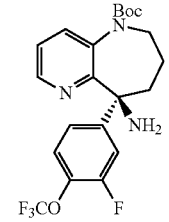 | (S)-tert-butyl 9-amino-9-(3-fluoro-4-(trifluoromethoxy)phenyl)-6,7,8,9-tetrahydro-5H-pyrido[3,2-b]azepine-5-carboxylate |
| 60 | | Intermediate 27 | 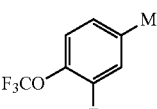 | A | 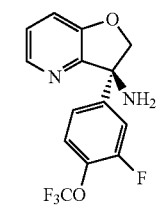 | (S)-3-(3-fluoro-4-(trifluoromethoxy)phenyl)-2,3-dihydrofuro[3,2-b]pyridin-3-amine |
| 61 | | Intermediate 28 | 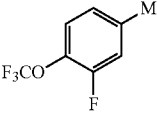 | A | 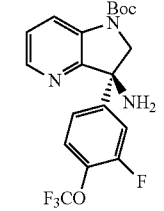 | (R)-tert-butyl 3-amino-3-(3-fluoro-4-(trifluoromethoxy)phenyl)-2,3-dihydro-1H-pyrrolo[3,2-b]pyridine-1-carboxylate |
| 62[10] | 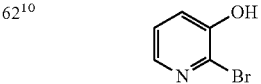 | 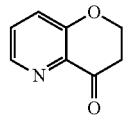 [SMILES: O=C1CCOc2cccnc21] | 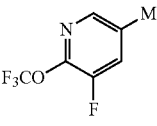 | A | 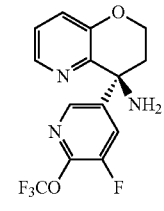 | (S)-4-(5-fluoro-6-(trifluoromethoxy)pyridin-3-yl)-3,4-dihydro-2H-pyrano[3,2-b]pyridin-4-amine |
| 63 | | 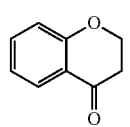 [SMILES: O=C1CCOc2ccccc21] | 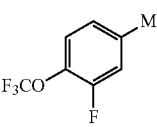 | A | 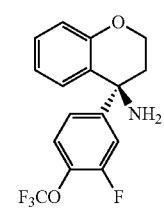 [SMILES: N[C@]1(c2ccc(OC(F)(F)F)c(F)c2)CCOc2ccccc21] | (S)-4-(3-fluoro-4-(trifluoromethoxy)phenyl)chroman-4-amine |

TABLE 6-continued

Prophetic Examples.

| Intermediate # | Starting Pyridine | Ketone Intermediate | Grignard | Grignard Procedure | Intermediate Structure | Intermediate Name |
|---|---|---|---|---|---|---|
| 64 | | (ketone structure) | 3-fluoro-4-(trifluoromethoxy)phenyl MgBr | A | (S)-tetrahydroquinolin-8-amine with 3-fluoro-4-(trifluoromethoxy)phenyl | (S)-8-(3-fluoro-4-(trifluoromethoxy)phenyl)-5,6,7,8-tetrahydroquinolin-8-amine |

[1] The starting pyridine is commercially available from: Frontier Scientific, CAS#23003-35-2.
[2] The starting pyridine is commercially available from: Capot Chemical Co. Ltd., CAS#1003711-30-5.
[3] The starting pyridine is commercially available from: Kingston Chemistry, Cat#KST-D1099.
[4] The starting pyridine is commercially available from: Kingston Chemistry, CAS#1020253-16-0, Cat#KST-G0368.
[5] The starting pyridine is commercially available from: Kingston Chemistry, CAS#127561-70-0, Cat#KST-F0151.
[6] The starting pyridine is commercially available from: Capot Chemical Co. Ltd., CAS#1093758-87-2.
[7] The starting pyridine is commercially available from: Cheminstock Ltd., Cat#C0410.
[8] The starting pyridine is commercially available from: Chemoraga, Inc., Cat#B00939.
[9] WO2009064418 patent application for ketone intermediate procedures.
[10] From intermediate 29.

General Amide Formation Procedure for Examples (82-110)

To a solution of intermediate amine hydrochloride, the corresponding carboxylic acid (1.2 eq), and DIPEA (2 eq) in DCM or DMF (1 mL) at room temperature is added an amide coupling reagent such as (HATU, TBTU, or EDCI) (1.2 eq.). The reaction is stirred for 1-24 h at room temperature. The reaction is diluted with DMF (1 mL), filtered through a syringe filter and purified by preperative reverse phase HPLC (gradient elution 10-100% MeCN/0.1% TFA in $H_2O$). The product containing fractions may then be combined and the solvent removed by lyophilzation to provide the target compound as the TFA salt; or the product is dissolved in MeOH (1 mL) and washed through PL-$HCO_3$ MP-resin, the resin is further washed with MeOH (2×0.4 mL). The combined filtrates are then concentrated and dried in vacuo to give the title compounds as the free base; or the product containing fractions are concentrated, the solids dissolved in DCM and the organic layer extracted with saturated aqueous $NaHCO_3$, the organic layer are dried, and concentrated to provide the title compounds as the free base.

TABLE 7

Examples 82-110 can be prepared via amide formation using methods analogous to those described above

| Ex # | Amine Intermediate | Acid Structure | Product Structure | Product Name |
|---|---|---|---|---|
| 82 | 33 | 6-oxo-1,6-dihydropyridine-3-carboxylic acid | (product structure) | (S)-N-(4-(3,4-dichlorophenyl)-3,4-dihydro-2H-pyrano[3,2-b]pyridin-4-yl)-6-oxo-1,6-dihydropyridine-3-carboxamide |
| 83 | 34 | 6-oxo-1,6-dihydropyridine-3-carboxylic acid | (product structure) | (S)-N-(4-(2-fluoro-4-(trifluoromethoxy)phenyl)-3,4-dihydro-2H-pyrano[3,2-b]pyridin-4-yl)-6-oxo-1,6-dihydropyridine-3-carboxamide |

TABLE 7-continued

Examples 82-110 can be prepared via amide formation using methods analogous to those described above

| Ex # | Amine Intermediate | Acid Structure | Product Structure | Product Name |
|---|---|---|---|---|
| 84 | 35 | | | (S)-N-(4-(2-chloro-4-(trifluoromethoxy)phenyl)-3,4-dihydro-2H-pyrano[3,2-b]pyridin-4-yl)-6-oxo-1,6-dihydropyridine-3-carboxamide |
| 85 | 36 | | | (S)-N-(4-(2-methyl-4-(trifluoromethoxy)phenyl)-3,4-dihydro-2H-pyrano[3,2-b]pyridin-4-yl)-6-oxo-1,6-dihydropyridine-3-carboxamide |
| 86 | 37 | | | (S)-N-(4-(3-chloro-4-(trifluoromethyl)phenyl)-3,4-dihydro-2H-pyrano[3,2-b]pyridin-4-yl)-6-oxo-1,6-dihydropyridine-3-carboxamide |
| 87 | 38 | | | (S)-N-(4-(3-chloro-4-(trifluoromethoxy)phenyl)-3,4-dihydro-2H-pyrano[3,2-b]pyridin-4-yl)-6-oxo-1,6-dihydropyridine-3-carboxamide |
| 88 | 39 | | | (S)-N-(4-(3-fluoro-4-(trifluoromethyl)phenyl)-3,4-dihydro-2H-pyrano[3,2-b]pyridin-4-yl)-6-oxo-1,6-dihydropyridine-3-carboxamide |

TABLE 7-continued

Examples 82-110 can be prepared via amide formation using methods analogous to those described above

| Ex # | Amine Intermediate | Acid Structure | Product Structure | Product Name |
|---|---|---|---|---|
| 89 | 40 | | | (S)-N-(4-(3-fluoro-4-(trifluoromethoxy)phenyl)-6-methyl-3,4-dihydro-2H-pyrano[3,2-b]pyridin-4-yl)-6-oxo-1,6-dihydropyridine-3-carboxamide |
| 90 | 41 | | | (S)-N-(4-(3-fluoro-4-(trifluoromethoxy)phenyl)-7-methyl-3,4-dihydro-2H-pyrano[3,2-b]pyridin-4-yl)-6-oxo-1,6-dihydropyridine-3-carboxamide |
| 91 | 42 | | | (S)-N-(4-(3-fluoro-4-(trifluoromethoxy)phenyl)-8-methyl-3,4-dihydro-2H-pyrano[3,2-b]pyridin-4-yl)-6-oxo-1,6-dihydropyridine-3-carboxamide |
| 92 | 43 | | | (S)-N-(4-(3-fluoro-4-(trifluoromethoxy)phenyl)-6-chloro-3,4-dihydro-2H-pyrano[3,2-b]pyridin-4-yl)-6-oxo-1,6-dihydropyridine-3-carboxamide |
| 93 | 44 | | | (S)-N-(4-(3-fluoro-4-(trifluoromethoxy)phenyl)-7-chloro-3,4-dihydro-2H-pyrano[3,2-b]pyridin-4-yl)-6-oxo-1,6-dihydropyridine-3-carboxamide |

TABLE 7-continued

Examples 82-110 can be prepared via amide formation using methods analogous to those described above

| Ex # | Amine Intermediate | Acid Structure | Product Structure | Product Name |
|---|---|---|---|---|
| 94 | 45 | | | (S)-N-(4-(3-fluoro-4-(trifluoromethoxy)phenyl)-8-chloro-3,4-dihydro-2H-pyrano[3,2-b]pyridin-4-yl)-6-oxo-1,6-dihydropyridine-3-carboxamide |
| 95 | 46 | | | (S)-N-(4-(3-fluoro-4-(trifluoromethoxy)phenyl)-6-fluoro-3,4-dihydro-2H-pyrano[3,2-b]pyridin-4-yl)-6-oxo-1,6-dihydropyridine-3-carboxamide |
| 96 | 47 | | | (S)-N-(4-(3-fluoro-4-(trifluoromethoxy)phenyl)-7-fluoro-3,4-dihydro-2H-pyrano[3,2-b]pyridin-4-yl)-6-oxo-1,6-dihydropyridine-3-carboxamide |
| 97 | 48 | | | (S)-N-(4-(3-fluoro-4-(trifluoromethoxy)phenyl)-8-fluoro-3,4-dihydro-2H-pyrano[3,2-b]pyridin-4-yl)-6-oxo-1,6-dihydropyridine-3-carboxamide |

TABLE 7-continued

Examples 82-110 can be prepared via amide formation using methods analogous to those described above

| Ex # | Amine Intermediate | Acid Structure | Product Structure | Product Name |
|---|---|---|---|---|
| 98 | 49 | | | (S)-N-(4-(3-fluoro-4-(trifluoromethoxy)phenyl)-6-methoxy-3,4-dihydro-2H-pyrano[3,2-b]pyridin-4-yl)-6-oxo-1,6-dihydropyridine-3-carboxamide |
| 99 | 50 | | | (S)-N-(4-(3-fluoro-4-(trifluoromethoxy)phenyl)-7-methoxy-3,4-dihydro-2H-pyrano[3,2-b]pyridin-4-yl)-6-oxo-1,6-dihydropyridine-3-carboxamide |
| 100 | 51 | | | (S)-N-(4-(3-fluoro-4-(trifluoromethoxy)phenyl)-8-methoxy-3,4-dihydro-2H-pyrano[3,2-b]pyridin-4-yl)-6-oxo-1,6-dihydropyridine-3-carboxamide |
| 101 | 52 | | | (S)-N-(4-([1,1'-biphenyl]-4-yl)-3,4-dihydro-2H-pyrano[3,2-b]pyridin-4-yl)-6-oxo-1,6-dihydropyridine-3-carboxamide |

TABLE 7-continued

Examples 82-110 can be prepared via amide formation using methods analogous to those described above

| Ex # | Amine Intermediate | Acid Structure | Product Structure | Product Name |
|---|---|---|---|---|
| 102 | 53 | | | (S)-N-(4-(3-fluoro-4-(trifluoromethoxy)phenyl)-2,2-dimethyl-3,4-dihydro-2H-pyrano[3,2-b]pyridin-4-yl)-6-oxo-1,6-dihydropyridine-3-carboxamide |
| 103 | 54 | | | (S)-N-(4'-(3-fluoro-4-(trifluoromethoxy)phenyl)-3',4'-dihydrospiro[cyclobutane-1,2'-pyrano[3,2-b]pyridin]-4'-yl)-6-oxo-1,6-dihydropyridine-3-carboxamide |
| 104 | 63 | | | (S)-N-(4-(3-fluoro-4-(trifluoromethoxy)phenyl)chroman-4-yl)-6-oxo-1,6-dihydropyridine-3-carboxamide |
| 105 | 64 | | | (S)-N-(8-(3-fluoro-4-(trifluoromethoxy)phenyl)-5,6,7,8-tetrahydroquinolin-8-yl)-6-oxo-1,6-dihydropyridine-3-carboxamide |
| 106 | 56 | | | (S)-N-(4-(3-fluoro-4-(trifluoromethoxy)phenyl)-1-methyl-1,2,3,4-tetrahydro-1,5-naphthyridin-4-yl)-6-oxo-1,6-dihydropyridine-3-carboxamide |

TABLE 7-continued

Examples 82-110 can be prepared via amide formation using methods analogous to those described above

| Ex # | Amine Intermediate | Acid Structure | Product Structure | Product Name |
|---|---|---|---|---|
| 107 | 57 | | | (S)-N-(1-acetyl-4-(3-fluoro-4-(trifluoromethoxy)phenyl)-1,2,3,4-tetrahydro-1,5-naphthyridin-4-yl)-6-oxo-1,6-dihydropyridine-3-carboxamide |
| 108 | 58 | | | (S)-N-(9-(3-fluoro-4-(trifluoromethoxy)phenyl)-6,7,8,9-tetrahydrooxepino[3,2-b]pyridin-9-yl)-6-oxo-1,6-dihydropyridine-3-carboxamide |
| 109 | 59 | | | (S)-N-(3-(3-fluoro-4-(trifluoromethoxy)phenyl)-2,3-dihydrofuro[3,2-b]pyridin-3-yl)-6-oxo-1,6-dihydropyridine-3-carboxamide |
| 110 | 62 | | | (S)-N-(4-(5-fluoro-6-(trifluoromethoxy)pyridin-3-yl)-3,4-dihydro-2H-pyrano[3,2-b]pyridin-4-yl)-6-oxo-1,6-dihydropyridine-3-carboxamide |

The amide coupling may also be followed by an additional step. For example, hydrolysis of an ester is exemplified in Example 75 and may be performed after the amide coupling to provide the compounds in Table 8.

TABLE 8

Examples 111-119 can be prepared via amide formation using methods analogous to those described above followed by ester hydrolysis.

| Ex # | Amine Intermediate | Acid Structure | Product Structure | Product Name |
|---|---|---|---|---|
| 111 | 33 | 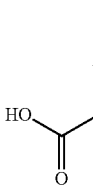 | 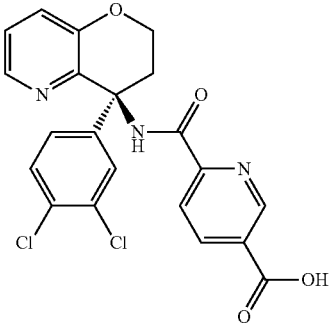 | (S)-6-((4-(3,4-dichlorophenyl)-3,4-dihydro-2H-pyrano[3,2-b]pyridin-4-yl)carbamoyl)nicotinic acid |
| 112 | 16 | 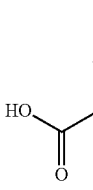 | 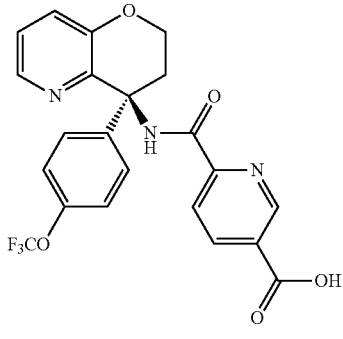 [SMILES: O=C(O)c1ccc(C(=O)N[C@]2(c3ccc(OC(F)(F)F)cc3)CCOc3cccnc32)nc1] | (S)-6-((4-(4-(trifluoromethoxy)phenyl)-3,4-dihydro-2H-pyrano[3,2-b]pyridin-4-yl)carbamoyl)nicotinic acid |
| 113 | 15 | 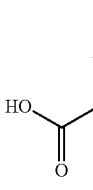 | 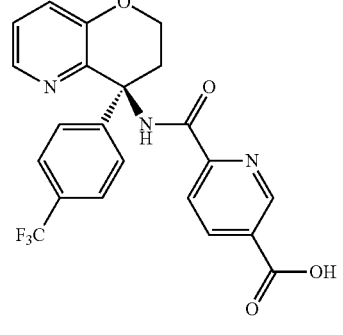 | (S)-6-((4-(4-(trifluoromethyl)phenyl)-3,4-dihydro-2H-pyrano[3,2-b]pyridin-4-yl)carbamoyl)nicotinic acid |
| 114 | 39 | 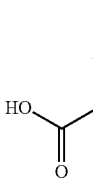 | 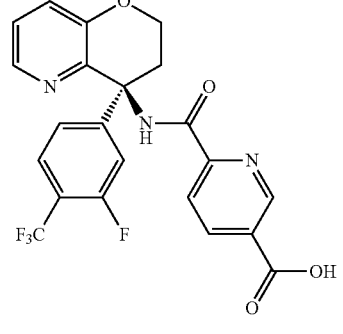 | (S)-6-((4-(3-fluoro-4-(trifluoromethyl)phenyl)-3,4-dihydro-2H-pyrano[3,2-b]pyridin-4-yl)carbamoyl)nicotinic acid |

TABLE 8-continued

Examples 111-119 can be prepared via amide formation using methods analogous to those described above followed by ester hydrolysis.

| Ex # | Amine Intermediate | Acid Structure | Product Structure | Product Name |
|---|---|---|---|---|
| 115 | 37 | | | (S)-6-((4-(3-chloro-4-(trifluoromethyl)phenyl)-3,4-dihydro-2H-pyrano[3,2-b]pyridin-4-yl)carbamoyl)nicotinic acid |
| 116 | 34 | | | (S)-6-((4-(2-fluoro-4-(trifluoromethoxy)phenyl)-3,4-dihydro-2H-pyrano[3,2-b]pyridin-4-yl)carbamoyl)nicotinic acid |
| 117 | 38 | | | (S)-6-((4-(3-chloro-4-(trifluoromethoxy)phenyl)-3,4-dihydro-2H-pyrano[3,2-b]pyridin-4-yl)carbamoyl)nicotinic acid |
| 118 | 63 | | | (S)-6-((4-(3-fluoro-4-(trifluoromethoxy)phenyl)chroman-4-yl)carbamoyl)nicotinic acid |

TABLE 8-continued

Examples 111-119 can be prepared via amide formation using methods analogous to those described above followed by ester hydrolysis.

| Ex # | Amine Intermediate | Acid Structure | Product Structure | Product Name |
|---|---|---|---|---|
| 119 | 64 |  | 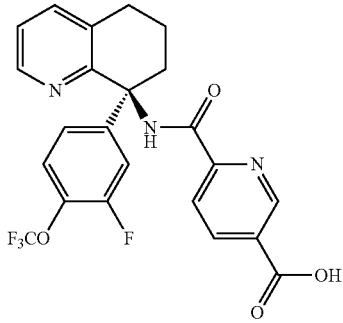 [SMILES: O=C(O)c1ccc(C(=O)N[C@]2(c3ccc(OC(F)(F)F)c(F)c3)CCCc3cccnc32)nc1] | (S)-6-((8-(3-fluoro-4-(trifluoromethoxy)phenyl)-5,6,7,8-tetrahydroquinolin-8-yl)carbamoyl)nicotinic acid |

Deprotection of a Boc protecting group may be performed after the amide coupling to provide the compounds in Table 9. The compounds may be synthesized according to the general procedure amide coupling procedure described above, followed by deprotection.

General Procedure for Boc Deprotection

To a solution of Boc protected material (1 eq) and DCM (0.2 M) is added 4M HCl in dioxane (5 eq.). After 1-24 h, the reaction can be washed with water and saturated NaHCO$_3$. The organic layer may then be concentrated in vacuo and purified by column chromatography to give the title compound.

TABLE 9

Examples 120-122 can be prepared via amide formation using methods analogous to those described above followed by ester hydrolysis.

| Ex # | Amine Intermediate | Acid Structure | Product Structure | Product Name |
|---|---|---|---|---|
| 120 | 55 | 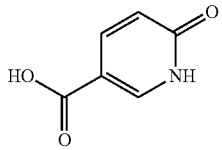 | 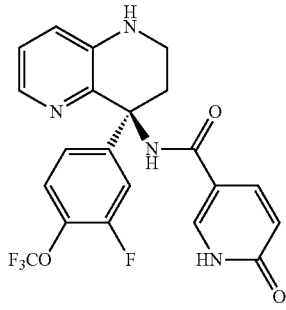 [SMILES: O=C(N[C@]1(c2ccc(OC(F)(F)F)c(F)c2)CCNc2cccnc21)c1ccc(=O)[nH]c1] | (S)-N-(4-(3-fluoro-4-(trifluoromethoxy)phenyl)-1,2,3,4-tetrahydro-1,5-naphthyridin-4-yl)-6-oxo-1,6-dihydropyridine-3-carboxamide |
| 121 | 59 | 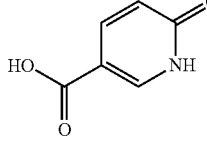 | 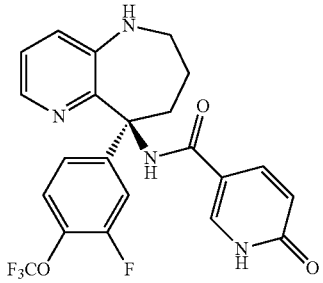 [SMILES: O=C(N[C@]1(c2ccc(OC(F)(F)F)c(F)c2)CCCNc2cccnc21)c1ccc(=O)[nH]c1] | (S)-N-(9-(3-fluoro-4-(trifluoromethoxy)phenyl)-6,7,8,9-tetrahydro-5H-pyrido[3,2-b]azepin-9-yl)-6-oxo-1,6-dihydropyridine-3-carboxamide |

TABLE 9-continued

Examples 120-122 can be prepared via amide formation using methods analogous to those described above followed by ester hydrolysis.

| Ex # | Amine Intermediate | Acid Structure | Product Structure | Product Name |
|---|---|---|---|---|
| 122 | 61 | 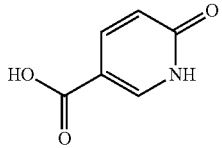 | 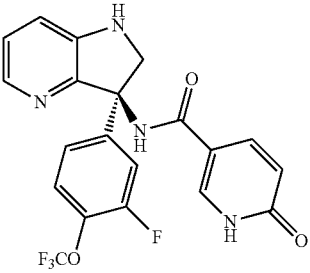 [SMILES: O=C(N[C@]1(c2ccc(OC(F)(F)F)c(F)c2)CNc2cccnc21)c1ccc(=O)[nH]c1] | (R)-N-(3-(3-fluoro-4-(trifluoromethoxy)phenyl)-2,3-dihydro-1H-pyrrolo[3,2-b]pyridin-3-yl)-6-oxo-1,6-dihydropyridine-3-carboxamide |

Stereochemistry

Absolute stereochemistry for Example 2, was determined by comparison of VCD spectra (VCD, Biotools, Inc.) (Stephens, P. J. et. al, Chirality 2008, 20, 643). Comparison of experimental VCD data with ab initio DFT calculations provide for the assigned absolute stereochemistry.

Assays

Luminescence Readout Assay for Measuring Intracellular Calcium.

A stable Chinese hamster ovary cell line expressing human TRPM8 was generated using tetracycline inducible T-REx™ expression system from Invitrogen, Inc. (Carlsbad, Calif.). In order to enable a luminescence readout based on intracellular increase in calcium (Le Poul et al., 2002), the cell line was also co-transfected with pcDNA3.1 plasmid containing jelly fish aequorin cDNA. Twenty four hours before the assay, cells were seeded in 96-well plates and TRPM8 expression was induced with 0.5 µg/ml tetracycline. On the day of the assay, culture media was removed and cells were incubated with assay buffer (Ham's F12 containing 30 mM HEPES) that contained 15 µM coelenterazine (P. J. K, Germany) for 2 h. Potential antagonists were added 2.5 min prior to the addition of agonist, 1 µM icilin, 100 µM L-menthol, or 1 min prior to the addition of cold buffer (<10° C.). The luminescence was measured by a CCD camera based FLASH-luminometer built by Amgen, Inc. A cooling device attached to FLASH luminometer was used for cold activation. Compound activity was calculated using either GraphPad Prism 4.01 (GraphPad Software Inc, San Diego, Calif.) or Genedata Screener.

The following compounds exhibit $IC_{50}$ values of less than 10 µM in the assay described above with icilin activation. Results are shown in Table 10. The prophetic examples may be tested using the same procedure and will be found to inhibit TRPM8.

TABLE 10 hTRPM8 $IC_{50}$'s for Examples 1-81.

| Example | $IC_{50}$ (µM) |
|---|---|
| 1 | 0.014 |
| 2 | 0.086 |
| 3 | 0.025 |
| 4 | 0.009 |
| 5 | 0.021 |
| 6 | 0.034 |
| 7 | 0.032 |
| 8 | 0.075 |
| 9 | 0.038 |
| 10 | 0.163 |
| 11 | 2.57 |
| 12 | 2.07 |
| 13 | 0.883 |
| 14 | 0.091 |
| 15 | 0.054 |
| 16 | 0.357 |
| 17 | 0.060 |
| 18 | 0.162 |
| 19 | 0.012 |
| 20 | 0.010 |
| 21 | 0.007 |
| 22 | 0.014 |
| 23 | 0.012 |
| 24 | 0.023 |
| 25 | 0.019 |
| 26 | 0.014 |
| 27 | 0.046 |
| 28 | 1.66 |
| 29 | 0.143 |
| 30 | 0.019 |
| 31 | 0.784 |
| 32 | 0.051 |
| 33 | 0.005 |
| 34 | 0.024 |
| 35 | 0.2 |
| 36 | 0.036 |
| 37 | 2.62 |
| 38 | 0.020 |
| 39 | 0.269 |
| 40 | 0.007 |
| 41 | 0.087 |
| 42 | 0.024 |
| 43 | 0.111 |
| 44 | 0.008 |
| 45 | 0.038 |
| 46 | 0.358 |
| 47 | 0.082 |
| 48 | 0.481 |
| 49 | 0.043 |
| 50 | 0.008 |
| 51 | 0.005 |
| 52 | 0.016 |
| 53 | 0.015 |
| 54 | 0.011 |
| 55 | 0.022 |
| 56 | 0.021 |
| 57 | 0.004 |
| 58 | 0.021 |

TABLE 10-continued hTRPM8 $IC_{50}$'s for Examples 1-81.

| Example | $IC_{50}$ (µM) |
|---|---|
| 59 | 0.013 |
| 60 | 0.125 |
| 61 | 0.006 |
| 62 | 0.051 |
| 63 | 0.019 |
| 64 | 0.335 |
| 65 | 0.012 |
| 66 | 0.017 |
| 67 | 0.293 |
| 68 | 0.023 |
| 69 | 0.036 |
| 70 | 1.35 |
| 71 | 0.143 |
| 72 | 0.112 |
| 73 | 0.019 |
| 74 | 0.025 |
| 75 | 0.014 |
| 76 | 0.206 |
| 77 | 1.34 |
| 78 | 0.058 |
| 79 | 0.334 |
| 80 | 0.021 |
| 81 | 0.124 |

Icilin Biochemical Challenge Models

Inhibition of Icilin Induced Jumping in Mice

Example compounds at doses ranging from 0.01 to 10 mg/kg may be administered to male C57BL/6 mice (18-25 g, Taconic, n=10/treatment) 1 h before icilin to assess the ability to block the spontaneous jumps induced by icilin (i.p. suspended in 100% PEG400 at 20 mg/kg, 5 mL/kg). The total number of jumps will be recorded during the 10 min post-icilin administration based on the number of photocell beam breaks from the vertical array of open field boxes (Kinder Scientific) while movement of the mice will be restricted within a clear Plexiglas® cylinder 9.5 cm diameter×30 cm height.

Inhibition of Icilin Induced Shaking in Rats

Example compounds at doses ranging from 0.01 to 3 mg/kg (p.o, suspended in 5% Tween80/Oralplus or suspended in 2% HPMC-1% Tween-80 pH2.2 with MSA, 5 mL/kg) can be administered to male Sprague Dawley rats (200-300 g, Harlan, n=6-8/treatment) 2 h before icilin to assess the ability to block the spontaneous wet-dog shake phenomena induced by icilin (i.p., suspended in 100% PEG400 at 0.5 mg/kg, 1 mL/kg or p.o., suspended in 2% HPMC-1% Tween-80 at 3 mg/kg, 2.5 mL/kg). Spontaneous wet-dog shakes may be counted manually by two blinded observers or using LABORAS automation (Metris) for 30 min post-icilin. The Example synthesized and prophetic compounds may be measured using these procedures and will be found to reduce the spontaneous wet dog shake phenomena indicued by icilin.

Cold Pressor Test (CPT) as a Translatable PD Model for TRPM8

The cold pressor test (CPT) was developed as a method to measure blood pressure response following exposure to a cold stimulus and has been used over 70 years in the diagnosis of hypertension and other cardiac autonomic disorders (Hines and Brown 1936). In healthy human subjects, the CPT is typically performed by immersing a subject's hand into ice water (0-5° C.) which triggers, through a vascular sympathetic activation of afferent pain and temperature neurons, an increase in blood pressure. With some modifications, this test has also been utilized in rat to delineate the medullary and spinal pathways mediating the cardio-vascular responses to cold pressor test and to identify neurotransmitters in these pathways (Sapru N et al 2008) or to characterize analgesic compounds (Koltzenburg M et al 2006 and Player M R et al 2011).

TRPM8 antagonists may be evaluated in rat CPT to determine whether they will attenuate the increase in blood pressure resulting from exposure to cold stimulation of the paws and ventral half of the body. Male Sprague-Dawley rats weighing 350-450 g may be instrumented with a unilateral carotid artery-cannula connected to a transducer for measuring blood pressure using a Digi-Med Blood Pressure Analyzer, Model 400 Animals may then be orally administrated with Vehicle (2% HPMC 1% Tween 80 pH 2.2 with MSA) or test compounds at 120 min prior to cold challenge and anesthetized with sodium pentobarbital at 60 mg/kg ip at 100 min prior to cold. Blood pressure may be recorded for 5 min for pre-cold baseline and additional 5 min during immersion of the paws and ventral half of body in ice water. Percent inhibition attributed to treatment with test compound may then be determined using the following Formula: [1−(cold evoked change in MBP/cold evoked change in MBP post-vehicle)]× 100. Plasma may be collected through artery catheter immediately after CPT for pk analysis and $IC_{50/90}$ determination.

REFERENCES

Hines, E A and Brown G E. The cold pressor test for measuring the reactability of the blood pressure. Am. Heart J. 1936, 11:1-9

Nakamura T, Kawabe K, and Sapru H. Cold pressor test in the rat: medullary and spinal pathways and neurotransmitters. Am J Physiol Heart Circ Physiol 2008, 295:H1780-H1787

Koltzenburg M, Pokorny R, Gasser U and Richarz U. Differential sensitivity of three experimental pain models in detecting the analgesic effects of transdermal fentanyl and buprenorphine. Pain 2006, 126:165-174

Parks D, Parsons W, Colburn R, Meegala S, Ballentine S, Illig C, Qin N, Liu Y, Hutchinson T, Lubin M, Stone D, Baker J, Schneider C, Ma J, Damiano B, Flores C, and Player M. Design and optimization of benzimidazole-containing transient receptor potentiate melastatin 8 (TRPM8) antagonists. J. Med. Chem. 2011, 54:233-247

CCI Model

Surgery—A chronic constriction injury (CCI) can be produced as previously described (Bennett & Xie, 1988). Under gaseous anesthesia with a mixture of isoflurane (3% for induction and 2% for maintenance) in $O_2$, the sciatic nerve can be exposed at the mid-thigh level proximal to the sciatic trifurcation. Four chromic gut ligatures (4-0) can be tied loosely around nerve, 1-2 mm apart such that the vascular supply will not be compromised.

Behavioral testing—A behavioral test can be performed to estimate cold-induced ongoing pain as previously described (Choi et al., 1994). The rat can be placed under a transparent plastic cover on an aluminum plate (IITC PE34, Woodland, Calif.) which can be kept at a cold temperature (5±0.5° C.). After 2 min of adaptation, the cumulative duration of time that the rat lifts its foot off the plate for the next 5 min can be measured. Foot lifts associated with locomotion or grooming are not counted. Seven to 9 days after the CCI surgery, baseline of the cold-induced ongoing pain can be measured. Any rat showing a cold-induced ongoing pain less than 100 sec out of 300 sec observation period can be eliminated from the study. Twenty four hours after the baseline measurement, test compound, positive control, morphine (2 mg/kg, Sigma, St. Louis) or a vehicle (saline or 2% HPMC/1% Tween 80) can be administered orally (test compound) or subcutaneously (morphine). Two hours (test compound) or 30 mins (morphine) after the drug administration, the cold-induced ongoing pain can be measured again.

Chung Model

Surgery—Spinal nerve ligation surgery can be performed as previously described (Kim & Chung, 1992). Briefly, under gaseous anesthesia with a mixture of isoflurane (3% for induction and 2% for maintenance) in $O_2$, the spinal nerve injury can be produced by ligating the left L5 and L6 spinal nerves taking special care to avoid any possible damage to the L4 spinal nerve or surrounding area. Additional treatments can be performed to increase the development of mechanical allodynia. First, L5 spinal nerve can be cut approximately 1 mm distal to the suture as described by Li et al. (2000). Second, immediately after ligation and cut, the L4 spinal nerve can be lightly manipulated by slightly stretching it with a fine hooked glass rod and gently sliding the hook back and forth 20 times along the nerve as described by Lee et al. (2003). The whole surgery procedure from anesthesia to the clipping of the incised skin can take at most 15 min.

Behavioral testing—Two weeks later, mechanical sensitivity can be measured by determining the median 50% foot withdrawal threshold for von Frey filaments using the up-down method (Chaplan et al., 1994). The rats can be placed under a plastic cover (9×9×20 cm) on a metal mesh floor. The area tested consists of the middle glabrous area between the footpads of the plantar surface of the hind paw. The plantar area can be touched with a series of 9 von Frey hairs with approximately exponentially incremental bending forces (von Frey values: 3.61, 3.8, 4.0, 4.2, 4.41, 4.6, 4.8, 5.0 and 5.2; equivalent to: 0.41, 0.63, 1.0, 1.58, 2.51, 4.07, 6.31, 10 and 15.8 g). The von Frey hair can be presented perpendicular to the plantar surface with sufficient force to cause slight bending, and held for approximately 3-4 sec. Abrupt withdrawal of the foot (paw flinching, shaking or licking for more than 1 sec) can be recorded as a response. Any rat showing a mechanical threshold of more than 3.16 g or less than 0.7 g after surgery can be eliminated from the study. After measuring basal threshold, test compound, positive control gabapentin (Sigma, St. Louis) or a vehicle (saline or 2% HPMC/1% Tween 80) can be administered orally (test compound) or intraperitoneally (gabapentin). The measurement of the tactile threshold can be reassessed at 1.5 and 2 h after drug administration.

Data—Since the von Frey filament set is calibrated on a logarithmic scale by the vendor (Stoelting) and our selection of 9 filaments for the up-down method is also based on near equal logarithmic intervals (Dixon et al., 1980), data can be treated using logarithmic values in every aspect (statistical treatment as well as plotting). However, an equivalent gram value scale is labeled on the Y-axis of the figures for convenience. Data are expressed as mean±standard error of the mean (S.E.M.).

For the treatment of TRPM8-receptor-diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating TRPM8-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$) alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound of Formula I having the structure:

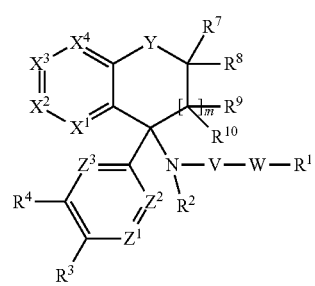

a pharmaceutically-acceptable salt thereof, a tautomer thereof, a pharmaceutically-acceptable salt of the tautomer, a stereoisomer thereof, or a mixture thereof, wherein:

V is —C(=O)—;
W is absent;
$X^1$ is —N—;
$X^2$ is —$CR^5$—;
$X^3$ is —$CR^5$—;
$X^4$ is —$CR^5$—;
Y is —O—;
$Z^1$ is selected from —$CR^6$— or —N—;
$Z^2$ is —$CR^6$—;
$Z^3$ is —$CR^6$—;
m is 1;
$R^1$ is $C_{1-6}$alk or a direct-bonded, $C_{1-2}$alk-linked, $C_{1-2}$alkO-linked, saturated, partially-saturated or unsaturated 3-, 4-, 5-, 6 -or 7-membered monocyclic or 7-, 8-, 9-, 10- or 11-membered bicyclic ring containing 0, 1, 2, 3 or 4 heteroatoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-6}$alkOH, $C_{1-6}$alk-C(=O)$R^a$, $C_{1-6}$alk-C(=O)O$R^a$, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, =S, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the ring is additionally substituted by 0 or 1 directly bonded, $SO_2$ linked, C(=O) linked or $CH_2$ linked saturated, partially-saturated or unsaturated 3-, 4-, 5-, 6- or 7-membered monocyclic ring containing 0, 1, 2, 3 or 4 heteroatoms selected from N, O and S, but containing no more than one O or S atom, and substituted by 0, 1, 2 or 3 groups selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —OR$^a$, —OC(=O)R$^a$, —SR$^a$, —S(=O)R$^a$, —S(=O)$_2$R$^a$, —S(=O)$_2$NR$^a$R$^a$, —NR$^a$R$^a$, and —N(R$^a$)C(=O)R$^a$;

R$^2$ is H or C$_{1-6}$alk;

R$^3$ is H, C$_{1-8}$alk, C$_{1-8}$alkOH, C$_{1-4}$haloalk, halo, cyano, R$^b$, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ or —NR$^a$C$_{2-6}$alkOR$^a$;

R$^4$ is H, C$_{1-6}$alk, —C$_{1-3}$haloalk, —OC$_{1-6}$alk, —OC$_{1-3}$haloalk, —N(C$_{1-6}$alk)C$_{1-6}$alk, —NHC$_{1-6}$alk, —NC(=O)C$_{1-6}$alk, —N(C$_{1-6}$alk)C$_{1-6}$alk, F, Cl, Br, CN, OH or NH$_2$; or R$^3$ and R$^4$ together form a four-atom unsaturated bridge containing 0 or 1 N atoms, wherein the bridge is substituted by 0, 1 or 2 R$^5$ substituents;

R$^5$ is, at each instance, independently selected from H, C$_{1-8}$alk, C$_{1-8}$alkOH, C$_{1-4}$haloalk, halo, cyano, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$ or —NR$^a$C$_{2-6}$alkOR$^a$;

R$^6$ is, at each instance, independently selected from H, halo, OR$^a$, C$_{1-6}$alk, or CF$_3$;

R$^7$ and R$^8$ are independently selected from H or C$_{1-6}$alk;

R$^9$ and R$^{10}$ are, at each instance, independently selected from H or C$_{1-6}$alk;

R$^a$ is independently, at each instance, H or R$^b$; and

R$^b$ is independently, at each instance, phenyl, benzyl or C$_{1-6}$alk, the phenyl, benzyl and C$_{1-6}$alk being substituted by 0, 1, 2 or 3 substituents selected from halo, oxo, C$_{1-4}$alk, C$_{1-3}$haloalk, —OC$_{1-4}$alk, —OH, —NH$_2$, —OC$_{1-4}$alk, —OC$_{1-4}$haloalk, —NHC$_{1-4}$alk, and —N(C$_{1-4}$alk)C$_{1-4}$alk;

wherein, the compound is not one of the following compounds, is not a salt thereof, is not a tautomer thereof, is not a salt of a tautomer, is not a stereoisomer thereof, and is not a salt of a stereoisomer:

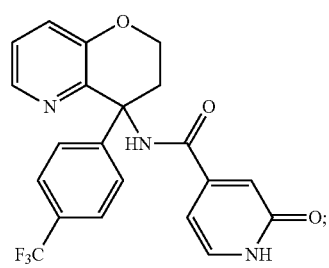

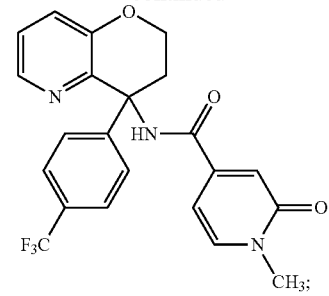

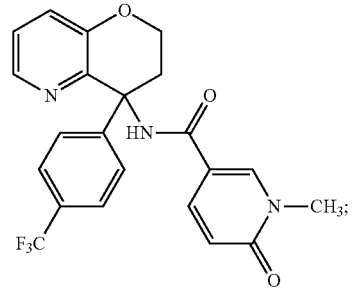

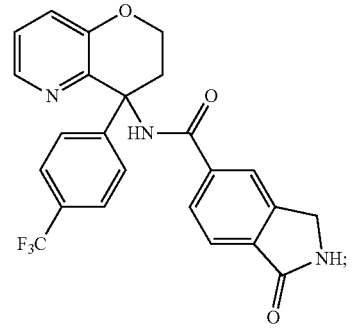

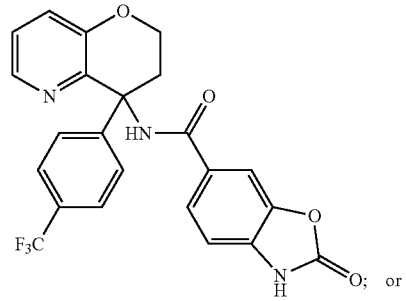

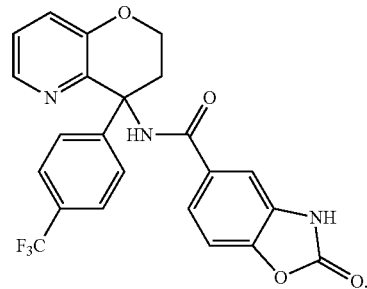 [SMILES: O=C(NC1(c2ccc(C(F)(F)F)cc2)CCOc2cccnc21)c1ccc2oc(=O)[nH]c2c1]

2. The compound of claim 1 or the pharmaceutically-acceptable salt thereof, the tautomer thereof, the pharmaceutically-acceptable salt of the tautomer, the stereoisomer thereof, or the mixture thereof, wherein R$^7$ and R$^8$ are both H.

3. The compound of claim 1 or the pharmaceutically-acceptable salt thereof, the tautomer thereof, the pharmaceutically-acceptable salt of the tautomer, the stereoisomer thereof, or the mixture thereof, wherein R$^7$, R$^8$, R$^9$, and R$^{10}$ are H; $R^2$ is H; $R^3$ is —$CH_3$, —F, —Cl, —$CF_3$, or —$OCF_3$; $R^4$ is —F, —Cl, or —$OCF_3$; and $R^1$ is a partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, but containing no more than one O or S atom, and the ring is substituted by 0, 1, 2 or 3 substituents independently selected from halo, oxo, $C_{1-6}$alk, $C_{1-6}$alkOH, $C_{1-6}$alk-C(=O)$R^a$, $C_{1-6}$alk-C(=O)O$R^a$, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, =S, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$ wherein the ring is additionally substituted by 0 or 1 directly bonded, $SO_2$ linked, C(=O) linked or $CH_2$ linked saturated, partially-saturated or unsaturated 3-, 4-, 5-, 6- or 7-membered monocyclic ring containing 0, 1, 2, 3 or 4 heteroatoms selected from N, O and S, but containing no more than one O or S atom, and substituted by 0, 1, 2 or 3 groups selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$.

4. The compound of claim 3 or the pharmaceutically-acceptable salt thereof, the tautomer thereof, the pharmaceutically-acceptable salt of the tautomer, the stereoisomer thereof, or the mixture thereof, wherein $R^5$ is H; 0 of $Z^1$, $Z^2$, and $Z^3$ are N; and $R^4$ is —F.

5. The compound of claim 4 or the pharmaceutically-acceptable salt thereof, the tautomer thereof, the pharmaceutically-acceptable salt of the tautomer, the stereoisomer thereof, or the mixture thereof, wherein $R^3$ is —$CF_3$ or —$OCF_3$.

6. The compound of claim 5 or the pharmaceutically-acceptable salt thereof, the tautomer thereof, the pharmaceutically-acceptable salt of the tautomer, the stereoisomer thereof, or the mixture thereof, wherein $R^6$ is H.

7. The compound of claim 1 or the pharmaceutically-acceptable salt thereof, the tautomer thereof, the pharmaceutically-acceptable salt of the tautomer, the stereoisomer thereof, or the mixture thereof, wherein $R^9$ and $R^{10}$ are H.

8. The compound of claim 1 or the pharmaceutically-acceptable salt thereof, the tautomer thereof, the pharmaceutically-acceptable salt of the tautomer, the stereoisomer thereof, or the mixture thereof, wherein the compound of Formula I has the Formula II:

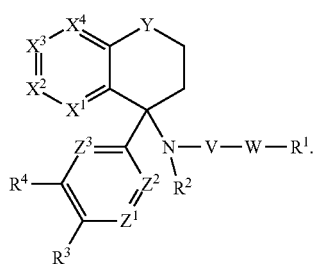

9. The compound of claim 8 or the pharmaceutically-acceptable salt thereof, the tautomer thereof, the pharmaceutically-acceptable salt of the tautomer, the stereoisomer thereof, or the mixture thereof, wherein the compound of Formula II has the Formula IIA:

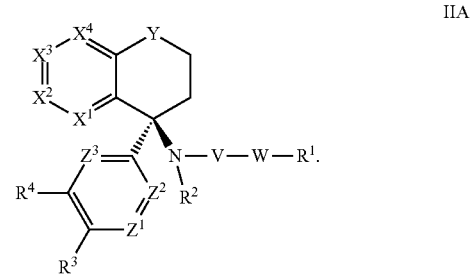

10. The compound of claim 1 or the pharmaceutically-acceptable salt thereof, the tautomer thereof, the pharmaceutically-acceptable salt of the tautomer, the stereoisomer thereof, or the mixture thereof, wherein 0 of $Z^1$, $Z^2$, and $Z^3$ are N.

11. The compound of claim 1 or the pharmaceutically-acceptable salt thereof, the tautomer thereof, the pharmaceutically-acceptable salt of the tautomer, the stereoisomer thereof, or the mixture thereof, wherein 1 of $Z^1$, $Z^2$, and $Z^3$ are N.

12. The compound claim 1 or the pharmaceutically-acceptable salt thereof, the tautomer thereof, the pharmaceutically-acceptable salt of the tautomer, the stereoisomer thereof, or the mixture thereof, wherein $R^2$ is H.

13. The compound of claim 1 or the pharmaceutically-acceptable salt thereof, the tautomer thereof, the pharmaceutically-acceptable salt of the tautomer, the stereoisomer thereof, or the mixture thereof, wherein $R^3$ is selected from H, $C_{1-8}$alk, $C_{1-8}$alkOH, $C_{1-4}$haloalk, halo, or —O$R^a$.

14. The compound of claim 1 or the pharmaceutically-acceptable salt thereof, the tautomer thereof, the pharmaceutically-acceptable salt of the tautomer, the stereoisomer thereof, or the mixture thereof, wherein $R^3$ is selected from —$CH_3$, —F, —Cl, —$CF_3$, or —$OCF_3$.

15. The compound of claim 1 or the pharmaceutically-acceptable salt thereof, the tautomer thereof, the pharmaceutically-acceptable salt of the tautomer, the stereoisomer thereof, or the mixture thereof, wherein $R^3$ is selected from —$CF_3$ or —$OCF_3$.

16. The compound of claim 1 or the pharmaceutically-acceptable salt thereof, the tautomer thereof, the pharmaceutically-acceptable salt of the tautomer, the stereoisomer thereof, or the mixture thereof, wherein $R^3$ is $R^b$ and $R^b$ is a phenyl substituted by 0, 1, 2 or 3 substituents selected from halo, $C_{1-4}$alk, $C_{1-3}$haloalk, —O$C_{1-4}$alk, —OH, —$NH_2$, —O$C_{1-4}$alk, —O$C_{1-4}$haloalk, —NH$C_{1-4}$alk, and —N($C_{1-4}$alk)$C_{1-4}$alk.

17. The compound of claim 1 or the pharmaceutically-acceptable salt thereof, the tautomer thereof, the pharmaceutically-acceptable salt of the tautomer, the stereoisomer thereof, or the mixture thereof, wherein $R^4$ is H.

18. The compound of claim 1 or the pharmaceutically-acceptable salt thereof, the tautomer thereof, the pharmaceutically-acceptable salt of the tautomer, the stereoisomer thereof, or the mixture thereof, wherein $R^4$ is selected from F, Cl, $C_{1-6}$alk, —O$C_{1-6}$alk, —O$C_{1-3}$haloalk, or —$C_{1-3}$haloalk.

19. The compound of claim 1 or the pharmaceutically-acceptable salt thereof, the tautomer thereof, the pharmaceutically-acceptable salt of the tautomer, the stereoisomer thereof, or the mixture thereof, wherein $R^4$ is selected from —F, —Cl, or —OCF$_3$.

20. The compound of claim 1 or the pharmaceutically-acceptable salt thereof, the tautomer thereof, the pharmaceutically-acceptable salt of the tautomer, the stereoisomer thereof, or the mixture thereof, wherein $R^4$ is —F.

21. The compound of claim 1 or the pharmaceutically-acceptable salt thereof, the tautomer thereof, the pharmaceutically-acceptable salt of the tautomer, the stereoisomer thereof, or the mixture thereof, wherein —$R^3$ is —OCF$_3$ and $R^4$ is —F.

22. The compound of claim 1 or the pharmaceutically-acceptable salt thereof, the tautomer thereof, the pharmaceutically-acceptable salt of the tautomer, the stereoisomer thereof, or the mixture thereof, wherein each instance of $R^5$ is H.

23. The compound of claim 1 or the pharmaceutically-acceptable salt thereof, the tautomer thereof, the pharmaceutically-acceptable salt of the tautomer, the stereoisomer thereof, or the mixture thereof, wherein each instance of $R^6$ is H.

24. The compound of claim 1 or the pharmaceutically-acceptable salt thereof, the tautomer thereof, the pharmaceutically-acceptable salt of the tautomer, the stereoisomer thereof, or the mixture thereof, wherein $R^1$ is the saturated, partially-saturated or unsaturated 3-, 4-, 5-, 6- or 7-membered monocyclic or 7-, 8-, 9-, 10- or 11-membered bicyclic ring and the monocyclic or bicyclic ring is substituted by 0, 1, 2, or 3 substituents, wherein the substituents are selected from F, Cl, Br, I, oxo, cyano, —CH$_3$, —CH$_2$CH$_3$, —CH$_2$CH$_2$CH$_3$, —C(H)(CH$_3$)$_2$, —CH$_2$C(H)(CH$_3$)$_2$, —CH$_2$C(H)=CH$_2$, —CH$_2$CO$_2$H, —CH$_2$CF$_3$, —C(OH)(CH$_3$)$_2$, —SO$_2$N(H)CH$_3$, —N(H)SO$_2$CH$_3$, —OCH$_3$, —OCF$_3$, —OH, —OCH$_2$CO$_2$H, —CH$_2$OH, —CH$_2$CH$_2$OH, —CH$_2$C(H)(CH$_3$)OH, —CO$_2$H, —CO$_2$CH$_3$, —CO$_2$CH$_2$CH$_3$, —CO$_2$C(CH$_3$)$_3$, —CO$_2$NH$_2$, —CO$_2$N(H)CH$_3$, —SO$_2$CH$_3$, —OC(=O)CH$_3$, —NH$_2$, —NHC(=O)CH$_3$, —N(CH$_3$)$_2$, —N(H)CH$_2$CH$_3$, —CF$_3$, —CHF$_2$, —CH$_2$C(H)(CF$_3$)OH, —CH$_2$C(CH$_3$)$_2$OH, —CH$_2$-phenyl, —C(=O)-phenyl, tetrazolyl, oxadiazolonyl, pyridyl, oxetanyl,

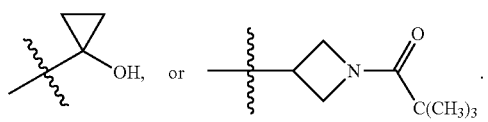 [SMILES: *C1(O)CC1 ; *C1CN(C(=O)C(C)(C)C)C1]

25. The compound of claim 1 or the pharmaceutically-acceptable salt thereof, the tautomer thereof, the pharmaceutically-acceptable salt of the tautomer, the stereoisomer thereof, or the mixture thereof, wherein $R^1$ is a phenyl, pyridyl, pyridinonyl, piperidinonyl, pyridazinonyl, pyrazinonyl, pyridazinyl, pyrimidinyl, pyrazinyl, tetradyrofuranyl, tetrahydropyranyl, thiazolyl, isothiazolyl, furanyl, thiophenyl, pyrazolyl, isoxazolyl, triazolyl, oxazolyl, imidazolyl, pyrrolidinyl, piperidinyl, cyclohexyl, cyclohexanonyl, quinolinyl, isoquinolinyl, naphthyridinyl, pyrrolopyridinyl, pyrrolopyrimidinyl, benzothiophenyl, pyrazolopyrimidinyl, triazolopyrimidinyl, indazolyl, tetrahydroindazolyl, tetrahydrocyclopentapyrazolyl, dihydropyrazolooxazinyl, indolinonyl, isoindolinonyl, benzooxazolonyl, oxazolopyridinonyl, benzoimidazolonyl, isoindolindionyl, tetrahydroquinolinyl, dihydroquinolinonyl, benzooxazinonyl, dihydrobenzooxazinonyl, dihydroindenonyl, benzothiazolyl, benzimidazolyl, imidazopyridinyl, tetrazolopyridinyl, quinolinonyl, quinoxalinyl, indolyl, or quinoxalindionyl substituted by 0, 1, 2, or 3 substituents.

26. The compound of claim 1 or the pharmaceutically-acceptable salt thereof, the tautomer thereof, the pharmaceutically-acceptable salt of the tautomer, the stereoisomer thereof, or the mixture thereof, wherein $R^1$ is a phenyl, pyridyl, pyridinonyl, pyrazinonyl, pyridazinyl, pyrimidinyl, tetrahydropyranyl, thiazolyl, isothiazolyl, imidazolyl, piperidinyl, quinolinyl, isoquinolinyl, indazolyl, indolinonyl, isoindolinonyl, benzooxazolonyl, dihydroquinolinonyl, imidazopyridinyl, quinolinonyl, indolyl substituted by 0, 1, 2, or 3 substituents.

27. The compound of claim 26 or the pharmaceutically-acceptable salt thereof, the tautomer thereof, the pharmaceutically-acceptable salt of the tautomer, the stereoisomer thereof, or the mixture thereof, wherein $R^1$ is a phenyl substituted by 0, or 1 substituent.

28. The compound of claim 26 or the pharmaceutically-acceptable salt thereof, the tautomer thereof, the pharmaceutically-acceptable salt of the tautomer, the stereoisomer thereof, or the mixture thereof, wherein $R^1$ is a pyridinonyl substituted by 0, or 1 substituent.

29. The compound of claim 26 or the pharmaceutically-acceptable salt thereof, the tautomer thereof, the pharmaceutically-acceptable salt of the tautomer, the stereoisomer thereof, or the mixture thereof, wherein $R^1$ is a pyridyl substituted by 0, or 1 substituent.

30. The compound of claim 26 or the pharmaceutically-acceptable salt thereof, the tautomer thereof, the pharmaceutically-acceptable salt of the tautomer, the stereoisomer thereof, or the mixture thereof, wherein $R^1$ is a benzooxazolonyl substituted by 0, or 1 substituent.

31. The compound of claim 26 or the pharmaceutically-acceptable salt thereof, the tautomer thereof, the pharmaceutically-acceptable salt of the tautomer, the stereoisomer thereof, or the mixture thereof, wherein $R^1$ is a quinolinyl substituted by 0, or 1 substituent.

32. The compound of claim 1 or the pharmaceutically-acceptable salt thereof, the tautomer thereof, the pharmaceutically-acceptable salt of the tautomer, the stereoisomer thereof, or the mixture thereof, wherein $R^1$ is a group of formula

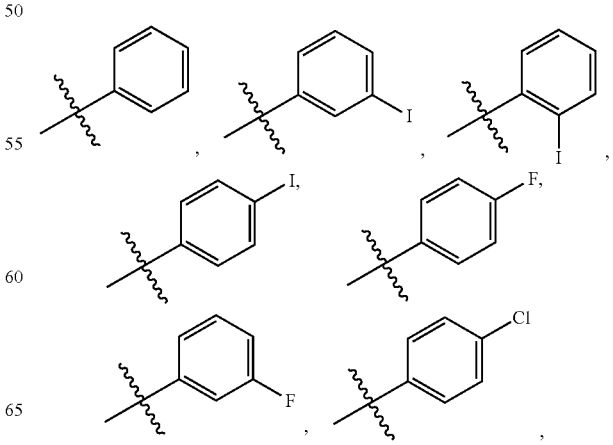

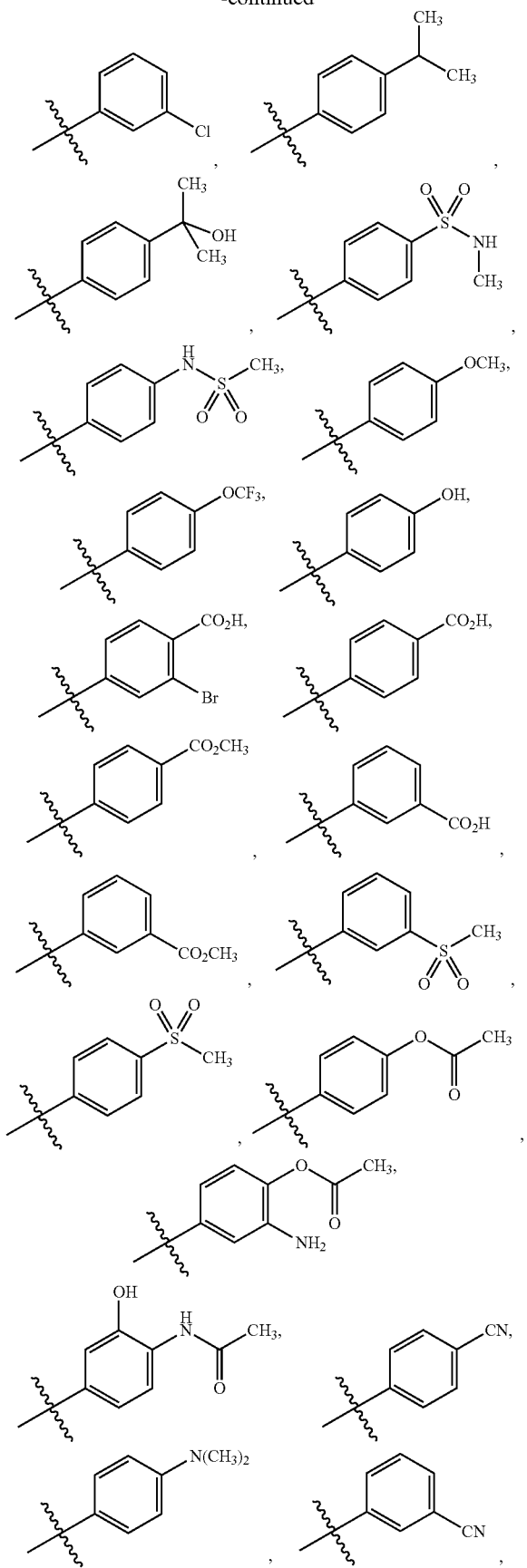
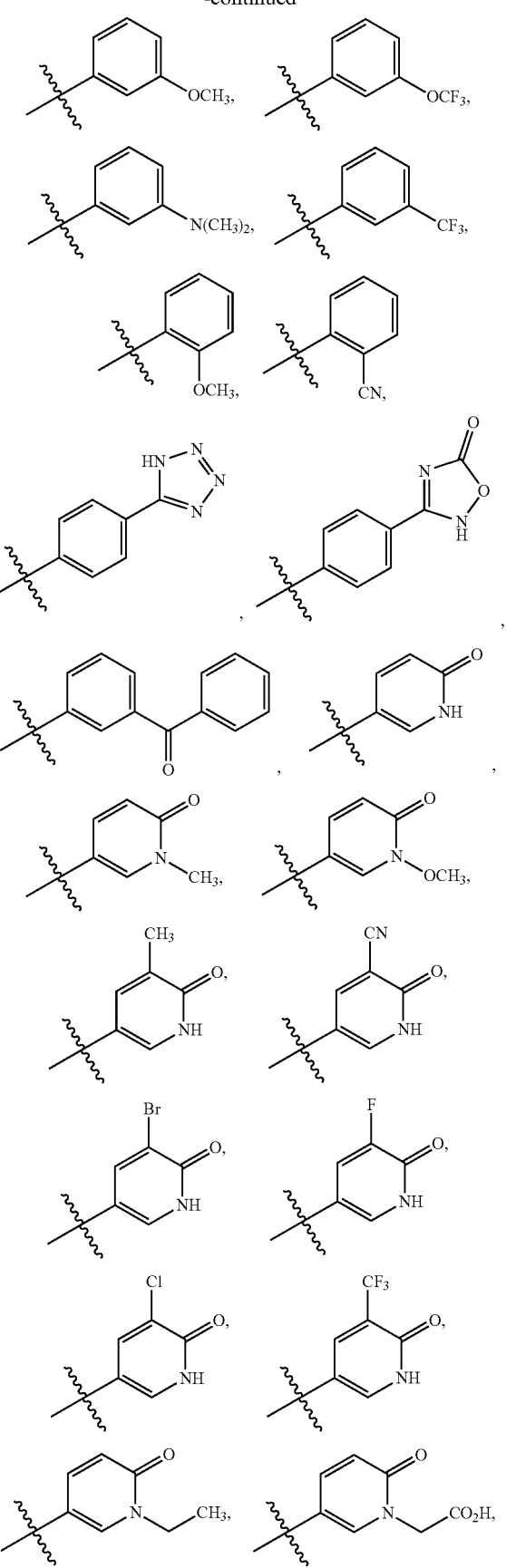

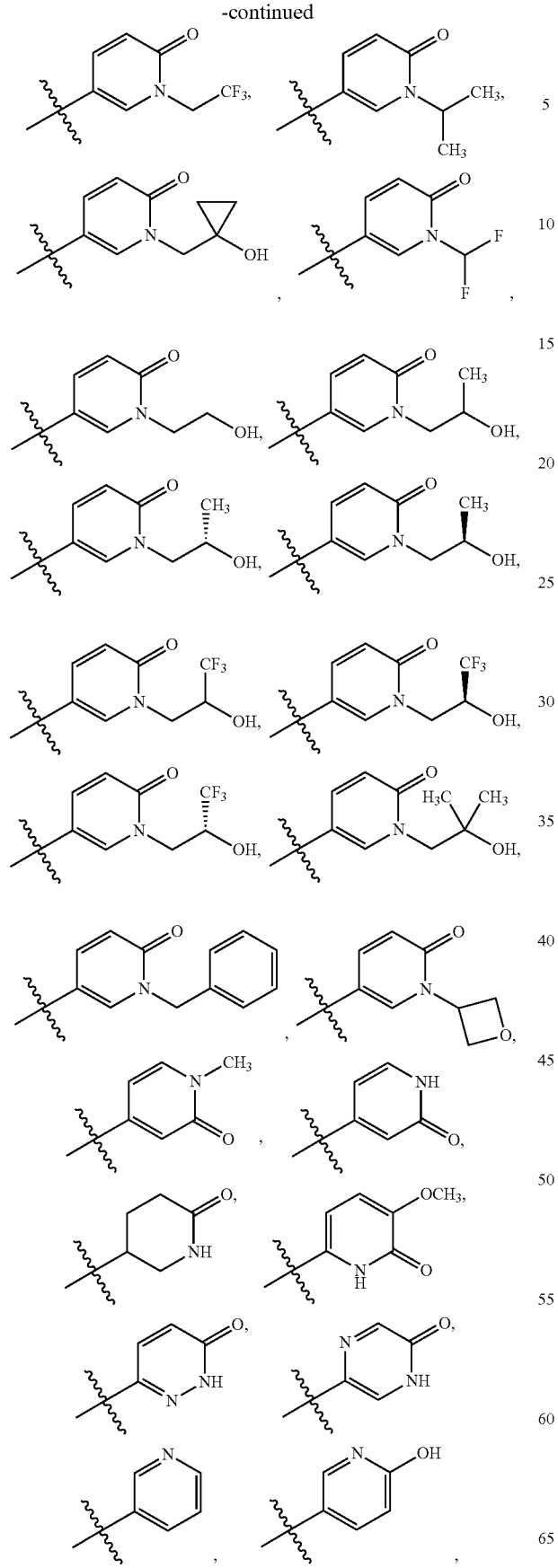
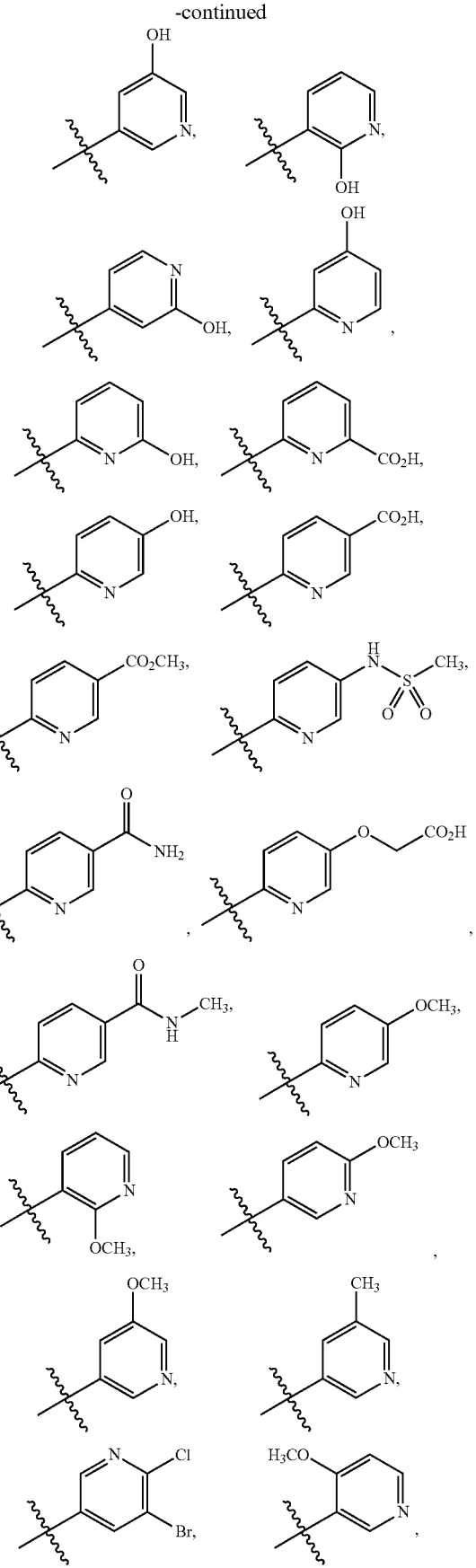

185
-continued
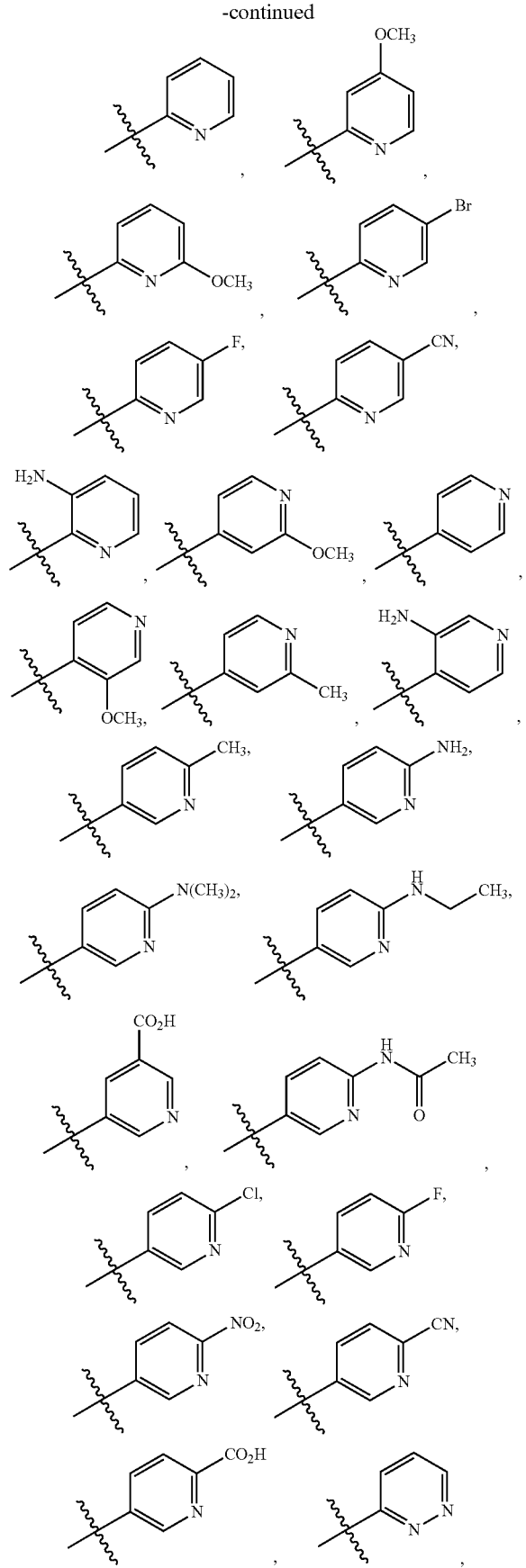
186
-continued
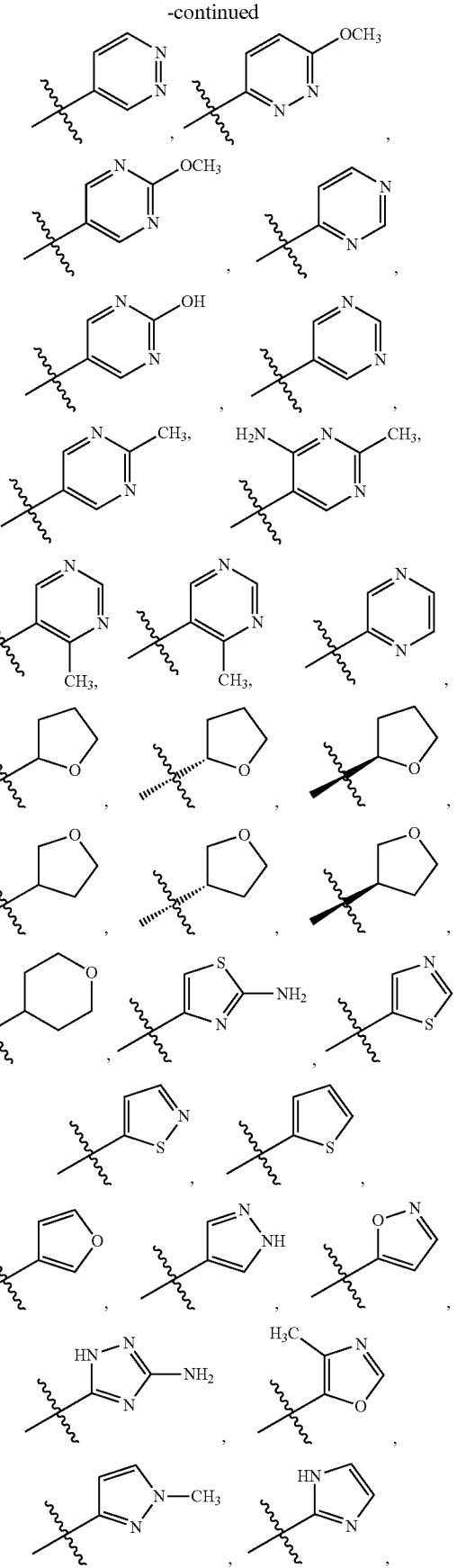

187
-continued
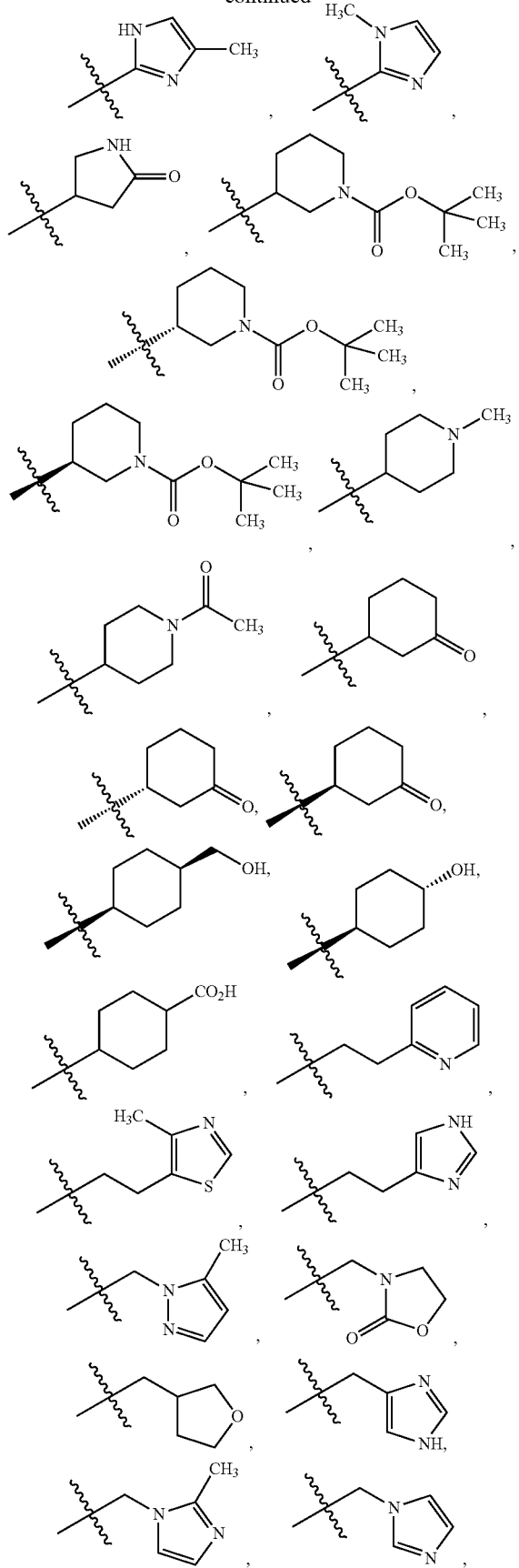
188
-continued
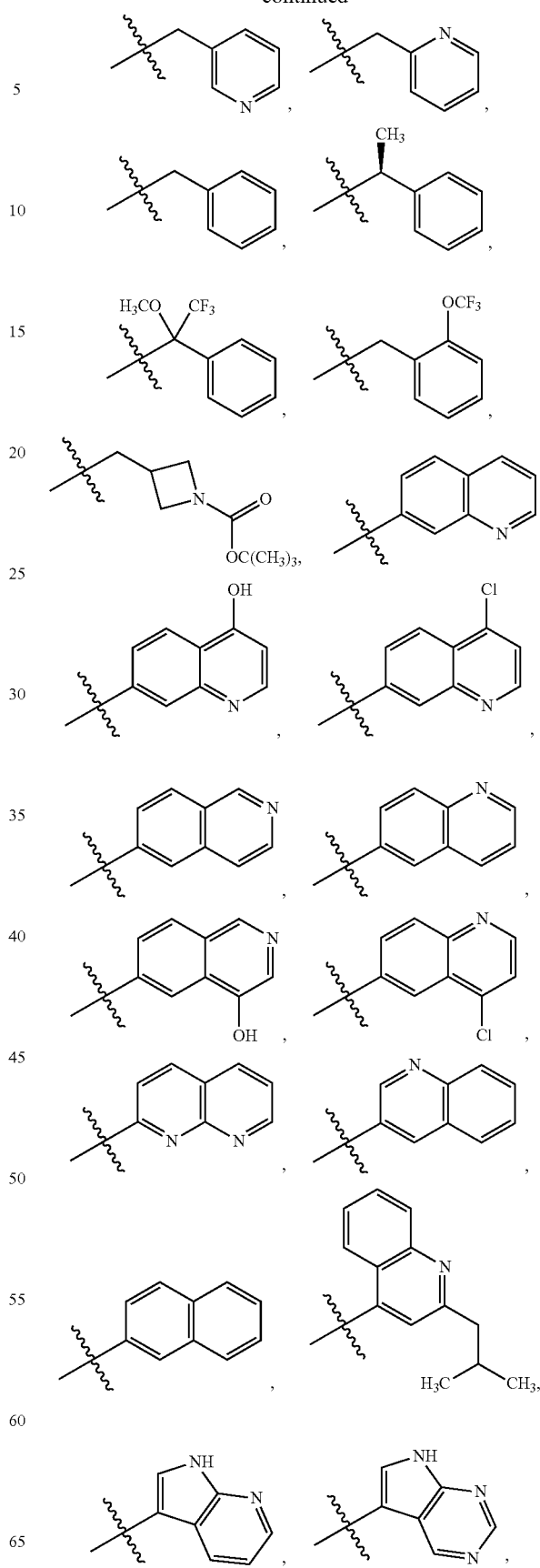

189
-continued
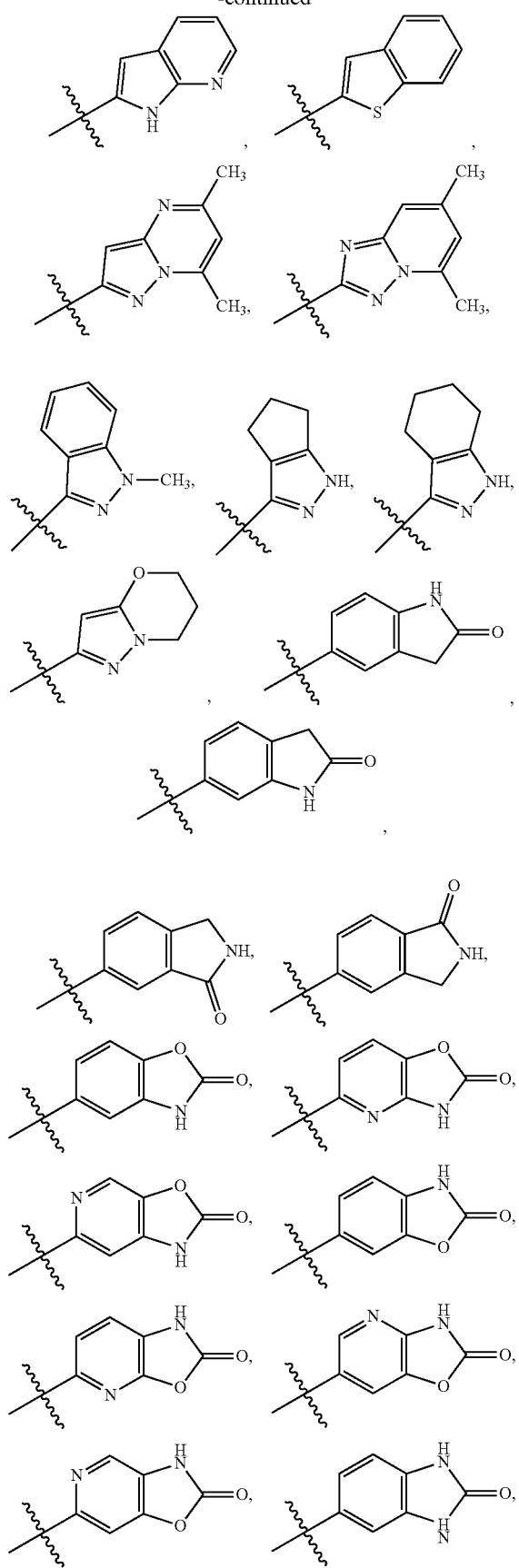
190
-continued
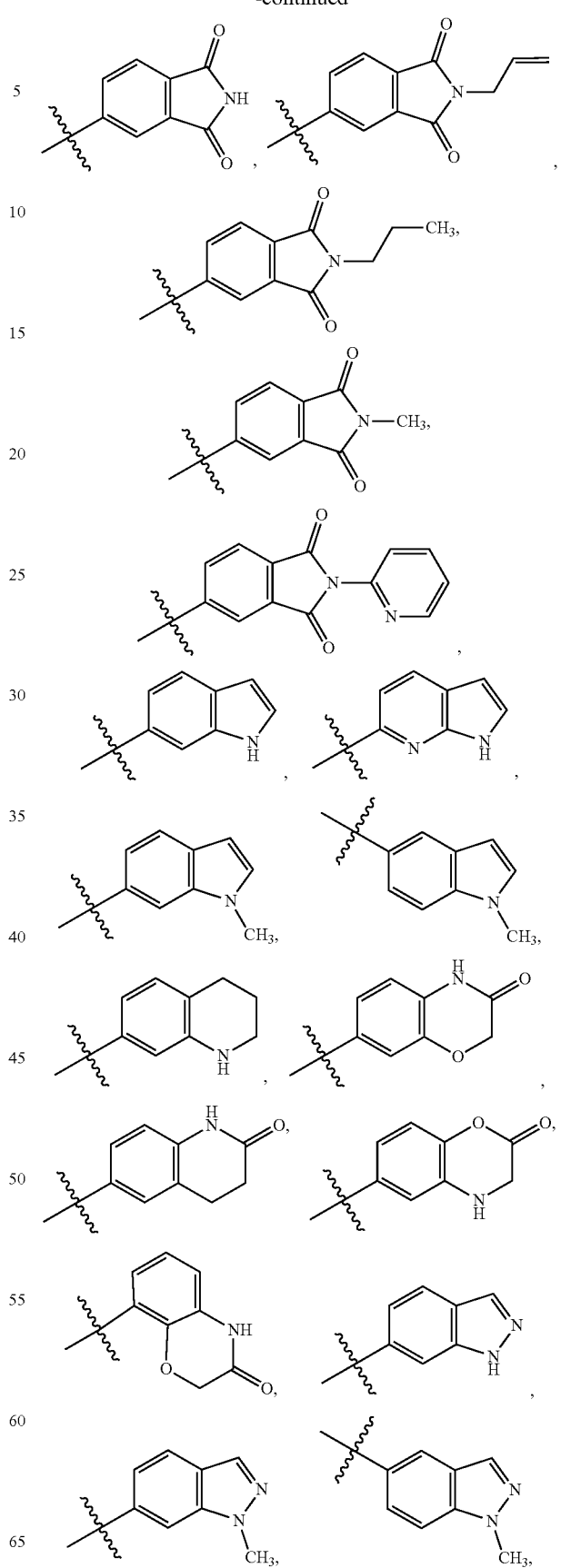

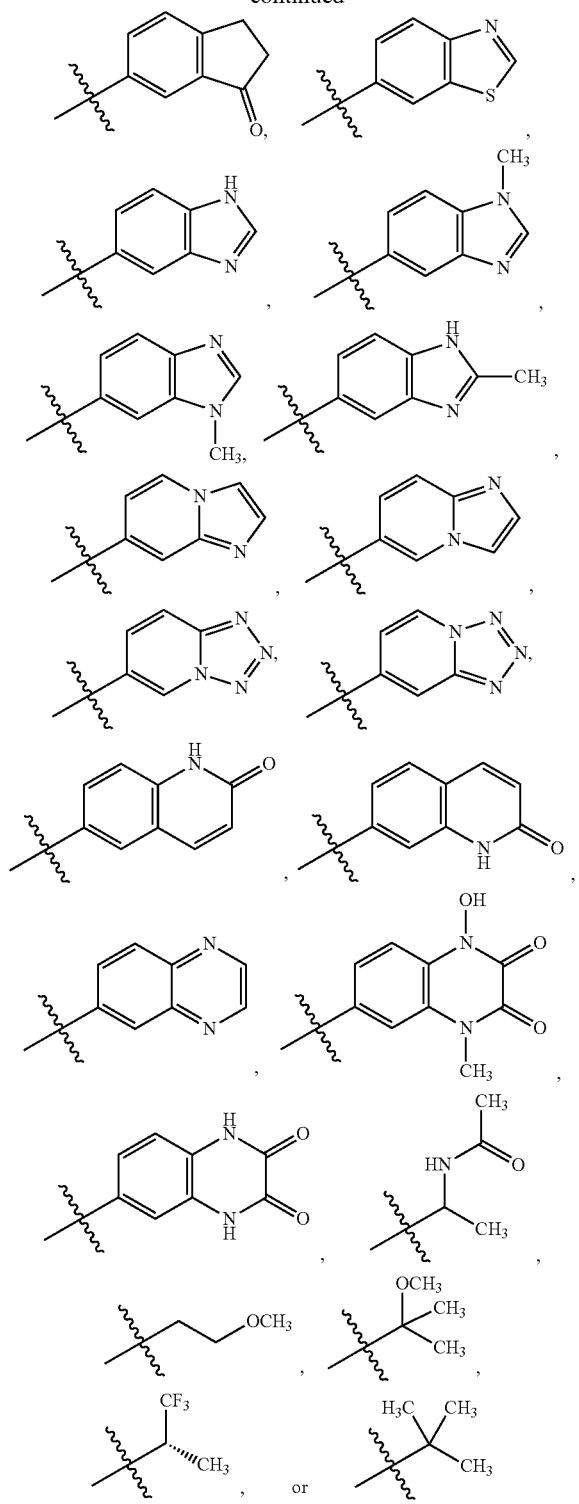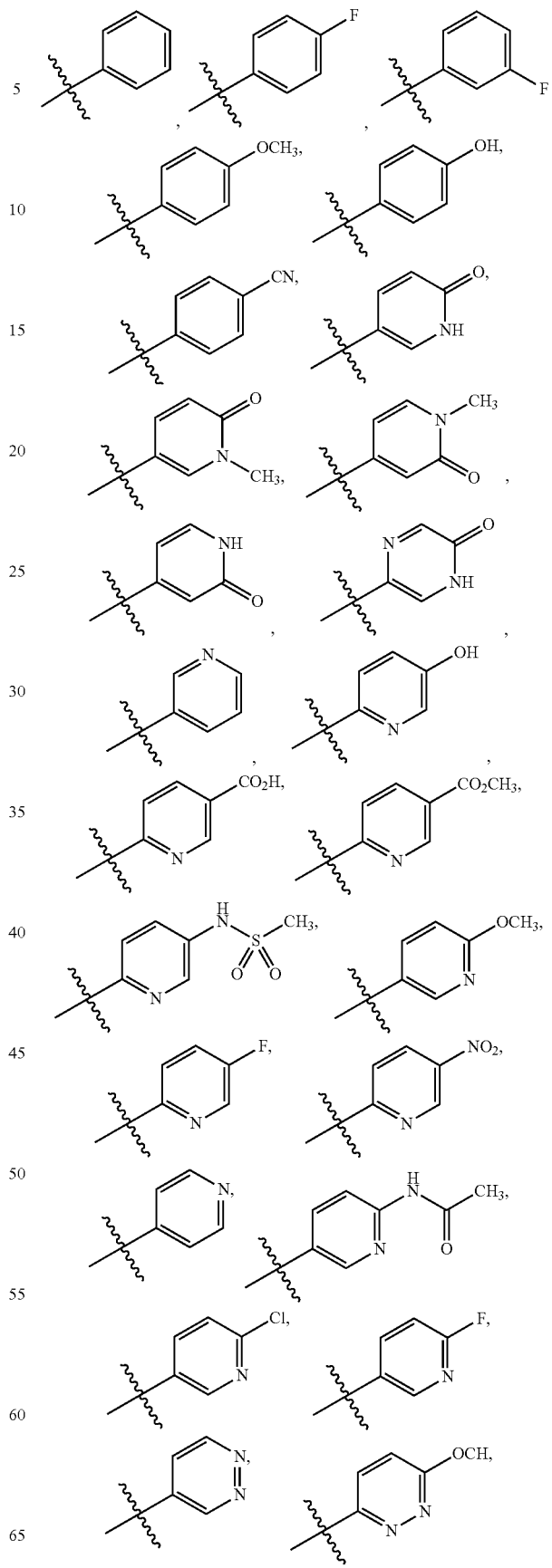
and the symbol ⁓, when drawn across a bond, indicates the point of attachment to the rest of the molecule.
33. The compound of claim 1 or the pharmaceutically-acceptable salt thereof, the tautomer thereof, the pharmaceutically-acceptable salt of the tautomer, the stereoisomer thereof, or the mixture thereof, wherein $R^1$ is a group of formula 193
-continued 194
-continued

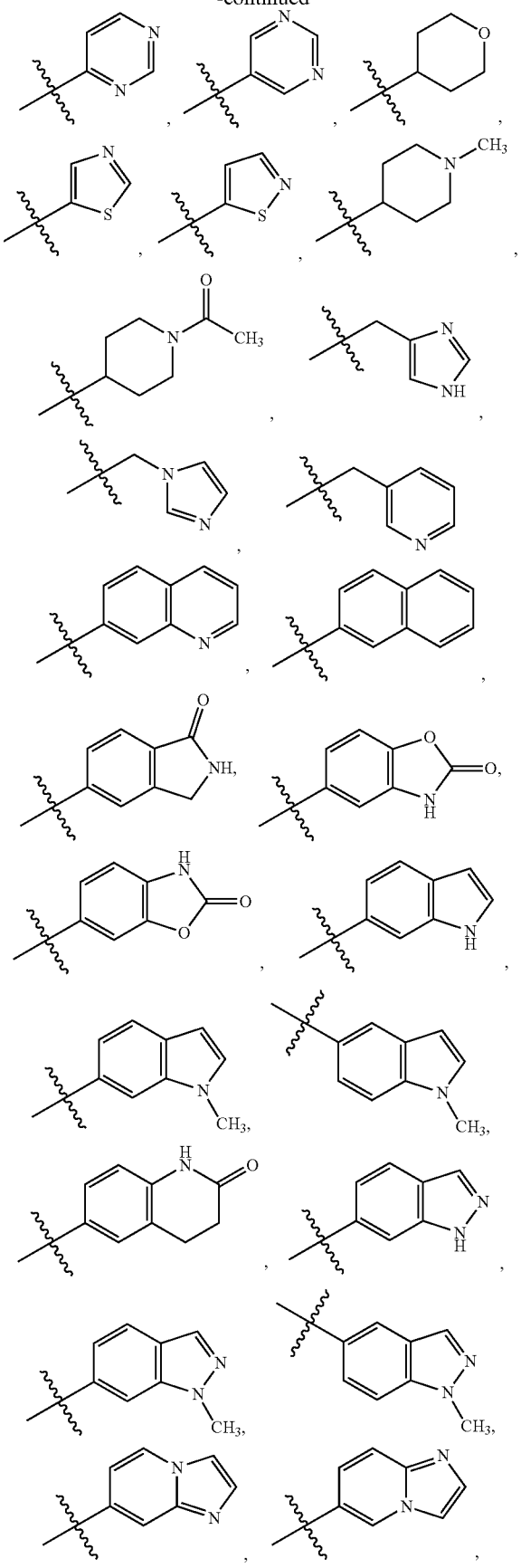

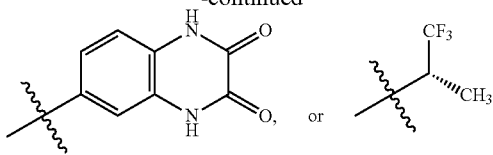

and the symbol ⌇, when drawn across a bond, indicates the point of attachment to the rest of the molecule.

34. The compound of claim 1 or the pharmaceutically-acceptable salt hereof, the tautomer thereof, the pharmaceutically-acceptable salt of the tautomer, the stereoisomer thereof, or the mixture thereof, wherein R¹ is a group of formula

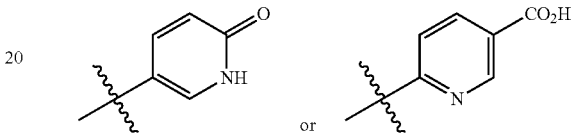

and the symbol ⌇, when drawn across a bond, indicates the point of attachment to the rest of the molecule.

35. The compound of claim 1 or the pharmaceutically-acceptable salt thereof, the tautomer thereof, the pharmaceutically-acceptable salt of the tautomer, the stereoisomer thereof, or the mixture thereof, wherein R¹ is

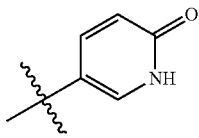 [SMILES: *c1ccc(=O)[nH]c1]

and the symbol ⌇, when drawn across a bond, indicates the point of attachment to the rest of the molecule.

36. The compound of claim 1 or the pharmaceutically-acceptable salt thereof, the tautomer thereof, the pharmaceutically-acceptable salt of the tautomer, the stereoisomer thereof, or the mixture thereof, wherein R¹ is

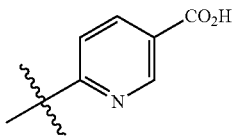 [SMILES: *c1ccc(C(=O)O)cn1]

and the symbol ⌇, when drawn across a bond, indicates the point of attachment to the rest of the molecule.

37. The compound of claim 1, wherein the compound is
(S)-N-(4-(4-(trifluoromethyl)phenyl)-3,4-dihydro-2H-pyrano[3,2-b]pyridin-4-yl)benzamide;
(S)-4-fluoro-N-(4-(4-(trifluoromethyl)phenyl)-3,4-dihydro-2H-pyrano[3,2-b]pyridin-4-yl)benzamide;
(S)-N-(4-(3,4-dichlorophenyl)-3,4-dihydro-2H-pyrano[3,2-b]pyridin-4-yl)benzamide;
(S)-4-hydroxy-N-(4-(4-(trifluoromethyl)phenyl)-3,4-dihydro-2H-pyrano[3,2-b]pyridin-4-yl)benzamide;
(S)-4-methoxy-N-(4-(4-(trifluoromethyl)phenyl)-3,4-dihydro-2H-pyrano[3,2-b]pyridin-4-yl)benzamide;

4-fluoro-N-(4-(3-fluoro-4-(trifluoromethoxy)phenyl)-3,4-dihydro-2H-pyrano[3,2-b]pyridin-4-yl)benzamide;
N-(4-(3-fluoro-4-(trifluoromethoxy)phenyl)-3,4-dihydro-2H-pyrano[3,2-b]pyridin-4-yl)benzamide;
4-fluoro-N-(4-(4-(trifluoromethoxy)phenyl)-3,4-dihydro-2H-pyrano[3,2-b]pyridin-4-yl)benzamide;
N-(4-(4-(trifluoromethoxy)phenyl)-3,4-dihydro-2H-pyrano[3,2-b]pyridin-4-yl)benzamide;
N-(4-(3,4-dichlorophenyl)-3,4-dihydro-2H-pyrano[3,2-b]pyridin-4-yl)-4-fluorobenzamide;
4-fluoro-N-(4-phenyl-3,4-dihydro-2H-pyrano[3,2-b]pyridin-4-yl)benzamide;
N-(4-phenyl-3,4-dihydro-2H-pyrano[3,2-b]pyridin-4-yl)benzamide;
N-(4-(6-(trifluoromethyl)pyridin-3-yl)-3,4-dihydro-2H-pyrano[3,2-b]pyridin-4-yl)benzamide;
(S)-N-(4-(4-chlorophenyl)-3,4-dihydro-2H-pyrano[3,2-b]pyridin-4-yl)benzamide;
(S)-N-(4-(4-chloro-3-fluorophenyl)-3,4-dihydro-2H-pyrano[3,2-b]pyridin-4-yl)benzamide;
(S)-N-(4-(4-fluorophenyl)-3,4-dihydro-2H-pyrano[3,2-b]pyridin-4-yl)benzamide;
(S)-N-(4-(3-(trifluoromethoxy)phenyl)-3,4-dihydro-2H-pyrano[3,2-b]pyridin-4-yl)benzamide;
(S)-N-(4-(p-tolyl)-3,4-dihydro-2H-pyrano[3,2-b]pyridin-4-yl)benzamide;
(S)-N-(4-(3-fluoro-4-(trifluoromethyl)phenyl)-3,4-dihydro-2H-pyrano[3,2-b]pyridin-4-yl)benzamide;
(S)-2-oxo-N-(4-(4-(trifluoromethyl)phenyl)-3,4-dihydro-2H-pyrano[3,2-b]pyridin-4-yl)-2,3-dihydrobenzo[d]oxazole-6-carboxamide;
(S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-6-carboxamide;
2-oxo-N-(4-(4-(trifluoromethoxy)phenyl)-3,4-dihydro-2H-pyrano[3,2-b]pyridin-4-yl)-2,3-dihydrobenzo[d]oxazole-6-carboxamide;
2-oxo-N-(4-(4-(trifluoromethoxy)phenyl)-3,4-dihydro-2H-pyrano[3,2-b]pyridin-4-yl)-2,3-dihydrobenzo[d]oxazole-5-carboxamide;
N-(4-(3,4-dichlorophenyl)-3,4-dihydro-2H-pyrano[3,2-b]pyridin-4-yl)-2-oxo-2,3-dihydrobenzo[d]oxazole-6-carboxamide;
N-(4-(3,4-dichlorophenyl)-3,4-dihydro-2H-pyrano[3,2-b]pyridin-4-yl)-2-oxo-2,3-dihydrobenzo[d]oxazole-5-carboxamide;
2-oxo-N-(4-phenyl-3,4-dihydro-2H-pyrano[3,2-b]pyridin-4-yl)-2,3-dihydrobenzo[d]oxazole-6-carboxamide;
2-oxo-N-(4-(6-(trifluoromethyl)pyridin-3-yl)-3,4-dihydro-2H-pyrano[3,2-b]pyridin-4-yl)-2,3-dihydrobenzo[d]oxazole-5-carboxamide;
(S)-N-(4-(4-(trifluoromethyl)phenyl)chroman-4-yl)benzamide;
methyl 6-((4-(3-fluoro-4-(trifluoromethoxy)phenyl)-3,4-dihydro-2H-pyrano[3,2-b]pyridin-4-yl)carbamoyl)nicotinate;
(S)-6-methoxy-N-(4-(4-(trifluoromethyl)phenyl)-3,4-dihydro-2H-pyrano[3,2-b]pyridin-4-yl)nicotinamide;
(S)-2-oxo-N-(4-(4-(trifluoromethyl)phenyl)-3,4-dihydro-2H-pyrano[3,2-b]pyridin-4-yl)-1,2,3,4-tetrahydroquinoline-6-carboxamide;
(S)-N-(4-(4-(trifluoromethyl)phenyl)-3,4-dihydro-2H-pyrano[3,2-b]pyridin-4-yl)-1H-indazole-6-carboxamide;
(S)-N-(4-(4-(trifluoromethyl)phenyl)-3,4-dihydro-2H-pyrano[3,2-b]pyridin-4-yl)pyrimidine-4-carboxamide;
(S)-N-(4-(4-(trifluoromethyl)phenyl)-3,4-dihydro-2H-pyrano[3,2-b]pyridin-4-yl)-1H-indole-6-carboxamide;
(S)-N-(4-(4-(trifluoromethyl)phenyl)-3,4-dihydro-2H-pyrano[3,2-b]pyridin-4-yl)pyridazine-4-carboxamide;
(S)-1-methyl-N-(4-(4-(trifluoromethyl)phenyl)-3,4-dihydro-2H-pyrano[3,2-b]pyridin-4-yl)-1H-indazole-6-carboxamide;
(S)-N-(4-(4-(trifluoromethyl)phenyl)-3,4-dihydro-2H-pyrano[3,2-b]pyridin-4-yl)thiazole-5-carboxamide;
(S)-5-hydroxy-N-(4-(4-(trifluoromethyl)phenyl)-3,4-dihydro-2H-pyrano[3,2-b]pyridin-4-yl)picolinamide;
(S)-N-(4-(4-(trifluoromethyl)phenyl)-3,4-dihydro-2H-pyrano[3,2-b]pyridin-4-yl)isothiazole-5-carboxamide;
(S)-1-methyl-N-(4-(4-(trifluoromethyl)phenyl)-3,4-dihydro-2H-pyrano[3,2-b]pyridin-4-yl)-1H-indole-5-carboxamide;
(S)-5-acetamido-N-(4-(4-(trifluoromethyl)phenyl)-3,4-dihydro-2H-pyrano[3,2-b]pyridin-4-yl)picolinamide;
(S)-1-methyl-N-(4-(4-(trifluoromethyl)phenyl)-3,4-dihydro-2H-pyrano[3,2-b]pyridin-4-yl)-1H-indazole-5-carboxamide;
(S)-5-oxo-N-(4-(4-(trifluoromethyl)phenyl)-3,4-dihydro-2H-pyrano[3,2-b]pyridin-4-yl)-4,5-dihydropyrazine-2-carboxamide;
(S)-N-(4-(4-(trifluoromethyl)phenyl)-3,4-dihydro-2H-pyrano[3,2-b]pyridin-4-yl)isonicotinamide;
(S)-6-methoxy-N-(4-(4-(trifluoromethyl)phenyl)-3,4-dihydro-2H-pyrano[3,2-b]pyridin-4-yl)pyridazine-3-carboxamide;
(S)-N-(4-(4-(trifluoromethyl)phenyl)-3,4-dihydro-2H-pyrano[3,2-b]pyridin-4-yl)nicotinamide;
(S)-N-(4-(4-(trifluoromethyl)phenyl)-3,4-dihydro-2H-pyrano[3,2-b]pyridin-4-yl)imidazo[1,2-a]pyridine-7-carboxamide;
(S)-N-(4-(3-fluoro-4-(trifluoromethoxy)phenyl)-3,4-dihydro-2H-pyrano[3,2-b]pyridin-4-yl)-5-oxo-4,5-dihydropyrazine-2-carboxamide;
(S)-N-(4-(3-fluoro-4-(trifluoromethoxy)phenyl)-3,4-dihydro-2H-pyrano[3,2-b]pyridin-4-yl)-5-hydroxypicolinamide;
(S)-N-(4-(3-fluoro-4-(trifluoromethoxy)phenyl)-3,4-dihydro-2H-pyrano[3,2-b]pyridin-4-yl)imidazo[1,2-a]pyridine-6-carboxamide;
(S)-N-(4-(3-fluoro-4-(trifluoromethoxy)phenyl)-3,4-dihydro-2H-pyrano[3,2-b]pyridin-4-yl)-1-methyl-1H-indazole-5-carboxamide;
(S)-N-(4-(3-fluoro-4-(trifluoromethoxy)phenyl)-3,4-dihydro-2H-pyrano[3,2-b]pyridin-4-yl)-2-oxo-1,2,3,4-tetrahydroquinoline-6-carboxamide;
(S)-5-fluoro-N-(4-(3-fluoro-4-(trifluoromethoxy)phenyl)-3,4-dihydro-2H-pyrano[3,2-b]pyridin-4-yl)picolinamide;
(S)-N-(4-(4-(trifluoromethyl)phenyl)-3,4-dihydro-2H-pyrano[3,2-b]pyridin-4-yl)quinoline-7-carboxamide;
(S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-5-carboxamide;
(S)-6-oxo-N-(4-(4-(trifluoromethoxy)phenyl)-3,4-dihydro-2H-pyrano[3,2-b]pyridin-4-yl)-1,6-dihydropyridine-3-carboxamide;
(S)-N-(4-(3-fluoro-4-(trifluoromethoxy)phenyl)-3,4-dihydro-2H-pyrano[3,2-b]pyridin-4-yl)-6-oxo-1,6-dihydropyridine-3-carboxamide;
(S)-6-oxo-N-(4-(4-(trifluoromethyl)phenyl)-3,4-dihydro-2H-pyrano[3,2-b]pyridin-4-yl)-1,6-dihydropyridine-3-carboxamide;

(S)-2-oxo-N-(4-(4-(trifluoromethyl)phenyl)-3,4-dihydro-2H-pyrano[3,2-b]pyridin-4-yl)-2,3-dihydrobenzo[d]oxazole-5-carboxamide;

(S)-N-(4-(3-fluoro-4-(trifluoromethoxy)phenyl)-3,4-dihydro-2H-pyrano[3,2-b]pyridin-4-yl)-5-nitropicolinamide;

(S)-N5-(4-(3-fluoro-4-(trifluoromethoxy)phenyl)-3,4-dihydro-2H-pyrano[3,2-b]pyridin-4-yl)-N2-methylpyridine-2,5-dicarboxamide;

(S)-N-(4-(3-fluoro-4-(trifluoromethoxy)phenyl)-3,4-dihydro-2H-pyrano[3,2-b]pyridin-4-yl)-2,3-dioxo-1,2,3,4-tetrahydroquinoxaline-6-carboxamide;

(S)-N-(4-(3-fluoro-4-(trifluoromethoxy)phenyl)-3,4-dihydro-2H-pyrano[3,2-b]pyridin-4-yl)-5-(methylsulfonamido)picolinamide;

(S)-6-((4-(3-fluoro-4-(trifluoromethoxy)phenyl)-3,4-dihydro-2H-pyrano[3,2-b]pyridin-4-yl)carbamoyl)nicotinic acid;

1-methyl-6-oxo-N-(4-(4-(trifluoromethyl)phenyl)-3,4-dihydro-2H-pyrano[3,2-b]pyridin-4-yl)-1,6-dihydropyridine-3-carboxamide;

1-oxo-N-(4-(4-(trifluoromethyl)phenyl)-3,4-dihydro-2H-pyrano[3,2-b]pyridin-4-yl)isoindoline-5-carboxamide; or (S)-N-(4-(naphthalen-2-yl)-3,4-dihydro-2H-pyrano[3,2-b]pyridin-4-yl)-6-oxo-1,6-dihydropyridine-3-carboxamide; or the pharmaceutically-acceptable salt thereof, the tautomer thereof, the pharmaceutically-acceptable salt of the tautomer, the stereoisomer thereof, or the mixture thereof.

38. The compound of claim 1, wherein the compound is (S)-N-(4-(4-(trifluoromethyl)phenyl)-3,4-dihydro-2H-pyrano[3,2-b]pyridin-4-yl)benzamide;

(S)-4-fluoro-N-(4-(4-(trifluoromethyl)phenyl)-3,4-dihydro-2H-pyrano[3,2-b]pyridin-4-yl)benzamide;

(S)-N-(4-(3,4-dichlorophenyl)-3,4-dihydro-2H-pyrano[3,2-b]pyridin-4-yl)benzamide;

(S)-4-hydroxy-N-(4-(4-(trifluoromethyl)phenyl)-3,4-dihydro-2H-pyrano[3,2-b]pyridin-4-yl)benzamide;

(S)-4-methoxy-N-(4-(4-(trifluoromethyl)phenyl)-3,4-dihydro-2H-pyrano[3,2-b]pyridin-4-yl)benzamide;

4-fluoro-N-(4-(3-fluoro-4-(trifluoromethoxy)phenyl)-3,4-dihydro-2H-pyrano[3,2-b]pyridin-4-yl)benzamide;

N-(4-(3-fluoro-4-(trifluoromethoxy)phenyl)-3,4-dihydro-2H-pyrano[3,2-b]pyridin-4-yl)benzamide;

4-fluoro-N-(4-(4-(trifluoromethoxy)phenyl)-3,4-dihydro-2H-pyrano[3,2-b]pyridin-4-yl)benzamide;

N-(4-(4-(trifluoromethoxy)phenyl)-3,4-dihydro-2H-pyrano[3,2-b]pyridin-4-yl)benzamide;

N-(4-(3,4-dichlorophenyl)-3,4-dihydro-2H-pyrano[3,2-b]pyridin-4-yl)-4-fluorobenzamide;

4-fluoro-N-(4-phenyl-3,4-dihydro-2H-pyrano[3,2-b]pyridin-4-yl)benzamide;

N-(4-phenyl-3,4-dihydro-2H-pyrano[3,2-b]pyridin-4-yl)benzamide;

N-(4-(6-(trifluoromethyl)pyridin-3-yl)-3,4-dihydro-2H-pyrano[3,2-b]pyridin-4-yl)benzamide;

(S)-N-(4-(4-chlorophenyl)-3,4-dihydro-2H-pyrano[3,2-b]pyridin-4-yl)benzamide;

(S)-N-(4-(4-chloro-3-fluorophenyl)-3,4-dihydro-2H-pyrano[3,2-b]pyridin-4-yl)benzamide;

(S)-N-(4-(4-fluorophenyl)-3,4-dihydro-2H-pyrano[3,2-b]pyridin-4-yl)benzamide;

(S)-N-(4-(3-(trifluoromethoxy)phenyl)-3,4-dihydro-2H-pyrano[3,2-b]pyridin-4-yl)benzamide;

(S)-N-(4-(p-tolyl)-3,4-dihydro-2H-pyrano[3,2-b]pyridin-4-yl)benzamide;

(S)-N-(4-(3-fluoro-4-(trifluoromethyl)phenyl)-3,4-dihydro-2H-pyrano[3,2-b]pyridin-4-yl)benzamide;

(S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-6-carboxamide;

2-oxo-N-(4-(4-(trifluoromethoxy)phenyl)-3,4-dihydro-2H-pyrano[3,2-b]pyridin-4-yl)-2,3-dihydrobenzo[d]oxazole-6-carboxamide;

2-oxo-N-(4-(4-(trifluoromethoxy)phenyl)-3,4-dihydro-2H-pyrano[3,2-b]pyridin-4-yl)-2,3-dihydrobenzo[d]oxazole-5-carboxamide;

N-(4-(3,4-dichlorophenyl)-3,4-dihydro-2H-pyrano[3,2-b]pyridin-4-yl)-2-oxo-2,3-dihydrobenzo[d]oxazole-6-carboxamide;

N-(4-(3,4-dichlorophenyl)-3,4-dihydro-2H-pyrano[3,2-b]pyridin-4-yl)-2-oxo-2,3-dihydrobenzo[d]oxazole-5-carboxamide;

2-oxo-N-(4-phenyl-3,4-dihydro-2H-pyrano[3,2-b]pyridin-4-yl)-2,3-dihydrobenzo[d]oxazole-6-carboxamide;

2-oxo-N-(4-(6-(trifluoromethyl)pyridin-3-yl)-3,4-dihydro-2H-pyrano[3,2-b]pyridin-4-yl)-2,3-dihydrobenzo[d]oxazole-5-carboxamide;

(S)-N-(4-(4-(trifluoromethyl)phenyl)chroman-4-yl)benzamide;

methyl 6-((4-(3-fluoro-4-(trifluoromethoxy)phenyl)-3,4-dihydro-2H-pyrano[3,2-b]pyridin-4-yl)carbamoyl)nicotinate;

(S)-6-methoxy-N-(4-(4-(trifluoromethyl)phenyl)-3,4-dihydro-2H-pyrano[3,2-b]pyridin-4-yl)nicotinamide;

(S)-2-oxo-N-(4-(4-(trifluoromethyl)phenyl)-3,4-dihydro-2H-pyrano[3,2-b]pyridin-4-yl)-1,2,3,4-tetrahydroquinoline-6-carboxamide;

(S)-N-(4-(4-(trifluoromethyl)phenyl)-3,4-dihydro-2H-pyrano[3,2-b]pyridin-4-yl)-1H-indazole-6-carboxamide;

(S)-N-(4-(4-(trifluoromethyl)phenyl)-3,4-dihydro-2H-pyrano[3,2-b]pyridin-4-yl)pyrimidine-4-carboxamide;

(S)-N-(4-(4-(trifluoromethyl)phenyl)-3,4-dihydro-2H-pyrano[3,2-b]pyridin-4-yl)-1H-indole-6-carboxamide;

(S)-N-(4-(4-(trifluoromethyl)phenyl)-3,4-dihydro-2H-pyrano[3,2-b]pyridin-4-yl)pyridazine-4-carboxamide;

(S)-1-methyl-N-(4-(4-(trifluoromethyl)phenyl)-3,4-dihydro-2H-pyrano[3,2-b]pyridin-4-yl)-1H-indazole-6-carboxamide;

(S)-N-(4-(4-(trifluoromethyl)phenyl)-3,4-dihydro-2H-pyrano[3,2-b]pyridin-4-yl)thiazole-5-carboxamide;

(S)-5-hydroxy-N-(4-(4-(trifluoromethyl)phenyl)-3,4-dihydro-2H-pyrano[3,2-b]pyridin-4-yl)picolinamide;

(S)-N-(4-(4-(trifluoromethyl)phenyl)-3,4-dihydro-2H-pyrano[3,2-b]pyridin-4-yl)isothiazole-5-carboxamide;

(S)-1-methyl-N-(4-(4-(trifluoromethyl)phenyl)-3,4-dihydro-2H-pyrano[3,2-b]pyridin-4-yl)-1H-indole-5-carboxamide;

(S)-5-acetamido-N-(4-(4-(trifluoromethyl)phenyl)-3,4-dihydro-2H-pyrano[3,2-b]pyridin-4-yl)picolinamide;

(S)-1-methyl-N-(4-(4-(trifluoromethyl)phenyl)-3,4-dihydro-2H-pyrano[3,2-b]pyridin-4-yl)-1H-indazole-5-carboxamide;

(S)-5-oxo-N-(4-(4-(trifluoromethyl)phenyl)-3,4-dihydro-2H-pyrano[3,2-b]pyridin-4-yl)-4,5-dihydropyrazine-2-carboxamide;

(S)-N-(4-(4-(trifluoromethyl)phenyl)-3,4-dihydro-2H-pyrano[3,2-b]pyridin-4-yl)isonicotinamide;

(S)-6-methoxy-N-(4-(4-(trifluoromethyl)phenyl)-3,4-dihydro-2H-pyrano[3,2-b]pyridin-4-yl)pyridazine-3-carboxamide;

(S)-N-(4-(4-(trifluoromethyl)phenyl)-3,4-dihydro-2H-pyrano[3,2-b]pyridin-4-yl)nicotinamide;
(S)-N-(4-(4-(trifluoromethyl)phenyl)-3,4-dihydro-2H-pyrano[3,2-b]pyridin-4-yl)imidazo[1,2-a]pyridine-7-carboxamide;
(S)-N-(4-(3-fluoro-4-(trifluoromethoxy)phenyl)-3,4-dihydro-2H-pyrano[3,2-b]pyridin-4-yl)-5-oxo-4,5-dihydropyrazine-2-carboxamide;
(S)-N-(4-(3-fluoro-4-(trifluoromethoxy)phenyl)-3,4-dihydro-2H-pyrano[3,2-b]pyridin-4-yl)-5-hydroxypicolinamide;
(S)-N-(4-(3-fluoro-4-(trifluoromethoxy)phenyl)-3,4-dihydro-2H-pyrano[3,2-b]pyridin-4-yl)imidazo[1,2-a]pyridine-6-carboxamide;
(S)-N-(4-(3-fluoro-4-(trifluoromethoxy)phenyl)-3,4-dihydro-2H-pyrano[3,2-b]pyridin-4-yl)-1-methyl-1H-indazole-5-carboxamide;
(S)-N-(4-(3-fluoro-4-(trifluoromethoxy)phenyl)-3,4-dihydro-2H-pyrano[3,2-b]pyridin-4-yl)-2-oxo-1,2,3,4-tetrahydroquinoline-6-carboxamide;
(S)-5-fluoro-N-(4-(3-fluoro-4-(trifluoromethoxy)phenyl)-3,4-dihydro-2H-pyrano[3,2-b]pyridin-4-yl)picolinamide;
(S)-N-(4-(4-(trifluoromethyl)phenyl)-3,4-dihydro-2H-pyrano[3,2-b]pyridin-4-yl)quinoline-7-carboxamide;
(S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-5-carboxamide;
(S)-6-oxo-N-(4-(4-(trifluoromethoxy)phenyl)-3,4-dihydro-2H-pyrano[3,2-b]pyridin-4-yl)-1,6-dihydropyridine-3-carboxamide;
(S)-N-(4-(3-fluoro-4-(trifluoromethoxy)phenyl)-3,4-dihydro-2H-pyrano[3,2-b]pyridin-4-yl)-6-oxo-1,6-dihydropyridine-3-carboxamide;
(S)-6-oxo-N-(4-(4-(trifluoromethyl)phenyl)-3,4-dihydro-2H-pyrano[3,2-b]pyridin-4-yl)-1,6-dihydropyridine-3-carboxamide;
(S)-N-(4-(3-fluoro-4-(trifluoromethoxy)phenyl)-3,4-dihydro-2H-pyrano[3,2-b]pyridin-4-yl)-5-nitropicolinamide;
(S)-N5-(4-(3-fluoro-4-(trifluoromethoxy)phenyl)-3,4-dihydro-2H-pyrano[3,2-b]pyridin-4-yl)-N2-methylpyridine-2,5-dicarboxamide;
(S)-N-(4-(3-fluoro-4-(trifluoromethoxy)phenyl)-3,4-dihydro-2H-pyrano[3,2-b]pyridin-4-yl)-2,3-dioxo-1,2,3,4-tetrahydroquinoxaline-6-carboxamide;
(S)-N-(4-(3-fluoro-4-(trifluoromethoxy)phenyl)-3,4-dihydro-2H-pyrano[3,2-b]pyridin-4-yl)-5-(methylsulfonamido)picolinamide; or
(S)-6-((4-(3-fluoro-4-(trifluoromethoxy)phenyl)-3,4-dihydro-2H-pyrano[3,2-b]pyridin-4-yl)carbamoyl)nicotinic acid; or the pharmaceutically-acceptable salt thereof, the tautomer thereof, the pharmaceutically-acceptable salt of the tautomer, the stereoisomer thereof, or the mixture thereof.

39. The compound of claim 1, wherein the compound is (S)-N-(4-(4-(trifluoromethyl)phenyl)-3,4-dihydro-2H-pyrano[3,2-b]pyridin-4-yl)benzamide;
(S)-N-(4-(3,4-dichlorophenyl)-3,4-dihydro-2H-pyrano[3,2-b]pyridin-4-yl)benzamide;
(S)-4-hydroxy-N-(4-(4-(trifluoromethyl)phenyl)-3,4-dihydro-2H-pyrano[3,2-b]pyridin-4-yl)benzamide;
(S)-4-methoxy-N-(4-(4-(trifluoromethyl)phenyl)-3,4-dihydro-2H-pyrano[3,2-b]pyridin-4-yl)benzamide;
4-fluoro-N-(4-(3-fluoro-4-(trifluoromethoxy)phenyl)-3,4-dihydro-2H-pyrano[3,2-b]pyridin-4-yl)benzamide;
N-(4-(3-fluoro-4-(trifluoromethoxy)phenyl)-3,4-dihydro-2H-pyrano[3,2-b]pyridin-4-yl)benzamide;
N-(4-(4-(trifluoromethoxy)phenyl)-3,4-dihydro-2H-pyrano[3,2-b]pyridin-4-yl)benzamide;
(S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-6-carboxamide;
2-oxo-N-(4-(4-(trifluoromethoxy)phenyl)-3,4-dihydro-2H-pyrano[3,2-b]pyridin-4-yl)-2,3-dihydrobenzo[d]oxazole-6-carboxamide;
2-oxo-N-(4-(4-(trifluoromethoxy)phenyl)-3,4-dihydro-2H-pyrano[3,2-b]pyridin-4-yl)-2,3-dihydrobenzo[d]oxazole-5-carboxamide;
N-(4-(3,4-dichlorophenyl)-3,4-dihydro-2H-pyrano[3,2-b]pyridin-4-yl)-2-oxo-2,3-dihydrobenzo[d]oxazole-6-carboxamide;
N-(4-(3,4-dichlorophenyl)-3,4-dihydro-2H-pyrano[3,2-b]pyridin-4-yl)-2-oxo-2,3-dihydrobenzo[d]oxazole-5-carboxamide;
2-oxo-N-(4-phenyl-3,4-dihydro-2H-pyrano[3,2-b]pyridin-4-yl)-2,3-dihydrobenzo[d]oxazole-6-carboxamide;
methyl 6-((4-(3-fluoro-4-(trifluoromethoxy)phenyl)-3,4-dihydro-2H-pyrano[3,2-b]pyridin-4-yl)carbamoyl)nicotinate;
(S)-N-(4-(4-(trifluoromethyl)phenyl)-3,4-dihydro-2H-pyrano[3,2-b]pyridin-4-yl)-1H-indazole-6-carboxamide;
(S)-N-(4-(4-(trifluoromethyl)phenyl)-3,4-dihydro-2H-pyrano[3,2-b]pyridin-4-yl)-1H-indole-6-carboxamide;
(S)-1-methyl-N-(4-(4-(trifluoromethyl)phenyl)-3,4-dihydro-2H-pyrano[3,2-b]pyridin-4-yl)-1H-indazole-6-carboxamide;
(S)-N-(4-(4-(trifluoromethyl)phenyl)-3,4-dihydro-2H-pyrano[3,2-b]pyridin-4-yl)thiazole-5-carboxamide;
(S)-5-hydroxy-N-(4-(4-(trifluoromethyl)phenyl)-3,4-dihydro-2H-pyrano[3,2-b]pyridin-4-yl)picolinamide;
(S)-1-methyl-N-(4-(4-(trifluoromethyl)phenyl)-3,4-dihydro-2H-pyrano[3,2-b]pyridin-4-yl)-1H-indole-5-carboxamide;
(S)-5-oxo-N-(4-(4-(trifluoromethyl)phenyl)-3,4-dihydro-2H-pyrano[3,2-b]pyridin-4-yl)-4,5-dihydropyrazine-2-carboxamide;
(S)-N-(4-(3-fluoro-4-(trifluoromethoxy)phenyl)-3,4-dihydro-2H-pyrano[3,2-b]pyridin-4-yl)imidazo[1,2-a]pyridine-6-carboxamide;
(S)-N-(4-(3-fluoro-4-(trifluoromethoxy)phenyl)-3,4-dihydro-2H-pyrano[3,2-b]pyridin-4-yl)-1-methyl-1H-indazole-5-carboxamide;
(S)-N-(4-(3-fluoro-4-(trifluoromethoxy)phenyl)-3,4-dihydro-2H-pyrano[3,2-b]pyridin-4-yl)-2-oxo-1,2,3,4-tetrahydroquinoline-6-carboxamide;
(S)-5-fluoro-N-(4-(3-fluoro-4-(trifluoromethoxy)phenyl)-3,4-dihydro-2H-pyrano[3,2-b]pyridin-4-yl)picolinamide;
(S)-N-(4-(4-(trifluoromethyl)phenyl)-3,4-dihydro-2H-pyrano[3,2-b]pyridin-4-yl)quinoline-7-carboxamide;
(S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-5-carboxamide;
(S)-6-oxo-N-(4-(4-(trifluoromethoxy)phenyl)-3,4-dihydro-2H-pyrano[3,2-b]pyridin-4-yl)-1,6-dihydropyridine-3-carboxamide;
(S)-N-(4-(3-fluoro-4-(trifluoromethoxy)phenyl)-3,4-dihydro-2H-pyrano[3,2-b]pyridin-4-yl)-6-oxo-1,6-dihydropyridine-3-carboxamide;

(S)-N5-(4-(3-fluoro-4-(trifluoromethoxy)phenyl)-3,4-dihydro-2H-pyrano[3,2-b]pyridin-4-yl)-N2-methylpyridine-2,5-dicarboxamide;

(S)-N-(4-(3-fluoro-4-(trifluoromethoxy)phenyl)-3,4-dihydro-2H-pyrano[3,2-b]pyridin-4-yl)-5-(methylsulfonamido)picolinamide;

(S)-6-((4-(3-fluoro-4-(trifluoromethoxy)phenyl)-3,4-dihydro-2H-pyrano[3,2-b]pyridin-4-yl)carbamoyl)nicotinic acid; or the pharmaceutically-acceptable salt thereof, the tautomer thereof, the pharmaceutically-acceptable salt of the tautomer, the stereoisomer thereof, or the mixture thereof.

40. The compound of claim 1, wherein the compound is (S)-N-(4-(4-(trifluoromethyl)phenyl)-3,4-dihydro-2H-pyrano[3,2-b]pyridin-4-yl)benzamide or the pharmaceutically-acceptable salt thereof, the tautomer thereof, the pharmaceutically-acceptable salt of the tautomer, the stereoisomer thereof, or the mixture thereof.

41. The compound of claim 1, wherein the compound is (S)-4-hydroxy-N-(4-(4-(trifluoromethyl)phenyl)-3,4-dihydro-2H-pyrano[3,2-b]pyridin-4-yl)benzamide or the pharmaceutically-acceptable salt thereof, the tautomer thereof, the pharmaceutically-acceptable salt of the tautomer, the stereoisomer thereof, or the mixture thereof.

42. The compound of claim 1, wherein the compound is (S)-6-((4-(3-fluoro-4-(trifluoromethoxy)phenyl)-3,4-dihydro-2H-pyrano[3,2-b]pyridin-4-yl)carbamoyl)nicotinic acid or the pharmaceutically-acceptable salt thereof, the tautomer thereof, the pharmaceutically-acceptable salt of the tautomer, the stereoisomer thereof, or the mixture thereof.

43. The compound of claim 1, wherein the compound is (S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-6-carboxamide or the pharmaceutically-acceptable salt thereof, the tautomer thereof, the pharmaceutically-acceptable salt of the tautomer, the stereoisomer thereof, or the mixture thereof.

44. The compound of claim 1, wherein the compound is 2-oxo-N-(4-(4-(trifluoromethoxy)phenyl)-3,4-dihydro-2H-pyrano[3,2-b]pyridin-4-yl)-2,3-dihydrobenzo[d]oxazole-6-carboxamide or the pharmaceutically-acceptable salt thereof, the tautomer thereof, the pharmaceutically-acceptable salt of the tautomer, the stereoisomer thereof, or the mixture thereof.

45. The compound of claim 1, wherein the compound is 2-oxo-N-(4-(4-(trifluoromethoxy)phenyl)-3,4-dihydro-2H-pyrano[3,2-b]pyridin-4-yl)-2,3-dihydrobenzo[d]oxazole-5-carboxamide or the pharmaceutically-acceptable salt thereof, the tautomer thereof, the pharmaceutically-acceptable salt of the tautomer, the stereoisomer thereof, or the mixture thereof.

46. The compound of claim 1, wherein the compound is (S)-N-(4-(3-fluoro-4-(trifluoromethoxy)phenyl)-3,4-dihydro-2H-pyrano[3,2-b]pyridin-4-yl)-6-oxo-1,6-dihydropyridine-3-carboxamide or the pharmaceutically-acceptable salt thereof, the tautomer thereof, the pharmaceutically-acceptable salt of the tautomer, the stereoisomer thereof, or the mixture thereof.

47. The compound of claim 1, wherein the compound is N-(4-(3,4-dichlorophenyl)-3,4-dihydro-2H-pyrano[3,2-b]pyridin-4-yl)-2-oxo-2,3-dihydrobenzo[d]oxazole-5-carboxamide or the pharmaceutically-acceptable salt thereof, the tautomer thereof, the pharmaceutically-acceptable salt of the tautomer, the stereoisomer thereof, or the mixture thereof.

48. The compound of claim 1, wherein the compound is 2-oxo-N-(4-phenyl-3,4-dihydro-2H-pyrano[3,2-b]pyridin-4-yl)-2,3-dihydrobenzo[d]oxazole-6-carboxamide or the pharmaceutically-acceptable salt thereof, the tautomer thereof, the pharmaceutically-acceptable salt of the tautomer, the stereoisomer thereof, or the mixture thereof.

49. The compound of claim 1, wherein the compound is (S)-N-(4-(3-fluoro-4-(trifluoromethoxy)phenyl)-3,4-dihydro-2H-pyrano[3,2-b]pyridin-4-yl)-5-(methylsulfonamido)picolinamide or the pharmaceutically-acceptable salt thereof, the tautomer thereof, the pharmaceutically-acceptable salt of the tautomer, the stereoisomer thereof, or the mixture thereof.

50. The compound of claim 1, wherein the compound is (S)-N5-(4-(3-fluoro-4-(trifluoromethoxy)phenyl)-3,4-dihydro-2H-pyrano[3,2-b]pyridin-4-yl)-N2-methylpyridine-2,5-dicarboxamide or the pharmaceutically-acceptable salt thereof, the tautomer thereof, the pharmaceutically-acceptable salt of the tautomer, the stereoisomer thereof, or the mixture thereof.

51. The compound of claim 1, wherein the compound is (S)-N-(4-(3-fluoro-4-(trifluoromethoxy)phenyl)-3,4-dihydro-2H-pyrano[3,2-b]pyridin-4-yl)-2-oxo-2,3-dihydrobenzo[d]oxazole-5-carboxamide or the pharmaceutically-acceptable salt thereof, the tautomer thereof, the pharmaceutically-acceptable salt of the tautomer, the stereoisomer thereof, or the mixture thereof.

52. The compound of claim 1, wherein the compound is (S)-5-hydroxy-N-(4-(4-(trifluoromethyl)phenyl)-3,4-dihydro-2H-pyrano[3,2-b]pyridin-4-yl)picolinamide or the pharmaceutically-acceptable salt thereof, the tautomer thereof, the pharmaceutically-acceptable salt of the tautomer, the stereoisomer thereof, or the mixture thereof.

53. The compound of claim 1, wherein the compound is (S)-2-oxo-N-(4-(4-(trifluoromethyl)phenyl)-3,4-dihydro-2H-pyrano[3,2-b]pyridin-4-yl)-1,2,3,4-tetrahydroquinoline-6-carboxamide or the pharmaceutically-acceptable salt thereof, the tautomer thereof, the pharmaceutically-acceptable salt of the tautomer, the stereoisomer thereof, or the mixture thereof.

54. The compound of claim 1, wherein the compound is methyl 6-((4-(3-fluoro-4-(trifluoromethoxy)phenyl)-3,4-dihydro-2H-pyrano[3,2-b]pyridin-4-yl)carbamoyl)nicotinate or the pharmaceutically-acceptable salt thereof, the tautomer thereof, the pharmaceutically-acceptable salt of the tautomer, the stereoisomer thereof, or the mixture thereof.

55. The compound of claim 1, wherein the compound is (S)-N-(4-(3,4-dichlorophenyl)-3,4-dihydro-2H-pyrano[3,2-b]pyridin-4-yl)-6-oxo-1,6-dihydropyridine-3-carboxamide;

(S)-N-(4-(2-fluoro-4-(trifluoromethoxy)phenyl)-3,4-dihydro-2H-pyrano[3,2-b]pyridin-4-yl)-6-oxo-1,6-dihydropyridine-3-carboxamide;

(S)-N-(4-(2-chloro-4-(trifluoromethoxy)phenyl)-3,4-dihydro-2H-pyrano[3,2-b]pyridin-4-yl)-6-oxo-1,6-dihydropyridine-3-carboxamide;

(S)-N-(4-(2-methyl-4-(trifluoromethoxy)phenyl)-3,4-dihydro-2H-pyrano[3,2-b]pyridin-4-yl)-6-oxo-1,6-dihydropyridine-3-carboxamide;

(S)-N-(4-(3-chloro-4-(trifluoromethyl)phenyl)-3,4-dihydro-2H-pyrano[3,2-b]pyridin-4-yl)-6-oxo-1,6-dihydropyridine-3-carboxamide;

(S)-N-(4-(3-chloro-4-(trifluoromethoxy)phenyl)-3,4-dihydro-2H-pyrano[3,2-b]pyridin-4-yl)-6-oxo-1,6-dihydropyridine-3-carboxamide;

(S)-N-(4-(3-fluoro-4-(trifluoromethyl)phenyl)-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-6-methyl-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-7-methyl-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-8-methyl-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-6-chloro-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-7-chloro-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-8-chloro-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-6-fluoro-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-7-fluoro-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-8-fluoro-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-6-methoxy-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-7-methoxy-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-8-methoxy-3,4-dihydro-2H-pyrano[3,2-b]pyridin-4-yl)-6-oxo-1,6-dihydropyridine-3-carboxamide;

(S)-N-(4-([1,1'-biphenyl]-4-yl)-3,4-dihydro-2H-pyrano[3,2-b]pyridin-4-yl)-6-oxo-1,6-dihydropyridine-3-carboxamide;

(S)-N-(4-(3-fluoro-4-(trifluoromethoxy)phenyl)-2,2-dimethyl-3,4-dihydro-2H-pyrano[3,2-b]pyridin-4-yl)-6-oxo-1,6-dihydropyridine-3-carboxamide;

(S)-N-(4-(5-fluoro-6-(trifluoromethoxy)pyridin-3-yl)-3,4-dihydro-2H-pyrano[3,2-b]pyridin-4-yl)-6-oxo-1,6-dihydropyridine-3-carboxamide;

(S)-6-((4-(3,4-dichlorophenyl)-3,4-dihydro-2H-pyrano[3,2-b]pyridin-4-yl)carbamoyl)nicotinic acid;

(S)-6-((4-(4-(trifluoromethoxy)phenyl)-3,4-dihydro-2H-pyrano[3,2-b]pyridin-4-yl)carbamoyl)nicotinic acid;

(S)-6-((4-(4-(trifluoromethyl)phenyl)-3,4-dihydro-2H-pyrano[3,2-b]pyridin-4-yl)carbamoyl)nicotinic acid;

(S)-6-((4-(3-fluoro-4-(trifluoromethyl)phenyl)-3,4-dihydro-2H-pyrano[3,2-b]pyridin-4-yl)carbamoyl)nicotinic acid;

(S)-6-((4-(3-chloro-4-(trifluoromethyl)phenyl)-3,4-dihydro-2H-pyrano[3,2-b]pyridin-4-yl)carbamoyl)nicotinic acid;

(S)-6-((4-(2-fluoro-4-(trifluoromethoxy)phenyl)-3,4-dihydro-2H-pyrano[3,2-b]pyridin-4-yl)carbamoyl)nicotinic acid;

(S)-6-((4-(3-chloro-4-(trifluoromethoxy)phenyl)-3,4-dihydro-2H-pyrano[3,2-b]pyridin-4-yl)carbamoyl)nicotinic acid; or (S)-6-((4-(3-fluoro-4-(trifluoromethoxy)phenyl)chroman-4-yl)carbamoyl)nicotinic acid; or the pharmaceutically-acceptable salt thereof, the tautomer thereof, the pharmaceutically-acceptable salt of the tautomer, the stereoisomer thereof, or the mixture thereof.

56. The compound of claim 1, wherein the compound is (S)-N-(4-(3-fluoro-4-(trifluoromethyl)phenyl)-3,4-dihydro-2H-pyrano[3,2-b]pyridin-4-yl)-6-oxo-1,6-dihydropyridine-3-carboxamide or the pharmaceutically-acceptable salt thereof, the tautomer thereof, the pharmaceutically-acceptable salt of the tautomer, the stereoisomer thereof, or the mixture thereof.

57. A pharmaceutical composition comprising the compound according to claim 1 or the pharmaceutically-acceptable salt thereof, the tautomer thereof, the pharmaceutically-acceptable salt of the tautomer, the stereoisomer thereof, or the mixture thereof, and a pharmaceutically-acceptable diluent or carrier.

* * * * *